US012215151B2

(12) United States Patent
Yoo et al.

(10) Patent No.: US 12,215,151 B2
(45) Date of Patent: Feb. 4, 2025

(54) METHODS OF TREATING CANCER USING ANTIBODIES AND MOLECULES THAT IMMUNOSPECIFICALLY BIND TO BTN1A1

(71) Applicant: STCUBE & CO., INC., Seoul (KR)

(72) Inventors: Stephen Sunghan Yoo, Centreville, VA (US); Yong-Sik Bong, Frederick, MD (US); Kyu Lee Han, Frederick, MD (US); Michael Joseph Surace, Germantown, MD (US)

(73) Assignee: STCUBE & CO., INC., Seoul (KR)

( * ) Notice: Subject to any disclaimer, the term of this patent is extended or adjusted under 35 U.S.C. 154(b) by 376 days.

(21) Appl. No.: 16/618,050

(22) PCT Filed: May 30, 2018

(86) PCT No.: PCT/US2018/035082

§ 371 (c)(1),
(2) Date: Nov. 27, 2019

(87) PCT Pub. No.: WO2018/222685

PCT Pub. Date: Dec. 6, 2018

(65) Prior Publication Data

US 2020/0131266 A1 Apr. 30, 2020

Related U.S. Application Data

(60) Provisional application No. 62/513,393, filed on May 31, 2017.

(51) Int. Cl.

| | |
|---|---|
| ***A61K 39/395*** | (2006.01) |
| ***A61N 5/10*** | (2006.01) |
| ***A61P 35/00*** | (2006.01) |
| ***C07K 16/28*** | (2006.01) |
| ***G01N 33/574*** | (2006.01) |
| *A61K 39/00* | (2006.01) |

(52) U.S. Cl.

CPC ............ *C07K 16/2803* (2013.01); *A61N 5/10* (2013.01); *A61P 35/00* (2018.01); *C07K 16/2818* (2013.01); *C07K 16/2827* (2013.01); *G01N 33/57415* (2013.01); *G01N 33/57423* (2013.01); *A61K 2039/505* (2013.01); *A61K 2039/507* (2013.01); *C07K 2317/565* (2013.01); *C07K 2317/73* (2013.01); *C07K 2317/76* (2013.01); *C07K 2317/92* (2013.01); *G01N 2333/70532* (2013.01)

(58) Field of Classification Search

None

See application file for complete search history.

(56) References Cited

U.S. PATENT DOCUMENTS

| | | | |
|---|---|---|---|
| 3,817,837 | A | 6/1974 | Rubenstein et al. |
| 3,850,752 | A | 11/1974 | Schuurs et al. |
| 3,939,350 | A | 2/1976 | Kronick et al. |
| 3,996,345 | A | 12/1976 | Ullman et al. |
| 4,016,043 | A | 4/1977 | Schuurs et al. |
| 4,018,653 | A | 4/1977 | Mennen |
| 4,179,337 | A | 12/1979 | Davis et al. |
| 4,196,265 | A | 4/1980 | Koprowski et al. |
| 4,275,149 | A | 6/1981 | Litman et al. |
| 4,277,437 | A | 7/1981 | Maggio |
| 4,366,241 | A | 12/1982 | Tom et al. |
| 4,424,279 | A | 1/1984 | Bohn et al. |
| 4,444,887 | A | 4/1984 | Hoffmann |
| 4,469,797 | A | 9/1984 | Albarella |
| 4,472,509 | A | 9/1984 | Gansow et al. |
| 4,485,045 | A | 11/1984 | Regen |
| 4,526,938 | A | 7/1985 | Churchill et al. |
| 4,544,545 | A | 10/1985 | Ryan et al. |
| 4,606,855 | A | 8/1986 | Deutsch et al. |
| 4,676,980 | A | 6/1987 | Segal et al. |
| 4,703,003 | A | 10/1987 | Struck |
| 4,716,111 | A | 12/1987 | Osband et al. |
| 4,741,900 | A | 5/1988 | Alvarez et al. |
| 4,742,159 | A | 5/1988 | Batz et al. |
| 4,767,720 | A | 8/1988 | Lingwood |
| 4,816,397 | A | 3/1989 | Boss et al. |
| 4,816,567 | A | 3/1989 | Cabilly et al. |

(Continued)

FOREIGN PATENT DOCUMENTS

| | | |
|---|---|---|
| EP | 0 592 106 B1 | 4/1994 |
| EP | 0 239 400 B1 | 8/1994 |

(Continued)

OTHER PUBLICATIONS

Jeong et al (Journal of Biological Chemistry, 2009, 284:22444-22456).*
Smith et al (Journal of Immunology, 2010, 184:3514-3525).*
O'Donnell et al (Cancer Treatment Reviews, Jan. 2017, 52:71-81).*
Stancovski et al, (PNAS, 1991, 88:8691-8695).*
Harwerth et al (Br. J. Cancer, 1993, 68:1140-1145).*
Horita et al (Scientific Reports, 2016, 6:35297, p. 1-8).*
Wang et al (Cancer Immunology Research, 2014, 2:846-856).*
Wang et al (OncoTargets and Therapy, 2016, 9:5023-5039).*
Sabatier et al (Oncotarget, 2014, 6:5549-5464).*

(Continued)

*Primary Examiner* — Laura B Goddard
(74) *Attorney, Agent, or Firm* — Jones Day

(57) ABSTRACT

Provided herein are methods for treating cancer using molecules having an antigen binding fragment that immunospecifically binds to BTN1A1, such as anti-BTN1A1 antibodies. These molecules include those having an antigen binding fragment that immunospecifically binds to glycosylated BTN1A1, such as anti-glycosylated BTN1A1 antibodies. Also included are molecules having an antigen binding fragment that immunospecifically bind to BTN1A1 dimers, such as anti-BTN1A1 dimer antibodies. Also provided are methods for treating anti-PD-1 therapy or anti-PD-L1 therapy resistant or refractory cancers.

20 Claims, 21 Drawing Sheets

Specification includes a Sequence Listing.

(56) References Cited

U.S. PATENT DOCUMENTS

| | | | |
|---|---|---|---|
| 4,867,973 | A | 9/1989 | Goers et al. |
| 4,870,287 | A | 9/1989 | Cole et al. |
| 4,880,078 | A | 11/1989 | Inoue et al. |
| 4,938,948 | A | 7/1990 | Ring et al. |
| 4,946,778 | A | 8/1990 | Ladner et al. |
| 4,980,286 | A | 12/1990 | Morgan et al. |
| 5,013,556 | A | 5/1991 | Woodle et al. |
| 5,021,236 | A | 6/1991 | Gries et al. |
| 5,091,513 | A | 2/1992 | Huston et al. |
| 5,128,326 | A | 7/1992 | Balazs et al. |
| 5,164,296 | A | 11/1992 | Blaustein et al. |
| 5,196,066 | A | 3/1993 | Kusuda et al. |
| 5,223,409 | A | 6/1993 | Ladner et al. |
| 5,225,539 | A | 7/1993 | Winter |
| 5,258,498 | A | 11/1993 | Huston et al. |
| 5,290,540 | A | 3/1994 | Prince et al. |
| 5,403,484 | A | 4/1995 | Ladner et al. |
| 5,413,923 | A | 5/1995 | Kucherlapati et al. |
| 5,420,253 | A | 5/1995 | Emery et al. |
| 5,427,908 | A | 6/1995 | Dower et al. |
| 5,516,637 | A | 5/1996 | Huang et al. |
| 5,530,101 | A | 6/1996 | Queen et al. |
| 5,545,806 | A | 8/1996 | Lonberg et al. |
| 5,565,332 | A | 10/1996 | Hoogenboom et al. |
| 5,569,825 | A | 10/1996 | Lonberg et al. |
| 5,571,698 | A | 11/1996 | Ladner et al. |
| 5,580,717 | A | 12/1996 | Dower et al. |
| 5,585,089 | A | 12/1996 | Queen et al. |
| 5,587,459 | A | 12/1996 | Uckun |
| 5,618,709 | A | 4/1997 | Gewirtz et al. |
| 5,624,821 | A | 4/1997 | Winter et al. |
| 5,625,126 | A | 4/1997 | Lonberg et al. |
| 5,627,052 | A | 5/1997 | Schrader |
| 5,633,425 | A | 5/1997 | Lonberg et al. |
| 5,648,239 | A | 7/1997 | Hawkins et al. |
| 5,656,434 | A | 8/1997 | Terano et al. |
| 5,658,727 | A | 8/1997 | Barbas et al. |
| 5,661,016 | A | 8/1997 | Lonberg et al. |
| 5,679,377 | A | 10/1997 | Bernstein et al. |
| 5,698,426 | A | 12/1997 | Huse |
| 5,728,868 | A | 3/1998 | Springer et al. |
| 5,733,743 | A | 3/1998 | Johnson et al. |
| 5,734,033 | A | 3/1998 | Reed |
| 5,739,169 | A | 4/1998 | Ocain et al. |
| 5,750,753 | A | 5/1998 | Kimae et al. |
| 5,760,395 | A | 6/1998 | Johnstone |
| 5,770,376 | A | 6/1998 | Bagrov |
| 5,780,225 | A | 7/1998 | Wigler et al. |
| 5,789,208 | A | 8/1998 | Sharon |
| 5,801,005 | A | 9/1998 | Cheever et al. |
| 5,807,715 | A | 9/1998 | Morrison et al. |
| 5,814,318 | A | 9/1998 | Lonberg et al. |
| 5,821,047 | A | 10/1998 | Garrard et al. |
| 5,821,337 | A | 10/1998 | Carter et al. |
| 5,824,311 | A | 10/1998 | Greene et al. |
| 5,830,880 | A | 11/1998 | Sedlacek et al. |
| 5,840,745 | A | 11/1998 | Buzzetti et al. |
| 5,843,597 | A | 12/1998 | Getz |
| 5,844,091 | A | 12/1998 | Blaustein et al. |
| 5,846,945 | A | 12/1998 | McCormick |
| 5,855,913 | A | 1/1999 | Hanes et al. |
| 5,858,657 | A | 1/1999 | Winter et al. |
| 5,861,155 | A | 1/1999 | Lin |
| 5,863,904 | A | 1/1999 | Nabel et al. |
| 5,871,907 | A | 2/1999 | Winter et al. |
| 5,872,223 | A | 2/1999 | Uckun |
| 5,874,064 | A | 2/1999 | Edwards et al. |
| 5,885,834 | A | 3/1999 | Epstein |
| 5,888,533 | A | 3/1999 | Dunn |
| 5,911,995 | A | 6/1999 | Uckun |
| 5,912,015 | A | 6/1999 | Bernstein et al. |
| 5,916,597 | A | 6/1999 | Lee et al. |
| 5,916,771 | A | 6/1999 | Hori et al. |
| 5,922,844 | A | 7/1999 | Hawkins et al. |
| 5,925,376 | A | 7/1999 | Heng |
| 5,934,272 | A | 8/1999 | Lloyd et al. |
| 5,939,598 | A | 8/1999 | Kucherlapati et al. |
| 5,945,155 | A | 8/1999 | Grill et al. |
| 5,958,769 | A | 9/1999 | Roberts et al. |
| 5,969,108 | A | 10/1999 | McCafferty et al. |
| 5,985,309 | A | 11/1999 | Edwards et al. |
| 5,985,877 | A | 11/1999 | Dionne et al. |
| 5,989,463 | A | 11/1999 | Tracy et al. |
| 5,998,596 | A | 12/1999 | Bergan et al. |
| 6,019,968 | A | 2/2000 | Platz et al. |
| 6,034,053 | A | 3/2000 | Uckun et al. |
| 6,040,305 | A | 3/2000 | Taveras et al. |
| 6,051,574 | A | 4/2000 | Anthony |
| 6,051,582 | A | 4/2000 | Taveras |
| 6,054,297 | A | 4/2000 | Carter et al. |
| 6,054,466 | A | 4/2000 | Ciccarone et al. |
| 6,057,300 | A | 5/2000 | Nabel et al. |
| 6,063,930 | A | 5/2000 | Dinsmore et al. |
| 6,066,738 | A | 5/2000 | Dinsmore et al. |
| 6,071,935 | A | 6/2000 | Lyssikatos |
| 6,077,853 | A | 6/2000 | Graham et al. |
| 6,080,870 | A | 6/2000 | Anthony et al. |
| 6,090,948 | A | 7/2000 | Dinsmore et al. |
| 6,093,737 | A | 7/2000 | Anthony et al. |
| 6,103,723 | A | 8/2000 | Bergman et al. |
| 6,124,295 | A | 9/2000 | Taveras et al. |
| 6,124,465 | A | 9/2000 | Bourzat et al. |
| 6,127,366 | A | 10/2000 | Kim et al. |
| 6,133,303 | A | 10/2000 | Bikker et al. |
| 6,143,766 | A | 11/2000 | Kaltenbronn |
| 6,159,984 | A | 12/2000 | Guzi et al. |
| 6,165,464 | A | 12/2000 | Hudziak et al. |
| 6,169,096 | B1 | 1/2001 | Venet et al. |
| 6,187,786 | B1 | 2/2001 | Venet et al. |
| 6,194,551 | B1 | 2/2001 | Idusogie et al. |
| 6,211,193 | B1 | 4/2001 | Remiszewski et al. |
| 6,218,372 | B1 | 4/2001 | Nabel et al. |
| 6,218,406 | B1 | 4/2001 | Bourzat et al. |
| 6,218,410 | B1 | 4/2001 | Uehata et al. |
| 6,225,322 | B1 | 5/2001 | Cooper et al. |
| 6,228,856 | B1 | 5/2001 | Njoroge et al. |
| 6,228,865 | B1 | 5/2001 | Doll et al. |
| 6,232,338 | B1 | 5/2001 | Davies et al. |
| 6,239,140 | B1 | 5/2001 | Cooper et al. |
| 6,242,196 | B1 | 6/2001 | Spiegelman et al. |
| 6,245,759 | B1 | 6/2001 | Bilodeau et al. |
| 6,248,756 | B1 | 6/2001 | Anthony et al. |
| 6,265,422 | B1 | 7/2001 | Bikker et al. |
| 6,268,363 | B1 | 7/2001 | Lee et al. |
| 6,271,242 | B1 | 8/2001 | Barbacid |
| 6,277,375 | B1 | 8/2001 | Ward |
| 6,277,832 | B1 | 8/2001 | Sugiyama et al. |
| 6,300,501 | B1 | 10/2001 | Dobrusin et al. |
| 6,331,415 | B1 | 12/2001 | Cabilly et al. |
| 6,335,156 | B1 | 1/2002 | Hermeking et al. |
| 6,342,487 | B1 | 1/2002 | Riou et al. |
| 6,342,765 | B1 | 1/2002 | Arnould |
| 6,362,188 | B1 | 3/2002 | Guzi et al. |
| 6,365,157 | B2 | 4/2002 | Rockwell et al. |
| 6,369,034 | B1 | 4/2002 | Doherty et al. |
| 6,372,747 | B1 | 4/2002 | Taveras et al. |
| 6,383,790 | B1 | 5/2002 | Shokat |
| 6,387,905 | B2 | 5/2002 | Njoroge et al. |
| 6,399,615 | B1 | 6/2002 | Guzi et al. |
| 6,399,633 | B1 | 6/2002 | Dumont et al. |
| 6,403,581 | B1 | 6/2002 | Ayral-Kaloustian et al. |
| 6,406,867 | B1 | 6/2002 | Yu et al. |
| 6,407,213 | B1 | 6/2002 | Carter et al. |
| 6,410,539 | B1 | 6/2002 | Arnould |
| 6,410,541 | B2 | 6/2002 | Remiszewski et al. |
| 6,414,145 | B1 | 7/2002 | Boyle et al. |
| 6,420,387 | B1 | 7/2002 | Venet et al. |
| 6,432,959 | B1 | 8/2002 | Cooper et al. |
| 6,436,960 | B1 | 8/2002 | Shin et al. |
| 6,440,974 | B2 | 8/2002 | Doll et al. |
| 6,451,812 | B1 | 9/2002 | End et al. |
| 6,458,935 | B1 | 10/2002 | Burns et al. |
| 6,639,055 | B1 | 10/2003 | Carter et al. |
| 6,709,659 | B1 | 3/2004 | Lok et al. |

(56) References Cited

U.S. PATENT DOCUMENTS 6,709,873 B1 3/2004 Yatscoff et al.
6,719,971 B1 4/2004 Carter et al.
6,753,407 B2 6/2004 Noga et al.
6,787,153 B1 9/2004 Hosokawa et al.
6,800,738 B1 10/2004 Carter et al.
6,814,965 B2 11/2004 Gao et al.
6,849,259 B2 2/2005 Haurum et al.
6,861,242 B2 3/2005 Canfield
6,861,572 B1 3/2005 Etches et al.
6,875,434 B1 4/2005 Schenk
6,891,024 B2 5/2005 Marsh
6,946,546 B2 9/2005 Vaughan et al.
6,982,323 B1 1/2006 Wang et al.
7,138,262 B1 11/2006 Daniel
7,407,659 B2 8/2008 Karumanchi et al.
7,943,743 B2 5/2011 Korman et al.
8,008,449 B2 8/2011 Korman et al.
8,178,098 B2 5/2012 Lahn et al.
8,354,509 B2 1/2013 Carven et al.
8,609,089 B2 12/2013 Langermann et al.
10,875,920 B2 * 12/2020 Yoo .......................... A61P 1/00
11,542,331 B2 1/2023 Yoo et al.
2003/0044407 A1 3/2003 Chang et al.
2003/0124652 A1 7/2003 Canfield
2005/0074403 A1 4/2005 Kayyem et al.
2005/0214860 A1 9/2005 Zhu et al.
2010/0028330 A1 2/2010 Collins et al.
2012/0039906 A1 2/2012 Olive
2012/0114649 A1 5/2012 Langermann et al.
2014/0242077 A1 8/2014 Choi et al.
2018/0355035 A1 * 12/2018 Yoo ......................... A61P 43/00
2020/0131269 A1 4/2020 Yoo et al.
2020/0148768 A1 5/2020 Yoo et al.
2023/0279112 A1 9/2023 Yoo et al.

FOREIGN PATENT DOCUMENTS

EP 0 519 596 B1 2/2005
GB 2 188 638 B 5/1990
GB 2 209 757 B 10/1990
WO WO 1988/07089 A1 9/1988
WO WO 1989/07142 A1 8/1989
WO WO 1990/02809 A1 3/1990
WO WO 1991/05548 A1 5/1991
WO WO 1991/09967 A1 7/1991
WO WO 1991/10737 A1 7/1991
WO WO 1991/10741 A1 7/1991
WO WO 1992/01047 A1 1/1992
WO WO 1992/18619 A1 10/1992
WO WO 1992/19244 A2 11/1992
WO WO 1992/22324 A1 12/1992
WO WO 1993/11236 A1 6/1993
WO WO 1995/15982 A2 6/1995
WO WO 1995/20401 A1 8/1995
WO WO 1996/20698 A2 7/1996
WO WO 1996/33735 A1 10/1996
WO WO 1996/34096 A1 10/1996
WO WO 1997/32572 A2 9/1997
WO WO 1997/33899 A1 9/1997
WO WO 1997/34911 A1 9/1997
WO WO 1997/38731 A1 10/1997
WO WO 1997/44013 A1 11/1997
WO WO 1998/16654 A1 4/1998
WO WO 1998/23289 A1 6/1998
WO WO 1998/24893 A2 6/1998
WO WO 1998/31346 A1 7/1998
WO WO 1998/46645 A2 10/1998
WO WO 1998/50433 A2 11/1998
WO WO 1999/15154 A1 4/1999
WO WO 1999/20253 A1 4/1999
WO WO 1999/23105 A1 5/1999
WO WO 1999/51642 A1 10/1999
WO WO 1999/58572 A1 11/1999
WO WO 1999/66903 A2 12/1999
WO WO 2000/42072 A2 7/2000
WO WO 2003/026494 A2 4/2003
WO WO 2004/028564 A2 4/2004
WO WO 2004/029092 A2 4/2004
WO WO 2004/029207 A2 4/2004
WO WO-2004056875 A1 * 7/2004 ................ A61P 1/04
WO WO 2006/121168 11/2006
WO WO 2007/005874 1/2007
WO WO 2008/076560 A2 6/2008
WO WO 2008/143665 A1 11/2008
WO WO 2008/143666 A2 11/2008
WO WO 2009/030884 A2 3/2009
WO WO 2009/101611 A1 8/2009
WO WO 2009/114335 A2 9/2009
WO WO 2010/027827 A2 3/2010
WO WO 2010/077634 A1 7/2010
WO WO 2010/106051 A1 9/2010
WO WO 2011/014438 A1 2/2011
WO WO 2011/066342 A2 6/2011
WO WO 2011/156520 A2 12/2011
WO WO 2015/013388 A2 1/2015
WO WO 2015/013389 A2 1/2015
WO WO 2015/100219 A1 7/2015
WO WO 2015/185875 A2 12/2015
WO WO 2016/160792 A1 10/2016
WO WO 2016/186177 A1 11/2016
WO WO 2017/096026 A1 6/2017
WO WO 2017/096051 A1 6/2017
WO WO 2017/172518 A1 10/2017
WO WO 2018/222689 A1 12/2018
WO WO 2018/226671 A1 12/2018

OTHER PUBLICATIONS

Abra et al., "The next generation of liposome delivery systems: recent experience with tumor-targeted, sterically-stabilized immunoliposomes and active-loading gradients," *J. Liposome Res.*, 12(1-2):1-3 (2002).

Al-Lazikani et al., "Standard conformations for the canonical structures of immunoglobulins," *J. Mol. Biol.*, 273:927-948 (1997).

Allen et al., "Large unilamellar liposomes with low uptake into the reticuloendothelial system," *FEBS Lett.*, 223:42-46 (1987).

Allen et al., "The use of glycolipids and hydrophilic polymoers in avoiding rapid uptake of liposomes by the mononuclear phagocyte system," *Adv. Drug Deliv. Rev*, 13: 285-309 (1994).

Allen et al., "Anti-body targeted stealth liposomes," *Stealth Liposomes*, 233-244 (1994).

Alley et al., "Antibody-drug conjugates: targeted drug delivery for cancer," *Curr. Opin. Chem. Biol.*, 14(4):529-537 (2010).

Ames et al., "Conversion of murine Fabs isolated from a combinatorial phage display library to full length immunoglobulins," *J. Immunol. Methods*, 184:177-186 (1995).

Arnon et al., "Monoclonal Antibodies For Immunotargeting of Drugs in Cancer Therapy," *Monoclonal Antibodies And Cancer Therapy*, 243-256 (1985).

Order, "Analysis, Results, and Future Prospective of the Therapeutic Use of Radiolabeled Antibody in Cancer Therapy," *Monoclonal Antibodies for Cancer Detection and Therapy*, 303-316 (1985).

Angal et al., "A single amino acid substitution abolishes the heterogeneity of chimeric mouse/human (IgG4) antibody," *Mol. Immunol.*, 30:105-108 (1993).

Arnett et al., "Immune modulation by butyrophilins," *Nat. Rev. Immunol.*, 14:559-569 (2014).

Aurrand-Lions et al., "Vanin-1, a novel GPI-linked perivascular molecule involved in thymus homing," *Immunity*, 5(5):391-405(1996).

Austin-Ward and Villaseca, "Gene therapy and its applications," *Rev. Med. Chil.*, 126(7):838-845 (1998). English Abstract.

Ausubel et al., "Preparation and Analysis of DNA,"*Current Protocols in Moleuclar Biology*, 1:2.10.2-2.10.3, 6.3.1-6.3.6 (1989).

Banghart et al., "Butyrophilin is expressed in mammary epithelial cells from a single-sized messenger RNA as a Type I membrane glycoprotein," *J. Biol. Chem.*, 273(7):4171-4179 (1998).

Barderas et al., "Affinity maturation of antibodies assisted by in silico modeling," *Proc. Natl. Acad. Sci. USA*, 105:9029-9034 (2008).

(56) References Cited

OTHER PUBLICATIONS

Bendas, "Immunoliposomes a Promising Approach to Targeting Cancer Therapy," *BioDrugs*, 15(4):215-224 (2001).
Bendig, "Humanization of Rodent Monoclonal Antibodies by CDR Grafting," *Methods: a Companion to Methods in Enzymology*, 8:83-93 (1995).
Better et al., "*Escherichia coli* secretion of an active chimeric antibody fragment," *Science*, 240:1041-1043 (1988).
Blume et al., "Liposomes for the sustained drug release in vivo," *Biochim. Biophys. Acta.*, 1029: 91-97 (1990).
Bollenbach et al., "Evolution and multilevel optimization of the genetic code," *Genome Res.*, 17:401-404 (2007).
Bostrom et al., "Improving antibody binding affinity and ificity for therapeutic development," *Methods Mol. Biol.*, 525:353-376 (2009).
Brahmer et al., "Safety and activity of anti-PD-L1 antibody in patients with advanced cancer," *N. Engl. J. Med.*, 66:2455-2465 (2012).
Brinkman et al., "Phage display of disulfide-stabilized Fv fragments," *J. Immunol. Methods*, 182:41-50 (1995).
Buchwald et al., "Long-term, continuous intravenous heparin administration by an implantable infusion pump in ambulatory patients with recurrent venous thrombosis," *Surgery*, 88(4):507-516 (1980).
Bukowski et al., "Signal transduction abnormalities in T lymphocytes from patients with advanced renal carcinoma: clinical relevance and effects of cytokine therapy," *Clin. Cancer Res.*, 4(10):2337-2347 (1998).
Burton et al., "Human antibodies from combinatorial libraries," *Adv. Immunol.*, 57:191-280 (1994).
Caron et al., "Engineered humanized dimeric forms of IgC are more effective antibodies," *J. Exp Med.*, 176:1191-95 (1992).
Carter et al., "Antibody-drug conjugates for cancer therapy," *Cancer J.*, 14(3):154-169 (2008).
Carter et al., "Humanization of an anti-p185HER2 antibody for human cancer therapy," *Proc. Natl. Acad. Sci. USA*, 89:4285-4289 (1992).
Carter et al., "Designer antibody-based therapeutics for oncology," *Amer. Assoc. Cancer Res. Educ. Book*, 1:147-154 (2005).
Chari, "Targeted cancer therapy: conferring ificity to cytotoxic drugs," *Acc. Chem. Res.*, 41(1):98-107 (2008).
Chen et al., "13II-labeled monoclonal antibody targeting neuropilin receptor type-2 for tumor SPECT imaging," *Int. J. Oncol.*, 50(2):649-659 (2016).
Chen et al., "Selection and analysis of an optimized anti-VEGF antibody: crystal structure of an affinity-matured Fab in complex with antigen," *J. Mol. Biol.*, 293:865-881 (1999).
Cheung et al., "Scanning N-glycosylation mutagenesis of membrane proteins," *Methods*, 41(4):451-459 (2007).
Chothia et al., "Canonical structures for the hypervariable regions of immunoglobulins," *J. Mol. Biol.*, 196:901-917 (1987).
Chothia et al., "Structural determinants in the sequences of immunoglobulin variable domain," *J. Mol. Biol.*, 278:457-479 (1998).
Christodoulides et al., "Immunization with recombinant class 1 outer-membrane protein from Neisseria meningitidis: influence of liposomes and adjuvants on antibody avidity, recognition of native protein and the induction of a bactericidal immune response against meningococci," *Microbiology*, 144:3027-3037 (1998).
Cleek et al., "Biodegradable Polymeric Carriers for a bFGF Antibody for Cardiovascular Application," *Pro. Int'l. Symp. Control. Rel. Bioact. Mater.*, 24:853-854 (1997).
Colman, "Effects of amino acid sequence changes on antibody-antigen interactions," *Research in Immunology*, 145:33-36 (1994).
Davidson et al., "Intralesional cytokine therapy in cancer: a pilot study of GM-CSF infusion in mesothelioma," *J Immunother.*, 21(5):389-398(1998).
Davies et al., "Expression of GnTIII in a recombinant anti-CD20 CHO production cell line: Expression of antibodies with altered glycoforms leads to an increase in ADCC through higher affinity for FC gamma RIII," *Biotechnol. Bioeng.*, 74:288-294 (2001).
Dernardo et al., "Comparison of 1,4,7,10-tetraazacyclododecane-N,N',N",N"'-tetraacetic acid (DOTA)-peptide-ChL6, a novel immunoconjugate with catabolizable linker, to 2-iminothiolane-2-[p-(bromoacetamido)benzyl]-DOTA-ChL6 in breast cancer xenografts.," *Clin Cancer Res.*, 4(10):2483-2490 (1998).
Desmyter et al., "Crystal structure of a camel single-domain VH antibody fragment in complex with lysozyme," *Nat. Struct. Biol.*, 3:803-811 (1996).
Dietrich et al., "Functional immobilization of a DNA-binding protein at a membrane interface via histidine tag and synthetic chelator lipids," *Biochemistry*, 35:1100-1105 (1996).
Dolcetti et al., "Measurement of myeloid cell immune suppressive activity," *Curr. Protoc. Immunol.*, 14.17.1-14.17.25 (2010).
Doronina et al., "Development of potent monoclonal antibody aurtistatin conjugates for cancer therapy," *Nat. Biotechnol.*, 21(7):778-784 (2003).
Ducry et al., "Antibody-drug conjugates: linking cytotoxic payloads to monoclonal antibodies," *Bioconjug. Chem.*, 21(1):5-13(2010).
During et al., "Controlled release of dopamine from a polymeric brain implant: in vivo characterization," *Ann. Neurol.*, 25(4):351-356 (1989).
Elbein et al., "Kifunensine, a potent inhibitor of the glycoprotein processing mannosidase I," J. Biol. Chem., 265(26):15599-15605 (1990).
Elliott et al., "Enhancement of therapeutic protein in vivo activities through glycoengineering," *Nat. Biotechnol.*, 21:414-421 (2003).
Eppstein et al., "Biological activity of liposome-encapsulated murine interferon gamma is mediated by a cell membrane receptor," *Proc. Natl. Acad. Sci. USA*, 82(11):3688-3692 (1985).
Finlay et al., "Affinity maturation of a humanized rat antibody for anti-RAGE therapy: comprehensive mutagenesis reveals a high level of mutational plasticity both inside and outside the complementarity-determining regions," *J. Mol. Biol.*, 388:541-558 (2009).
Foote et al., "Antibody framework residues affecting the conformation of the hypervariable loops," *J. Mol. Biol.*, 224(2):487-499 (1992).
Huse, "Combinatorial anitbody expression libraris in filamentous phage," *Antibody Engineering: a Practical Guide*, 103-120 (1991).
Fujihara et al., "Galectin-9 in cancer therapy," *Recent Patents on Endocrine, Metabolic and Immune Drug Discovery*, 7(2):130-137 (2013).
Gillies et al., "High-level expression of chimeric antibodies using adapted cDNA variable region cassettes," *J. Immunol. Methods*, 125:191-202 (1989).
Glaser et al., "Antibody engineering by codon-based mutagenesis in a filamentous phage vector system," *J. Immunol.*, 149:3903-3913 (1992).
Goodson, "Dental Applications," Medical Applications of Controlled Release, 2:115-138 (1984).
Grosjean et al., "Preferential codon usage in prokaryotic genes: the optimal codon-anticodon interaction energy and the selective codon usage in efficiently expressed genes," *Gene*, 18:199-209 (1982).
Gustchina et al., "Affinity maturation by targeted diversification of the CDR-H2 loop of a monoclonal Fab derived from a synthetic naïve human antibody library and directed against the internal trimeric coiled-coil of gp41 yields a set of Fabs with improved HIV-1 neutralization potency and breadth," *Virology*, 393:112-119 (2009).
Hackel et al., "Stability and CDR composition biases enrich binder functionality landscapes," *J. Mol. Biol.*, 401:84-96 (2010).
Hamers-Casterman et al., "Naturally occurring antibodies devoid of light chains," *Nature*, 363:446-448 (1993).
Hamid et al., "Safety and tumor responses with lambrolizumab (anti-PD-1) in melanoma," *N. Eng. J. Med.*, 369(2):134-144 (2013).
Hanibuchi et al., "Therapeutic efficacy of mouse-human chimeric anti-ganglioside GM2 monoclonal antibody against multiple organ micrometastases of human lung cancer in NK cell-depleted SCID mice," *Int. J. Cancer*, 78(4):480-485 (1998).
Hansen et al., "Attachment of antibodies to sterically stabilized liposomes: evaluation, comparison and optimization of coupling procedures," *Biochim. Biophys. Acta.*, 1239(2):133-144 (1995).
Helenius et al., "Intracellular functions of N-linked glycans," *Science*, 291(5512):2364-2369 (2001).
Hellstrand et al., "Histamine and cytokine therapy," *Acta Oncol.*, 37(4):347-353(1998).

(56) References Cited

OTHER PUBLICATIONS

Hellstrom et al., "Antibodies for Drug Delivery", *Controlled Drug Delivery*, 623-653 (1987).
Hollander, "Immunotherapy for B-Cell lymphoma: current status and prospective advances," *Front. Immunol.*, 3:3. doi: 10.3389/fimmu.2012.00003 (2012).
Honegger et al., "Yet another numbering scheme for immunoglobulin variable domains: an automatic modeling and analysis tool," *J. Mol. Biol.*, 309(3):657-670 (2001).
Howard et al., "Intracerebral drug delivery in rats with lesion-induced memory deficits," *J. Neurosurg.*, 71(1):105-112 (1989).
Hu et al., "Minibody: a novel engineered anti-carcinoembryonic antigen antibody fragment (single-chain Fv-CH3) which exhibits rapid, high-level targeting of xenografts," *Cancer Res.*, 56:3055-3061 (1996).
Hui et al., "Pathways for potentiation of immunogenicity during adjuvant-assisted immunizations with Plasmodium falciparum major merozoite surface protein 1," *Infect. Immun.*, 66(11):5329-5336(1998).
Huston et al., "Antigen recognition and targeted delivery by the single-chain Fv," *Cell Biophys.*, 22:189-224 (1993).
Huston et al., "Protein engineering of single-chain Fv analogs and fusion proteins," *Methods Enzymol.*, 203:46-88 (1991).
Hwang et al., "Hepatic uptake and degradation of unilamellar sphingomyelin/cholesterol liposomes: a kinetic study," *Proc. Natl. Acad. Sci. USA*, 77:4030-4034 (1980).
Jeong et al., "The PRY/SPRY/B30.2 domain of butyrophilin 1A1 (BTN1A1) binds to xanthine oxidoreductase: implicaitons for the function of BTN1A1 in the mammary gland and other tissues," *J. Biol. Chem.*, 284(33):22444-22456 (2009).
Jestin et al., "Optimization models and the structure of the genetic code," *J. Mol. Evol.*, 69:452-457 (2009).
Joliot et al., "Antennapedia homeobox peptide regulates neural morphogenesis," *Proc. Natl. Acad. Sci. USA*, 88(5):1864-1868 (1991).
Jones et al., "Replacing the complementarity-determining regions in a human antibody with those from a mouse," *Nature*, 321(6069):522-525 (1986).
Kabat et al., "Unusual distributions of amino acids in complementarity-determining (hypervariable) segments of heavy and light chains of immunoglobulins and their possible roles in specificity of antibody-combining sites," *J. Biol. Chem.*, 252:6609-6616 (1977).
Kabat, "The structural basis of antibody complementarity," *Adv. Protein Chem.*, 32:1-75 (1978).
Kantarjian et al., "Treatment of philadelphia chromosome-positive, accelerated-phase chronic myelogenous leukemia with imatinib mesylate," *Clin. Cancer Res.*, 8:2167-2176 (2002).
Katoh et al., "Mafft: a novel method for rapid multiple sequence alignment based on fast Fourier transform," *Nucleic Acids Res.*, 30(14):3059-3066 (2002).
Kettleborough et al., "Isolation of tumor cell-specific single-chain Fv from immunized mice using phage-antibody libraries and the re-construction of whole antibodies from these antibody fragments," *Eur. J. Immunol.*, 24:952-958 (1994).
Khantasup et al., "Design and generation of humanized single-chain Fv derived from mouse hybridoma for potential targeting application," *Monoclonal Antibodies in Immunodiganosi and Immunotherapy*, 34(6):404-417 (2015).
Klibanov et al., "Activity of amphipathic poly(ethylene glycol) 5000 to prolong the circulation time of liposomes depends on the liposome size and is unfavorable for immunoliposome binding to target," *Biochim Biophys Acta*, 1062(2):142-148 (1991).
Klibanov et al., "Amphipathic polyethyleneglycols effectively prolong the circulation time of liposomes," *FEBS Letts.*, 268(1):235-237 (1990).
Knappik et al., "An improved affinity tag based on the FLAG peptide for the detection and purification of recombinant antibody fragments," *Biotechniques*, 17(4):754-761 (1994).
Krause et al., "An insertion mutation that distorts antibody binding site architecture enhances function of a human antibody," *MBio*, 2:e000345-10, 1-8 (2011).
Kuan et al., "Affinity-matured anti-glycoprotein NMB recombinant immunotoxins targeting malignant gliomas and melanomas," *Int. J. Cancer*, 129:111-121 (2011).
Kurland et al., "Optimization of translation accuracy," *Prog. Nucleic Acid Res. Mol. Biol.*, 31:191-219 (1984).
Lam et al., "Microencapsulation of recombinant humanized monoclonal antibody for local delivery," *Proc. Int'l. Symp. Control Rel. Bioact. Mater.*, 24:759-760 (1997).
Langer et al., "New methods of drug delivery," *Science*, 249(4976):1527-1533 (1990).
Larocca et al., "Aktl is essential for postnatal mammary gland development, function, and the expression of Btn1a1," *PLoS One*, 6(9):e24432 (2011).
Lebrero-Fernandez et al., "Altered expression of butyrophilin (BTN) and BTN-like (BTNL) genes in intestinal inflammation and colon cancer: BTN and BTNL genes in inflammation and cancer," *Immunity Inflammation Dis.*, 4(2):191-200 (2016).
Lefranc et al., "IMGT, the international ImMunoGeneTics database," *Nucleic Acids Res.*, 27(1):209-212 (1999).
Levy et al., "Inhibition of calcification of bioprosthetic heart valves by local controlled-release diphosphonate," *Science*, 228(4696):190-192 (1985).
Litzinger et al., "Effect of liposome size on the circulation time and intraorgan distribution of amphipathic poly(ethylene glycol)-containing liposomes," *Biochim. Biophys. Acta*, 1190:99-107 (1994).
Lonberg et al., "Human antibodies from transgenic mice," *Int. Rev. Immunol.*, 13:65-93 (1995).
Loughrey et al., "A non-covalent method of attaching antibodies to liposomes," *Biochim. Biophys. Acta*, 901:157-160 (1987).
Lowry et al., "Protein measurement with the folin phenol reagent," *J. Biol. Chem.*, 193:265-275 (1951).
Marchler-Bauer et al., "CDD: a conserved domain database for the functional annotation of proteins," *Nucleic Acids Res.*, 39:D225-D229 (2011).
Martin et al., "Structural families in loops of homologous proteins: automatic classification, modelling and application to antibodies," *J. Mol. Biol.*, 263(5):800-815 (1996).
Martin et al., "Irreversible coupling of immunoglobulin fragments to preformed vesicles. an improved method for liposome targeting," *J. Biol. Chem.*, 257(1):286-288 (1982).
La Mar et al., "Proton nuclear magnetic resonance investigation of the nature of solution conformational equilibria of monomeric insect deoxyhemoglobins," *Biochemistry*, 20(15):4429-4438 (1981).
Maruyama et al., "Effect of molecular weight in amphipathic polyethyleneglycol on prolonging the circulation time of large unilamellar liposomes," *Chem. Pharm. Bull.*, 39: 1620-1622 (1991).
Maruyama, "In vivo targeting by liposomes," *Biol. Pharm. Bull.*, 23(7): 791-799 (2000).
Mohammad et al., "A new tubulin polymerization inhibitor, auristatin PE, induces tumor regression in a human Waldenstrom's macroglobulinemia xenograft model," *Int. J. Oncol.*, 15:367-372 (1999).
Mohammad et al., "Bryostatin 1 induces differentiation and potentiates the antitumor effect of Auristatin PE in a human pancreatic tumor (PANC-1) xenograft model," *Anticancer Drugs*, 12:735-740 (2001).
Montgomery et al., "Affinity maturation and characterization of a human monoclonal antibody against HIV-1 gp41," *MAbs*, 1:462-474 (2009).
Morea et al., "Antibody modeling: implications for engineering and design," *Methods*, 20:267-279 (2000).
Morrison et al., "Chimeric human antibody molecules: mouse antigen-binding domains with human constant region domains," *Proc. Natl. Acad. Sci. USA*, 81(21):6851-6855 (1984).
Morrison, "Transfectomas provide novel chimeric antibodies," *Science*, 229:1202-1207 (1985).
Mueller et al., "Humanized porcine VCAM-specific monoclonal antibodies with chimeric IgG2/G4 constant regions block human leukocyte binding to porcine endothelial cells," *Mol. Immunol.*, 34:441-452 (1997).

(56) References Cited

OTHER PUBLICATIONS

Mullinax et al., "Expression of a heterodimeric Fab antibody protein in one cloning step," *Biotechniques*, 12:864-869 (1992).
Murali et al., "Antibody like peptidomimetics as large scale immunodetection probes," *Cell Mol. Biol.* (*Noisy-le grand*), 49:209-216 (2003).
Mustapha et al., "Evaluation of galectin-9 blocking monclonal antibodies as novel immune-chckpoint inhibitors via the targeting of regulatory T cells in cancer," *Eur. J. Immunol.*, 26(Suppl 1):16 (2016).
Ning et al., "Intratumoral radioimmunotherapy of a human colon cancer xenograft using a sustained-release gel," *Radiother. Oncol.*, 39:179-189 (1996).
Niwa et al., "Defucosylated Chimeric Anti-CC Chemokine Receptor 4 IgG1 with Enhanced Antibody-Dependent Cellular Cytotoxicity Shows Potent Therapeutic Activity to T-Cell Leukemia and Lympoma,"*Cancer Res.*, 64:2127-33 (2004).
Ogg et al., "Expression of butyrophilin (Btn1a1) in lactating mammary gland is essential for the regulated secretion of milk-lipid droplets,"*Proc. Natl. Acad. Sci. USA*, 101(27):10084-10089 (2004).
Oi et al., "Chimeric Antibodies," *BioTechniques*, 4:214-221 (1986).
Okazaki et al., "Fucose depletion from human IgG1 oligosaccharide enhances binding enthalpy and association rate between IgG1 andFcγRIIIa," *J. Mol. Biol.*, 336:1239-1249 (2004).
Olive D, "B7/ butyrophilin family members are leading the race for immune intervention," *Exp. Opin. Ther. Patents*, 17(3):357-359 (2007).
Padlan, "A possible procedure for reducing the immunogenicity of antibody variable domains while preserving their ligand-binding properties," *Mol. Immunol.*, 28:489-498 (1991).
Park et al., "Immunoliposomes for cancer treatment,"*Adv. Pharmacol.*, 40:399-435 (1997).
Park, "Tumor-directed targeting of liposomes," *Bioscience Rep.*, 22(2): 267-281 (2002).
Paul, "Structure and function of immunoglobulins," *Fundamental Immunology*, 292-295 (1993).
Persic et al., "An integrated vector system for the eukaryotic expression of antibodies or their fragments after selection from phage display libraries," *Gene*, 187:9-19 (1997).
Peterson et al., "Enzymatic cleavage of peptide-linked radiolabels from immunoconjugates,"*Bioconjug. Chem.*, 10(4):553-557 (1999).
Pluckthun et al., "Expression of functional antibody Fv and Fab fragments in *Escherichia coli*," *Methods Enzymol.*, 178:497-515 (1989).
Presta, "Antibody engineering," *Curr. Opin. Struct. Biol.*, 2:593-596 (1992).
Presta, "Molecular engineering and design of therapeutic antibodies," *Curr. Opin. Immunol.*, 20:460-470 (2008).
Qin et al., "Interferon-β gene therapy inhibits tumor formation and causes regression of established tumors in immune-deficient mice," *Proc Natl Acad Sci USA*, 95(24):14411-14416 (1998).
Langer et al., "Chemical and physical structure of polymers as carriers for controlled release of bioactive agents: a review," *J. Macromol. Sci. Rev. Macromol. Chem.*, 23:61-126 (1983).
Ravetch et al., "Fc receptors, " *Annu. Rev. Immunol.*, 9:457-492 (1991).
Riechmann et al., "Reshaping human antibodies for therapy," *Nature*, 332(6162):323-327 (1988).
Robenek et al., "Butyrophilin controls milk fat globule secretion," *Proc. Natl. Acad. Sci. USA*, 103(27):10385-10390 (2006).
Roguska et al., "Humanization of murine monoclonal antibodies through variable domain resurfacing," *Proc. Natl. Acad. Sci. USA*, 91:969-973 (1994).
Rothman et al., "Antibody-dependent cytotoxicity mediated by natural killer cells is enhanced by castanospermine-induced alterations of IgG glycosylation," *Molecular Immunology*26:1113-1123 (1989).
Routledge et al., "The effect of aglycosylation on the immunogenicity of a humanized therapeutic CD3 monoclonal antibody," *Transplantation*, 60:847-853 (1995).
Rudikoff et al., "Single amino acid substitution altering antigen-binding specificity," *Proc. Natl. Acad. Sci. USA*, 79(6):1979-1983 (1982).
Sali et al., "Comparative protein modelling by satisfaction of spatial restraints," *J. Molec. Biol.*, 234:779-815(1993).
Sarter et al., "Btn2a2, a T cell immunomodulatory molecule coregulated with MHC class II genes," *J. Exp. Med.*, 213(2):177-187 (2016).
Saudek et al., "A preliminary trial of the programmable implantable medication system for insulin delivery," *N.Engl. J. Med.* 321(9):574-579 (1989).
Sawai et al., "Direct production of the Fab fragment derived from the sperm immobilizing antibody using polymerase chain reaction and cDNA expression vectors," *Am. J. Reprod. Immunol.*, 34:26-34 (1995).
Schier et al., "Isolation of picomolar affinity anti-c-erbB-2 single-chain Fv by molecular evolution of the complementarity determining regions in the center of the antibody binding site," *J. Mol. Biol.*, 263:551-567 (1996).
Schwarz et al., "Mechanisms and principles of N-linked protein glycosylation," *Curr. Opin. Struct. Biol.*, 21:576-582 (2011).
Sefton, "Inplantable pumps," *CRC Crit. Ref Biomed. Eng.* 14:201-240 (1987).
Senter, "Potent antibody drug conjugates for cancer therapy," *Curr. Opin. Chem. Biol.*, 13(3):235-244 (2009).
Shields et al., "Lack of fucose on human IgG1 N-linked oligosaccharide improves binding to human Fcgamma RIII and antibody-dependent cellular toxicity,"*J. Biol. Chem.*, 277:26733-26740 (2002).
Shinkawa et al., "The absence of fucose but not the presence of galactose or bisecting N-acetylglucosamine of human IgG1 complex-type oligosaccharides shows the critical role of enhancing antibody-dependent cellular cytotoxicity,"*J Biol. Chem.*, 278:3466-73 (2003).
Shopes, "A genetically engineered human IgG mutant with enhanced cytolytic activity," *Immunol.*, 148:2918-2922 (1992).
Shu et al., "Secretion of a single-gene-encoded immunoglobulin from myeloma cells," *Proc. Natl. Acad. Sci. USA*, 90:7995-7999 (1993).
Skerra et al., "Assembly of a functional immunoglobulin Fv fragment in *Escherichia coli*," *Science*, 240: 1038-1041 (1988).
Smith et al., "BTN1A1, the mammary gland butyrophilin, and BTN2A2 are both inhibitors of T cell activation," *J. Immunol.*, 184(7):3514-3525 (2010).
Song et al., "Antibody mediated lung targeting of long-circulating emulsions," *PDA J. Pharm. Sci. Tech.*, 50:372-377 (1996).
Søreide, "Receiver-operating characteristic curve analysis in diagnostic, prognostic and predictive biomarker research," *J. Clin. Pathol.*, 62(1):1-5 (2009).
Steffer et al., "Butyrophilin, a milk protein, modulates the encephalitogenic T cell response to myelin oligodendrocyte glycoprotein in experimental autoimmune encephalomyelitis," *J. Immunol.*, 165(5):2859-2865 (2000).
Steidl et al., "In vitro affinity maturation of human GM-CSF antibodies by targeted CDR-diversification,"*Mol. Immunol.*, 46:135-144 (2008).
Stevenson et al., "A chimeric antibody with dual Fc regions (bisFabFc) prepared by mannipulations at the IgG hinge," *Anticancer Drug Design*, 3:219-30 (1989).
Studnicka et al., "Human-engineered monoclonal antibodies retain full specific binding activity by preserving non-CDR complementarity-modulating residues," *Protein Eng.*, 7:805-814 (1994).
Swann et al., "Considerations for the development of therapeutic monoclonal antibodies," *Curr. Opin. Immunol.*, 20:493-499 (2008).
Takahashi et al., "Human Fas ligand: gene structure, chromosomal location and species specificity,"*Int. Immunol.*, 6:1567-1574 (1994).
Tao et al., "Studies of aglycosylated chimeric mouse-human IgG. Role of carbohydrate in the structure and effector functions mediated by the human IgG constant region," *J. Immunol.*, 143:2595-2601 (1989).
Taylor et al., "A transgenic mouse that expresses a diversity of human sequence heavy and light chain immunoglobulins," *Nucleic Acids Res.*, 20:6287-6295 (1992).
Taylor et al., "Cloning and sequence analysis of human butyrophilin reveals a potential receptor function," *Biochim. Biophys. Acta.*, 1306(1):1-4 (1996).

(56) References Cited

OTHER PUBLICATIONS

Teicher, "Antibody-drug conjugate targets," *Curr. Cancer Drug Targets*, 9(8):982-1004 (2009).
Thorpe et al., "The preparation and cytotoxic properties of antibody-toxin conjugates," *Immunol. Rev.*, 62:119-158 (1982).
Thorpe, "Antibody Carriers of Cytotoxic Agents in Cancer Therapy: a Review", *Monoclonal Antibodies '84: Biological and Clinical Applications*, 475-506 (1985).
Topalian et al., "Safety, activity, and immune correlates of anti-PD-1 antibody in cancer," *N. Engl. J. Med.*, 366(26):2443-2454 (2012).
Torchilin et al., "How do polymers prolong circulation time of liposomes," *J. Liposome Res.*, 6: 99-116 (1996).
Umana et al., "Engineered glycoforms of an antineuroblastoma IgG1 with optimized antibody-dependent cellular cytotoxic activity," *Nature Biotechnology*, 17:176-180 (1999).
Vingerhoeds et al., "Immunoliposomes in vivo," *Immunomethods*, 4(3):259-272 (1994).
Wall et al., "Modulation of cIAP-1 by novel antitubulin agents when combined with bryostatin 1 results in increased apoptosis in the human early pre-B acute lymphoblastic leukemia cell line Reh," *Biochem. Biophys. Res. Commun.*, 266:76-80 (1999).
Wallick et al., "Glycosylation of a VH residue of a monoclonal antibody against alpha (1—6) dextran increases its affinity for antigen," *J. Exp. Med.*, 168:1099-1109 (1988).
Wilson et al., "The structure of an antigenic determinant in a protein," *Cell*, 37:767-778 (1984).
Wohlgemuth et al., Evolutionary optimization of speed and accuracy of decoding on the ribosome, *Philos. Trans. R. Soc. Lond. B. Biol. Sci.*, 366:2979-2986 (2011).
Wolff et al., "Monoclonal Antibody Homodimers: Enhanced Antitumor Activity in Nude Mice," *Cancer Research*, 53:2560-2565 (1993).
Woyke et al., "Effect of auristatin PHE on microtubule integrity and nuclear localization in Cryptococcus neoformans," *Antimicrob. Agents Chemother.*, 46:3802-3808 (2002).
Woyke et al., "In vitro activities and postantifungal effects of the potent dolastatin 10 derivative auristatin PHE," *Antimcrob. Agents Chemother.*, 45:3580-3584 (2001).
Wu et al., "Receptor-mediated in vitro gene transformation by a soluble DNA carrier system," *J. Biol. Chem.*, 262(10):4429-4432 (1987).
Wu et al., "Stepwise in vitro affinity maturation of Vitaxin, an alphav beta3-specific humanized mAb," *Proc. Natl. Acad. Sci. USA*, 95:6037-6042 (1998).
Yelton et al., "Affinity maturation of the BR96 anti-carcinoma antibody by codon-based mutagenesis," *J. Immunol.*, 155:1994-2004 (1995).
Zimmerman et al., "A triglycine linker improves tumor uptake and biodistributions of 67-Cu-labeled anti-neuroblastoma MAb chCE7 F(ab')2 fragments," *Nucl. Med. Biol.*, 26(8):943-950 (1999).
Cedeno-Laurent et al., "Galectin-1 research in T cell immunity: Past, present and future," Clin Immunol 142(2)107-116 (2012).
Paliard et al., "Simultaneous production of IL-2, IL-4, and IFN-gamma by activated human CD4+ and CD8+ T cell clones" J Immunol 141:849-855 (1988).
The Human Protein Atlas, BTN1A1 expression in blood cell (2021).

* cited by examiner

| ka (1/Ms) | kd (1/s) | KD (M) |
|---|---|---|
| 7.19E+04 | 1.80E-04 | 2.50E-09 |

| ka (1/Ms) | kd (1/s) | KD (M) |
|---|---|---|
| 7.13E+03 | 2.24E-04 | 3.14E-08 |

METHODS OF TREATING CANCER USING ANTIBODIES AND MOLECULES THAT IMMUNOSPECIFICALLY BIND TO BTN1A1

CROSS REFERENCE TO RELATED APPLICATIONS

This application is the U.S. national stage application of PCT/US2018/035082, filed May 30, 2018, which claims the benefit of U.S. Provisional Application No. 62/513,393, filed May 31, 2017; the disclosure of each of which is incorporated herein by reference in its their entirety.

REFERENCE TO A SEQUENCE LISTING

This application is being filed with a computer readable form (CRF) copy of a Sequence Listing named 13532-019-999 ST25.txt, created on Nov. 27, 2019, and being 113,893 bytes in size; which is incorporated herein by reference in its entirety.

1. FIELD

The present invention relates in general to the field of cancer immunology and molecular biology. Provided herein are methods for treating cancer using anti-BTN1A1 antibodies or other molecules having an antigen binding fragment that immunospecifically bind to BTN1A1. In some embodiments, the cancer is resistant or refractory to an anti-PD-1 therapy or an anti-PD-L1 therapy.

2. BACKGROUND

The immune system of humans and other mammals protects them against infections and diseases. A number of stimulatory and inhibitory ligands and receptors provide a tight control system to maximize immune response against infection while limiting self-immunity. Recently, therapeutics that modulate immune response, such as anti-PD1 or anti-PDL1 antibodies, were found to be effective in some cancer treatments. However, development of new therapeutics that safely and effectively treat diseases by modulating the immune system remain an urgent need, especially for anti-PD1 therapy or anti-PD-L1 therapy resistant or refractory cancers. The methods described herein meet these needs and provide other related advantages.

3. SUMMARY

In one aspect, provided herein is a method of treating an anti-PD-1 therapy or anti-PD-L1 therapy resistant or refractory cancer in a subject, including administering to the subject a therapeutically effective amount of a molecule including an antigen binding fragment that immunospecifically binds to BTN1A1.

In another aspect, provided herein is a method of treating cancer in a subject, comprising administering to the subject a therapeutically effective amount of a molecule comprising an antigen binding fragment that immunospecifically binds to BTN1A1 in combination with a radiation therapy.

In some embodiments, the radiation therapy is a high-dose radiation therapy.

In another aspect, provided herein is a method of killing or inhibiting the proliferation of a cancer cell resistant to an anti-PD-1 therapy or an anti-PD-L1 therapy, including contacting the cell with an effective amount of a molecule including an antigen binding fragment that immunospecifically binds to BTN1A1.

In another aspect, provided herein is a method of treating cancer, including (i) obtaining a sample including cancer cells from the subject having the cancer; (ii) determining the level of BTN1A1 in the sample; (iii) diagnosing the subject as being likely to be responsive to a molecule including an antigen binding fragment that immunospecifically binds to BTN1A1, if the level of BTN1A1 in the sample is higher than or equal to a BTN1A1 reference level, and (iv) administering to the subject a therapeutically effective amount of the molecule including an antigen binding fragment that immunospecifically binds to BTN1A1.

In another aspect, provided herein is a method of treating cancer, including (i) obtaining a sample including cancer cells from the subject having the cancer; (ii) determining the level of PD-L1 in the sample; (iii) diagnosing the subject as being likely to be responsive to a molecule including an antigen binding fragment that immunospecifically binds to BTN1A1, if the level of PD-L1 in the sample is lower than or equal to a PD-L1 reference level, and (iv) administering to the subject a therapeutically effective amount of the molecule including an antigen binding fragment that immunospecifically binds to BTN1A1.

In another aspect, provided herein is a method of treating an anti-PD1 therapy or anti-PD-L1 therapy resistant or refractory cancer, including (i) obtaining a sample including cancer cells from the subject having the anti-PD1 therapy or anti-PD-L1 therapy resistant or refractory cancer; (ii) determining the level of BTN1A1 in the sample; (iii) diagnosing the subject as being likely to be responsive to a molecule including an antigen binding fragment that immunospecifically binds to BTN1A1, if the level of BTN1A1 in the sample is higher than or equal to a BTN1A1 reference level, and (iv) administering to the subject a therapeutically effective amount of the molecule including an antigen binding fragment that immunospecifically binds to BTN1A1.

In another aspect, provided herein is a method of treating an anti-PD1 therapy or anti-PD-L1 therapy resistant or refractory cancer, including (i) obtaining a sample including cancer cells from the subject having the anti-PD1 therapy or anti-PD-L1 therapy resistant or refractory cancer cancer; (ii) determining the level of BTN1A1 or PD-L1 in the sample; (iii) diagnosing the subject as being likely to be responsive to a molecule including an antigen binding fragment that immunospecifically binds to BTN1A1, if the level of BTN1A1 in the sample is higher than or equal to a BTN1A1 reference level or if the level of PD-L1 in the sample is equal to or lower than a PD-L1 reference level, and (iv) administering to the subject a therapeutically effective amount of the molecule including an antigen binding fragment that immunospecifically binds to BTN1A1.

In another aspect, provided herein is a method of treating cancer, including obtaining a sample including cancer cells from the subject having the cancer; determining the level of BTN1A1 and/or PD-L1 in the sample; diagnosing the subject as being likely to be responsive to a molecule including an antigen binding fragment that immunospecifically binds to BTN1A1, if the level of BTN1A1 in the sample is higher than or equal to a BTN1A1 reference level and/or if the level of PD-L1 in the sample is equal to or lower than a PD-L1 reference level, and administering to the subject a therapeutically effective amount of the molecule including an antigen binding fragment that immunospecifically binds to BTN1A1.

In some embodiments, the cancer is an anti-PD-1 therapy or anti-PD-L1 therapy resistant or refractory cancer.

In some embodiments, the cancer is a breast cancer or a lung cancer.

In some embodiments, the cancer is a mammary carcinoma or a Lewis lung carcinoma.

In some embodiments, the method includes determining the level of BTN1A1 in the sample.

In some embodiments, the method includes determining the level of PD-L1 in the sample.

In some embodiments, the method includes determining the levels of BTN1A1 and PD-L1 in the sample.

In some embodiments, the the subject is diagnosted as being likely to be responsive to a molecule including an antigen binding fragment that immunospecifically binds to BTN1A1, if the level of BTN1A1 in the sample is higher than a BTN1A1 reference level.

In some embodiments, the subject is diagnosted as being likely to be responsive to a molecule including an antigen binding fragment that immunospecifically binds to BTN1A1, if the level of PD-L1 in the sample is lower than a PD-L1 reference level.

In some embodiments, the subject is diagnosed as being likely to be responsive to a molecule including an antigen binding fragment that immunospecifically binds to BTN1A1, if the level of BTN1A1 in the sample is higher than a BTN1A1 reference level and if the level of PD-L1 is lower than a PD-L1 reference level.

In some embodiments, determining the level of BTN1A1 or PD-L1 in the sample includes analyzing the level of a BTN1A1 or PD-L1 protein in a tissue sample by immunocytochemistry.

In some embodiments, the antigen binding fragment that immunospecifically binds to BTN1A1 preferentially binds a BTN1A1 dimer over a BTN1A1 monomer.

In some embodiments, the molecule including an antigen binding fragment that immunospecifically binds to BTN1A1 is STC810.

In some embodiments, the molecule including an antigen binding fragment that immunospecifically binds to BTN1A1 is STC2714.

In another aspect, provided herein is a method of treating cancer in a subject, including administering to the subject a therapeutically effective amount of a molecule including an antigen binding fragment that immunospecifically binds to BTN1A1 and a therapeutically effective amount of an anti-PD-1 therapy or an anti-PD-L1 therapy.

In some embodiments, the method includes administering an anti-PD-1 therapy.

In some embodiments, the method includes administering an anti-PD-L1 therapy.

In some embodiments, the method includes administering an anti-PD-1 therapy and an anti-PD-L1 therapy.

In some embodiments, the molecule including the antigen binding fragment that immunospecifically binds to BTN1A1 and the anti-PD-1 therapy or anti-PD-L1 therapy are formulated together.

In some embodiments, the molecule including the antigen binding fragment that immunospecifically binds to BTN1A1 and the anti-PD-1 therapy or anti-PD-L1 therapy are formulated separately.

In some embodiments, the molecule including the antigen binding fragment that immunospecifically binds to BTN1A1 and the anti-PD-1 therapy or anti-PD-L1 therapy are administered independently at the same time or separately within time intervals, optionally followed by one or more cycles of repeat dosing.

In some embodiments, the antigen binding fragment that immunospecifically binds to BTN1A1 preferentially binds a BTN1A1 dimer over a BTN1A1 monomer.

In some embodiments, the molecule including an antigen binding fragment that immunospecifically binds to BTN1A1 is STC810.

In some embodiments, the molecule including an antigen binding fragment that immunospecifically binds to BTN1A1 is STC2714.

In some embodiments, the treatment produces at least one therapeutic effect, such as a reduction in size of a tumor, a reduction in number of metastatic lesions over time, a complete response, a partial response, or a stable disease.

In some embodiments, the cancer is a breast cancer, a neuroendocrine prostate cancer (NEPC), a diffuse large B-cell lymphoma, a melanoma, a cancer from the National Cancer Institute cancer panel (NCI 60), a uveal melanoma, a pancreas cancer, an ovarian cancer, a uterine cancer, a lung adenocarcinoma, a desmoplastic small-round-cell tumor, a bladder cancer, a colorectal cancer, a lung squamous cell carcinoma, a liver cancer, a lung cancer, a stomach cancer, a cholangiocarcinoma, an esophagus squamous cell carcinoma, a head and neck cancer, a sarcoma, a prostate cancer, a liver cancer, a pancreas cancer, a pheochromocytoma or paraganglioma (PCPG), a cervical cancer, a glioma, or a acute myeloid leukemia (AML).

In some embodiments, the anti-PD-1 therapy or the anti-PD-L1 therapy includes an anti-PD-1 or anti-PD-L1 antibody or antibody fragment, or a soluble PD-1 or PD-L1 ligand, or Fc-fusion protein thereof.

In some embodiments, the anti-PD-1 therapy includes nivolumab (Opdivo), pembrolizumab (Keytruda), pidilizumab, AMP-514, or AMP-224.

In some embodiments, the anti-PD-1 therapy includes an anti-PD-1 antibody provided in International Application No. PCT/US2016/64394.

In some embodiments, the anti-PD-L1 therapy includes YW243.55.S70, MPDL3280A, MEDI-4736, MSB-0010718C, or MDX-1105.

In some embodiments, the anti-PD-L1 therapy includes an antibody provided in International Application No. PCT/US2016/024691, and International Application No. PCT/US2017/024027.

In some embodiments, the antigen binding fragment that immunospecifically binds to BTN1A1 preferentially binds glycosylated BTN1A1 over non-glycosylated BTN1A1.

In some embodiments, the antigen binding fragment preferentially binds BTN1A1 dimers over BTN1A1 monomers.

In some embodiments, the molecule including an antigen binding fragment that immunospecifically binds to BTN1A1 is STC810.

In some embodiments, the molecule including an antigen binding fragment that immunospecifically binds to BTN1A1 is STC2714.

In some embodiments, the antigen binding fragment includes (a) a heavy chain variable ($V_H$) region including (1) a $V_H$ CDR1 having an amino acid sequence selected from the group consisting of SEQ ID NOS: 7, 10, 13, 16, 35, 38, 41, 44, 63, 66, 69, and 72; (2) a $V_H$ CDR2 having an amino acid sequence selected from the group consisting of SEQ ID NOS: 8, 11, 14, 17, 36, 39, 42, 45, 64, 67, 70, and 73; and (3) a $V_H$ CDR3 having an amino acid sequence selected from the group consisting of SEQ ID NOS: 9, 12, 15, 18, 37, 40, 43, 46, 65, 68, 71, and 74; or (b) a light chain variable ($V_L$) region including (1) a $V_L$ CDR1 having an amino acid sequence selected from the group consisting of SEQ ID NOS: 19, 22, 25, 28, 47, 50, 53, 56, 75, 78, 81, and 84; (2) a $V_L$ CDR2 having an amino acid sequence selected from the group consisting of SEQ ID NOS: 20, 23, 26, 29, 48, 51, 54, 57, 76, 79, 82, and 85; and (3) a $V_L$ CDR3 having an amino acid sequence selected from the group consisting of SEQ ID NOS: 21, 24, 27, 30, 49, 52, 55, 58, 77, 80, 83, and 86.

In some embodiments, the antigen binding fragment includes a heavy chain variable ($V_H$) region including (1) a $V_H$ CDR1 having an amino acid sequence selected from the group consisting of SEQ ID NOS: 7, 10, 13, 16, 35, 38, 41, 44, 63, 66, 69, and 72; (2) a $V_H$ CDR2 having an amino acid sequence selected from the group consisting of SEQ ID NOS: 8, 11, 14, 17, 36, 39, 42, 45, 64, 67, 70, and 73; and (3) a $V_H$ CDR3 having an amino acid sequence selected from the group consisting of SEQ ID NOS: 9, 12, 15, 18, 37, 40, 43, 46, 65, 68, 71, and 74.

In some embodiments, the heavy chain variable ($V_H$) region includes (a) (1) a $V_H$ CDR1 having an amino acid sequence of SEQ ID NOS: 7, 35 or 63; (2) a $V_H$ CDR2 having an amino acid sequence of SEQ ID NOS: 8, 36 or 64; and (3) a $V_H$ CDR3 having an amino acid sequence of SEQ ID NOS: 9, 37 or 65; (b) (1) a $V_H$ CDR1 having an amino acid sequence of SEQ ID NOS: 10, 38 or 66; (2) a $V_H$ CDR2 having an amino acid sequence of SEQ ID NOS: 11, 39 or 67; and (3) a $V_H$ CDR3 having an amino acid sequence of SEQ ID NOS: 12, 40 or 68; (c)(1) a $V_H$ CDR1 having an amino acid sequence of SEQ ID NOS: 13, 41 or 69; (2) a $V_H$ CDR2 having an amino acid sequence of SEQ ID NOS: 14, 42 or 70; and (3) a $V_H$ CDR3 having an amino acid sequence of SEQ ID NOS: 15, 43 or 71; or (d) (1) a $V_H$ CDR1 having an amino acid sequence of SEQ ID NOS: 16, 44 or 72; (2) a $V_H$ CDR2 having an amino acid sequence of SEQ ID NOS: 17, 45 or 73; and (3) a $V_H$ CDR3 having an amino acid sequence of SEQ ID NOS: 18, 46 or 74.

In some embodiments, the heavy chain variable ($V_H$) region includes the amino acid sequence of SEQ ID NOS: 3, 31, or 59.

In some embodiments, the antigen binding fragment includes a light chain variable ($V_L$) region including: (1) a $V_L$ CDR1 having an amino acid sequence selected from the group consisting of SEQ ID NOS: 19, 22, 25, 28, 47, 50, 53, 56, 75, 78, 81, and 84; (2) a $V_L$ CDR2 having an amino acid sequence selected from the group consisting of SEQ ID NOS: 20, 23, 26, 29, 48, 51, 54, 57, 76, 79, 82, and 85; and (3) a $V_L$ CDR3 having an amino acid sequence selected from the group consisting of SEQ ID NOS: 21, 24, 27, 30, 49, 52, 55, 58, 77, 80, 83, and 86.

In some embodiments, the light chain variable ($V_L$) region includes (a) (1) a $V_L$ CDR1 having an amino acid sequence of SEQ ID NOS: 19, 47 or 75; (2) a $V_L$ CDR2 having an amino acid sequence of SEQ ID NOS: 20, 48 or 76; and (3) a $V_L$ CDR3 having an amino acid sequence of SEQ ID NOS: 21, 49 or 77; (b) (1) a $V_L$ CDR1 having an amino acid sequence of SEQ ID NOS: 22, 50 or 78; (2) a $V_L$ CDR2 having an amino acid sequence of SEQ ID NOS: 23, 51 or 79; and (3) a $V_L$ CDR3 having an amino acid sequence of SEQ ID NOS: 24, 52 or 80; (c)(1) a $V_L$ CDR1 having an amino acid sequence of SEQ ID NOS: 25, 53 or 81; (2) a $V_L$ CDR2 having an amino acid sequence of SEQ ID NOS: 26, 54 or 82; and (3) a $V_L$ CDR3 having an amino acid sequence of SEQ ID NOS: 27, 55 or 83; or (d) (1) a $V_L$ CDR1 having an amino acid sequence of SEQ ID NOS: 28, 56 or 84; (2) a $V_L$ CDR2 having an amino acid sequence of SEQ ID NOS: 29, 57 or 85; and (3) a $V_L$ CDR3 having an amino acid sequence of SEQ ID NOS: 30, 58 or 86.

In some embodiments, the light chain variable ($V_L$) region includes the amino acid sequence of SEQ ID NOS: 5, 35, 61, 89, 117 or 145.

In some embodiments, the antigen binding fragment includes (a) a heavy chain variable ($V_H$) region including (1) a $V_H$ CDR1 having an amino acid sequence selected from the group consisting of SEQ ID NOS: 7, 10, 13, 16, 35, 38, 41, 44, 63, 66, 69, and 72; (2) a $V_H$ CDR2 having an amino acid sequence selected from the group consisting of SEQ ID NOS: 8, 11, 14, 17, 36, 39, 42, 45, 64, 67, 70, and 73; and (3) a $V_H$ CDR3 having an amino acid sequence selected from the group consisting of SEQ ID NOS: 9, 12, 15, 18, 37, 40, 43, 46, 65, 68, 71, and 74; and (b) a light chain variable ($V_L$) region including (1) a $V_L$ CDR1 having an amino acid sequence selected from the group consisting of SEQ ID NOS: 19, 22, 25, 28, 47, 50, 53, 56, 75, 78, 81, or 84; (2) a $V_L$ CDR2 having an amino acid sequence selected from the group consisting of SEQ ID NOS: 20, 23, 26, 29, 48, 51, 54, 57, 76, 79, 82, or 85; and (3) a $V_L$ CDR3 having an amino acid sequence selected from the group consisting of SEQ ID NOS: 21, 24, 27, 30, 49, 52, 55, 58, 77, 80, 83, or 86.

In some embodiments, the antigen binding fragment includes (i) (a) a heavy chain variable ($V_H$) region including (1) a $V_H$ CDR1 having an amino acid sequence of SEQ ID NOS: 7, 35 or 63; (2) a $V_H$ CDR2 having an amino acid sequence of SEQ ID NOS: 8, 36 or 64; and (3) a $V_H$ CDR3 having an amino acid sequence of SEQ ID NOS: 9, 37 or 65; and (b) a light chain variable ($V_L$) region including (1) a $V_L$ CDR1 having an amino acid sequence of SEQ ID NOS: 19, 47 or 75; (2) a $V_L$ CDR2 having an amino acid sequence of SEQ ID NOS: 20, 48 or 76; and (3) a $V_L$ CDR3 having an amino acid sequence of SEQ ID NOS: 21, 49 or 77; (ii) (a) a heavy chain variable ($V_H$) region including (1) a $V_H$ CDR1 having an amino acid sequence of SEQ ID NOS: 10, 38 or 66; (2) a $V_H$ CDR2 having an amino acid sequence of SEQ ID NOS: 11, 39 or 67; and (3) a $V_H$ CDR3 having an amino acid sequence of SEQ ID NOS: 12, 40 or 68; and (b) a light chain variable ($V_L$) region including (1) a $V_L$ CDR1 having an amino acid sequence of SEQ ID NOS: 22, 50 or 78; (2) a $V_L$ CDR2 having an amino acid sequence of SEQ ID NOS: 23, 51 or 79; and (3) a $V_L$ CDR3 having an amino acid sequence of SEQ ID NOS: 24, 52 or 80; (iii) (a) a heavy chain variable ($V_H$) region including (1) a $V_H$ CDR1 having an amino acid sequence of SEQ ID NOS: 13, 41 or 69; (2) a $V_H$ CDR2 having an amino acid sequence of SEQ ID NOS: 14, 42 or 70; and (3) a $V_H$ CDR3 having an amino acid sequence of SEQ ID NOS: 15, 43 or 71; and (b) a light chain variable ($V_L$) region including (1) a $V_L$ CDR1 having an amino acid sequence of SEQ ID NOS: 25, 53 or 81; (2) a $V_L$ CDR2 having an amino acid sequence of SEQ ID NOS: 26, 54 or 82; and (3) a $V_L$ CDR3 having an amino acid sequence of SEQ ID NOS: 27, 55 or 83; or (iv) (a) a heavy chain variable ($V_H$) region including (1) a $V_H$ CDR1 having an amino acid sequence of SEQ ID NOS: 16, 44 or 72; (2) a $V_H$ CDR2 having an amino acid sequence of SEQ ID NOS: 17, 45 or 73; and (3) a $V_H$ CDR3 having an amino acid sequence of SEQ ID NOS: 18, 46 or 74; and (b) a light chain variable ($V_L$) region including (1) a $V_L$ CDR1 having an amino acid sequence of SEQ ID NOS: 28, 56 or 84; (2) a $V_L$ CDR2 having an amino acid sequence of SEQ ID NOS: 29, 57 or 85; and (3) a $V_L$ CDR3 having an amino acid sequence of SEQ ID NOS: 30, 58 or 86.

In some embodiments, the $V_H$ region includes the amino acid sequence of SEQ ID NO: 3 and the $V_L$ region includes the amino acid sequence of SEQ ID NO: 5.

In some embodiments, the $V_H$ region includes the amino acid sequence of SEQ ID NO: 31 and the $V_L$ region includes the amino acid sequence of SEQ ID NO: 33.

In some embodiment, the $V_H$ region includes the amino acid sequence of SEQ ID NO: 59 and the $V_L$ region includes the amino acid sequence of SEQ ID NO: 61.

In some embodiments, the molecule including the antigen binding fragment that immunospecifically binds to BTN1A1 is STC703, STC810, or STC820, or a humanized variant thereof.

In some embodiments, the molecule including the antigen binding fragment that immunospecifically binds to BTN1A1 is STC703 or STC81, or a humanized variant thereof.

In some embodiments, the molecule including the antigen binding fragment that immunospecifically binds to BTN1A1 is STC810, or a humanized variant thereof.

In some embodiments, the antigen binding fragment includes (a) a heavy chain variable ($V_H$) region including (1) a $V_H$ CDR1 having an amino acid sequence selected from the group consisting of SEQ ID NOS: 225, 228, 231, and 234; (2) a $V_H$ CDR2 having an amino acid sequence selected from the group consisting of SEQ ID NOS: 226, 229, 232, and 235; and (3) a $V_H$ CDR3 having an amino acid sequence selected from the group consisting of SEQ ID NOS: 227, 230, 233, and 236; or (b) a light chain variable ($V_L$) region including (1) a $V_L$ CDR1 having an amino acid sequence selected from the group consisting of SEQ ID NOS: 237, 240, 243, and 246; (2) a $V_L$ CDR2 having an amino acid sequence selected from the group consisting of SEQ ID NOS: 238, 241, 244, and 247; and (3) a $V_L$ CDR3 having an amino acid sequence selected from the group consisting of SEQ ID NOS: 239, 242, 245, and 248.

In some embodiments, the antigen binding fragment includes a heavy chain variable ($V_H$) region including (1) a $V_H$ CDR1 having an amino acid sequence selected from the group consisting of SEQ ID NOS: 225, 228, 231, and 234; (2) a $V_H$ CDR2 having an amino acid sequence selected from the group consisting of SEQ ID NOS: 226, 229, 232, and 235; and (3) a $V_H$ CDR3 having an amino acid sequence selected from the group consisting of SEQ ID NOS: 227, 230, 233, and 236.

In some embodiments, the heavy chain variable ($V_H$) region includes (a) (1) a $V_H$ CDR1 having an amino acid sequence of SEQ ID NO: 225; (2) a $V_H$ CDR2 having an amino acid sequence of SEQ ID NO: 226; and (3) a $V_H$ CDR3 having an amino acid sequence of SEQ ID NO: 227; (b)(1) a $V_H$ CDR1 having an amino acid sequence of SEQ ID NO: 228; (2) a $V_H$ CDR2 having an amino acid sequence of SEQ ID NO: 229; and (3) a $V_H$ CDR3 having an amino acid sequence of SEQ ID NO: 230; c)(1) a $V_H$ CDR1 having an amino acid sequence of SEQ ID NO: 231; (2) a $V_H$ CDR2 having an amino acid sequence of SEQ ID NO: 232; and (3) a $V_H$ CDR3 having an amino acid sequence of SEQ ID NO: 233; or (d)(1) a $V_H$ CDR1 having an amino acid sequence of SEQ ID NO: 234; (2) a $V_H$ CDR2 having an amino acid sequence of SEQ ID NO: 235; and (3) a $V_H$ CDR3 having an amino acid sequence of SEQ ID NO: 236.

In some embodiments, the heavy chain variable ($V_H$) region includes the amino acid sequence of SEQ ID NO: 221.

In some embodiments, the antigen binding fragment includes a light chain variable ($V_L$) region including: (1) a $V_L$ CDR1 having an amino acid sequence selected from the group consisting of SEQ ID NOS: 237, 240, 243, and 246; (2) a $V_L$ CDR2 having an amino acid sequence selected from the group consisting of SEQ ID NOS: 238, 241, 244, and 247; and (3) a $V_L$ CDR3 having an amino acid sequence selected from the group consisting of SEQ ID NOS: 239, 242, 245, and 248.

In some embodiments, the light chain variable ($V_L$) region includes (a)(1) a $V_L$ CDR1 having an amino acid sequence of SEQ ID NO: 237; (2) a $V_L$ CDR2 having an amino acid sequence of SEQ ID NO: 238; and (3) a $V_L$ CDR3 having an amino acid sequence of SEQ ID NO: 239; (b) (1) a $V_L$ CDR1 having an amino acid sequence of SEQ ID NO: 240; (2) a $V_L$ CDR2 having an amino acid sequence of SEQ ID NO: 241; and (3) a $V_L$ CDR3 having an amino acid sequence of SEQ ID NO: 242; (c) (1) a $V_L$ CDR1 having an amino acid sequence of SEQ ID NO: 243; (2) a $V_L$ CDR2 having an amino acid sequence of SEQ ID NO: 244; and (3) a $V_L$ CDR3 having an amino acid sequence of SEQ ID NO: 245; or (d)(1) a $V_L$ CDR1 having an amino acid sequence of SEQ ID NO: 246; (2) a $V_L$ CDR2 having an amino acid sequence of SEQ ID NO: 247; and (3) a $V_L$ CDR3 having an amino acid sequence of SEQ ID NO: 248.

In some embodiments, the light chain variable ($V_L$) region includes the amino acid sequence of SEQ ID NO: 223.

In some embodiments, the antigen binding fragment includes (a) a heavy chain variable ($V_H$) region including (1) a $V_H$ CDR1 having an amino acid sequence selected from the group consisting of SEQ ID NO: 225, 228, 231, and 234; (2) a $V_H$ CDR2 having an amino acid sequence selected from the group consisting of SEQ ID NOS: 226, 229, 232, and 235; and (3) a $V_H$ CDR3 having an amino acid sequence selected from the group consisting of SEQ ID NOS: 227, 230, 233, and 236; and (b) a light chain variable ($V_L$) region including (1) a $V_L$ CDR1 having an amino acid sequence selected from the group consisting of SEQ ID NOS: 237, 240, 243, and 246; (2) a $V_L$ CDR2 having an amino acid sequence selected from the group consisting of SEQ ID NOS: 238, 241, 244, and 247; and (3) a $V_L$ CDR3 having an amino acid sequence selected from the group consisting of SEQ ID NOS: 239, 242, 245, and 248.

In some embodiments, the antigen binding fragment includes (i) (a) a heavy chain variable ($V_H$) region including (1) a $V_H$ CDR1 having an amino acid sequence of SEQ ID NO: 225; (2) a $V_H$ CDR2 having an amino acid sequence of SEQ ID NO: 226; and (3) a $V_H$ CDR3 having an amino acid sequence of SEQ ID NO: 227; and (b) a light chain variable ($V_L$) region including (1) a $V_L$ CDR1 having an amino acid sequence of SEQ ID NO: 237; (2) a $V_L$ CDR2 having an amino acid sequence of SEQ ID NO: 238; and (3) a $V_L$ CDR3 having an amino acid sequence of SEQ ID NO: 239; (ii) (a) a heavy chain variable ($V_H$) region including (1) a $V_H$ CDR1 having an amino acid sequence of SEQ ID NO: 228; (2) a $V_H$ CDR2 having an amino acid sequence of SEQ ID NO: 229; and (3) a $V_H$ CDR3 having an amino acid sequence of SEQ ID NO: 230; and (b) a light chain variable ($V_L$) region including (1) a $V_L$ CDR1 having an amino acid sequence of SEQ ID NO: 240; (2) a $V_L$ CDR2 having an amino acid sequence of SEQ ID NO: 241; and (3) a $V_L$ CDR3 having an amino acid sequence of SEQ ID NO: 242; (iii) (a) a heavy chain variable ($V_H$) region including (1) a $V_H$ CDR1 having an amino acid sequence of SEQ ID NO: 231; (2) a $V_H$ CDR2 having an amino acid sequence of SEQ ID NO: 232; and (3) a $V_H$ CDR3 having an amino acid sequence of SEQ ID NO: 233; and (b) a light chain variable ($V_L$) region including (1) a $V_L$ CDR1 having an amino acid sequence of SEQ ID NO: 243; (2) a $V_L$ CDR2 having an amino acid sequence of SEQ ID NO: 244; and (3) a $V_L$ CDR3 having an amino acid sequence of SEQ ID NO: 245; or (iv) (a) a heavy chain variable ($V_H$) region including (1) a $V_H$ CDR1 having an amino acid sequence of SEQ ID NO:

234; (2) a $V_H$ CDR2 having an amino acid sequence of SEQ ID NO: 235; and (3) a $V_H$ CDR3 having an amino acid sequence of SEQ ID NO: 236; and (b) a light chain variable ($V_L$) region including (1) a $V_L$ CDR1 having an amino acid sequence of SEQ ID NO: 246; (2) a $V_L$ CDR2 having an amino acid sequence of SEQ ID NO: 247; and (3) a $V_L$ CDR3 having an amino acid sequence of SEQ ID NO: 248.

In some embodiments, the $V_H$ region includes the amino acid sequence of SEQ ID NO: 221 and the $V_L$ region includes the amino acid sequence of SEQ ID NO: 223.

In some embodiments, the molecule including the antigen binding fragment that immunospecifically binds to BTN1A1 is STC2714, or a humanized variant thereof.

In some embodiments, the binding to BTN1A1 competitively blocks the binding of the molecules provided herein to BTN1A1 in a dose-dependent manner.

In some embodiments, the molecule including the antigen binding fragment that immunospecifically binds to BTN1A1 binds to glycosylated BTN1A1 with a dissociation constant ($K_D$) of no more than 1 μM.

In some embodiments, the molecule including the antigen binding fragment that immunospecifically binds to BTN1A1 binds to glycosylated BTN1A1 with a dissociation constant ($K_D$) of no more than 500 nM, no more than 400 nM, no more than 300 nM, no more than 200 nM, no more than 100 nM, no more than 50 nM, no more than 10 nM, or no more than 5 nM.

In some embodiments, the molecule including the antigen binding fragment that immunospecifically binds to BTN1A1 binds to a BTN1A1 dimer with a dissociation constant ($K_D$) of no more than 1 μM.

In some embodiments, the molecule including the antigen binding fragment that immunospecifically binds to BTN1A1 binds to a BTN1A1 dimer with a dissociation constant ($K_D$) of no more than 500 nM, no more than 400 nM, no more than 300 nM, no more than 200 nM, no more than 100 nM, no more than 50 nM, no more than 10 nM, or no more than 5 nM.

In some embodiments, the molecule including the antigen binding fragment that immunospecifically binds to BTN1A1 is an antibody.

In some embodiments, the antibody is a monoclonal antibody.

In some embodiments, the antibody is a human antibody or a humanized antibody.

In some embodiments, the antibody is an IgG, IgM, or IgA.

In some embodiments the molecule including the antigen binding fragment that immunospecifically binds to BTN1A1 is a Fab', a F(ab')2, a F(ab')3, a monovalent scFv, a bivalent scFv, or a single domain antibody.

In some embodiments, the molecule including the antigen binding fragment that immunospecifically binds to BTN1A1 is recombinantly produced.

4. BRIEF DESCRIPTION OF THE DRAWINGS

The following drawings form part of the present specification and are included to further demonstrate certain embodiments of the present invention. The invention can be better understood by reference to one or more of these drawings in combination with the detailed description of specific embodiments presented herein.

FIG. 1—BTN1A1 expression across human cancers. FIG. 1 depicts a bar diagram illustrating BTN1A1 expression across a variety of human cancer types, according to cBioPortal. The frequency of mutations (green), deletions (blue), amplifications (red), or multiple aberrations (grey) is plotted by cancer type. CAN=copy number aberration.

FIGS. 2A-D—Mutually exclusive expression of BTN1A1 and PD-L1 in cancer tissues. FIGS. 2A-D show exemplary images of lung squamous carcinoma (FIG. 2A), prostate adenocarcinoma (FIG. 2B), pancreatic adenocarcinoma (FIG. 2C), and hepatocellular carcinoma (FIG. 2D) paraffin-embedded tissue samples. Two samples are shown for each tissue type (top and bottom rows of FIGS. 2A-D). Different slices from each sample were stained with PD-L1 (left columns in FIGS. 2A-D) or BTN1A1 (right columns in FIGS. 2A-D).

FIGS. 3A-D—Mutually exclusive expression of BTN1A1 and PD-L1 in cancer tissues. FIGS. 3A-D show fluorescence microscope images of an exemplary human lung squamous cell carcinoma tissue slice. FIG. 3A shows fluorescence staining for PD-L1 (green). FIG. 3B shows fluorescence staining for BTN1A1 (red). FIG. 3C shows fluorescence staining for cytokeratin (purple). FIG. 3D shows a merged image overlaying the images of FIGS. 3A-C.

FIGS. 4A-D—Mutually exclusive expression of BTN1A1 and PD-L1 in cancer tissues. FIGS. 4A-D show further fluorescence microscope images of an additional exemplary human lung squamous cell carcinoma tissue slice. FIG. 4A shows fluorescence staining for PD-L1 (green). FIG. 4B shows fluorescence staining for BTN1A1 (red). FIG. 4C shows fluorescence staining for cytokeratin (purple). FIG. 4D shows a merged image overlaying the images of FIGS. 4A-C. DAPI=fluorescent stain (4',6-diamidino-2-phenylindole).

FIG. 5A and FIG. 5B—STC810 synergizes with anti-PD-1 antibody to induce IL-2 and IFNγ secretion in mixed lymphocyte reaction. FIG. 5A and FIG. 5B show bar diagrams illustrating the effect of indicated antibody treatments on a mixed lymphocyte culture with respect to IL-2 (FIG. 5A) or IFNγ (FIG. 5B) secretion.

FIGS. 6A-C—Surface plasmon resonance analysis of BTN1A1-Fc binding to immobilized STC1011, STC1012, or STC1029 MAb. FIG. 6A, FIG. 6B, and FIG. 6C: Sensorgrams showing real-time binding of soluble BTN1A1-Fc protein (2-64 nM with 2-fold dilution) to STC1011 (FIG. 6A), STC1012 (FIG. 6B), or STC1029 (FIG. 6C) immobilized on a Protein A-CM5 chip (BIAcore). Flow cells without any immobilized protein were used as the controls for non-specific binding and were subtracted from the test flow cells.

FIGS. 7A-C—fluorescence labeled STC1012 is internalized by cells overexpressing glycosylated mouse BTN1A1 WT or non-glycosylated mouse BTN1A1 2NQ. FIG. 7A shows representative images from a IncuCyte ZOOM® live cell analysis. Red fluorescence indicating internalized phRodo™-labeled STC1012 is visible in the middle panel in the top row (293T mBTN1A1 (WT)) and in the top right panel (293T mBTN1A1 (2NQ)) and not visible in the control panels. FIG. 7B shows a graph plotting internalized STC1012-phRodo™ fluorescence over time. Increasing internalized STC810-phRodo™ fluorescence is observed in cells expressing glycosylated BTN1A1 WT and in cells expressing non-glycosylated BTN1A1 2NQ. FIG. 7C shows results from a control experiment using pHRodo™—labeled control mIgG1.

FIG. 8A and FIG. 8B—anti-mBTN1A1 antibody promotes proliferation of T-cells co-cultured with mBTN1A1-overexpressing 4T1 cells. FIG. 8A and FIG. 8B show results of a 4T1-BTN1A1—mouse splenocyte co-culture experiment. 4T1 cells overexpressing BTN1A1 were co-cultured with mouse splenocytes and indicated anti-mouse BTN1A1 antibodies. FIG. 8A shows results of a flow cytometry analysis of proliferating T-cells in the co-culture. FIG. 8B shows a bar diagram illustrating the effects of STC1011, STC1012, and STC1029 on T-cell proliferation in the co-culture. CFSE=fluorescent stain (5(6)-carboxyfluorescein N-hydroxysuccinimidyl ester).

FIG. 9—Dosing schedule for PD-1/PD-L1 therapy refractory cancer models. FIG. 9 shows a graph illustrating the dosing schedule for anti-BTN1A1 antibody administration to Balb/c mice bearing a mammary carcinoma (4T1) implant or C57BL/6 mice bearing a Lewis lung carcinoma (LLC) implant. Sac=time mice are sacrificed.

FIG. 10—STC1012 is efficacious in PD-1/PD-L1 therapy refractory breast cancer model. FIG. 10 shows a scatter plot illustrating progressing 4T1 tumor growth in Balb/c mice that were treated with anti-mouse BTN1A1 antibody STC1012 or an IgG antibody-control. Tumor volume in individual animals is plotted over time.

FIG. 11—STC1012 is efficacious in PD-1/PD-L1 therapy refractory lung cancer model (days 6-16). FIG. 11 shows a scatter plot illustrating progressing LLC tumor growth in C57BL/6 mice that were treated with anti-mouse BTN1A1 antibody STC1012 or an IgG antibody-control. Tumor volume in individual animals is plotted over time (days 6-16).

FIG. 12—STC1012 is efficacious in PD-1/PD-L1 therapy refractory lung cancer model (days 6-29). FIG. 12 shows a scatter plot illustrating progressing LLC tumor growth in C57BL/6 mice that were treated with anti-mouse BTN1A1 antibody STC1012 or an IgG antibody-control. Tumor volume in individual animals is plotted over time (days 6-29).

FIG. 13A—Epitope mapping of BTN1A1-Fc. STC810 and BTN1A1 (ECD)-Fc were subject to Ag-Ab cross-linking and analyzed by high-mass MALDI. FIG. 13A shows the amino acid residues of BTN1A1 (ECD)-Fc that were cross-linked to STC810, including R41, K42, K43, T185 and K188.

FIG. 13B—Epitope mapping of BTN1A1-His. STC810 and BTN1A1 (ECD)-His were subject to Ag-Ab cross-linking and analyzed by high-mass MALDI. FIG. 13B shows the amino acid residues of BTN1A1 (ECD)-His that were cross-linked to STC810, including R68, K78, T175, 5179 and T185.

FIG. 14—T cell killing effect of BTN1A1 antibody. FIG. 14 shows a graph plotting T cell mediated apoptosis of PC3 human prostate cancer cells in the presence of STC810, STC2602, STC2714 or STC2781 BTN1A1 antibody along with a negative control.

FIG. 15—Dimer-specific binding of BTN1A1 antibody. FIG. 15 first panel from the left is an image of Coomassie blue stained SDS-PAGE gel, showing locations of monomer and dimer forms of the BTN1A1 protein in both native and reduced conditions along with a size standard. The second through fifth panels show wester blots visualizing the monomer and dimer forms of the BTN1A1 protein in both native and reduced conditions using STC810, STC2602, STC2714 and STC 2781 antibody, respectively.

FIG. 16-B—Binding affinity ($K_D$) of STC2714 to monomer and dimer form of BTN1A1. FIG. 16A: Sensorgrams showing real-time binding of soluble BTN1A1-Fc protein (FIG. 16A) (2-64 nm with 2-fold dilution) to STC2714 immobilized on a Protein A-CM5 chip (Biacore). FIG. 16B: Sensorgrams showing real-time binding of soluble BTN1A1-His protein (2-64 nm with 2-fold dilution) to STC2714 immobilized on a Protein A-CM5 chip (Biacore).

5. DETAILED DESCRIPTIONS

The B7 family of co-stimulatory molecules can drive the activation and inhibition of immune cells. A related family of molecules—the buryrophilins—also have immunomodulatory functions similar to B7 family members. Butyrophilin, subfamily 1, member A1 ("BTN1A1") is a type I membrane glycoprotein and a major component of milk fat globule membrane, and has structural similarities to the B7 family. BTN1A1 is known as a major protein regulating the formation of fat droplets in the milk. (Ogg et al. *PNAS,* 101(27):10084-10089 (2004)). BTN1A1 is expressed in immune cells, including T cells. Treatment with recombinant BTN1A1 was found to inhibit T cell activation and protect animal models of EAE. (Stefferl et al., *J. Immunol.* 165(5):2859-65 (2000)).

BTN1A1 is also specifically and highly expressed in cancer cells. The BTN1A1 expressed in cancer cells is generally glycosylated. The expression of BTN1A1 can be used to aid cancer diagnosis as well as to evaluate the efficacy of a cancer treatment.

This disclosure is based, at least in part, on the surprising finding that BTN1A1 is expressed across a variety of cancer cells. See, e.g., Example 1.

This disclosure is based, at least in part, on the surprising finding that expression of BTN1A1 and PD-L1 is mutually exclusive in certain cancers. See, e.g., Example 2.

This disclosure is based, at least in part, on the surprising finding that anti-BTN1A1 antibodies can synergize with anti-PD1 antibodies in the activation of certain lymphocytes. See, e.g., Example 3.

This disclosure is further based, at least in part, on the surprising finding that molecules that can immunospecifically bind to BTN1A1 are efficacious in the treatment of cancers that are refractory to anti-PD1 and anti-PD-L1 therapies. See, e.g., Example 4.

Provided herein are methods for treating cancer using anti-BTN1A1 antibodies and other molecules that can immunospecifically bind to BTN1A1. In some embodiments, the cancer is an anti-PD-1 therapy or an anti-PD-L1 therapy refractory cancer. Also provided are methods for cancer diagnosis and for selecting patients using anti-BTN1A1 antibodies and other molecules that can immunospecifically bind to BTN1A1.

5.1. Definitions

As used herein, and unless otherwise specified, the articles "a," "an," and "the" refer to one or to more than one of the grammatical object of the article. By way of example, an antibody refers to one antibody or more than one antibodies.

As used herein, and unless otherwise specified, the term "Butyrophilin, subfamily 1, member A1" or "BTN1A1" refers to BTN1A1 from any vertebrate source, including mammals such as primates (e.g., humans, cynomolgus monkey (cyno)), dogs, and rodents (e.g., mice and rats). Unless otherwise specified, BTN1A1 also includes various BTN1A1 isoforms, related BTN1A1 polypeptides, including SNP variants thereof, as well as different modified forms of BTN1A1, including but not limited to phosphorylated BTN1A1, glycosylated BTN1A1, and ubiquitinated BTN1A1. As used herein, glycosylated BTN1A1 include BTN1A1 with N55, N215, and/or N449 glycosylation.

An exemplary amino acid sequence of human BTN1A1 (BC096314.1 GI: 64654887), is provided below with the potential glycosylation sites bolded and underlined:

(SEQ ID NO: 1)
MAVFPSSGLPRCLLTLILLQLPKLDSAPFDVIGPPEPILAVVGEDAKLPCR
LSPNASAEHLELRWFRKKVSPAVLVHRDGREQEAEQMPEYRGRATLVQDGI
AKGRVALRIRGVRVSDDGEYTCFFREDGSYEEALVHLKVAALGSDPHISMQ
VQENGEICLECTSVGWYPEPQVQWRTSKGEKFPSTSESRNPDEEGLFTVAA
SVIIRDTSAKNVSCYIQNLLLGQEKKVEISIPASSLPRLTPWIVAVAVILM
VLGLLTIGSIFFTWRLYNERPRERRNEFSSKERLLEELKWKKATLHAVDVT
LDPDTAHPHLFLYEDSKSVRLEDSRQKLPEKTERFDSWPCVLGRETFTSGR
HYWEVEVGDRTDWAIGVCRENVMKKGFDPMTPENGFWAVELYGNGYWALTP
LRTPLPLAGPPRRVGIFLDYESGDISFYNMNDGSDIYTFSNVTFSGPLRPF
FCLWSSGKKPLTICPIADGPERVTVIANAQDLSKEIPLSPMGEDSAPRDAD
TLHSKLIPTQPSQGAP

An exemplary encoding nucleic acid sequence of human BTN1A1 (BC096314.1 GI: 64654887), is provided below:

(SEQ ID NO: 2)
ATGGCAGTTTTCCCAAGCTCCGGTCTCCCCAGATGTCTGCTCACCCTCATT
CTCCTCCAGCTGCCCAAACTGGATTCAGCTCCCTTTGACGTGATTGGACCC
CCGGAGCCCATCCTGGCCGTTGTGGGTGAGGACGCCAAGCTGCCCTGTCGC
CTGTCTCCGAACGCGAGCGCCGAGCACTTGGAGCTACGCTGGTTCCGAAAG
AAGGTTTCGCCGGCCGTGCTGGTGCATAGGGACGGGCGCGAGCAGGAAGCC
GAGCAGATGCCCGAGTACCGCGGGCGGGCGACGCTGGTCCAGGACGGCATC
GCCAAGGGGCGCGTGGCCTTGAGGATCCGTGGCGTCAGAGTCTCTGACGAC
GGGGAGTACACGTGCTTTTTCAGGGAGGATGGAAGCTACGAAGAAGCCCTG
GTGCATCTGAAGGTGGCTGCTCTGGGCTCTGACCCTCACATCAGTATGCAA
GTTCAAGAGAATGGAGAAATCTGTCTGGAGTGCACCTCAGTGGGATGGTAC
CCAGAGCCCCAGGTGCAGTGGAGAACTTCCAAGGGAGAGAAGTTTCCATCT
ACATCAGAGTCCAGGAATCCTGATGAAGAAGGTTTGTTCACTGTGGCTGCT
TCAGTGATCATCAGAGACACTTCTGCGAAAAATGTGTCCTGCTACATCCAG
AATCTCCTTCTTGGCCAGGAGAAGAAAGTAGAAATATCCATACCAGCTTCC
TCCCTCCCAAGGCTGACTCCCTGGATAGTGGCTGTGGCTGTCATCCTGATG
GTTCTAGGACTTCTCACCATTGGGTCCATATTTTTCACTTGGAGACTATAC
AACGAAAGACCCAGAGAGAGGAGGAATGAATTCAGCTCTAAAGAGAGACTC
CTGGAAGAACTCAAATGGAAAAAGGCTACCTTGCATGCAGTTGATGTGACT
CTGGACCCAGACACAGCTCATCCCCACCTCTTTCTTTATGAGGATTCAAAA
TCTGTTCGACTGGAAGATTCACGTCAGAAACTGCCTGAGAAAACAGAGAGA
TTTGACTCCTGGCCCTGTGTGTTGGGCCGTGAGACCTTCACCTCAGGAAGG
CATTACTGGGAGGTGGAGGTGGGAGACAGGACTGACTGGGCAATCGGCGTG
TGTAGGGAGAATGTGATGAAGAAAGGATTTGACCCCATGACTCCTGAGAAT
GGGTTCTGGGCTGTAGAGTTGTATGGAAATGGGTACTGGGCCCTCACTCCT

-continued

CTCCGGACCCCTCTCCCATTGGCAGGGCCCCCACGCCGGGTTGGGATTTTC
CTAGACTATGAATCAGGAGACATCTCCTTCTACAACATGAATGATGGATCT
GATATCTATACTTTCTCCAATGTCACTTTCTCTGGCCCCCTCCGGCCCTTC
TTTTGCCTATGGTCTAGCGGTAAAAAGCCCCTGACCATCTGCCCAATTGCT
GATGGGCCTGAGAGGGTCACAGTCATTGCTAATGCCCAGGACCTTTCTAAG
GAGATCCCATTGTCCCCCATGGGGGAGGACTCTGCCCCTAGGGATGCAGAC
ACTCTCCATTCTAAGCTAATCCCTACCCAACCCAGCCAAGGGGCACCTTAA

An exemplary amino acid sequence of an exemplary dimeric BTN1A1 extracellular domain construct (BTN1A1-ECD-Fc) is provided below.

(SEQ ID NO: 189)
APFDVIGPPEPILAVVGEDAELPCRLSPNASAEHLELRWFRKKVSPAVLV
HRDGREQEAEQMPEYRGRATLVQDGIAKGRVALRIRGVRVSDDGEYTCFF
REDGSYEEALVHLKVAALGSDPHISMQVQENGEICLECTSVGWYPEPQVQ
WRTSKGEKFPSTSESRNPDEEGLFTVAASVIIRDTSAKNVSCYIQNLLLG
QEKKVEISIPASSLPRDKTHTCPPCPAPELLGGPSVFLFPPKPKDTLMIS
RTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPS
REEMTKNQVSLTCLVKGFYPSDIAVEWESNGQPENNYKTTPPVLDSDGSF
FLYSKLTVDKSRWQQGNVFSCSVMHEALHNHYTQKSLSLSPGK

An exemplary amino acid sequence of an exemplary monomeric BTN1A1 extracellular domain construct (BTN1A1-His6) is provided below.

(SEQ ID NO: 190)
APFDVIGPPEPILAVVGEDAELPCRLSPNASAEHLELRWFRKKVSPAVLV
HRDGREQEAEQMPEYRGRATLVQDGIAKGRVALRIRGVRVSDDGEYTCFF
REDGSYEEALVHLKVAALGSDPHISMQVQENGEICLECTSVGWYPEPQVQ
WRTSKGEKFPSTSESRNPDEEGLFTVAASVIIRDTSAKNVSCYIQNLLLG
QEKKVEISIPASSLPRHHHHHH

An exemplary amino acid sequence of mouse BTN1A1 (GenBank: AAH11497.1), is provided below with the potential glycosylation sites bolded and underlined:

(SEQ ID NO: 191)
MAVPTNSCLLVCLLTLTVLQLPTLDSAAPFDVTAPQEPVLALVGSDAELT
CGFSPNASSEYMELLWFRQTRSKAVLLYRDGQEQEGQQMTEYRGRATLAT
AGLLDGRATLLIRDVRVSDQGEYRCLFKDNDDFEEAAVYLKVAAVGSDPQ
ISMTVQENGEMELECTSSGWYPEPQVQWRTGNREMLPSTSESKKHNEEGL
FTVAVSMMIRDSSIKNMSCCIQNILLGQGKEVEISLPAPFVPRLTPWIVA
VAIILLALGFLTIGSIFFTWKLYKERSSLRKKEFGSKERLLEELRCKKTV
LHEVDVTLDPDTAHPHLFLYEDSKSVRLEDSRQILPDRPERFDSWPCVLG
RETFTSGRHYWEVEVGDRTDWAIGVCRENVVKKGFDPMTPDNGFWAVELY

-continued

GNGYWALTPLRTSLRLAGPPRRVGVFLDYDAGDISFYNMSNGSLIYTFPS

ISFSGPLRPFFCLWSCGKKPLTICSTANGPEKVTVIANVQDDIPLSPLGE

GCTSGDKDTLHSKLIPFSPSQAAP

An exemplary encoding nucleic acid sequence of mouse BTN1A1 (GenBank: BC011497.1), is provided below:

(SEQ ID NO: 192)

ATGGCAGTTCCCACCAACTCCTGCCTCCTGGTCTGTCTGCTCACCCTCA

CTGTCCTACAGCTGCCCACGCTGGATTCGGCAGCTCCCTTCGATGTGACC

GCACCTCAGGAGCCAGTGTTGGCCCTAGTGGGCTCAGATGCCGAGCTGAC

CTGTGGCTTTTCCCCAAACGCGAGCTCAGAATACATGGAGCTGCTGTGGT

TTCGACAGACGAGGTCGAAAGCGGTACTTCTATACCGGGATGGCCAGGAG

CAGGAGGGCCAGCAGATGACGGAGTACCGCGGGAGGGCGACGCTGGCGAC

AGCCGGGCTTCTAGACGGCCGCGCTACTCTGCTGATCCGAGATGTCAGGG

TCTCAGACCAGGGGGAGTACCGGTGCCTTTTCAAAGACAACGACGACTTC

GAGGAGGCCGCCGTATACCTCAAAGTGGCTGCTGTGGGTTCAGATCCTCA

AATCAGTATGACGGTTCAAGAGAATGGAGAAATGGAGCTGGAGTGCACCT

CCTCTGGATGGTACCCAGAGCCTCAGGTGCAGTGGAGAACAGGCAACAGA

GAGATGCTACCATCCACGTCAGAGTCCAAGAAGCATAATGAGGAAGGCCT

GTTCACTGTGGCAGTTTCAATGATGATCAGAGACAGCTCCATAAAGAACA

TGTCCTGCTGCATCCAGAATATCCTCCTTGGCCAGGGGAAGGAAGTAGAG

ATCTCCTTACCAGCTCCCTTCGTGCCAAGGCTGACTCCCTGGATAGTAGC

TGTGGCTATCATCTTACTGGCCTTAGGATTTCTCACCATTGGGTCCATAT

TTTTCACTTGGAAACTATACAAGGAAAGATCCAGTCTGCGGAAGAAGGAA

TTTGGCTCTAAAGAGAGACTTCTGGAAGAACTCAGATGCAAAAAGACTGT

ACTGCATGAAGTTGACGTGACTCTGGATCCAGACACAGCCCACCCCCACC

TCTTCCTGTATGAAGATTCAAAGTCAGTTCGATTGGAAGATTCACGTCAG

ATCCTGCCTGATAGACCAGAGAGATTTGACTCCTGGCCCTGTGTGTTGGG

CCGTGAGACCTTTACTTCAGGGAGACATTACTGGGAGGTGGAGGTGGGAG

ATAGAACTGACTGGGCCATTGGTGTGTGTAGGGAGAATGTGGTGAAGAAA

GGGTTTGACCCCATGACTCCTGATAATGGGTTCTGGGCTGTGGAGTTGTA

TGGAAATGGGTACTGGGCCCTCACCCCACTCAGGACCTCTCTCCGATTAG

CAGGGCCCCCTCGCAGAGTTGGGGTTTTTCTGGACTATGACGCAGGAGAC

ATTTCCTTCTACAACATGAGTAACGGATCTCTTATCTATACTTTCCCTAG

CATCTCTTTCTCTGGCCCCCTCCGTCCCTTCTTTTGTCTGTGGTCCTGTG

GTAAAAAGCCCCTGACCATCTGTTCAACTGCCAATGGGCCTGAGAAAGTC

ACAGTCATTGCTAATGTCCAGGACGACATTCCCTTGTCCCCGCTGGGGGA

AGGCTGTACTTCTGGAGACAAAGACACTCTCCATTCTAAACTGATCCCGT

TCTCACCTAGCCAAGCGGCACCATAA

As used herein, and unless otherwise specified, the terms "Programmed Death 1," "Programmed Cell Death 1," "Protein PD-1," "PD-1," "PD-1 polypeptide," or "PD1" encompass a polypeptide ("polypeptide" and "protein" are used interchangeably herein), including any native polypeptide, from any vertebrate source, including mammals such as primates (e.g., humans and cynomolgus monkeys (cynomolgus)), dogs, and rodents (e.g., mice and rats), unless otherwise indicated. In certain embodiments, the terms include "related PD-1 polypeptides," including SNP variants thereof. The term "PD-1" also encompasses "full-length," unprocessed PD-1 as well as any form of PD-1 that results from processing in the cell. NCBI Reference Sequence NP_005009.2 provides and exemplary human PD-L1 amino acid sequence. GenBank™ accession number L27440.1 provides an exemplary human PD-1 nucleic acid sequence.

As used herein, and unless otherwise specified, the term "anti-PD-1 therapy" encompasses any inhibitor of PD-1. In some embodiments, an anti-PD-1 therapy can include an anti-PD-1 antibody or antigen binding fragment thereof, an inhibitory nucleic acid, or a soluble PD-1 ligand (e.g., a soluble PD-L1), or a fusion-protein thereof (e.g., an Fc-fusion protein). In some embodiments, the anti-PD-1 therapy includes nivolumab (Opdivo), pembrolizumab (Keytruda), pidilizumab, AMP-514, or AMP-224.

In some embodiments, the anti-PD-1 therapy includes Nivolumab (CAS Registry Number: 946414-94-4). Nivolumab is also known as MDX-1 106, MDX-1 106-04, ONO-4538, or BMS-936558. Nivolumab is a fully human IgG4 monoclonal antibody that specifically blocks PD-1. Nivolumab (clone 5C4) and other human monoclonal antibodies that specifically bind to PD-1 are disclosed in U.S. Pat. No. 8,008,449 and WO2006/121 168.

In some embodiments, the anti-PD-1 therapy includes Pembrolizumab. Pembrolizumab is also known as KEYTRUDA®, lambrolizumab, Merck 3745, MK-3475 or SCH-900475. Pembrolizumab is a humanized IgG4 monoclonal antibody that binds to PD-1. Pembrolizumab is disclosed, e.g., in Hamid, O. et al. (2013) New England Journal of Medicine 369 (2): 134-44, WO2009/1 14335, and U.S. Pat. No. 8,354,509.

In some embodiments, the anti-PD-1 therapy is Pidilizumab. Pidilizumab, also known as CT-011 (CureTech), is a humanized IgG1 monoclonal antibody that binds to PD-1. Pidilizumab and other humanized anti-PD-1 monoclonal antibodies are disclosed in WO2009/101611.

In some embodiments, the anti-PD-1 therapy includes an anti-PD-1 antibody provided in International Application No. PCT/US2016/64394.

Additional anti-PD 1 antibodies that can be useful as anti-PD1 therapies are disclosed in U.S. Pat. No. 8,609,089, US 2010028330, and/or US 201201 14649.

In some embodiments, the anti-PD-1 therapy includes the fusion protein AMP 514 (Amplimmune). AMP-224, also known as B7-DCIg is, e.g., disclosed in WO2010/027827 and WO201 1/066342. AMP-224 is a PD-L2 Fc fusion soluble receptor that blocks the interaction between PD1 and B7-H1.

In some embodiments, the anti-PD-1 therapy includes an immunoadhesin (e.g., an immunoadhesin including an extracellular or PD-1 binding portion of PD-L1 or PD-L2 fused to a constant region (e.g., an Fc region of an immunoglobulin sequence)). In some embodiments, the anti-PD-1 therapy includes the fusion protein AMP-224 (Fc-fusion of PD-L2).

As used herein, and unless otherwise specified, the terms "Programmed Death 1 Ligand 1," "Programmed Cell Death 1 Ligand 1," "Protein PD-L1," "PD-L1," "PD-L1 polypeptide," or "PD1-L1" encompass a polypeptide ("polypeptide" and "protein" are used interchangeably herein), including any native polypeptide, from any vertebrate source, including mammals such as primates (e.g., humans and cynomolgus monkeys (cynomolgus)), dogs, and rodents (e.g., mice and rats), unless otherwise indicated. In certain embodiments, the terms include "related PD-L1 polypeptides," including SNP variants thereof. The term "PD-L1" also encompasses "full-length," unprocessed PD-L1 as well as any form of PD-L1 that results from processing in the cell. NCBI Reference Sequence NP 054862.1 provides and exemplary human PD-L1 amino acid sequence. GenBank™ accession number NM_014143 provides an exemplary human PD-1 nucleic acid sequence.

As used herein, and unless otherwise specified, the term "anti-PD-L1 therapy" encompasses any inhibitor of PD-L1. In some embodiments, an anti-PD-1 therapy can include an anti-PD-L1 antibody or antigen binding fragment thereof, an inhibitory nucleic acid, or a soluble PD-L1 ligand (e.g., a soluble PD-1), or a fusion-protein thereof (e.g., an Fc-fusion protein). In some embodiments, the anti-PD-L1 therapy includes YW243.55.S70, MPDL3280A, MEDI-4736, MSB-0010718C, or MDX-1105.

In some embodiments, the anti-PD-L1 therapy includes MDX-1105. MDX-1105, is also known as BMS-936559. See, e.g., WO2007/005874.

In some embodiments, the PD-L1 therapy includes the antibody YW243.55.570, as described, e.g., in WO 2010/077634 (heavy and light chain variable region sequences shown in SEQ ID NOS: 20 and 21, respectively).

In some embodiments, the PD-L1 therapy includes MDPL3280A (Genentech/Roche). MDPL3280A is a human Fc optimized IgG1 monoclonal antibody that binds to PD-L1. MDPL3280A and other human monoclonal antibodies to PD-L1 are disclosed, e.g., in U.S. Pat. No. 7,943,743 and U.S. Publication No.: 20120039906.

In some embodiments, the anti-PD-L1 therapy includes the antibody MSB0010718C (Merck Serono). MSB0010718C is also known as A09-246-2.

In some embodiments, the anti-PD-L1 therapy includes MDPL3280A (Genentech/Roche), a human Fc optimized IgG1 monoclonal antibody that binds to PD-L1. MDPL3280A and other human monoclonal antibodies to PD-L1 are disclosed in U.S. Pat. No. 7,943,743 and U.S. Publication No.: 20120039906.

In some embodiments, the anti-PD-L1 therapy includes an antibody provided in International Application No. PCT/US2016/024691, published as WO 2016/160792 A1, and International Application No. PCT/US2017/024027.

As used herein, and unless otherwise specified, the term "antibody" refers to a polypeptide product of B cells within the immunoglobulin (or "Ig") class of polypeptides that is able to bind to a specific molecular antigen and is composed of two identical pairs of polypeptide chains, whereby each pair has one heavy chain (about 50-70 kDa) and one light chain (about 25 kDa) and each amino-terminal portion of each chain includes a variable region of about 100 to about 130 or more amino acids and each carboxy-terminal portion of each chain includes a constant region (See Borrebaeck (ed.) (1995) *Antibody Engineering*, Second Edition, Oxford University Press.; Kuby (1997) *Immunology*, Third Edition, W.H. Freeman and Company, New York). Here, the specific molecular antigen includes the target BTN1A1, which can be a BTN1A1 polypeptide, BTN1A1 fragment or BTN1A1 epitope. Antibodies provided herein include, but are not limited to, monoclonal antibodies, synthetic antibodies, recombinantly produced antibodies, bi-specific antibodies, multispecific antibodies, human antibodies, humanized antibodies, camelized antibodies, chimeric antibodies, intrabodies, anti-idiotypic (anti-Id) antibodies.

As used herein, and unless otherwise specified, the term "monoclonal antibody" refers to an antibody that is the product of a single cell clone or hybridoma or a population of cells derived from a single cell. A monoclonal antibody also is intended to refer to an antibody produced by recombinant methods from heavy and light chain encoding immunoglobulin genes to produce a single molecular immunoglobulin species. Amino acid sequences for antibodies within a monoclonal antibody preparation are substantially homogeneous and the binding activity of antibodies within such a preparation exhibit substantially the same antigen binding activity. In contrast, polyclonal antibodies are obtained from different B cells within a population, which are a combination of immunoglobulin molecules that bind a specific antigen. Each immunoglobulin of the polyclonal antibodies can bind a different epitope of the same antigen. Methods for producing both monoclonal antibodies and polyclonal antibodies are well known in the art (Harlow and Lane., *Antibodies: A Laboratory Manual*, Cold Spring Harbor Laboratory Press (1989) and Borrebaeck (ed.), *Antibody Engineering: A Practical Guide*, W.H. Freeman and Co., Publishers, New York, pp. 103-120 (1991)).

As used herein, and unless otherwise specified, the term "human antibody" refers to an antibody that has a human variable region and/or a human constant region or a portion thereof corresponding to human germline immunoglobulin sequences. Such human germline immunoglobulin sequences are described by Kabat et al. (1991) *Sequences of Proteins of Immunological Interest*, Fifth Edition, U.S. Department of Health and Human Services, NIH Publication No. 91-3242. Here, a human antibody can include an antibody that binds to BTN1A1 and is encoded by a nucleic acid sequence that is a naturally occurring somatic variant of the human germline immunoglobulin nucleic acid sequence.

As used herein, and unless otherwise specified, the term "chimeric antibody" refers to an antibody that a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA*, 81:6851-6855 (1984)).

As used herein, and unless otherwise specified, the term "humanized antibody" refers to chimeric antibodies that include human immunoglobulins (e.g., recipient antibody) in which the native Complementarity Determining Region ("CDR") residues are replaced by residues from the corresponding CDR of a nonhuman species (e.g., donor antibody) such as mouse, rat, rabbit or nonhuman primate having the desired specificity, affinity, and capacity. In some instances, one or more FR region residues of the human immunoglobulin are replaced by corresponding nonhuman residues. Furthermore, humanized antibodies can have residues that are not found in the recipient antibody or in the donor antibody. These modifications are made to further refine antibody performance. A humanized antibody heavy or light chain can have substantially all of at least one or more variable regions, in which all or substantially all of the CDRs correspond to those of a nonhuman immunoglobulin and all or substantially all of the FRs are those of a human immunoglobulin sequence. The humanized antibody can have at least a portion of an immunoglobulin constant region (Fc), typically that of a human immunoglobulin. For further details, see, Jones et al., *Nature*, 321:522-525 (1986); Riechmann et al., *Nature*, 332:323-329 (1988); and Presta, *Curr.*

*Op. Struct. Biol.,* 2:593-596 (1992); Carter et al., *Proc. Natl. Acd. Sci. USA* 89:4285-4289 (1992); and U.S. Pat. Nos. 6,800,738, 6,719,971, 6,639,055, 6,407,213, and 6,054,297.

As used herein, and unless otherwise specified, the term “recombinant antibody” refers to an antibody that is prepared, expressed, created or isolated by recombinant means. Recombinant antibodies can be antibodies expressed using a recombinant expression vector transfected into a host cell, antibodies isolated from a recombinant, combinatorial antibody library, antibodies isolated from an animal (e.g., a mouse or cow) that is transgenic and/or transchromosomal for human immunoglobulin genes (see, e.g., Taylor, L. D. et al., *Nucl. Acids Res.* 20:6287-6295(1992)) or antibodies prepared, expressed, created or isolated by any other means that involves splicing of immunoglobulin gene sequences to other DNA sequences. Such recombinant antibodies can have variable and constant regions, including those derived from human germline immunoglobulin sequences (see Kabat, E. A. et al. (1991) *Sequences of Proteins of Immunological Interest*, Fifth Edition, U.S. Department of Health and Human Services, NIH Publication No. 91-3242). The recombinant antibodies can also be subjected to in vitro mutagenesis (or, when an animal transgenic for human Ig sequences is used, in vivo somatic mutagenesis) and thus the amino acid sequences of the $V_H$ and $V_L$ regions of the recombinant antibodies can be sequences that, while derived from and related to human germline $V_H$ and $V_L$ sequences, do not naturally exist within the human antibody germline repertoire in vivo.

As used herein, and unless otherwise specified, a “neutralizing antibody” refers to an antibody that blocks the binding the BTN1A1 with its natural ligands and inhibits the signaling pathways mediated by BTN1A1 and/or its other physiological activities. The IC50 of a neutralizing antibody refers to the concentration of the antibody that is required to neutralize 50% of BTN1A1 in a neutralization assay. The IC50 of the neutralizing antibody can range between 0.01-10 μg/ml in the neutralization assay.

As used herein, and unless otherwise specified, the term “antigen binding fragment” and similar terms refer to a portion of an antibody which includes the amino acid residues that immunospecifically bind to an antigen and confer on the antibody its specificity and affinity for the antigen. An antigen binding fragment can be referred to as a functional fragment of an antibody. An antigen binding fragment can be monovalent, bivalent, or multivalent.

Molecules having an antigen binding fragment include, for example, an Fd, Fv, Fab, F(ab'), $F(ab)_2$, $F(ab')_2$, single chain Fv (scFv), diabody, triabody, tetrabody, minibody, or a single domain antibody. A scFv can be monovalent scFv or bivalent scFv. Other molecules having an antigen binding fragment can include, for example, heavy or light chain polypeptides, variable region polypeptides or CDR polypeptides or portions thereof so long as such antigen binding fragments retain binding activity. Such antigen binding fragments can be found described in, for example, Harlow and Lane, *Antibodies: A Laboratory Manual*, Cold Spring Harbor Laboratory, New York (1989); Myers (ed.), *Molec. Biology and Biotechnology: A Comprehensive Desk Reference*, New York: VCH Publisher, Inc.; Huston et al., *Cell Biophysics,* 22:189-224 (1993); Plückthun and Skerra, *Meth. Enzymol.,* 178:497-515 (1989) and in Day, E. D., *Advanced Immunochemistry*, Second Ed., Wiley-Liss, Inc., New York, NY (1990). An antigen binding fragment can be a polypeptide having an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

The heavy chain of an antibody refers to a polypeptide chain of about 50-70 kDa, whereby the amino-terminal portion includes a variable region of about 120 to 130 or more amino acids and a carboxy-terminal portion that includes a constant region. The constant region can be one of five distinct types, referred to as alpha (α), delta (δ), epsilon (ε), gamma (γ) and mu (μ), based on the amino acid sequence of the heavy chain constant region. The distinct heavy chains differ in size: α, δ and γ contain approximately 450 amino acids, while μ and c contain approximately 550 amino acids. When combined with a light chain, these distinct types of heavy chains give rise to five well known classes of antibodies, IgA, IgD, IgE, IgG and IgM, respectively, including four subclasses of IgG, namely IgG1, IgG2, IgG3 and IgG4. A heavy chain can be a human heavy chain.

The light chain of an antibody refers to a polypeptide chain of about 25 kDa, whereby the amino-terminal portion includes a variable region of about 100 to about 110 or more amino acids and a carboxy-terminal portion that includes a constant region. The approximate length of a light chain is 211 to 217 amino acids. There are two distinct types, referred to as kappa (κ) of lambda (λ) based on the amino acid sequence of the constant domains. Light chain amino acid sequences are well known in the art. A light chain can be a human light chain.

The variable domain or variable region of an antibody refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable domains differ extensively in sequence between different antibodies. The variability in sequence is concentrated in the CDRs while the less variable portions in the variable domain are referred to as framework regions (FR). The CDRs of the light and heavy chains are primarily responsible for the interaction of the antibody with antigen. Numbering of amino acid positions used herein is according to the EU Index, as in Kabat et al. (1991) *Sequences of proteins of immunological interest*. (U.S. Department of Health and Human Services, Washington, D.C.) $5^{th}$ ed. A variable region can be a human variable region.

A CDR refers to one of three hypervariable regions (H1, H2 or H3) within the non-framework region of the immunoglobulin (Ig or antibody) $V_H$ β-sheet framework, or one of three hypervariable regions (L1, L2 or L3) within the non-framework region of the antibody $V_L$ β-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains (Kabat et al., *J. Biol. Chem.* 252:6609-6616 (1977); Kabat, *Adv. Prot. Chem.* 32:1-75 (1978)). CDR region sequences also have been defined structurally by Chothia as those residues that are not part of the conserved β-sheet framework, and thus are able to adapt different conformations (Chothia and Lesk, *J. Mol. Biol.* 196:901-917 (1987)). Both terminologies are well recognized in the art. The positions of CDRs within a canonical antibody variable domain have been determined by comparison of numerous structures (Al-Lazikani et al., *J. Mol. Biol.* 273:927-948 (1997); Morea et al., *Methods* 20:267-279 (2000)). Because the number of residues within a hypervariable region varies in different antibodies, additional residues relative to the canonical positions are conventionally numbered with a, b, c and so forth next to the residue number in the canonical variable domain numbering scheme (Al-Lazikani et al., supra (1997)). Such nomenclature is similarly well known to those skilled in the art.

For example, CDRs defined according to standard designations are set forth in the Table 1 below.

TABLE 1

CDR Definitions

| | Exemplary (Kabat + Chothia) | IMGT | Kabat | AbM | Chothia | Contact |
|---|---|---|---|---|---|---|
| $V_H$ CDR1 | 26-35 | 27-38 | 31-35 | 26-35 | 26-32 | 30-35 |
| $V_H$ CDR2 | 50-65 | 56-65 | 50-65 | 50-58 | 53-55 | 47-58 |
| $V_H$ CDR3 | 95-102 | 105-117 | 95-102 | 95-102 | 96-101 | 93-101 |
| $V_L$ CDR1 | 24-34 | 27-38 | 24-34 | 24-34 | 26-32 | 30-36 |
| $V_L$ CDR2 | 50-56 | 56-65 | 50-56 | 50-56 | 50-52 | 46-55 |
| $V_L$ CDR3 | 89-97 | 105-117 | 89-97 | 89-97 | 91-96 | 89-96 |

One or more CDRs also can be incorporated into a molecule either covalently or noncovalently to make it an immunoadhesin. An immunoadhesin can incorporate the CDR(s) as part of a larger polypeptide chain, can covalently link the CDR(s) to another polypeptide chain, or can incorporate the CDR(s) noncovalently. The CDRs permit the immunoadhesin to bind to a particular antigen of interest.

The "framework" or "FR" residues refer to those variable domain residues flanking the CDRs. FR residues are present, e.g., in chimeric, humanized, human, domain antibodies, diabodies, linear antibodies, and bispecific antibodies. FR residues are those variable domain residues other than the hypervariable region residues herein defined.

As used herein, and unless otherwise specified, the term "isolated" as used in reference to an antibody means the antibody is substantially free of cellular material or other contaminating proteins from the cell or tissue source and/or other contaminant components from which the antibody is derived, or substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, or 5% (by dry weight) of heterologous protein (also referred to herein as a "contaminating protein"). In certain embodiments, when the antibody is recombinantly produced, it is substantially free of culture medium, e.g., culture medium represents less than about 20%, 10%, or 5% of the volume of the protein preparation. In certain embodiments, when the antibody is produced by chemical synthesis, it is substantially free of chemical precursors or other chemicals, e.g., it is separated from chemical precursors or other chemicals which are involved in the synthesis of the protein. Accordingly such preparations of the antibody have less than about 30%, 20%, 10%, 5% (by dry weight) of chemical precursors or compounds other than the antibody of interest. Contaminant components can also include, but are not limited to, materials that would interfere with therapeutic uses for the antibody, and may include enzymes, hormones, and other proteinaceous or nonproteinaceous solutes. In certain embodiments, the antibody will be purified (1) to greater than 95% by weight of antibody as determined by the Lowry method (Lowry et al. J. Bio. Chem. 193: 265-275, 192

1), such as 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step. In a specific embodiment, antibodies provided herein are isolated As used herein, and unless otherwise specified, the term "polynucleotide," "nucleotide," nucleic acid" "nucleic acid molecule" and other similar terms are used interchangeable and include DNA, RNA, mRNA and the like.

As used herein, and unless otherwise specified, the term "isolated" as used in reference to a nucleic acid molecule means the nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, a nucleic acid molecule(s) encoding an antibody provided herein is isolated or purified.

As used herein and unless otherwise specified, the term "bind" or "binding" refers to an interaction between molecules. Interactions can be, for example, non-covalent interactions including hydrogen bonds, ionic bonds, hydrophobic interactions, and/or van der Waals interactions. The strength of the total non-covalent interactions between an antibody and a single epitope of a target molecule, such as BTN1A1, is the affinity of the antibody for that epitope. "Binding affinity" generally refers to the strength of the sum total of noncovalent interactions between a single binding site of a molecule (e.g., a binding protein such as an antibody) and its binding partner (e.g., an antigen).

The affinity of a binding molecule X, such as an antibody, for its binding partner Y, such as the antibody's cognate antigen can generally be represented by the dissociation constant ($K_D$). Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. The "$K_D$" or "$K_D$ value" can be measured by assays known in the art, for example by a binding assay. The $K_D$ can be measured in a radiolabeled antigen binding assay (MA), for example, performed with the Fab version of an antibody of interest and its antigen (Chen, et al., (1999) *J Mol. Biol.* 293:865-881). The $K_D$ or $K_D$ value can also be measured by using surface plasmon resonance assays by Biacore, using, for example, a BIAcore™-2000 or a BIAcore™-3000 BIAcore, Inc., Piscataway, NJ), or by biolayer interferometry using, for example, the OctetQK384 system (ForteBio, Menlo Park, CA).

As used herein, and unless otherwise specified, a molecule is said to be able to "immunospecifically bind" a second molecule if such binding exhibits the specificity and affinity of an antibody to its cognate antigen. An antibody immunospecifically binds to a target region or conformation ("epitope") of an antigen if such binding involves the antigen recognition site of the antibody. An antibody that immunospecifically binds to a particular antigen can bind to other antigens with lower affinity if the other antigen has some sequence or conformational similarity that is recognized by the antigen recognition site as determined by, e.g., immunoassays, BIACORE® assays, or other assays known in the art. An antibody in general do not bind to a totally unrelated antigen. Some antibodies (and their antigen binding fragments) does not cross-react with other antigens. Antibodies can also bind to other molecules in a way that is not immunospecific, such as to FcR receptors, by virtue of binding domains in other regions/domains of the antibody that do not involve the antigen recognition site, such as the Fc region.

An antibody or antigen binding fragment that immunospecifically binds to an antigen or an epitope of an antigen that includes a glycosylation site can bind to the antigen or the epitope in both glycosylated form or unglycosylated form. In some embodiments, the antibody or antigen binding fragment preferentially binds the glycosylated antigen or epitope over the unglycosylated antigen or epitope. The preferential binding can be determined by binding affinity. For example, an antibody or antigen binding fragment that preferentially binds glycosylated BTN1A1 over unglycosylated BTN1A1 can bind to glycosylated BTN1A1 with a $K_D$ less than the $K_D$ exhibited relative to unglycosylated BTN1A1. In some embodiments, the antibody or antigen binding fragment binds to glycosylated BTN1A1 with a $K_D$ less than half of the $K_D$ exhibited relative to unglycosylated BTN1A1. In some embodiments, the antibody or antigen binding fragment binds to glycosylated BTN1A1 with $K_D$ at least 10 times less than the $K_D$ exhibited relative to unglycosylated BTN1A1. In some embodiments, the antibody or antigen binding fragment binds to glycosylated BTN1A1 with $K_D$ that is about 75%, about 50%, about 25%, about 10%, about 5%, about 2.5%, or about 1% of the $K_D$ exhibited relative to unglycosylated BTN1A1.

An antibody or antigen binding fragment that immunospecifically binds to BTN1A1 can bind to a BTN1A1 monomer or a BTN1A1 dimer. In some embodiments, the antibody or antigen binding fragment preferentially binds a BTN1A1 dimer over a BTN1A1 monomers. BTN1A1 binding can occur, e.g., to a cell surface expressed BTN1A1 or to a soluble BTN1A1 domain construct, such as a BTN1A1 extracellular domain (ECD) construct (e.g., flag-tagged BTN1A1-ECD or a BTN1A1-CED-Fc fusion construct). In some embodiments, the BTN1A1 monomer or dimer is glycosylated at one or more positions. In some embodiments, the antibody or antigen binding fragment binds to BTN1A1 dimer with a $K_D$ less than half of the $K_D$ exhibited relative to a BTN1A1 monomer. In some embodiments, the antibody or antigen binding fragment binds to aBTN1A1 dimer with a $K_D$ at least 10 times less than the $K_D$ exhibited relative to a BTN1A1 monomer. In some embodiments, the antibody or antigen binding fragment binds to a BTN1A1 dimer with a $K_D$ that is about 75%, about 50%, about 25%, about 10%, about 5%, about 2.5%, or about 1% of the $K_D$ exhibited relative to aBTN1A1 monomer.

The preferential binding can also be determined by binding assays and be indicated by, for example, mean fluorescence intensity ("MFI"). For example, an antibody or antigen binding fragment that preferentially binds the glycosylated BTN1A1 can bind to glycosylated BTN1A1 with an MFI that is higher than the MFI as exhibited relative to unglycosylated BTN1A1. In some embodiments, the antibody or antigen binding fragment binds to glycosylated BTN1A1 with an MFI that is at least twice as high as the MFI as exhibited relative to unglycosylated BTN1A1. In some embodiments, antibody or the antigen binding fragment binds to glycosylated BTN1A1 with an MFI that is at least three times as high as the MFI as exhibited relative to unglycosylated BTN1A1. In some embodiments, antibody or the antigen binding fragment binds to glycosylated BTN1A1 with an MFI that is at least five times, at least ten times, at least fifteen times, or at least twenty times as high as the MFI as exhibited relative to unglycosylated BTN1A1.

As used herein, and unless otherwise specified, a molecule is said to "immunospecifically mask" glycosylation of an antigen or epitope, or a specified glycosylation site thereof, refers to its ability to either (1) block the glycosylation site of an unglycosylated antigen or epitope so that the antigen or epitope cannot be glycosylated, or (2) bind to the glycosylated antigen or epitope or at the specified glycosylation site of the glycosylated antigen or epitope and prevent the physiological effect of the glycosylation, such as the downstream signaling mediated by the glycosylation. For example, an antibody or antigen binding fragment that immunospecifically masks BTN1A1 glycosylation refers to the antibody or antigen binding fragment that (1) either blocks the glycosylation site of an unglycosylated BTN1A1 and prevents its glycosylation or (2) binds to glycosylated BTN1A1 and prevents the physiological effects of the glycosylation, such as the immunosuppressive effect mediated by the glycosylation. For another example, an antibody or antigen binding fragment that immunospecifically masks BTN1A1 glycosylation at N55 and N215 refers to the antibody or antigen binding fragment that either (1) blocks N55 and N215 of an unglycosylated BTN1A1 and prevents the glycosylation of N55 and N215 or (2) binds to BTN1A1 glycosylated at N55 and N215 and prevent the physiological effect of the glycosylation, such as the immunosuppressive effect mediated by the glycosylation.

As used herein, and unless otherwise specified, the term "carrier" refers to a diluent, adjuvant (e.g., Freund's adjuvant (complete or incomplete)), excipient, stabilizers or vehicle with which a therapeutic agent is administered. A "pharmaceutically acceptable carrier" is a carrier that is nontoxic to the cell or mammal being exposed thereto at the dosages and concentrations employed, which can be sterile liquids, such as water and oils, including those of petroleum, animal, vegetable or synthetic origin, such as peanut oil, soybean oil, mineral oil, sesame oil and the like.

As used herein, and unless otherwise specified, the term "vector" refers to a substance that is used to introduce a nucleic acid molecule into a host cell. Vectors applicable for use include, for example, expression vectors, plasmids, phage vectors, viral vectors, episomes and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more nucleic acid molecules are to be co-expressed (e.g. both an antibody heavy and light chain), both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the nucleic acid molecule is expressed in a sufficient amount to produce the desired product (e.g. an anti-BTN1A1 antibody provided herein), and it is further understood that expression levels can be optimized to obtain sufficient expression using methods well known in the art.

As used herein, and unless otherwise specified, the term "host cell" refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, and unless otherwise specified, the term "subject" refers to an animal that is the object of treatment, observation and/or experiment. "Animal" includes vertebrates and invertebrates, such as fish, shellfish, reptiles, birds, and, in particular, mammals. "Mammal" includes, but not limited to, mice, rats, rabbits, guinea pigs, dogs, cats, sheep, goats, cows, horses, primates, such as monkeys, chimpanzees, apes, and humans.

As used herein, and unless otherwise specified, the term "cancer" or "cancerous" refers to the physiological condition in mammals that is typically characterized by unregulated cell growth. Examples of cancer include, but are not limited to, hematological cancers and solid tumors.

As used herein, and unless otherwise specified, the term "treat," "treating," "treatment," when used in reference to a cancer patient, refer to an action that reduces the severity of the cancer, or retards or slows the progression of the cancer, including (a) inhibiting the cancer growth, or arresting development of the cancer, and (b) causing regression of the cancer, or delaying or minimizing one or more symptoms associated with the presence of the cancer.

As used herein, and unless otherwise specified, the term "resistant" or "refractory" refers to a circumstance where patients, even after intensive treatment, have residual cancer cells (e.g., lung cancer or breast cancer cells) in a tissue or an organ (e.g., lung or breast).

The term "responsiveness" or "responsive" when used in reference to a treatment refers to the degree of effectiveness of the treatment in lessening or decreasing the symptoms of a disease, e.g., an anti-PD1 therapy or an anti-PD-L1 therapy resistant or refractory cancer, being treated. For example, the term "increased responsiveness" when used in reference to a treatment of a cell or a subject refers to an increase in the effectiveness in lessening or decreasing the symptoms of the disease compared to a reference treatment (e.g., of the same cell or subject, or of a different cell or subject) when measured using any methods known in the art. In certain embodiments, the increase in the effectiveness is at least about 5%, at least about 10%, at least about 20%, at least about 30%, at least about 40%, or at least about 50%.

As used herein, the terms "effective subject response," "effective patient response," and "effective patient tumor response" refer to any increase in the therapeutic benefit to the patient. An "effective patient tumor response" can be, for example, about 5%, about 10%, about 25%, about 50%, or about 100% decrease in the rate of progress of the tumor. An "effective patient tumor response" can be, for example, about 5%, about 10%, about 25%, about 50%, or about 100% decrease in the physical symptoms of a cancer. An "effective patient tumor response" can also be, for example, about 5%, about 10%, about 25%, about 50%, about 100%, about 200%, or more increase in the response of the patient, as measured by any suitable means, such as gene expression, cell counts, assay results, tumor size, etc.

An improvement in the cancer or cancer-related disease can be characterized as a complete or partial response. "Complete response" refers to an absence of clinically detectable disease with normalization of any previously abnormal radiographic studies, bone marrow, and cerebrospinal fluid (CSF) or abnormal monoclonal protein measurements. "Partial response" refers to at least about 10%, about 20%, about 30%, about 40%, about 50%, about 60%, about 70%, about 80%, or about 90% decrease in all measurable tumor burden (i.e., the number of malignant cells present in the subject, or the measured bulk of tumor masses or the quantity of abnormal monoclonal protein) in the absence of new lesions. The term "treatment" contemplates both a complete and a partial response.

The term "likelihood" generally refers to an increase in the probability of an event. The term "likelihood" when used in reference to the effectiveness of a patient tumor response generally contemplates an increased probability that the rate of tumor progress or tumor cell growth will decrease. The term "likelihood" when used in reference to the effectiveness of a patient tumor response can also generally mean the increase of indicators, such as mRNA or protein expression, that may evidence an increase in the progress in treating the tumor.

The term "predict" generally means to determine or tell in advance. When used to "predict" the effectiveness of a cancer treatment, for example, the term "predict" can mean that the likelihood of the outcome of the cancer treatment can be determined at the outset, before the treatment has begun, or before the treatment period has progressed substantially.

The term "monitor," as used herein, generally refers to the overseeing, supervision, regulation, watching, tracking, or surveillance of an activity. For example, the term "monitoring the effectiveness of a compound" refers to tracking the effectiveness in treating cancer in a patient or in a tumor cell culture. Similarly, the term "monitoring," when used in connection with patient compliance, either individually, or in a clinical trial, refers to the tracking or confirming that the patient is actually taking a drug being tested as prescribed. The monitoring can be performed, for example, by following the expression of mRNA or protein biomarkers.

"Tumor," as used herein, refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

As used herein, and unless otherwise specified, the term "therapeutically effective amount" refers to the amount of an agent (e.g., an antibody described herein or any other agent described herein) that is sufficient to reduce and/or ameliorate the severity and/or duration of a given disease, disorder or condition, and/or a symptom related thereto. A therapeutically effective amount of an agent, including a therapeutic agent, can be an amount necessary for (i) reduction or amelioration of the advancement or progression of a given disease, disorder, or condition, (ii) reduction or amelioration of the recurrence, development or onset of a given disease, disorder or conditions, and/or (iii) to improve or enhance the prophylactic or therapeutic effect of another therapy (e.g., a therapy other than the administration of an antibody provided herein). A therapeutically effective amount of a substance/molecule/agent of the present disclosure (e.g., an anti-BTN1A1 antibody) can vary according to factors such as the disease state, age, sex, and weight of the individual, and the ability of the substance/molecule/agent, to elicit a desired response in the individual. A therapeutically effective amount encompasses an amount in which any toxic or detrimental effects of the substance/molecule/agent are outweighed by the therapeutically beneficial effects.

As used herein, and unless otherwise specified, the term "administer" or "administration" refers to the act of injecting or otherwise physically delivering a substance as it exists outside the body into a patient, such as by mucosal, intradermal, intravenous, intramuscular delivery and/or any other method of physical delivery described herein or known in the art. When a disease, disorder or condition, or a symptom thereof, is being treated, administration of the substance typically occurs after the onset of disease, disorder or condition or symptoms thereof. When a disease, disorder or condition, or symptoms thereof, are being prevented, administration of the substance typically occurs before the onset of the disease, disorder or condition or symptoms thereof.

A "biological marker" or "biomarker" is a substance whose detection indicates a particular biological state, such as, for example, the presence of cancer. In some embodiments, biomarkers can be determined individually. In other embodiments, several biomarkers can be measured simultaneously. In some embodiments of the methods provided herein, BTN1A1 is a biomarker indicating the presence of cancer. In some embodiments PD-L1 is a biomarker indicating the presence of cancer. In some embodiments, BTN1A1 and PD-L1 can be used in combination to indicate the presence of a cancer (e.g., an anti-PD1 or anti-PD-L1 therapy resistant or refractory cancer that is responsive to treatment with, e.g., an anti-BTN1A1 antibody).

In some embodiments, a "biomarker" indicates a change in the level of mRNA expression that may correlate with the risk or progression of a disease, or with the susceptibility of the disease to a given treatment. In some embodiments, the biomarker is a nucleic acid, such as mRNA or cDNA (e.g., BTN1A1 or PD-L1 mRNA or cDNA).

In additional embodiments, a "biomarker" indicates a change in the level of polypeptide or protein expression that may correlate with the risk or progression of a disease, or patient's susceptibility to treatment. In some embodiments, the biomarker can be a polypeptide or protein, or a fragment thereof (e.g., BTN1A1 or PD-L1 protein). The relative level of specific proteins can be determined by methods known in the art. For example, antibody based methods, such as an immunoblot, enzyme-linked immunosorbent assay (ELISA), or other methods can be used.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from the RNA molecule to give a protein, a polypeptide, or a portion thereof.

The term "level" refers to the amount, accumulation, or rate of a biomarker molecule (e.g., BTN1A1 or PD-L1). A level can be represented, for example, by the amount or the rate of synthesis of a messenger RNA (mRNA) encoded by a gene, the amount or the rate of synthesis of a polypeptide or protein encoded by a gene, or the amount or the rate of synthesis of a biological molecule accumulated in a cell or biological fluid. The term "level" refers to an absolute amount of a molecule in a sample or a relative amount of the molecule, determined under steady-state or non-steady-state conditions.

The terms "determining," "measuring," "evaluating," "assessing," and "assaying" as used herein generally refer to any form of measurement, and include determining whether an element is present or not. These terms include quantitative and/or qualitative determinations. Assessing may be relative or absolute. "Assessing the presence of" can include determining the amount of something present, as well as determining whether it is present or absent.

The term "sample" as used herein relates to a material or mixture of materials, typically, although not necessarily, in fluid form, containing one or more components of interest.

"Biological sample" as used herein refers to a sample obtained from a biological subject, including a sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, and cells isolated from a mammal. Exemplary biological samples include but are not limited to cell lysate, a cell culture, a cell line, a tissue, oral tissue, gastrointestinal tissue, an organ, an organelle, a biological fluid, a blood sample, a urine sample, a skin sample, and the like. Preferred biological samples include, but are not limited to, whole blood, partially purified blood, PBMC, tissue biopsies, and the like.

5.2 Molecules Having an Antigen Binding Fragment that Immunospecifically Bind to BTN1A1

Molecules having an antigen binding fragment that immunospecifically binds to BTN1A1, which are useful in the methods provided herein, are described, e.g., in International Patent Application No. PCT/US2016/064436 and in U.S. Provisional Application entitled "ANTIBODIES AND MOLECULES THAT IMMUNOSPECIFICALLY BIND TO BTN1A1 AND THERAPEUTIC USES THEREOF," filed May 31, 2017, which are incorporated herein by reference in their entireties.

Provided herein are molecules having an antigen binding fragment that immunospecifically binds to BTN1A1, including anti-BTN1A1 antibodies. In some embodiments, the antigen binding fragment that immunospecifically binds BTN1A1 binds to a fragment, or an epitope of BTN1A1. In some embodiments, the antigen binding fragment immunospecifically binds to a BTN1A1 dimer. In some embodiments, the BTN1A1 epitope can be a linear epitope. In some embodiments, the BTN1A1 epitope can be a conformation epitope. In some embodiments, the BTN1A1 epitope is found in a BTN1A1 dimer and not found in a BTN1A1 monomer. In some embodiments, the molecules provided herein that have an antigen binding fragment that immunospecifically binds to BTN1A1 inhibit the immune suppressive function of BTN1A1.

N-glycosylation is a posttranslational modification that is initiated in the endoplasmic reticulum (ER) and subsequently processed in the Golgi (Schwarz and Aebi, *Curr. Opin. Struc. Bio.,* 21(5):576-582 (2011). This type of modification is first catalyzed by a membrane-associated oligosaccharyl transferase (OST) complex that transfers a preformed glycan composed of oligosaccharides to an asparagine (Asn) side-chain acceptor located within the NXT motif (-Asn-X-Ser/Thr-) (Cheung and Reithmeier, *Methods,* 41:451-459 2007); Helenius and Aebi, Science, 291 (5512):2364-9 (2001). The addition or removal of saccharides from the preformed glycan is mediated by a group of glycotransferases and glycosidases, respectively, which tightly regulate the N-glycosylation cascade in a cell- and location-dependent manner.

In some embodiments, the molecules have an antigen binding fragment that selectively binds to one or more glycosylation motifs of BTN1A1. In some embodiments, the antigen binding fragment immunospecifically binds to a glycopeptide having a glycosylation motif and the adjacent peptide. In some embodiments, the antigen binding fragment immunospecifically binds to a peptide sequence that is located near one or more of the glycosylation motifs in three dimensions. In some embodiments, the antigen binding fragment selectively binds one or more glycosylation motifs of a BTN1A1 dimer over the one or more glycosylations motifs of a BTN1A1 monomer.

In some embodiments, the antigen binding fragment binds to glycosylated BTN1A1 (e.g., a glycosylated BTN1A1 dimer) with $K_D$ less than at least 30%, 40%, 50%, 60%, 70%, 80%, or 90% of the $K_D$ exhibited relative to unglycosylated BTN1A1. In certain embodiments, the antigen binding fragment binds to glycosylated BTN1A1 with $K_D$ less than 50% of the $K_D$ exhibited relative to unglycosylated BTN1A1. In some embodiments, the antigen binding fragment binds to glycosylated BTN1A1 with $K_D$ that is less than 1%, 2%, 3%, 4%, 5%, 6%, 7%, 8%, 9%, 10%, 15%, 20%, 30%, 40%, 50% of the $K_D$ exhibited relative to unglycosylated BTN1A1. In some embodiments, the antigen binding fragment binds to glycosylated BTN1A1 with $K_D$ at least 10 times less than the $K_D$ exhibited relative to unglycosylated BTN1A1.

The specific glycosylation sites of a particular BTN1A1 isoform or variant can vary from amino acids at position 55, 215, or 449 of that particular BTN1A1 isoform or variant. In those circumstances, a person of ordinary skill in the art would be able to determine the glycosylation sites of any particular BTN1A1 isoform or variant that correspond to N55, N215, and N449 of the human BTN1A1 exemplified above based on sequence alignment and other common knowledge in the art. As such, provided herein are also molecules having an antigen binding fragment that immunospecifically binds to a glycosylated form of a BTN1A1 isoform or variant relative to the unglycosylated BTN1A1 isoform or variant. The glycosylated sites of a BTN1A1 isoform or variant can be the corresponding sites of N55, N215, and N449 of human BTN1A1 sequence as provided above.

In some embodiments, the molecules have an antigen binding fragment that immunospecifically binds to glycosylated BTN1A1 (e.g., a glycosylated BTN1A1 dimer). In some embodiments, the antigen binding fragment immunospecifically binds to BTN1A1 glycosylated at positions N55, N215, and/or N449. In some embodiments, the antigen binding fragment immunospecifically binds to BTN1A1 glycosylated at position N55. In some embodiments, the antigen binding fragment immunospecifically binds to BTN1A1 glycosylated at position N215. In some embodiments, the antigen binding fragment immunospecifically binds to BTN1A1 glycosylated at position N449. In some embodiments, the antigen binding fragment immunospecifically binds to one or more glycosylation motifs. In some embodiments, the antigen binding fragment immunospecifically binds to BTN1A1 glycosylated at positions N55 and N215. In some embodiments, the antigen binding fragments immunospecifically binds to BTN1A1 glycosylated at positions N215 and N449. In some embodiments, the antigen binding fragments immunospecifically binds to BTN1A1 glycosylated at positions N55 and N449. In some embodiments, the antigen binding fragments immunospecifically binds to BTN1A1 glycosylated at positions N55, N215 and N449.

In some embodiments, the molecules have an antigen binding fragment that immunospecifically binds to glycosylated BTN1A1, whereby the antigen binding fragment preferentially binds glycosylated BTN1A1 (e.g., a glycosylated BTN1A1 dimer) over non-glycosylated BTN1A1. In some embodiments, the antigen binding fragments preferentially bind to BTN1A1 glycosylated at positions N55, N215, and/or N449 over non-glycosylated BTN1A1. In some embodiments, the antigen binding fragments preferentially bind to BTN1A1 glycosylated at position N55 over non-glycosylated BTN1A1. In some embodiments, the antigen binding fragments preferentially bind to BTN1A1 glycosylated at position N215 over non-glycosylated BTN1A1. In some embodiments, the antigen binding fragments preferentially bind to BTN1A1 glycosylated at position N449 over non-glycosylated BTN1A1. In some embodiments, the antigen binding fragments preferentially bind to one or more glycosylation motifs. In some embodiments, the antigen binding fragments preferentially binds BTN1A1 glycosylated at positions N55 and N215 over non-glycosylated BTN1A1. In some embodiments, the antigen binding fragments preferentially bind to BTN1A1 glycosylated at positions N215 and N449 over non-glycosylated BTN1A1. In some embodiments, the antigen binding fragments preferentially bind to BTN1A1 glycosylated at positions N55 and N449 over non-glycosylated BTN1A1. In some embodiments, the antigen binding fragments preferentially binds BTN1A1 glycosylated at positions N55, N215 and N449 over non-glycosylated BTN1A1.

The preferential binding can be determined by binding affinity. For example, an antibody or antigen binding fragment that preferentially binds to the glycosylated BTN1A1 (e.g., a glycosylated BTN1A1 dimer) can bind to glycosylated BTN1A1 with a $K_D$ less than the $K_D$ exhibited relative to unglycosylated BTN1A1. In some embodiments, the antibody or antigen binding fragment binds to glycosylated BTN1A1 with $K_D$ less than half of the $K_D$ exhibited relative to unglycosylated BTN1A1. In some embodiments, the antibody or antigen binding fragment binds to glycosylated BTN1A1 with $K_D$ at least 2 times less than the $K_D$ exhibited relative to unglycosylated BTN1A1. In some embodiments, the antibody or antigen binding fragment binds to glycosylated BTN1A1 with $K_D$ at least 5 times less than the $K_D$ exhibited relative to unglycosylated BTN1A1. In some embodiments, the antibody or antigen binding fragment binds to glycosylated BTN1A1 with $K_D$ at least 10 times less than the $K_D$ exhibited relative to unglycosylated BTN1A1. In some embodiments, the antibody or antigen binding fragment binds to glycosylated BTN1A1 with $K_D$ at least 15 times less than the $K_D$ exhibited relative to unglycosylated BTN1A1. In some embodiments, the antibody or antigen binding fragment binds to glycosylated BTN1A1 with $K_D$ at least 20 times less than the $K_D$ exhibited relative to unglycosylated BTN1A1. In some embodiments, the antibody or antigen binding fragment binds to glycosylated BTN1A1 with $K_D$ at least 25 times less than the $K_D$ exhibited relative to unglycosylated BTN1A1. In some embodiments, the antibody or antigen binding fragment binds to glycosylated BTN1A1 with $K_D$ at least 30 times less than the $K_D$ exhibited relative to unglycosylated BTN1A1. In some embodiments, the antibody or antigen binding fragment binds to glycosylated BTN1A1 with $K_D$ at least 40 times less than the $K_D$ exhibited relative to unglycosylated BTN1A1. In some embodiments, the antibody or antigen binding fragment binds to glycosylated BTN1A1 with $K_D$ at least 50 times less than the $K_D$ exhibited relative to unglycosylated BTN1A1. In some embodiments, the antibody or antigen binding fragment binds to glycosylated BTN1A1 with $K_D$ that is about 75% of the $K_D$ exhibited relative to unglycosylated BTN1A1. In some embodiments, the antibody or antigen binding fragment binds to glycosylated BTN1A1 with $K_D$ that is about 50% of the $K_D$ exhibited relative to unglycosylated BTN1A1. In some embodiments, the antibody or antigen binding fragment binds to glycosylated BTN1A1 with $K_D$ that is about 25% of the $K_D$ exhibited relative to unglycosylated BTN1A1. In some embodiments, the antibody or antigen binding fragment binds to glycosylated BTN1A1 with $K_D$ that is about 10% of the $K_D$ exhibited relative to unglycosylated BTN1A1. In some embodiments, the antibody or antigen binding fragment binds to glycosylated BTN1A1 with $K_D$ that is about 5% of the $K_D$ exhibited relative to unglycosylated BTN1A1. In some embodiments, the antibody or antigen binding fragment binds to glycosylated BTN1A1 with $K_D$ that is about 2.5% of the $K_D$ exhibited relative to unglycosylated BTN1A1. In some embodiments, the antibody or antigen binding fragment binds to glycosylated BTN1A1 with $K_D$ that is about 1% of the $K_D$ exhibited relative to unglycosylated BTN1A1.

The preferential binding can also be determined by in a binding assay as indicated by, for example, fluorescence intensity ("MFI"). For example, an antibody or antigen binding fragment that preferentially binds to the glycosylated BTN1A1 (e.g., a glycosylated BTN1A1 dimer) can bind to glycosylated BTN1A1 with an MFI that is higher than the MFI as exhibited relative to unglycosylated BTN1A1. In some embodiments, the antibody or antigen binding fragment binds to glycosylated BTN1A1 with an MFI that is at least twice as high as the MFI as exhibited relative to unglycosylated BTN1A1. In some embodiments, antibody or the antigen binding fragment binds to glycosylated BTN1A1 with an MFI that is at least two times as high as the MFI as exhibited relative to unglycosylated BTN1A1. In some embodiments, antibody or the antigen binding fragment binds to glycosylated BTN1A1 with an MFI that is at least three times as high as the MFI as exhibited relative to unglycosylated BTN1A1. In some embodiments, antibody or the antigen binding fragment binds to glycosylated BTN1A1 with an MFI that is at least five times as high as the MFI as exhibited relative to unglycosylated BTN1A1. In some embodiments, antibody or the antigen binding fragment binds to glycosylated BTN1A1 with an MFI that is at least ten times as high as the MFI as exhibited relative to unglycosylated BTN1A1. In some embodiments, antibody or the antigen binding fragment binds to glycosylated BTN1A1 with an MFI that is at least fifteen times as high as the MFI as exhibited relative to unglycosylated BTN1A1. In some embodiments, antibody or the antigen binding fragment binds to glycosylated BTN1A1 with an MFI that is at least twenty times as high as the MFI as exhibited relative to unglycosylated BTN1A1. In some embodiments, antibody or the antigen binding fragment binds to glycosylated BTN1A1 with an MFI that is at least twenty-five times as high as the MFI as exhibited relative to unglycosylated BTN1A1. In some embodiments, antibody or the antigen binding fragment binds to glycosylated BTN1A1 with an MFI that is at least thirty times as high as the MFI as exhibited relative to unglycosylated BTN1A1. In some embodiments, antibody or the antigen binding fragment binds to glycosylated BTN1A1 with an MFI that is at least fourty times as high as the MFI as exhibited relative to unglycosylated BTN1A1. In some embodiments, antibody or the antigen binding fragment binds to glycosylated BTN1A1 with an MFI that is at least fifty times as high as the MFI as exhibited relative to unglycosylated BTN1A1.

In some embodiments, the antigen binding fragments immunospecifically mask BTN1A1 glycosylation (e.g., in a glycosylated BTN1A1 dimer) at positions N55, N215, and/or N449. In some embodiments, the antigen binding fragments immunospecifically mask BTN1A1 glycosylation at position N55. In some embodiments, the antigen binding fragments immunospecifically mask BTN1A1 glycosylation at position N215. In some embodiments, the antigen binding fragments immunospecifically mask BTN1A1 glycosylation at position N449. In some embodiments, the antigen binding fragments immunospecifically mask one or more glycosylation motifs of BTN1A1. In some embodiments, the antigen binding fragments immunospecifically mask BTN1A1 glycosylation at positions N55 and N215. In some embodiments, the antigen binding fragments immunospecifically mask BTN1A1 glycosylation at positions N215 and N449. In some embodiments, the antigen binding fragments immunospecifically mask BTN1A1 glycosylation at positions N55 and N449. In some embodiments, the antigen binding fragments immunospecifically mask BTN1A1 glycosylation at positions N55, N215 and N449

In some embodiments, the molecules have an antigen binding fragment that selectively binds to a BTN1A1 dimer over a BTN1A1 monomer. In some embodiments, the BTN1A1 dimer is expressed at the surface of a cell. In some embodiments, the BTN1A1 dimer is a soluble protein fragment of BTN1A1, e.g., an extracellular domain construct of BTN1A1, such as an Fc-fusion protein construct (e.g., BTN1A1-ECD-Fc). In some embodiments, the BTN1A1 monomer is an extracellular domain construct of BTN1A1, such as a Flag-tagged or a His6-tagged BTN1A1-ECD construct. In some embodiments, the molecules selectively binding to a BTN1A1 dimer are molecules provided herein that selectively bind to glycosylated BTN1A1. In some embodiments, preferential binding to a BTN1A1 dimer over a BTN1A1 monomer is determined by determining preferential binding to a BTN1A1-ECD-Fc construct over a BTN1A1-ECD-His6 or a BTN1A1-ECD-Flag construct, e.g., using a surface plasmon resonance assay (e.g., BIAcore).

In some embodiments, the antigen binding fragment binds to a BTN1A1 dimer (e.g., a glycosylated BTN1A1 dimer) with $K_D$ less than at least 30%, 40%, 50%, 60%, 70%, 80%, or 90% of the $K_D$ exhibited relative to a BTN1A1 monomer (e.g., a glycosylated BTN1A1 monomer). In certain embodiments, the antigen binding fragment binds to a BTN1A1 dimer (e.g., a glycosylated BTN1A1 dimer) with $K_D$ less than 50% of the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ that is less than 1%, 2%, 3%, 4%, 5%, 6%, 7%, 8%, 9%, 10%, 15%, 20%, 30%, 40%, 50% of the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ at least 10 times less than the $K_D$ exhibited relative to a BTN1A1 monomer (e.g., a glycosylated BTN1A1 monomer).

The preferential binding can be determined by binding affinity. For example, an antibody or antigen binding fragment that preferentially binds to the BTN1A1 dimer (e.g., a glycosylated BTN1A1 dimer) can bind to a BTN1A1 dimer (e.g., a glycosylated BTN1A1 dimer) with a $K_D$ less than the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with $K_D$ less than half of the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with $K_D$ at least 2 times less than the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with $K_D$ at least 5 times less than the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with $K_D$ at least 10 times less than the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with $K_D$ at least 15 times less than the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with $K_D$ at least 20 times less than the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with $K_D$ at least 25 times less than the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with $K_D$ at least 30 times less than the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with $K_D$ at least 40 times less than the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with $K_D$ at least 50 times less than the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with a $K_D$ that is about 75% of the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with a $K_D$ that is about 50% of the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with a $K_D$ that is about 25% of the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with a $K_D$ that is about 10% of the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with $K_D$ that is about 5% of the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with $K_D$ that is about 2.5% of the $K_D$ exhibited relative to a BTN1A1 monomer (e.g., a glycosylated BTN1A1 monomer). In some embodiments, the antibody or antigen binding fragment binds to a BTN1A1 dimer with a $K_D$ that is about 1% of the $K_D$ exhibited relative to a BTN1A1 monomer (e.g., a glycosylated BTN1A1 monomer).

The preferential binding can also be determined by in a binding assay as indicated by, for example, fluorescence intensity ("MFI"). For example, an antibody or antigen binding fragment that preferentially binds to the BTN1A1 dimer (e.g., a glycosylated BTN1A1 dimer) can bind to a BTN1A1 monomer (e.g., a glycosylated BTN1A1 monomer) with an MFI that is higher than the MFI as exhibited relative to the BTN1A1 monomer. In some embodiments, the antibody or antigen binding fragment binds to a BTN1A1 dimer (e.g., a glycosylated BTN1A1 dimer) with an MFI that is at least twice as high as the MFI as exhibited relative to a BTN1A1 monomer (e.g., a glycosylated BTN1A1 monomer). In some embodiments, antibody or the antigen binding fragment binds to a BTN1A1 dimer (e.g., a glycosylated BTN1A1 dimer) with an MFI that is at least three times as high as the MFI as exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with an MFI that is at least five times as high as the MFI as exhibited relative to a BTN1A1 monomer (e.g., a glycosylated BTN1A1 monomer). In some embodiments, the antibody or the antigen binding fragment binds to a BTN1A1 dimer (e.g., a glycosylated BTN1A1 dimer) with an MFI that is at least ten times as high as the MFI as exhibited relative to a BTN1A1 monomer (e.g., a glycosylated BTN1A1 monomer). In some embodiments, the antibody or the antigen binding fragment binds to a BTN1A1 dimer (e.g., a glycosylated BTN1A1 dimer) with an MFI that is at least fifteen times as high as the MFI as exhibited relative to a BTN1A1 monomer (e.g., a glycosylated BTN1A1 monomer). In some embodiments, the antibody or the antigen binding fragment binds to a BTN1A1 dimer (e.g., a glycosylated BTN1A1 dimer) with an MFI that is at least twenty times as high as the MFI as exhibited relative to a BTN1A1 monomer (e.g., a glycosylated BTN1A1 monomer). In some embodiments, the antibody or the antigen binding fragment binds to a BTN1A1 dimer (e.g., a glycosylated BTN1A1 dimer) with an MFI that is at least twenty-five times as high as the MFI as exhibited relative to a BTN1A1 monomer (e.g., a glycosylated BTN1A1 monomer). In some embodiments, the antibody or the antigen binding fragment binds to a BTN1A1 dimer (e.g., a glycosylated BTN1A1 dimer) with an MFI that is at least thirty times as high as the MFI as exhibited relative to a BTN1A1 monomer (e.g., a glycosylated BTN1A1 monomer). In some embodiments, the antibody or the antigen binding fragment binds to a BTN1A1 dimer (e.g., a glycosylated BTN1A1 dimer) with an MFI that is at least fourty times as high as the MFI as exhibited relative to a BTN1A1 monomer (e.g., a glycosylated BTN1A1 monomer). In some embodiments, the antibody or the antigen binding fragment binds to a BTN1A1 dimer (e.g., a glycosylated BTN1A1 dimer) with an MFI that is at least fifty times as high as the MFI as exhibited relative to a BTN1A1 monomer (e.g., a glycosylated BTN1A1 monomer).

In some embodiments, the antibody or antigen binding fragment preferentially binds a glycosylated dimer BTN1A1 over a glycosylated monomer BTN1A1. The two BTN1A1 monomers in a glycosylated BTN1A1 dimer can be independently glycosylated at the same positions or at different positions. In some embodiments, one of the monomers in a BTN1A1 dimer is not glycosylated. A glycosylated BTN1A1 monomer in a glycosylated BTN1A1 dimer can be glycosylated at positions N55, N215, and/or N449. In some embodiments, a glycosylated BTN1A1 monomer is glycosylated at position N55. In some embodiments, a glycosylated BTN1A1 monomer is glycosylated at position N215. In some embodiments, a glycosylated BTN1A1 monomer is glycosylated at position N449. In some embodiments, a glycosylated BTN1A1 monomer is glycosylated at positions N55 and N215. In some embodiments, a glycosylated BTN1A1 monomer is glycosylated at positions N55 and N449. In some embodiments, a glycosylated BTN1A1 monomer is glycosylated at positions N215 and N449. In some embodiments, a glycosylated BTN1A1 monomer is glycosylated at positions N55 N215, and N449.

5.2.1. Antibodies and Other Molecules Having an Antigen Binding Fragment

In some embodiments, the anti-BTN1A1 antibody or anti-glycosylated BTN1A1 antibody or anti-BTN1A1 dimer antibody can be an IgG, IgM, IgA, IgD, or IgE. The anti-BTN1A1 antibody or anti-glycosylated BTN1A1 antibody or anti-BTN1A1 dimer antibody can also be a chimeric antibody, an affinity matured antibody, a humanized antibody, or a human antibody. The anti-BTN1A1 antibody or anti-glycosylated BTN1A1 antibody or anti-BTN1A1 dimer antibody can also be a camelized antibody, an intrabody, an anti-idiotypic (anti-Id) antibody. In some embodiments, the anti-BTN1A1 antibody or anti-glycosylated BTN1A1 antibody or anti-BTN1A1 dimer antibody can be a polyclonal antibody or monoclonal antibody. In some embodiments, the anti-BTN1A1 antibody is STC703, STC810, STC820, or a humanized variant thereof.

Antibodies can be produced from any animal source, including birds and mammals. In some embodiments, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is hereby incorporated by reference in its entirety. These techniques are further described in Marks (1992); *Stemmer* (1994); Gram et al. (1992); Barbas et al. (1994); and Schier et al. (1996); which are hereby incorporated by reference in their entireties.

Methods for producing polyclonal antibodies in various animal species, as well as for producing monoclonal antibodies of various types, including humanized, chimeric, and fully human, are well known in the art. For example, the following U.S. patents provide enabling descriptions of such methods and are herein incorporated by reference: U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; 6,891,024; 7,407,659; and 8,178,098, which are hereby incorporated by reference in their entireties.

The molecules having an antigen binding fragment that immunospecifically binds BTN1A1 or specifically binds glycosylated BTN1A1 or specifically binds BTN1A1 dimers, including the anti-BTN1A1 antibodies or anti-glycosylated BTN1A1 antibodies or anti-BTN1A1 dimer antibody (e.g., STC703, STC810, STC2714), can also be produced by any method known in the art useful for the production of polypeptides, e.g., in vitro synthesis, recombinant DNA production, and the like. The humanized antibodies can be produced by recombinant DNA technology. The antibodies described herein can also be produced using recombinant immunoglobulin expression technology. The recombinant production of immunoglobulin molecules, including humanized antibodies are described in U.S. Pat. No. 4,816,397 (Boss et al.), U.S. Pat. Nos. 6,331,415 and 4,816,567 (both to Cabilly et al.), U.K. patent GB 2,188,638 (Winter et al.), and U.K. patent GB 2,209,757; which are hereby incorporated by reference in their entireties. Techniques for the recombinant expression of immunoglobulins, including humanized immunoglobulins, can also be found, in Goeddel et al., Gene Expression Technology Methods in Enzymology Vol. 185 Academic Press (1991), and Borreback, Antibody Engineering, W. H. Freeman (1992); which are hereby incorporated by reference in their entireties. Additional information concerning the generation, design and expression of recombinant antibodies can be found in Mayforth, Designing Antibodies, Academic Press, San Diego (1993).

In certain embodiments, the anti-BTN1A1 antibody or anti-glycosylated BTN1A1 antibody or anti-BTN1A1 dimer antibody is a human antibody. Human antibodies can be made by a variety of methods known in the art including phage display methods described above using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Human antibodies can be produced using transgenic mice which are incapable of expressing functional endogenous immunoglobulins, but which can express human immunoglobulin genes. For example, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a BTN1A1 polypeptide, or a glycosylated BTN1A1 polypeptide, or a BTN1A1 polypeptide dimer. Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, therapeutically useful IgG, IgA, IgM and IgE antibodies can be produced. For an overview of this technology for producing human antibodies, see Lonberg and Huszar (1995, *Int. Rev. Immunol.* 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

In some embodiments, the anti-BTN1A1 antibody or anti-glycosylated BTN1A1 antibody or anti-BTN1A1 dimer antibody is a chimeric antibody, for example, an antibody having antigen binding sequences from a non-human donor grafted to a heterologous non-human, human or humanized sequence (e.g., framework and/or constant domain sequences). In one embodiment, the non-human donor is a rat. In one embodiment, an antigen binding sequence is synthetic, e.g., obtained by mutagenesis (e.g., phage display screening of a human phage library, etc.). In one embodiment, a chimeric antibody can have murine V regions and human C regions. In one embodiment, the murine light chain V region is fused to a human kappa light chain. In one embodiment, the murine heavy chain V region is fused to a human IgG1 C region.

Methods for producing chimeric antibodies are known in the art. See e.g., Morrison, 1985, *Science* 229:1202; Oi et al., 1986, *BioTechniques* 4:214; Gillies et al., 1989, *J. Immunol. Methods* 125:191-202; and U.S. Pat. Nos. 6,311,415, 5,807,715, 4,816,567, and 4,816,397; all of which are hereby incorporated by references in their entireties. Chimeric antibodies including one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519,596; Padlan, 1991, *Molecular Immunology* 28(4/5):489-498; Studnicka et al., 1994, *Protein Engineering* 7:805; and Roguska et al., 1994, *Proc. Natl. Acad. Sci. USA* 91:969), and chain shuffling (U.S. Pat. No. 5,565,332); all of which are hereby incorporated by references in their entireties.

An exemplary process for the production of the recombinant chimeric anti-BTN1A1 antibodies can include the following: a) constructing, by conventional molecular biology methods, an expression vector that encodes and expresses an antibody heavy chain in which the CDRs and variable region of the murine anti-BTN1A1 (or anti-glycosylated BTN1A1 or anti-BTNA1 dimer) monoclonal antibody are fused to an Fc region derived from a human immunoglobulin, thereby producing a vector for the expression of a chimeric antibody heavy chain; b) constructing, by conventional molecular biology methods, an expression vector that encodes and expresses an antibody light chain of the murine anti-BTN1A1 (or anti-glycosylated BTN1A1 or anti-BTN1A1 dimer) monoclonal antibody, thereby producing a vector for the expression of chimeric antibody light chain; c) transferring the expression vectors to a host cell by conventional molecular biology methods to produce a transfected host cell for the expression of chimeric antibodies; and d) culturing the transfected cell by conventional cell culture techniques so as to produce chimeric antibodies.

An exemplary process for the production of the recombinant humanized anti-BTN1A1 antibodies can include the following: a) constructing, by conventional molecular biology methods, an expression vector that encodes and expresses an antibody heavy chain in which the CDRs and a minimal portion of the variable region framework that are required to retain donor antibody binding specificity are derived from a non-human immunoglobulin, such as the murine anti-BTN1A1 (or anti-glycosylated BTN1A1, or anti-BTN1A1 dimer) monoclonal antibody, and the remainder of the antibody is derived from a human immunoglobulin, thereby producing a vector for the expression of a humanized antibody heavy chain; b) constructing, by conventional molecular biology methods, an expression vector that encodes and expresses an antibody light chain in which the CDRs and a minimal portion of the variable region framework that are required to retain donor antibody binding specificity are derived from a non-human immunoglobulin, such as the murine anti-BTN1A1 (or anti-glycosylated BTN1A1 or anti-BTN1A1 dimer) monoclonal antibody, and the remainder of the antibody is derived from a human immunoglobulin, thereby producing a vector for the expression of humanized antibody light chain; c) transferring the expression vectors to a host cell by conventional molecular biology methods to produce a transfected host cell for the expression of humanized antibodies; and d) culturing the transfected cell by conventional cell culture techniques so as to produce humanized antibodies.

With respect to either exemplary method, host cells can be co-transfected with such expression vectors, which can contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains can include cDNA or genomic DNA or both. The host cell used to express the recombinant antibody can be either a bacterial cell such as *Escherichia coli*, or more preferably a eukaryotic cell (e.g., a Chinese hamster ovary (CHO) cell or a HEK-293 cell). The choice of expression vector is dependent upon the choice of host cell, and can be selected so as to have the desired expression and regulatory characteristics in the selected host cell. Other cell lines that can be used include, but are not limited to, CHO-K1, NSO, and PER.C6 (Crucell, Leiden, Netherlands). Furthermore, codon usage can by optimized when host cell is selected to account for species specific codon usage bias and enhance protein expression. For example, for CHO cell expression the DNA encoding the antibodies can incorporate codons used preferentially by *Cricetulus griseus* (from where Chinese Hamster ovaries cells are derived. Methods of codon optimization may be employed to facilitate improved expression by a desired host cell (see, e.g., Wohlgemuth, I. et al., *Philos. Trans. R. Soc. Lond. B Biol. Sci.* 366(1580): 2979-2986 (2011); Jestin, J. L. et al., *J. Mol. Evol.* 69(5): 452-457 (2009); Bollenbach, T. et al., *Genome Res.* 17(4): 401-404(2007); Kurland, C. G. et al., *Prog. Nucleic Acid Res. Mol. Biol.* 31:191-219 (1984); Grosjean, H. et al., *Gene* 18(3): 199-209(1982)).

In some embodiments, the anti-BTN1A1 antibodies or anti-glycosylated BTN1A1 or anti-BTN1A1 dimer antibodies can be monoclonal antibodies. In some embodiments, the anti-BTN1A1 antibodies or anti-glycosylated BTN1A1 antibodies or anti-BTN1A1 dimer antibodies can be polyclonal antibodies. Animals can be inoculated with an antigen, such as a BTN1A1 polypeptide or glycosylated BTN1A1 polypeptide, or BTN1A1 dimer polypeptide in order to produce antibodies specific for a BTN1A1 polypeptide or a glycosylated BTN1A1 polypeptide or a BTN1A1 dimer. Frequently an antigen is bound or conjugated to another molecule to enhance the immune response. A conjugate can be any peptide, polypeptide, protein, or non-proteinaceous substance bound to an antigen that is used to elicit an immune response in an animal. Antibodies produced in an animal in response to antigen inoculation have a variety of non-identical molecules (polyclonal antibodies) made from a variety of individual antibody producing B lymphocytes. Given the correct conditions for polyclonal antibody production in an animal, most of the antibodies in the animal's serum recognize the collective epitopes on the antigenic compound to which the animal has been immunized.

This specificity can be further enhanced by affinity purification to select only those antibodies that recognize the antigen or epitope of interest. The methods for generating monoclonal antibodies (MAbs) can begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and can provide certain advantages. Mice (e.g., BALB/c mice) are routinely used and generally give a high percentage of stable fusions.

Hybridoma technology involves the fusion of a single B lymphocyte from a mouse previously immunized with a BTN1A1 polypeptide or glycosylated BTN1A1 polypeptide or BTN1A1 dimer polypeptide with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) can be produced.

In one embodiment, the antibody is an immunoglobulin single variable domain derived from a camelid antibody, preferably from a heavy chain camelid antibody, devoid of light chains, which are known as VHH domain sequences or Nanobodies™. A Nanobody™ (Nb) is the smallest functional fragment or single variable domain (VHH) of a naturally occurring single-chain antibody and is known to the person skilled in the art. They are derived from heavy chain only antibodies seen in camelids (Hamers-Casterman et al., *Nature,* 363(6428):446-8 (1993); Desmyter et al., *Nat Struct Biol.,* 3(9):803-11. (1996)). In the family of "camelids," immunoglobulins devoid of light polypeptide chains are found. "Camelids" include old world camelids (*Camelus bactrianus* and *Camelus dromedarius*) and new world camelids (for example, *Lama paccos, Lama glama, Lama guanicoe* and *Lama vicugna*). The single variable domain heavy chain antibody is herein designated as a Nanobody™ or a VHH antibody. The small size and unique biophysical properties of Nbs excel conventional antibody fragments for the recognition of uncommon or hidden epitopes and for binding into cavities or active sites of protein targets. Further, Nbs can be designed as multi-specific and multivalent antibodies, attached to reporter molecules, or humanzied. Nbs are stable, survive the gastro-intestinal system and can easily be manufactured.

Unifying two antigen binding sites of different specificity into a single construct, bispecific antibodies have the ability to bring together two discreet antigens with exquisite specificity and therefore have great potential as therapeutic agents. Bispecific antibodies can be made by fusing two hybridomas, each capable of producing a different immunoglobulin. Bispecific antibodies can also be produced by joining two scFv antibody fragments while omitting the Fc portion present in full immunoglobulins. Each scFv unit in such constructs can be made up of one variable domain from each of the heavy (VH) and light (VL) antibody chains, joined with one another via a synthetic polypeptide linker, the latter often being genetically engineered so as to be minimally immunogenic while remaining maximally resistant to proteolysis. Respective scFv units can be joined by a number of techniques including incorporation of a short (usually less than 10 amino acids) polypeptide spacer bridging the two scFv units, thereby creating a bispecific single chain antibody. The resulting bispecific single chain antibody is therefore a species containing two VH/VL pairs of different specificity on a single polypeptide chain, whereby the VH and VL domains in a respective scFv unit are separated by a polypeptide linker long enough to allow intramolecular association between these two domains, and whereby the thusly formed scFv units are contiguously tethered to one another through a polypeptide spacer kept short enough to prevent unwanted association between, for example, the VH domain of one scFv unit and the VL of the other scFv unit.

Examples of molecules having an antigen binding fragment that immunospecifically binds to BTN1A1 or glycosylated BTN1A1 or BTN1A1 dimer, include, without limitation: (i) the Fab fragment, consisting of VL, VH, CL, and CH1 domains; (ii) the "Fd" fragment consisting of the VH and CH1 domains; (iii) the "Fv" fragment consisting of the VL and VH domains of a single antibody; (iv) the "dAb" fragment, which consists of a VH domain; (v) isolated CDR regions; (vi) F(ab')2 fragments, a bivalent fragment including two linked Fab fragments; (vii) single chain Fv molecules ("scFv"), whereby a VH domain and a VL domain are linked by a peptide linker that allows the two domains to associate to form a binding domain; (viii) bi-specific single chain Fv dimers (see U.S. Pat. No. 5,091,513); and (ix) diabodies, multivalent, or multispecific fragments constructed by gene fusion (U.S. Patent Appln. Publn. No. 20050214860). Fv, scFv, or diabody molecules may be stabilized by the incorporation of disulfide bridges linking the VH and VL domains. Minibodies having a scFv joined to a CH3 domain can also be made (Hu et al., *Cancer Res.,* 56(13):3055-61(1996)).

Antibody-like binding peptidomimetics are also contemplated in embodiments. Murali et al., *Cell Mol. Biol.,* 49 (2):209-216 (2003) describe "antibody like binding peptidomimetics" (ABiPs), which are peptides that act as pared-down antibodies and have certain advantages of longer serum half-life as well as less cumbersome synthesis methods, which is hereby incorporated by reference in its entirety.

5.2.2. Anti-BTN1A1 Antibodies

A total of 68 mouse monoclonal antibodies that immunospecifically bind to human BTN1A1 were cloned and characterized (Table 7). In addition, 3 mouse monoclonal antibodies that immunospecifically bind to mouse BTN1A1 were cloned and characterized (see Example 4). For example, the antibodies designated as STC703, STC810 and STC820 showed glycosylation specific binding with high affinity ($K_D$ between STC703 and hBTN1A1-Fc was determined to be 286 nM by Biacore, ($K_D$ between STC810 and hBTN1A1-Fc was determined to be 0.92 nM by Biacore, and $K_D$ between STC820 and hBTN1A1-His was determined to be 16.2 nM by Biacore). STC703 and STC810 were found to preferentially bind BTN1A1 dimers over BTN1A1 monomers. STC703, STC810, and STC820 were found to preferentially bind human BTN1A1 over mouse BTN1A1. STC1011, STC1012, and STC1029 were found to preferentially bind mouse BTN1A1 over human BTN1A1. Treatment with a monoclonal anti-BTN1A1 antibody enhanced T-cell dependent apoptosis of cancer cells, inhibited proliferation of cancer cells, and also resulted in glycosylation dependent internalization of BTN1A1 to lysosomes. Accordingly, provided herein are also anti-BTN1A1 antibodies with specific sequence features, anti-BTN1A1 antibodies that immunospecifically bind to specific epitopes, as well as the uses thereof in cancer treatment.

In some embodiments, an anti-BTN1A1 antibody provided herein includes a VH domain, VL domain, VH CDR1, VH CDR2, VH CDR3, VL CDR1, VL CDR2, and/or VL CDR3 of monoclonal antibody STC703, STC810, STC820, STC1011, STC1012, STC1029, STC2602, STC2714, STC2739, STC2778, or STC2781, described herein, or a humanized variant thereof. In certain embodiments, the anti-BTN1A1 antibody can further include a VH FR1, VH FR2, VH FR3, VH FR4, VL FR1, VL FR2, VL FR3, and/or VL FR4 of a human germline immunoglobulin amino acid sequence or a variant thereof.

In some embodiments, an anti-BTN1A1 antibody provided herein includes a VH domain, VL domain, VH CDR1, VH CDR2, VH CDR3, VL CDR1, VL CDR2, and/or VL CDR3 of monoclonal antibody STC703, STC810, STC820, STC1011, STC1012, STC1029, STC2602, STC2714, STC2739, STC2778, or STC2781 described herein, or a humanized variant thereof. In certain embodiments, the anti-BTN1A1 antibody can further include a VH FR1, VH FR2, VH FR3, VH FR4, VL FR1, VL FR2, VL FR3, and/or VL FR4 of a human germline immunoglobulin amino acid sequence or a variant thereof.

In some embodiments, an anti-BTN1A1 antibody provided herein includes a VH domain, VL domain, VH CDR1, VH CDR2, VH CDR3, VL CDR1, VL CDR2, and/or VL CDR3 of monoclonal antibody STC703 or STC810 described herein, or a humanized variant thereof. In certain embodiments, the anti-BTN1A1 antibody can further include a VH FR1, VH FR2, VH FR3, VH FR4, VL FR1, VL FR2, VL FR3, and/or VL FR4 of a human germline immunoglobulin amino acid sequence or a variant thereof.

In some embodiments, an anti-BTN1A1 antibody provided herein includes a VH domain, VL domain, VH CDR1, VH CDR2, VH CDR3, VL CDR1, VL CDR2, and/or VL CDR3 of monoclonal antibody STC820 described herein, or a humanized variant thereof. In certain embodiments, the anti-BTN1A1 antibody can further include a VH FR1, VH FR2, VH FR3, VH FR4, VL FR1, VL FR2, VL FR3, and/or VL FR4 of a human germline immunoglobulin amino acid sequence or a variant thereof.

In some embodiments, an anti-BTN1A1 antibody provided herein includes a VH domain, VL domain, VH CDR1, VH CDR2, VH CDR3, VL CDR1, VL CDR2, and/or VL CDR3 of monoclonal antibody STC1011, STC1012, or STC1029 described herein, or a humanized variant thereof. In certain embodiments, the anti-BTN1A1 antibody can further include a VH FR1, VH FR2, VH FR3, VH FR4, VL FR1, VL FR2, VL FR3, and/or VL FR4 of a human germline immunoglobulin amino acid sequence or a variant thereof.

In some embodiments, an anti-BTN1A1 antibody provided herein includes a VH domain, VL domain, VH CDR1, VH CDR2, VH CDR3, VL CDR1, VL CDR2, and/or VL CDR3 of monoclonal antibody STC2602, STC2714, STC2739, STC2778, or STC2781 described herein, or a humanized variant thereof. In certain embodiments, the anti-BTN1A1 antibody can further include a VH FR1, VH FR2, VH FR3, VH FR4, VL FR1, VL FR2, VL FR3, and/or VL FR4 of a human germline immunoglobulin amino acid sequence or a variant thereof.

In some embodiments, an anti-BTN1A1 antibody provided herein includes a VH domain, VL domain, VH CDR1, VH CDR2, VH CDR3, VL CDR1, VL CDR2, and/or VL CDR3 of monoclonal antibody STC2714 described herein, or a humanized variant thereof. In certain embodiments, the anti-BTN1A1 antibody can further include a VH FR1, VH FR2, VH FR3, VH FR4, VL FR1, VL FR2, VL FR3, and/or VL FR4 of a human germline immunoglobulin amino acid sequence or a variant thereof.

In some embodiments, the anti-BTN1A1 antibody includes less than six CDRs. In some embodiments, the antibody includes or consists of one, two, three, four, or five CDRs selected from the group consisting of VH CDR1, VH CDR2, VH CDR3, VL CDR1, VL CDR2, and/or VL CDR3. In specific embodiments, the antibody includes or consists of one, two, three, four, or five CDRs selected from the group consisting of VH CDR1, VH CDR2, VH CDR3, VL CDR1, VL CDR2, and/or VL CDR3 of the monoclonal antibody STC703, STC810, STC820, STC1011, STC1012, STC1029, STC2602, STC2714, STC2739, STC2778, or STC2781, described herein, or a humanized variant thereof. In specific embodiments, the antibody further includes a VH FR1, VH FR2, VH FR3, VH FR4, VL FR1, VL FR2, VL FR3, and/or VL FR4 of a human germline immunoglobulin amino acid sequence or a variant thereof.

In some embodiments, the anti-BTN1A1 antibody includes less than six CDRs. In some embodiments, the antibody includes or consists of one, two, three, four, or five CDRs selected from the group consisting of VH CDR1, VH CDR2, VH CDR3, VL CDR1, VL CDR2, and/or VL CDR3. In specific embodiments, the antibody includes or consists of one, two, three, four, or five CDRs selected from the group consisting of VH CDR1, VH CDR2, VH CDR3, VL CDR1, VL CDR2, and/or VL CDR3 of the monoclonal antibody STC703, STC810, STC820, STC1011, STC1012, STC1029, STC2602, STC2714, STC2739, STC2778, or STC2781, described herein, or a humanized variant thereof.

In specific embodiments, the antibody further includes a VH FR1, VH FR2, VH FR3, VH FR4, VL FR1, VL FR2, VL FR3, and/or VL FR4 of a human germline immunoglobulin amino acid sequence or a variant thereof.

In some embodiments, the anti-BTN1A1 antibody includes less than six CDRs. In some embodiments, the antibody includes or consists of one, two, three, four, or five CDRs selected from the group consisting of VH CDR1, VH CDR2, VH CDR3, VL CDR1, VL CDR2, and/or VL CDR3. In specific embodiments, the antibody includes or consists of one, two, three, four, or five CDRs selected from the group consisting of VH CDR1, VH CDR2, VH CDR3, VL CDR1, VL CDR2, and/or VL CDR3 of the monoclonal antibody STC703, or STC810 described herein, or a humanized variant thereof. In specific embodiments, the antibody further includes a VH FR1, VH FR2, VH FR3, VH FR4, VL FR1, VL FR2, VL FR3, and/or VL FR4 of a human germline immunoglobulin amino acid sequence or a variant thereof.

In some embodiments, the anti-BTN1A1 antibody includes less than six CDRs. In some embodiments, the antibody includes or consists of one, two, three, four, or five CDRs selected from the group consisting of VH CDR1, VH CDR2, VH CDR3, VL CDR1, VL CDR2, and/or VL CDR3. In specific embodiments, the antibody includes or consists of one, two, three, four, or five CDRs selected from the group consisting of VH CDR1, VH CDR2, VH CDR3, VL CDR1, VL CDR2, and/or VL CDR3 of the monoclonal antibody STC820 described herein, or a humanized variant thereof. In specific embodiments, the antibody further includes a VH FR1, VH FR2, VH FR3, VH FR4, VL FR1, VL FR2, VL FR3, and/or VL FR4 of a human germline immunoglobulin amino acid sequence or a variant thereof.

In some embodiments, the anti-BTN1A1 antibody includes less than six CDRs. In some embodiments, the antibody includes or consists of one, two, three, four, or five CDRs selected from the group consisting of VH CDR1, VH CDR2, VH CDR3, VL CDR1, VL CDR2, and/or VL CDR3. In specific embodiments, the antibody includes or consists of one, two, three, four, or five CDRs selected from the group consisting of VH CDR1, VH CDR2, VH CDR3, VL CDR1, VL CDR2, and/or VL CDR3 of the monoclonal antibody STC1011, STC1012, or STC1029 described herein, or a humanized variant thereof. In specific embodiments, the antibody further includes a VH FR1, VH FR2, VH FR3, VH FR4, VL FR1, VL FR2, VL FR3, and/or VL FR4 of a human germline immunoglobulin amino acid sequence or a variant thereof.

In some embodiments, the anti-BTN1A1 antibody includes less than six CDRs. In some embodiments, the antibody includes or consists of one, two, three, four, or five CDRs selected from the group consisting of VH CDR1, VH CDR2, VH CDR3, VL CDR1, VL CDR2, and/or VL CDR3. In specific embodiments, the antibody includes or consists of one, two, three, four, or five CDRs selected from the group consisting of VH CDR1, VH CDR2, VH CDR3, VL CDR1, VL CDR2, and/or VL CDR3 of the monoclonal antibody STC2602, STC2714, STC2739, STC2778, or STC2781 described herein, or a humanized variant thereof. In specific embodiments, the antibody further includes a VH FR1, VH FR2, VH FR3, VH FR4, VL FR1, VL FR2, VL FR3, and/or VL FR4 of a human germline immunoglobulin amino acid sequence or a variant thereof.

In some embodiments, the anti-BTN1A1 antibody includes less than six CDRs. In some embodiments, the antibody includes or consists of one, two, three, four, or five CDRs selected from the group consisting of VH CDR1, VH CDR2, VH CDR3, VL CDR1, VL CDR2, and/or VL CDR3. In specific embodiments, the antibody includes or consists of one, two, three, four, or five CDRs selected from the group consisting of VH CDR1, VH CDR2, VH CDR3, VL CDR1, VL CDR2, and/or VL CDR3 of the monoclonal antibody STC2714 described herein, or a humanized variant thereof. In specific embodiments, the antibody further includes a VH FR1, VH FR2, VH FR3, VH FR4, VL FR1, VL FR2, VL FR3, and/or VL FR4 of a human germline immunoglobulin amino acid sequence or a variant thereof.

In some embodiments, the antibody is a humanized antibody, a monoclonal antibody, a recombinant antibody, an antigen binding fragment or any combination thereof.

In some embodiments, the antibody is a humanized monoclonal antibody, or antigen binding fragment thereof.

In some embodiments, provided herein are antibodies, including humanized antibodies, (i) that competitively block (e.g., in a dose-dependent manner) an anti-BTN1A1 antibody provided herein from binding to a BTN1A1 polypeptide (e.g., a cell surface-expressed or soluble BTN1A1), a BTN1A1 fragment, or a BTN1A1 epitope and/or (ii) that bind to a BTN1A1 epitope that is bound by an anti-BTN1A1 antibody (e.g., humanized anti-BTN1A1 antibodies) provided herein. In some embodiments, the antibody competitively blocks (e.g., in a dose-dependent manner) monoclonal antibody STC703, STC810, STC820, STC1011, STC1012, STC1029, STC2602, STC2714, STC2739, STC2778, or STC2781, described herein or a humanized variant thereof from binding to a BTN1A1 polypeptide (e.g., a cell surface-expressed or soluble BTN1A1), a BTN1A1 fragment, or a BTN1A1 epitope. In other embodiments, the antibody binds to a BTN1A1 epitope that is bound (e.g., recognized) by monoclonal antibody BTN1A1 described herein or a humanized variant thereof (e.g. humanized anti-BTN1A1 antibodies).

In some embodiments, provided herein are antibodies, including humanized antibodies, (i) that competitively block (e.g., in a dose-dependent manner) an anti-BTN1A1 antibody provided herein from binding to a BTN1A1 polypeptide (e.g., a cell surface-expressed or soluble BTN1A1), a BTN1A1 fragment, or a BTN1A1 epitope and/or (ii) that bind to a BTN1A1 epitope that is bound by an anti-BTN1A1 antibody (e.g., humanized anti-BTN1A1 antibodies) provided herein. In some embodiments, the antibody competitively blocks (e.g., in a dose-dependent manner) monoclonal antibody STC703, STC810, STC820, STC1011, STC1012, STC1029, STC2602, STC2714, STC2739, STC2778, or STC2781, described herein or a humanized variant thereof from binding to a BTN1A1 polypeptide (e.g., a cell surface-expressed or soluble BTN1A1), a BTN1A1 fragment, or a BTN1A1 epitope. In other embodiments, the antibody binds to a BTN1A1 epitope that is bound (e.g., recognized) by monoclonal antibody BTN1A1 described herein or a humanized variant thereof (e.g. humanized anti-BTN1A1 antibodies).

In some embodiments, provided herein are antibodies, including humanized antibodies, (i) that competitively block (e.g., in a dose-dependent manner) an anti-BTN1A1 antibody provided herein from binding to a BTN1A1 polypeptide (e.g., a cell surface-expressed or soluble BTN1A1), a BTN1A1 fragment, or a BTN1A1 epitope and/or (ii) that bind to a BTN1A1 epitope that is bound by an anti-BTN1A1 antibody (e.g., humanized anti-BTN1A1 antibodies) provided herein. In some embodiments, the antibody competitively blocks (e.g., in a dose-dependent manner) monoclonal antibody STC703 or STC810 described herein or a humanized variant thereof from binding to a BTN1A1 polypeptide (e.g., a cell surface-expressed or soluble BTN1A1), a BTN1A1 fragment, or a BTN1A1 epitope. In other embodiments, the antibody binds to a BTN1A1 epitope that is bound (e.g., recognized) by monoclonal antibody BTN1A1 described herein or a humanized variant thereof (e.g. humanized anti-BTN1A1 antibodies).

In some embodiments, provided herein are antibodies, including humanized antibodies, (i) that competitively block (e.g., in a dose-dependent manner) an anti-BTN1A1 antibody provided herein from binding to a BTN1A1 polypeptide (e.g., a cell surface-expressed or soluble BTN1A1), a BTN1A1 fragment, or a BTN1A1 epitope and/or (ii) that bind to a BTN1A1 epitope that is bound by an anti-BTN1A1 antibody (e.g., humanized anti-BTN1A1 antibodies) provided herein. In some embodiments, the antibody competitively blocks (e.g., in a dose-dependent manner) monoclonal antibody STC820 described herein or a humanized variant thereof from binding to a BTN1A1 polypeptide (e.g., a cell surface-expressed or soluble BTN1A1), a BTN1A1 fragment, or a BTN1A1 epitope. In other embodiments, the antibody binds to a BTN1A1 epitope that is bound (e.g., recognized) by monoclonal antibody BTN1A1 described herein or a humanized variant thereof (e.g. humanized anti-BTN1A1 antibodies).

In some embodiments, provided herein are antibodies, including humanized antibodies, (i) that competitively block (e.g., in a dose-dependent manner) an anti-BTN1A1 antibody provided herein from binding to a BTN1A1 polypeptide (e.g., a cell surface-expressed or soluble BTN1A1), a BTN1A1 fragment, or a BTN1A1 epitope and/or (ii) that bind to a BTN1A1 epitope that is bound by an anti-BTN1A1 antibody (e.g., humanized anti-BTN1A1 antibodies) provided herein. In some embodiments, the antibody competitively blocks (e.g., in a dose-dependent manner) monoclonal antibody STC1011, STC1012, or STC1029 described herein or a humanized variant thereof from binding to a BTN1A1 polypeptide (e.g., a cell surface-expressed or soluble BTN1A1), a BTN1A1 fragment, or a BTN1A1 epitope. In other embodiments, the antibody binds to a BTN1A1 epitope that is bound (e.g., recognized) by monoclonal antibody BTN1A1 described herein or a humanized variant thereof (e.g. humanized anti-BTN1A1 antibodies).

In some embodiments, provided herein are antibodies, including humanized antibodies, (i) that competitively block (e.g., in a dose-dependent manner) an anti-BTN1A1 antibody provided herein from binding to a BTN1A1 polypeptide (e.g., a cell surface-expressed or soluble BTN1A1), a BTN1A1 fragment, or a BTN1A1 epitope and/or (ii) that bind to a BTN1A1 epitope that is bound by an anti-BTN1A1 antibody (e.g., humanized anti-BTN1A1 antibodies) provided herein. In some embodiments, the antibody competitively blocks (e.g., in a dose-dependent manner) monoclonal antibody STC2602, STC2714, STC2739, STC2778, or STC2781 described herein or a humanized variant thereof from binding to a BTN1A1 polypeptide (e.g., a cell surface-expressed or soluble BTN1A1), a BTN1A1 fragment, or a BTN1A1 epitope. In other embodiments, the antibody binds to a BTN1A1 epitope that is bound (e.g., recognized) by monoclonal antibody BTN1A1 described herein or a humanized variant thereof (e.g. humanized anti-BTN1A1 antibodies).

In some embodiments, provided herein are antibodies, including humanized antibodies, (i) that competitively block (e.g., in a dose-dependent manner) an anti-BTN1A1 antibody provided herein from binding to a BTN1A1 polypeptide (e.g., a cell surface-expressed or soluble BTN1A1), a BTN1A1 fragment, or a BTN1A1 epitope and/or (ii) that bind to a BTN1A1 epitope that is bound by an anti-BTN1A1 antibody (e.g., humanized anti-BTN1A1 antibodies) provided herein. In some embodiments, the antibody competitively blocks (e.g., in a dose-dependent manner) monoclonal antibody STC2714 described herein or a humanized variant thereof from binding to a BTN1A1 polypeptide (e.g., a cell surface-expressed or soluble BTN1A1), a BTN1A1 fragment, or a BTN1A1 epitope. In other embodiments, the antibody binds to a BTN1A1 epitope that is bound (e.g., recognized) by monoclonal antibody BTN1A1 described herein or a humanized variant thereof (e.g. humanized anti-BTN1A1 antibodies).

TABLE 2a

Sequences of heavy chain variable (VH) region and light chain variable (VL) region of mouse monoclonal anti-human BTN1A1 antibody STC703

| | DNA sequence | Protein sequence |
|---|---|---|
| Heavy chain | CAGGGTCAGATGCAGCAGTCTGGAGCT GAGCTGGTGAAGCCTGGGGCTTCAGTG AAGCTGTCCTGCAAGACTTCTGGCTTC ACCTTCAGCAGTAGGTATATAAGTTGG TTGAAGCAGAAGCCTCGACAGAGTCTT GAGTGGATTGCATGGATTTATGCTGGA ACTGGTGGCACTAGTTATAATCAGAAG TTCACAGGCAAGGCCCAACTGACTGTA GACACATCCTCCAGCACAGCCTACATG CAACTCAGCAGCCTGACATCTGAGGAC TCTGCCATCTATTACTGTGCAAGACGG AGGGGACTAGGGTACTTTGACTACTGG GGCCAAGGCACCACTCTCACAGTCTCC TCA (SEQ ID NO: 4) | QGQMQQSGAELVKPGA SVKLSCKTSGFTFSSR YISWLKQKPRQSLEWI AWIYAGTGGTSYNQKF TGKAQLTVDTSSSTAY MQLSSLTSEDSAIYYC ARRRGLGYFDYWGQGT TLTVSS (SEQ ID NO: 3) |
| Kappa Light chain | GACATCCAGATGACTCAGTCTCCAGCC TCCCTATCTGTGTCTGTGGGAGAAACT GTCACCATCACATGTCGAGCAAGTGAG AATATTTACAGTAATTTAGCATGGTAT CAGCAGAAACAGGGAAAATCTCCTCAG CTCCTGGTCTATGCTGCAACAAACTTA GCAGATGGTGTGCCATCAAGGTTCAGT GGCAGTGGATCAGGCACACAGTTTTCC CTCAAGATCAACAGCCTGCAGTCTGAA GATTTTGGGAATTATTACTGTCAACAT TTTTGGGGTTCTCCGTGGACGTTCGGT GGAGGCACCAAGCTGGAAATCAAA (SEQ ID NO: 6) | DIQMTQSPASLSVSVG ETVTITCRASENIYSN LAWYQQKQGKSPQLLV YAATNLADGVPSRFSG SGSGTQFSLKINSLQS EDFGNYYCQHFWGSPW TFGGGTKLEIK (SEQ ID NO: 5) |

TABLE 2b

CDR Sequences of mouse monoclonal anti-human BTN1A1 antibody STC703

| | Region definition | CDR1 | CDR2 | CDR3 |
|---|---|---|---|---|
| Heavy chain | Chothia | GFTFSSR (SEQ ID NO: 7) | YAGTGG (SEQ ID NO: 8) | RRGLGYFDY (SEQ ID NO: 9) |
| | AbM | GFTFSSR YIS (SEQ ID NO: 10) | WIYAGTGGTS (SEQ ID NO: 11) | RRGLGYFDY (SEQ ID NO: 12) |
| | Kabat | SRYIS (SEQ ID NO: 13) | WIYAGTGGTS YNQKFTG (SEQ ID NO: 14) | RRGLGYFDY (SEQ ID NO: 15) |
| | Contact | SSRYIS (SEQ ID NO: 16) | WIAWIYAGTG GTS (SEQ ID NO: 17) | ARRRGLGYFD (SEQ ID NO: 18) |
| Kappa light chain | Chothia | RASENIY SNLA (SEQ ID NO: 19) | AATNLAD (SEQ ID NO: 20) | QHFWGSPWT (SEQ ID NO: 21) |

TABLE 2b-continued

CDR Sequences of mouse monoclonal anti-human BTN1A1 antibody STC703

| Region definition | CDR1 | CDR2 | CDR3 |
|---|---|---|---|
| AbM | RASENIYSNLA (SEQ ID NO: 22) | AATNLAD (SEQ ID NO: 23) | QHFWGSPWT (SEQ ID NO: 24) |
| Kabat | RASENIYSNLA (SEQ ID NO: 25) | AATNLAD (SEQ ID NO: 26) | QHFWGSPWT (SEQ ID NO: 27) |
| Contact | YSNLAWY (SEQ ID NO: 28) | LLVYAATNLA (SEQ ID NO: 29) | QHFWGSPW (SEQ ID NO: 30) |

TABLE 3a

Sequences of heavy chain variable (VH) region and light chain variable (VL) region of mouse monoclonal anti-human BTN1A1 antibody STC810

| | DNA sequence | Protein sequence |
|---|---|---|
| Heavy chain | GAGGTCCAGCTGCAGCAGTCTGGACCTGAGCTGGTGAAGCCTGGGGCTTCAGTGAAGATATCCTGCAAGGCTTCTGGATACACATTCACTCACTACAACATGGACTGGGTGAAGCAGAGCCATGGAAAGAGCCTTGAATGGATTGGATATATTTATCCTTCCAATGGTGGTACTGGCTACAACCAGAAATTCAAGAGCAGGGCCACATTGACTGTAGACAAGTCCTCCAGCACAGCCTACATGGAACTCCACAGCCTGACATCTGAGGACTCTGCAGTCTATTACTGTGCAAGAGGGGCCTATCACTACGGTAGTTCCTACGCCTACTGGTACTTCGATGTCTGGGGCGCAGGGACCACGGTCACCGTCTCCTCA (SEQ ID NO: 32) | EVQLQQSGPELVKPGASVKISCKASGYTFTHYNMDWVKQSHGKSLEWIGYIYPSNGGTGYNQKFKSRATLTVDKSSSTAYMELHSLTSEDSAVYYCARGAYHYGSSYAYWYFDVWGAGTTVTVSS (SEQ ID NO: 31) |
| Kappa Light chain | GATATCCAGATGACACAGACTACATCCTCCCTGTCTGCCTCTCTGGGAGACAGAGTCACCATCAGTTGCAGTGCAAGTCAGGACATTAGCAATTATTTAAACTGGTATCAGCAGAAACCAGATGAAACTGTTAAACTCCTGATCTCTTACACATCAAGTTTACACTCAGGAGTCCCATCAAGATTCAGTGGCAGTGGGTCTGGGACAGATTATTCTCTCACCATCAGCAACCTGGCACCTGAAGATATTGCCACTTACTATTGTCAGCAGTCTAGTAAGCTTCCATTCACGTTCGGCTCGGGGACAGAGTTGGAAATAAAACGGGCT (SEQ ID NO: 34) | DIQMTQTTSSLSASLGDRVTISCSASQDISNYLNWYQQKPDETVKLLISYTSSLHSGVPSRFSGSGSGTDYSLTISNLAPEDIATYYCQQSSKLPFTFGSGTELEIKRA (SEQ ID NO: 33) |

TABLE 3b

CDR Sequences of mouse monoclonal anti-human BTN1A1 antibody STC810

| | Region definition | CDR1 | CDR2 | CDR3 |
|---|---|---|---|---|
| Heavy chain | Chothia | GYTFTHY (SEQ ID NO: 35) | YPSNGG (SEQ ID NO: 36) | GAYHYGSSYAYWYFDV (SEQ ID NO: 37) |
| | AbM | GYTFTHYNMD (SEQ ID NO: 38) | YIYPSNGGTG (SEQ ID NO: 39) | GAYHYGSSYAYWYFDV (SEQ ID NO: 40) |

TABLE 3b-continued

CDR Sequences of mouse monoclonal anti-human BTN1A1 antibody STC810

| | Region definition | CDR1 | CDR2 | CDR3 |
|---|---|---|---|---|
| | Kabat | HYNMD (SEQ ID NO: 41) | YIYPSNGGTGYNQKFKS (SEQ ID NO: 42) | GAYHYGSSYAYWYFDV (SEQ ID NO: 43) |
| | Contact | THYNMD (SEQ ID NO: 44) | WIGYIYPSNGGTG (SEQ ID NO: 45) | ARGAYHYGSSYAYWYFD (SEQ ID NO: 46) |
| Kappa light chain | Chothia | SASQDISNYLN (SEQ ID NO: 47) | YTSSLHS (SEQ ID NO: 48) | QQSSKLPFT (SEQ ID NO: 49) |
| | AbM | SASQDISNYLN (SEQ ID NO: 50) | YTSSLHS (SEQ ID NO: 51) | QQSSKLPFT (SEQ ID NO: 52) |
| | Kabat | SASQDISNYLN (SEQ ID NO: 53) | YTSSLHS (SEQ ID NO: 54) | QQSSKLPFT (SEQ ID NO: 55) |
| | Contact | SNYLNWY (SEQ ID NO: 56) | LLISYTSSLH (SEQ ID NO: 57) | QQSSKLPF (SEQ ID NO: 58) |

TABLE 4a

Sequences of heavy chain variable (VH) region and light chain variable (VL) region of mouse monoclonal anti-human BTN1A1 antibody STC820

| | DNA sequence | Protein sequence |
|---|---|---|
| Heavy chain | CAGGGTCAGATGCAGCAGTCTGGAGCTGAGCTGGTGAAGCCTGGGGCTTCAGTGAAGCTGTCCTGCAAGACTTCTGGCTTCACCTTCAGCAGTAGGTATATAAGTTGGTTGAAGCAGAAGCCTCGACAGAGTCTTGAGTGGATTGCATGGATTTATGCTGGAACTGGTGGTACTAGCTATAATCAGAAGTTCACAGGCAAGGCCCAACTGACTGTAGACACATCCTCCAGCACAGCCTACATGCAACTCAGCAGCCTGACATCTGAGGACTCTGCCATCTATTACTGTGCAAGACGAAGGGGCGGCGGTTACTTTGACTACTGGGGCCAAGGCACCACTCTCACAGTCTCCTCA (SEQ ID NO: 60) | QGQMQQSGAELVKPGASVKLSCKTSGFTFSSRYISWLKQKPRQSLEWIAWIYAGTGGTSYNQKFTGKAQLTVDTSSSTAYMQLSSLTSEDSAIYYCARRRGGGYFDYWGQGTTLTVSS (SEQ ID NO: 59) |
| Kappa Light chain | GACATCCAGATGACTCAGTCTCCAGCCTCCCTATCTGTATCTGTGGGAGAAACTGTCACCATCACATGTCGAGCAAGTGAGAATATTTTCAGTAATTTAGCATGGTATCAGCAGAAACAGGGAAAATCTCCTCAGCTCCTGGTCTATGCTGCAACAAACTTAGCAGATGGTGTGCCATCAAGGTTCAGTGGCAGTGGATCAGGCACACAGTATTCCCTCAAGATCAACAGCCTGCAGTCTGAGGATTTTGGGAGTTATTACTGTCAACATTTTTGGGGTTCTCCGTGGACGTTCGGTGGAGGCACCAAGCTGGAAATCAAA (SEQ ID NO: 62) | DIQMTQSPASLSVSVGETVTITCRASENIFSNLAWYQQKQGKSPQLLVYAATNLADGVPSRFSGSGSGTQYSLKINSLQSEDFGSYYCQHFWGSPWTFGGGTKLEIK (SEQ ID NO: 61) |

TABLE 4b

CDR Sequences of mouse monoclonal anti-human BTN1A1 antibody STC820

| | Region definition | CDR1 | CDR2 | CDR3 |
|---|---|---|---|---|
| Heavy chain | Chothia | GFTFSSR (SEQ ID NO: 63) | YAGTGG (SEQ ID NO: 64) | RRGGGYFDY (SEQ ID NO: 65) |
| | AbM | GFTFSSRYIS (SEQ ID NO: 66) | WIYAGTGGTS (SEQ ID NO: 67) | RRGGGYFDY (SEQ ID NO: 68) |
| | Kabat | SRYIS (SEQ ID NO: 69) | WIYAGTGGTSYNQKFTG (SEQ ID NO: 70) | RRGGGYFDY (SEQ ID NO: 71) |
| | Contact | SSRYIS (SEQ ID NO: 72) | WIAWIYAGTGGTS (SEQ ID NO: 73) | ARRRGGGYFD (SEQ ID NO: 74) |
| Kappa light chain | Chothia | RASENIFSNLA (SEQ ID NO: 75) | AATNLAD (SEQ ID NO: 76) | QHFWGSPWT (SEQ ID NO: 77) |
| | AbM | RASENIFSNLA (SEQ ID NO: 78) | AATNLAD (SEQ ID NO: 79) | QHFWGSPWT (SEQ ID NO: 80) |
| | Kabat | RASENIFSNLA (SEQ ID NO: 81) | AATNLAD (SEQ ID NO: 82) | QHFWGSPWT (SEQ ID NO: 83) |
| | Contact | FSNLAW (SEQ ID NO: 84) | LLVYAATNLA (SEQ ID NO: 85) | QHFWGSPW (SEQ ID NO: 86) |

TABLE 5b

CDR Sequences of mouse monoclonal anti-human BTN1A1 antibody STC1011

| | Region definition | CDR1 | CDR2 | CDR3 |
|---|---|---|---|---|
| Heavy chain | Chothia | GYTFTDY (SEQ ID NO: 91) | SPNNGGT (SEQ ID NO: 92) | EPDLLYYFDY (SEQ ID NO: 93) |
| | AbM | GYTFTDYYMD (SEQ ID NO: 94) | YISPNNGGTK (SEQ ID NO: 95) | EPDLLYYFDY (SEQ ID NO: 96) |
| | Kabat | DYYMD (SEQ ID NO: 97) | YISPNNGGTKYNQKFKG (SEQ ID NO: 98) | EPDLLYYFDY (SEQ ID NO: 99) |
| | Contact | TDYYMD (SEQ ID NO: 100) | SLEWIGYISPNNGGTK (SEQ ID NO: 101) | AREPDLLYYFD (SEQ ID NO: 102) |
| Kappa light chain | Chothia | SASQDISNYLN (SEQ ID NO: 103) | YTSSLHS (SEQ ID NO: 104) | QQSSKLPFT (SEQ ID NO: 105) |
| | AbM | SASQDISNYLN (SEQ ID NO: 106) | YTSSLHS (SEQ ID NO: 107) | QQSSKLPFT (SEQ ID NO: 108) |
| | Kabat | SASQDISNYLN (SEQ ID NO: 109) | YTSSLHS (SEQ ID NO: 110) | QQSSKLPFT (SEQ ID NO: 111) |
| | Contact | SNYLNWY (SEQ ID NO: 112) | LLISYTSSLH (SEQ ID NO: 113) | QQSSKLPF (SEQ ID NO: 114) |

TABLE 5a

Sequences of heavy chain variable (VH) region and light chain variable (VL) region of mouse monoclonal anti-mouse BTN1A1 antibody STC1011

| | DNA sequence | Protein sequence |
|---|---|---|
| Heavy chain | GAGGTCCAGCTGCAACAGTCTGGACCTGAGCTGGTGAAGCCTGGGGATTCAGTGAAGATGTCCTGCAAGGCTTCTGGCTACACATTCACTGACTACTACATGGACTGGGTGAAGCAGAGCCATGGAAAGAGCCTTGAGTGGATTGGATATATTTCTCCTAACAATGGTGGTACTAAGTACAATCAGAAGTTCAAGGGCAAGGCCACATTGACTGTTGACAAGTCCTCCAGCACAGCCTACATGGAGCTCCACAGCCTGACATCTGAGGACTCTGCAGTCTATTACTGTGCAAGAGAGCCCGACCTGCTTTACTACTTTGACTACTGGGGCCAAGGCACCACTCTCACAGTCTCCTCAG (SEQ ID NO: 88) | EVQLQQSGPELVKPGDSVKMSCKASGYTFTDYYMDWVKQSHGKSLEWIGYISPNNGGTKYNQKFKGKATLTVDKSSSTAYMELHSLTSEDSAVYYCAREPDLLYYFDYWGQGTTLTVSS (SEQ ID NO: 87) |
| Kappa Light chain | GACATTGTGATGTCACAGTCTCCATCCTCCCTAGCTGTGTCAGTTGGAGAGAAGGTTATTATGAGCTGCAAGTCCAGTCAGAGCCTTTTATATTTTAGCAATCAAAAGAACTACTTGGCCTGGTACCAGCAGAAACCAGGGCAGTCTCCTAGACTGCTGATTTACTGGGCATCCACTAGGGAATCTGGGGTCCCTGATCGCTTCACAGGCAGTGGATCTGGGACAGATTTCACTCTCACCATCAGCAGTGTGAAGGCTGAAGACCTGGCAGTTTATTACTGTCAGCAATATTATAGCTATCCGTGGACGTTCGGTGGAGGCACCAAGCTGGAAATCAAAC (SEQ ID NO: 90) | DIVMSQSPSSLAVSVGEKVIMSCKSSQSLLYFSNQKNYLAWYQQKPGQSPRLLIYWASTRESGVPDRFTGSGSGTDFTLTISSVKAEDLAVYYCQQYYSYPWTFGGGTKLEIK (SEQ ID NO: 89) |

TABLE 6a

Sequences of heavy chain variable (VH) region and light chain variable (VL) region of mouse monoclonal anti-mouse BTN1A1 antibody STC1012

| | DNA sequence | Protein sequence |
|---|---|---|
| Heavy chain | GAAGTGATGCTGGTGGAGTCTGGGGGAGCCTTAGTGAAGCCTGGAGGGTCCCTGAAACTCTCCTGTGCAGCCTCTGGATTCACTTTCAGCAATTATGTCATGTCTTGGGTTCGCCAGACTCCAGAGAAGAGGCTGGAGTGGGTCGCAACCATTAGTAGTGGTGGTAGTTACACCAATTATCCAGACAGTGTGAAGGGTCGATTCATCATCTCCAGAGACAATGCCAGGAACACCCTGTACCTGCAAATGAGCAGTCTGAGGTCTGAGGACACGGCCATATATTACTGTGTAAGAGAGGGGGATGGTTTCTACGTCTTTGACTACTGGGGCCTAGGCACCACTCTCACAGTCTCCTCA (SEQ ID NO: 116) | EVMLVESGGALVKPGGSLKLSCAASGFTFSNYVMSWVRQTPEKRLEWVATISSGGSYTNYPDSVKGRFIISRDNARNTLYLQMSSLRSEDTAIYYCVREGDGFYVFDYWGLGTTLTVSS (SEQ ID NO: 115) |
| Kappa Light chain | GACATTGTGATGTCACAGTCTCCATCCTCCCTAGCTGTGTCAGTTGGAGAGAAGGTTATTATGAGCTGCAAGTCCAGTCAGAGCCTTTTATATAGTGGCAATCAAAAGAACTACTTGGCCTGGTACCAGCAGAAACCAGGGCAGTCTCCTAAACTGCTGATTTACTGGGCATCCACTAGGGAATCTGGGGTCCCTGATCGCTTCACAGGCAGTGGATCTGGGACAGATTTCACTCTCACCATCAGCAGTGTGAAGGCTGAAGACCTGGCAGTTTATTACTGTCAGCAATATTATAGCTATCCGTGGACGTTCGGTGGAGGCACCAAGCTGGAAATCAAA (SEQ ID NO: 118) | DIVMSQSPSSLAVSVGEKVIMSCKSSQSLLYSGNQKNYLAWYQQKPGQSPKLLIYWASTRESGVPDRFTGSGSGTDFTLTISSVKAEDLAVYYCQQYYSYPWTFGGGTKLEIK (SEQ ID NO: 117) |

TABLE 6b

CDR Sequences of mouse monoclonal anti-mouse BTN1A1 antibody STC1012

| | Region definition | CDR1 | CDR2 | CDR3 |
|---|---|---|---|---|
| Heavy chain | Chothia | GFTFSNY (SEQ ID NO: 119) | SSGGSY (SEQ ID NO: 120) | EGDGFYVFDY (SEQ ID NO: 121) |
| | AbM | GFTFSNYVMS (SEQ ID NO: 122) | TISSGGSYTN (SEQ ID NO: 123) | EGDGFYVFDY (SEQ ID NO: 124) |
| | Kabat | NYVMS (SEQ ID NO: 125) | TISSGGSYTNYPDSVKG (SEQ ID NO: 126) | EGDGFYVFDY (SEQ ID NO: 127) |
| | Contact | SNYVMS (SEQ ID NO: 128) | WVATISSGGSYTN (SEQ ID NO: 129) | VREGDGFYVFD (SEQ ID NO: 130) |
| Kappa light chain | Chothia | KSSQSLLYSGNQKNYLA (SEQ ID NO: 131) | WASTRES (SEQ ID NO: 132) | QQYYSYPWT (SEQ ID NO: 133) |
| | AbM | KSSQSLLYSGNQKNYLA (SEQ ID NO: 134) | WASTRES (SEQ ID NO: 135) | QQYYSYPWT (SEQ ID NO: 136) |
| | Kabat | KSSQSLLYSGNQKNYLA (SEQ ID NO: 137) | WASTRES (SEQ ID NO: 138) | QQYYSYPWT (SEQ ID NO: 139) |
| | Contact | LYSGNQKNYLAWY (SEQ ID NO: 140) | LLIYWASTRE (SEQ ID NO: 141) | QQYYSYPW (SEQ ID NO: 142) |

TABLE 7a

Sequences of heavy chain variable (VH) region and light chain variable (VL) region of mouse monoclonal anti-mouse BTN1A1 Antibody STC1029

| | DNA sequence | Protein sequence |
|---|---|---|
| Heavy chain | GAGGTTCAGCTGCAGCAGTCTGGACCTGAGCTGGTGAAGCCTGGGGCTTCAGTGAAGATATCCTGCAAGGCTTCTGGTTACTCATTTACTGGCTACTTTATGAACTGGGTGAAACAGAGCCATGGAAAGAGCCTTGAGTGGATTGGACGTATTAATCCTTATAATGGTGATACTTTTTACAACCAGAAGTTCAAGGACAAGGCCACATTAACTGTAGACACATCCTCTAGCACAGCCCACATGGAGCTCCGGAGCCTGACATCTGAGGAGTCTGCAGTCTATTATTGTGCAAGATGGACTACGGTAATAAACTTTGACTACCGGGGCCAAGGCACCACTCTCACAGTCTCCTCA (SEQ ID NO: 144) | EVQLQQSGPELVKPGASVKISCKASGYSFTGYFMNWVKQSHGKSLEWIGRINPYNGDTFYNQKFKDKATLTVDTSSSTAHMELRSLTSEESAVYYCARWTTVINFDYWGQGTTLTVSS (SEQ ID NO: 143) |
| Kappa light chain | AGTATTGTGATGACCCAGACTCCCAAATTCCTGCTTGTGTCAGCAGGAGACAGGGTTACCATAACCTGCAAGGCCAGTCAGAGTGTGAGTTATGATGTAGTTTGGTACCAACAGAAGCCAGGGCAGTCTCCTAAACTGCTGATGTATTATGTATCCAATCGCTACACTGGAGTCCCTGATCGCTTCACTGGCAGTGGATATGGGACGGATTTCACTTTCACCATCAGCACTGTGCAGGCTGAAGACCTGGCAGTTTATTTCTGTCAGCAGGATTATAGCTCTCCTCCGACGTTCGGTGGAGGCACCAAGCTGGAAATCAAA (SEQ ID NO: 146) | SIVMTQTPKFLLVSAGDRVTITCKASQSVSYDVVWYQQKPGQSPKLLMYYVSNRYTGVPDRFTGSGYGTDFTFTISTVQAEDLAVYFCQQDYSSPPTFGGGTKLEIK (SEQ ID NO: 145) |

TABLE 7b

CDR Sequences of mouse monoclonal anti-mouse BTN1A1 antibody STC1029

| | Region definition | CDR1 | CDR2 | CDR3 |
|---|---|---|---|---|
| Heavy chain | Chothia | GYSFTGY (SEQ ID NO: 147) | NPYNGD (SEQ ID NO: 148) | WTTVINFDY (SEQ ID NO: 149) |
| | AbM | GYSFTGYFMN (SEQ ID NO: 150) | RINPYNGDTF (SEQ ID NO: 151) | WTTVINFDY (SEQ ID NO: 152) |
| | Kabat | GYFMN (SEQ ID NO: 153) | RINPYNGDTFYNQKFKD (SEQ ID NO: 154) | WTTVINFDY (SEQ ID NO: 155) |
| | Contact | TGYFMN (SEQ ID NO: 156) | WIGRINPYNGDTF (SEQ ID NO: 157) | ARWTTVINFD (SEQ ID NO: 158) |
| Kappa light chain | Chothia | KASQSVSYDVV (SEQ ID NO: 159) | YVSNRYT (SEQ ID NO: 160) | QQDYSSPPT (SEQ ID NO: 161) |
| | AbM | KASQSVSYDVV (SEQ ID NO: 162) | YVSNRYT (SEQ ID NO: 163) | QQDYSSPPT (SEQ ID NO: 164) |
| | Kabat | KASQSVSYDVV (SEQ ID NO: 165) | YVSNRYT (SEQ ID NO: 166) | QQDYSSPPT (SEQ ID NO: 167) |
| | Contact | SYDVVWY (SEQ ID NO: 168) | LLMYYVSNRY (SEQ ID NO: 169) | QQDYSSPP (SEQ ID NO: 170) |

TABLE 8a

Sequences of heavy chain variable (VH) region and light chain variable (VL) region of mouse monoclonal anti-mouse BTN1A1 Antibody STC2602

| | DNA sequence | Protein sequence |
|---|---|---|
| Heavy chain | gaagtccagctgcagcagtctggacctgagctggtgaagcctgg ggcttcagtgaagatatcctgcaaggcttctggtttttctttcattgg ctactacatagactgggtgaagcagagtcctggaaagagccttga gtggattggatatatttatccttccaatggtgaaaccagctaccacc agaagtgcaagggcaaggccacattgactgtagacaaatcctcc agcacagtcaacatgcagctcaacagtctgacatctgaggactct gcagtctattactgtgcaagatatggtaactacgactggttcttcgat gtctggggcgcagggaccacggtcaccgtttcctca (SEQ ID NO: 194) | EVQLQQSGPELVKPGASVKIS CKASGFSFIGYYIDWVKQSPG KSLEWIGYIYPSNGETSYHQK CKGKATLTVDKSSSTVNMQL NSLTSEDSAVYYCARYGNYD WFFDVWGAGTTVTVSS (SEQ ID NO: 193) |
| Kappa light chain | caaattgttctcacccagtctccagcaatcatgtctgcatctccagg ggagaaggtcaccataacctgcagtgccagttcaagtgtaagtta catgcactggttccagcagaagccaggcacttctcccaaattttgg atttatagcacatccaacctggcttctggagtccctattcgcttcagt ggcagtggatctgggacctcttactctctcacaatcagccgaatgg aggctgaagatgctgccacttattactgccagcaaaggagtagtta cccgtacacgttcggaggggggaccaagctggaaataaaacgg (SEQ ID NO: 196) | QIVLTQSPAIMSASPGEKVTIT CSASSSVSYMHWFQQKPGTS PKFWIYSTSNLASGVPIRFSGS GSGTSYSLTISRMEAEDAATY YCQQRSSYPYTFGGGTKLEIK (SEQ ID NO: 195) |

TABLE 8b

CDR Sequences of mouse monoclonal anti-mouse BTN1A1 antibody STC2602

| | Region definition | CDR1 | CDR2 | CDR3 |
|---|---|---|---|---|
| Heavy chain | Chothia | GFSIGY (SEQ ID NO: 197) | YPSNGE (SEQ ID NO: 198) | YGNYDWFFDV (SEQ ID NO: 199) |
| | AbM | GFSIGYYID (SEQ ID NO: 200) | YIYPSNGETS (SEQ ID NO: 201) | YGNYDWFFDV (SEQ ID NO: 202) |
| | Kabat | GYYID (SEQ ID NO: 203) | YIYPSNGETSYHQ KCKG (SEQ ID NO: 204) | YGNYDWFFDV (SEQ ID NO: 205) |
| | Contact | IGYYID (SEQ ID NO: 206) | WIGYIYPSNGETS (SEQ ID NO: 207) | ARYGNYDWFFD (SEQ ID NO: 208) |
| Kappa light chain | Chothia | SASSSVSYMH (SEQ ID NO: 209) | STSNLAS (SEQ ID NO: 210) | QQRSSYPYT (SEQ ID NO: 211) |
| | AbM | SASSSVSYMH (SEQ ID NO: 212) | STSNLAS (SEQ ID NO: 213) | QQRSSYPYT (SEQ ID NO: 214) |
| | Kabat | SASSSVSYMH (SEQ ID NO: 215) | STSNLAS (SEQ ID NO: 216) | QQRSSYPYT (SEQ ID NO: 217) |
| | Contact | SYMHWF (SEQ ID NO: 218) | FWIYSTSNLA (SEQ ID NO: 219) | QQRSSYPY (SEQ ID NO: 220) |

TABLE 9a

Sequences of heavy chain variable (VH) region and light chain variable (VL) region of mouse monoclonal anti-mouse BTN1A1 Antibody STC2714

| | DNA sequence | Protein sequence |
|---|---|---|
| Heavy chain | cagatccagttggtgcagtctggacctgagctgaagaagcctgg agcgacagtcaagatctcctgcaaggcttctggatataccttcaca atctttggaatgaactgggtgaagcaggctccaggaaagggttta gagtggatgggctggataaacaccaacactggagagccaacata tgctgaagagttcaagggacggtttgccttctctttggaaacctctg ccagcactgcctttttgcagatcaacaacctcaaaaatgaggaca cggctacatatttctgtgcaagagtggggtactacgactttgactac tggggccaaggcaccactctcacagtctcctca (SEQ ID NO: 222) | QIQLVQSGPELKKPGATVKIS CKASGYTFTIFGMNWVKQAP GKGLEWMGWINTNTGEPTY AEEFKGRFAFSLETSASTAFL QINNLKNEDTATYFCARVGY YDFDYWGQGTTLTVSS (SEQ ID NO: 221) |

TABLE 9a-continued

Sequences of heavy chain variable (VH) region and light chain variable (VL) region of mouse monoclonal anti-mouse BTN1A1 Antibody STC2714

| | DNA sequence | Protein sequence |
|---|---|---|
| Kappa light chain | gatgttgtgatgacccagactccactcactttgtcggttaccgttgg acaaccagcctccatctcttgcaagtcaagtcagagcctcttagat agtgatggaaagacatttttgaattggttcttacagaggccaggcc agtctccaaagcgcctaatctatctggtgtctaaaaaggactctgg agtccctgacaggttcactggcagtggagcagggacagatttcac actgaaaatcagcagagtggaggctgaggatttgggagtttattat tgccggcaaggtacacattttccgtggacgttcggtggaggcacc aggctggaaatcaaa (SEQ ID NO: 224) | DVVMTQTPLTLSVTVGQPASI SCKSSQSLLDSDGKTFLNWFL QRPGQSPKRLIYLVSKKDSGV PDRFTGSGAGTDFTLKISRVE AEDLGVYYCRQGTHFPWTFG GGTRLEIK (SEQ ID NO: 223) |

TABLE 9b

CDR Sequences of mouse monoclonal anti-mouse BTN1A1 antibody STC2714

| | Region definition | CDR1 | CDR2 | CDR3 |
|---|---|---|---|---|
| Heavy chain | Chothia | GYTFFIF (SEQ ID NO: 225) | NTNTGE (SEQ ID NO: 226) | VGYYDFDY (SEQ ID NO: 227) |
| | AbM | GYTFFIFGMN (SEQ ID NO: 228) | WINTNTGEPT (SEQ ID NO: 229) | VGYYDFDY (SEQ ID NO: 230) |
| | Kabat | IFGMN (SEQ ID NO: 231) | WINTNTGEPTYAE EFKG (SEQ ID NO: 232) | VGYYDFDY (SEQ ID NO: 233) |
| | Contact | TIFGMN (SEQ ID NO: 234) | WMGWINTNTGEPT (SEQ ID NO: 235) | ARVGYYDFD (SEQ ID NO: 236) |
| Kappa light chain | Chothia | KSSQSLLDSDGKT FLN (SEQ ID NO: 237) | LVSKKDS (SEQ ID NO: 238) | RQGTHFPWT (SEQ ID NO: 239) |
| | AbM | KSSQSLLDSDGKT FLN (SEQ ID NO: 240) | LVSKKDS (SEQ ID NO: 241) | RQGTHFPWT (SEQ ID NO: 242) |
| | Kabat | KSSQSLLDSDGKT FLN (SEQ ID NO: 243) | LVSKKDS (SEQ ID NO: 244) | RQGTHFPWT (SEQ ID NO: 245) |
| | Contact | LDSDGKTFLNWFL (SEQ ID NO: 246) | RLIYLVSKKD (SEQ ID NO: 247) | RQGTHFPW (SEQ ID NO: 248) |

TABLE 10a

Sequences of heavy chain variable (VH) region and light chain variable (VL) region of mouse monoclonal anti-mouse BTN1A1 Antibody STC2739

| | DNA sequence | Protein sequence |
|---|---|---|
| Heavy chain | caggtacaactgaagcagtcaggacctggcctagtgcagccctc acagagcctgtccatcacctgcacagtctctggtttctcattaacta cccatggtgtaaactgggttcgccagtctccaggaaagggtctgg agtggctgggagtgatatggagtggtggaagcacagactataat gcagctttcatatccagactgagcatcagcaaggacaattccaag agccaagttttctttaaaatgaacagtctgcaagctaatgacacag ccatatattactgtgccagaccctactactatggagctatggactac tggggtcaaggaacctcagtcaccgtctcctca (SEQ ID NO: 250) | QVQLKQSGPGLVQPSQSLSIT CTVSGFSLTTHGVNWVRQSP GKGLEWLGVIWSGGSTDYN AAFISRLSISKDNSKSQVFFK MNSLQANDTAIYYCARPYYY GAMDYWGQGTSVTVSS (SEQ ID NO: 249) |
| Kappa light chain | caaattgttctcacccagtctccatcaatcatgtctgcatctccagg ggagaaggtcaccataacctgcagtgccagctcaagtgtaagtta catacactggttccagcagaagccaggcacttctcccaaactctg gatctatagcacatccaacctggcttctggagtccctgctcgcttca gtggcagtggatctgggacctcttactctctcacaatcagccgaat ggaggctgaagatgctgccacttattactgccagcaaaggagtat ttacccgctcacgttcggtgctgggaccaagctggagctgaaa (SEQ ID NO: 252) | QIVLTQSPSIMSASPGEKVTIT CSASSSVSYIHWFQQKPGTSP KLWIYSTSNLASGVPARFSGS GSGTSYSLTISRMEAEDAATY YCQQRSIYPLTFGAGTKLELK (SEQ ID NO: 251) |

TABLE 10b

CDR Sequences of mouse monoclonal anti-mouse BTN1A1 antibody STC2739

| | Region definition | CDR1 | CDR2 | CDR3 |
|---|---|---|---|---|
| Heavy chain | Chothia | GFSLTTH (SEQ ID NO: 253) | WSGGS (SEQ ID NO: 254) | PYYYGAMDY (SEQ ID NO: 255) |
| | AbM | GFSLTTHGVN (SEQ ID NO: 256) | VIWSGGSTD (SEQ ID NO: 257) | PYYYGAMDY (SEQ ID NO: 258) |
| | Kabat | THGVN (SEQ ID NO: 259) | VIWSGGSTDYNAA FIS (SEQ ID NO: 260) | PYYYGAMDY (SEQ ID NO: 261) |
| | Contact | TTHGVN (SEQ ID NO: 262) | VWGVIWSGGSTD (SEQ ID NO: 263) | ARPYYYGAMD (SEQ ID NO: 264) |
| Kappa light chain | Chothia | SASSSVSYIH (SEQ ID NO: 265) | STSNLAS (SEQ ID NO: 266) | QQRSIYPLT (SEQ ID NO: 267) |
| | AbM | SASSSVSYIH (SEQ ID NO: 268) | STSNLAS (SEQ ID NO: 269) | QQRSIYPLT (SEQ ID NO: 270) |
| | Kabat | SASSSVSYIH (SEQ ID NO: 271) | STSNLAS (SEQ ID NO: 272) | QQRSIYPLT (SEQ ID NO: 273) |
| | Contact | SYIHWF (SEQ ID NO: 274) | LWIYSTSNLA (SEQ ID NO: 275) | QQRSIYPL (SEQ ID NO: 276) |

TABLE 11a

Sequences of heavy chain variable (VH) region and light chain variable (VL) region of mouse monoclonal anti-mouse BTN1A1 Antibody STC2778

| | DNA sequence | Protein sequence |
|---|---|---|
| Heavy chain | cagatccagttggtgcagtctggacctgagctgaagaagcctgg agagacagtcaagatctcctgcaaggcttctgggtatagcttcaca aactatggaatgaactgggtgaagcaggctccaggaaagggttt aaagtggatgggctggataaatatctacactggagagacaacata tggtgatgatttcaagggacggtttgccttctctttggaaacctctgc cagcactgcctatttgcagatcaacaacctcagaagtgaggacac ggctacatatttctgtgtaagagggggactatgattatgtactgg ggccaaggcaccactctcacagtctcctca (SEQ ID NO: 278) | QIQLVQSGPELKKPGETVKIS CKASGYSFTNYGMNWVKQA PGKGLKWMGWINIYTGETTY GDDFKGRFAFSLETSASTAYL QINNLRSEDTATYFCVRGGT MIMYWGQGTTLTVSS (SEQ ID NO: 277) |
| Kappa light chain | gatattgtgctaactcagtctccagccaccctgtctgtgactccagg agatagcgtcagtctttcctgcagggccagccaaagtattagcaa caacctacactggcatcaacaaaaatcacatgagtctccaaggctt ctcatcaagtatgcttcccagtccatgtctgggatcccctccaggtt cagtggcagtggatcagggacagatttcactctcagtatcaacagt gtggagactgaagattttggaatgtatttctgtcaacagagtgaca gctggccgctcacgttcggtgctgggaccaagctggagctgaaa (SEQ ID NO: 280) | DIVLTQSPATLSVTPGDSVSL SCRASQSISNNLHWHQQKSH ESPRLLIKYASQSMSGIPSRFS GSGSGTDFTLSINSVETEDFG MYFCQQSDSWPLTFGAGTKL ELK (SEQ ID NO: 279) |

TABLE 11b

CDR Sequences of mouse monoclonal anti-mouse BTN1A1 antibody STC2778

| | Region definition | CDR1 | CDR2 | CDR3 |
|---|---|---|---|---|
| Heavy chain | Chothia | GYSFTNY (SEQ ID NO: 281) | NIYTGE (SEQ ID NO: 282) | GGTMIMY (SEQ ID NO: 283) |
| | AbM | GYSFTNYGMN (SEQ ID NO: 284) | WINIYTGETT (SEQ ID NO: 285) | GGTMIMY (SEQ ID NO: 286) |
| | Kabat | NYGMN (SEQ ID NO: 287) | WINIYTGETTYGD DFKG (SEQ ID NO: 288) | GGTMIMY SEQ ID NO: 289) |
| | Contact | TNYGMN (SEQ ID NO: 290) | WMGWINIYTGETT (SEQ ID NO: 291) | VRGGTMIM (SEQ ID NO: 292) |

TABLE 11b-continued

CDR Sequences of mouse monoclonal anti-mouse BTN1A1 antibody STC2778

| | Region definition | CDR1 | CDR2 | CDR3 |
|---|---|---|---|---|
| Kappa light chain | Chothia | RASQSISNNLH (SEQ ID NO: 293) | YASQSMS (SEQ ID NO: 294) | QQSDSWPLT (SEQ ID NO: 295) |
| | AbM | RASQSISNNLH (SEQ ID NO: 296) | YASQSMS (SEQ ID NO: 297) | QQSDSWPLT (SEQ ID NO: 298) |
| | Kabat | RASQSISNNLH (SEQ ID NO: 299) | YASQSMS (SEQ ID NO: 300) | QQSDSWPLT (SEQ ID NO: 301) |
| | Contact | SNNLHWH (SEQ ID NO: 302) | LLIKYASQSM (SEQ ID NO: 303) | QQSDSWPL (SEQ ID NO: 304) |

TABLE 12a

Sequences of heavy chain variable (VH) region and light chain variable (VL) region of mouse monoclonal anti-mouse BTN1A1 Antibody STC2781

| | DNA sequence | Protein sequence |
|---|---|---|
| Heavy chain | cagatccagttggtgcagtctggacctgagctgaagaagcctggagagacagtcaagatctcctgcaaggcttctgggtatagcttcacaaactatggaatgaactgggtgaagcaggctccaggaaagggtttaaagtggatgggctggataaatatctacactggagagacaacatatggtgatgatttcaagggacggtttgccttctctttggaaacctctgccagcactgcctatttgcagatcaacaacctcaaaagtgaggacacggctacatatttctgtgtaagaggggggactatgattatgtactggggccaaggcaccactctcacagtctcctca (SEQ ID NO: 306) | QIQLVQSGPELKKPGETVKISCKASGYSFTNYGMNWVKQAPGKGLKWMGWINIYTGETTYGDDFKGRFAFSLETSASTAYLQINNLKSEDTATYFCVRGGTMIMYWGQGTTLTVSS (SEQ ID NO: 305) |
| Kappa light chain | gacattgtgctgacacagtctcctgcttccttagctgtatctctggggcagagggccaccatctcatacagggccagcaaaagtgtcagtacatctggctatagttatatgcactggaaccaacagaaaccaggacagccacccagactcctcatctatcttgtatccaacctagaatctggggtccctgccaggttcagtggcagtgggtctgggacagacttcaccctcaacatccatcctgtggaggaggaggatgctgcaacctattactgtcagcacattagggagctttacacgttcggaggggggaccaagctggaaataaaa (SEQ ID NO: 308) | DIVLTQSPASLAVSLGQRATISYRASKSVSTSGYSYMHWNQQKPGQPPRLLIYLVSNLESGVPARFSGSGSGTDFTLNIHPVEEEDAATYYCQHIRELTFGGGTKLEIK (SEQ ID NO: 307) |

TABLE 12b

CDR Sequences of mouse monoclonal anti-mouse BTN1A1 antibody STC2781

| | Region definition | CDR1 | CDR2 | CDR3 |
|---|---|---|---|---|
| Heavy chain | Chothia | GYSFTNY (SEQ ID NO: 309) | NIYTGE (SEQ ID NO: 310) | GGTMIMY (SEQ ID NO: 311) |
| | AbM | GYSFTNYGMN (SEQ ID NO: 312) | WINIYTGETT (SEQ ID NO: 313) | GGTMIMY (SEQ ID NO: 314) |
| | Kabat | NYGMN (SEQ ID NO: 315) | WINIYTGETTYGDDFKG (SEQ ID NO: 316) | GGTMIMY (SEQ ID NO: 317) |
| | Contact | TNYGMN (SEQ ID NO: 318) | WMGWINIYTGETT (SEQ ID NO: 319) | VRGGTMIM (SEQ ID NO: 320) |
| Kappa light chain | Chothia | RASKSVSTSGYSYMH (SEQ ID NO: 321) | LVSNLES (SEQ ID NO: 322) | QHIRELYT (SEQ ID NO: 323) |
| | AbM | RASKSVSTSGYSYMH (SEQ ID NO: 324) | LVSNLES (SEQ ID NO: 325) | QHIRELYT (SEQ ID NO: 326) |
| | Kabat | RASKSVSTSGYSYMH (SEQ ID NO: 327) | LVSNLES (SEQ ID NO: 328) | QHIRELYT (SEQ ID NO: 329) |
| | Contact | STSGYSYMHWN (SEQ ID NO: 330) | LLIYLVSNLE (SEQ ID NO: 331) | QHIRELY (SEQ ID NO: 332) |

Accordingly, provided herein are molecules having an antigen binding fragment that immunospecifically binds to BTN1A1 or glycosylated BTN1A1 with the following sequence features. In some embodiments, the molecules provided herein have an antigen binding fragment that has (a) a heavy chain variable (VH) region including: (1) a VH CDR1 having an amino acid sequence of SEQ ID NOS: 7, 10, 13, 16, 35, 38, 41, 44, 63, 66, 69, or 72; (2) a VH CDR2 having an amino acid sequence SEQ ID NOS: 8, 11, 14, 17, 36, 39, 42, 45, 64, 67, 70, or 73; and (3) a VH CDR3 having an amino acid sequence of SEQ ID NOS: 9, 12, 15, 18, 37, 40, 43, 46, 65, 68, 71, or 74; and/or (b) a light chain variable (VL) region including: (1) a VL CDR1 having an amino acid sequence of SEQ ID NOS: 19, 22, 25, 28, 47, 50, 53, 56, 75, 78, 81, or 84; (2) a VL CDR2 having an amino acid sequence of SEQ ID NOS: 20, 23, 26, 29, 48, 51, 54, 57, 76, 79, 82, or 85; and (3) a VL CDR3 having an amino acid sequence of SEQ ID NOS: 21, 24, 27, 30, 49, 52, 55, 58, 77, 80, 83, or 86.

In some embodiments, provided herein are antibodies having (a) a heavy chain variable (VH) region including: (1) a VH CDR1 having an amino acid sequence of SEQ ID NOS: 7, 10, 13, 16, 35, 38, 41, 44, 63, 66, 69, or 72; (2) a VH CDR2 having an amino acid sequence SEQ ID NOS: 8, 11, 14, 17, 36, 39, 42, 45, 64, 67, 70, or 73; and (3) a VH CDR3 having an amino acid sequence of SEQ ID NOS: 9, 12, 15, 18, 37, 40, 43, 46, 65, 68, 71, or 74; and (b) a light chain variable (VL) region including: (1) a VL CDR1 having an amino acid sequence of SEQ ID NOS: 19, 22, 25, 28, 47, 50, 53, 56, 75, 78, 81, or 84; (2) a VL CDR2 having an amino acid sequence of SEQ ID NOS: 20, 23, 26, 29, 48, 51, 54, 57, 76, 79, 82, or 85; and (3) a VL CDR3 having an amino acid sequence of SEQ ID NOS: 21, 24, 27, 30, 49, 52, 55, 58, 77, 80, 83, or 86. The antibody can be a monoclonal antibody. The antibody can be a humanized antibody.

In another aspect, provided herein are molecules having an antigen binding fragment that immunospecifically binds to BTN1A1 or glycosylated BTN1A1 with the following sequence features. In some embodiments, the molecules provided herein have an antigen binding fragment that has (a) a heavy chain variable (VH) region including: (1) a VH CDR1 having an amino acid sequence of SEQ ID NOS: 91, 94, 97, 100, 119, 122, 125, 128, 147, 150, 153, or 156; (2) a VH CDR2 having an amino acid sequence SEQ ID NOS: 92, 95, 98, 101, 120, 123, 126, 129, 148, 151, 154, or 157; and (3) a VH CDR3 having an amino acid sequence of SEQ ID NOS: 93, 96, 99, 102, 121, 124, 127, 130, 149, 152, 155, or 158; and/or (b) a light chain variable (VL) region including: (1) a VL CDR1 having an amino acid sequence of SEQ ID NOS: 103, 106, 109, 112, 131, 134, 137, 140, 159, 162, 165, or 168; (2) a VL CDR2 having an amino acid sequence of SEQ ID NOS: 104, 107, 110, 113, 132, 135, 138, 141, 160, 163, 166, or 169; and (3) a VL CDR3 having an amino acid sequence of SEQ ID NOS: 105, 108, 111, 114, 133, 136, 139, 142, 161, 164, 167, or 170.

In some embodiments, provided herein are antibodies having (a) a heavy chain variable (VH) region including: (1) a VH CDR1 having an amino acid sequence of SEQ ID NOS: 91, 94, 97, 100, 119, 122, 125, 128, 147, 150, 153, or 156; (2) a VH CDR2 having an amino acid sequence SEQ ID NOS: 92, 95, 98, 101, 120, 123, 126, 129, 148, 151, 154, or 157; and (3) a VH CDR3 having an amino acid sequence of SEQ ID NOS: 93, 96, 99, 102, 121, 124, 127, 130, 149, 152, 155, or 158; and (b) a light chain variable (VL) region including: (1) a VL CDR1 having an amino acid sequence of SEQ ID NOS: 103, 106, 109, 112, 131, 134, 137, 140, 159, 162, 165, or 168; (2) a VL CDR2 having an amino acid sequence of SEQ ID NOS: 104, 107, 110, 113, 132, 135, 138, 141, 160, 163, 166, or 169; and (3) a VL CDR3 having an amino acid sequence of SEQ ID NOS: 105, 108, 111, 114, 133, 136, 139, 142, 161, 164, 167, or 170. The antibody can be a monoclonal antibody. The antibody can be a humanized antibody.

Accordingly, provided herein are molecules having an antigen binding fragment that immunospecifically binds to BTN1A1 or glycosylated BTN1A1 with the following sequence features. In some embodiments, the molecules provided herein have an antigen binding fragment that has (a) a heavy chain variable (VH) region including: (1) a VH CDR1 having an amino acid sequence of SEQ ID NOS: 197, 200, 203, or 206; (2) a VH CDR2 having an amino acid sequence SEQ ID NOS: 198, 201, 204, or 207; and (3) a VH CDR3 having an amino acid sequence of SEQ ID NOS: 199, 202, 205, or 208; and/or (b) a light chain variable (VL) region including: (1) a VL CDR1 having an amino acid sequence of SEQ ID NOS: 209, 212, 215, or 218; (2) a VL CDR2 having an amino acid sequence of SEQ ID NOS: 210, 213, 216, or 219; and (3) a VL CDR3 having an amino acid sequence of SEQ ID NOS: 211, 214, 217, or 220.

In some embodiments, provided herein are antibodies having (a) a heavy chain variable (VH) region including: (1) a VH CDR1 having an amino acid sequence of SEQ ID NOS: 197, 200, 203, or 206; (2) a VH CDR2 having an amino acid sequence SEQ ID NOS: 198, 201, 204, or 207; and (3) a VH CDR3 having an amino acid sequence of SEQ ID NOS: 199, 202, 205, or 208; and (b) a light chain variable (VL) region including: (1) a VL CDR1 having an amino acid sequence of SEQ ID NOS: 209, 212, 215, or 218; (2) a VL CDR2 having an amino acid sequence of SEQ ID NOS: 210, 213, 216, or 219; and (3) a VL CDR3 having an amino acid sequence of SEQ ID NOS: 211, 214, 217, or 220. The antibody can be a monoclonal antibody. The antibody can be a humanized antibody.

Accordingly, provided herein are molecules having an antigen binding fragment that immunospecifically binds to BTN1A1 or glycosylated BTN1A1 with the following sequence features. In some embodiments, the molecules provided herein have an antigen binding fragment that has (a) a heavy chain variable (VH) region including: (1) a VH CDR1 having an amino acid sequence of SEQ ID NOS: 225, 228, 231, or 234; (2) a VH CDR2 having an amino acid sequence SEQ ID NOS: 226, 229, 232, or 235; and (3) a VH CDR3 having an amino acid sequence of SEQ ID NOS: 227, 230, 233, or 236; and/or (b) a light chain variable (VL) region including: (1) a VL CDR1 having an amino acid sequence of SEQ ID NOS: 237, 240, 243, or 246; (2) a VL CDR2 having an amino acid sequence of SEQ ID NOS: 238, 241, 244, or 247; and (3) a VL CDR3 having an amino acid sequence of SEQ ID NOS: 239, 242, 245, or 248.

In some embodiments, provided herein are antibodies having (a) a heavy chain variable (VH) region including: (1) a VH CDR1 having an amino acid sequence of SEQ ID NOS: 225, 228, 231, or 234; (2) a VH CDR2 having an amino acid sequence SEQ ID NOS: 226, 229, 232, or 235; and (3) a VH CDR3 having an amino acid sequence of SEQ ID NOS: 227, 230, 233, or 236; and (b) a light chain variable (VL) region including: (1) a VL CDR1 having an amino acid sequence of SEQ ID NOS: 237, 240, 243, or 246; (2) a VL CDR2 having an amino acid sequence of SEQ ID NOS: 238, 241, 244, or 247; and (3) a VL CDR3 having an amino acid sequence of SEQ ID NOS: 239, 242, 245, or 248. The antibody can be a monoclonal antibody. The antibody can be a humanized antibody.

Accordingly, provided herein are molecules having an antigen binding fragment that immunospecifically binds to BTN1A1 or glycosylated BTN1A1 with the following sequence features. In some embodiments, the molecules provided herein have an antigen binding fragment that has (a) a heavy chain variable (VH) region including: (1) a VH CDR1 having an amino acid sequence of SEQ ID NOS: 253, 256, 259, or 262; (2) a VH CDR2 having an amino acid sequence SEQ ID NOS: 254, 257, 260, or 263; and (3) a VH CDR3 having an amino acid sequence of SEQ ID NOS: 255, 258, 261, or 264; and/or (b) a light chain variable (VL) region including: (1) a VL CDR1 having an amino acid sequence of SEQ ID NOS: 265, 268, 271, or 274; (2) a VL CDR2 having an amino acid sequence of SEQ ID NOS: 266, 269, 272, or 275; and (3) a VL CDR3 having an amino acid sequence of SEQ ID NOS: 267, 270, 273, or 276.

In some embodiments, provided herein are antibodies having (a) a heavy chain variable (VH) region including: (1) a VH CDR1 having an amino acid sequence of SEQ ID NOS: 253, 256, 259, or 262; (2) a VH CDR2 having an amino acid sequence SEQ ID NOS: 254, 257, 260, or 263; and (3) a VH CDR3 having an amino acid sequence of SEQ ID NOS: 255, 258, 261, or 264; and (b) a light chain variable (VL) region including: (1) a VL CDR1 having an amino acid sequence of SEQ ID NOS: 265, 268, 271, or 274; (2) a VL CDR2 having an amino acid sequence of SEQ ID NOS: 266, 269, 272, or 275; and (3) a VL CDR3 having an amino acid sequence of SEQ ID NOS: 267, 270, 273, or 276. The antibody can be a monoclonal antibody. The antibody can be a humanized antibody.

Accordingly, provided herein are molecules having an antigen binding fragment that immunospecifically binds to BTN1A1 or glycosylated BTN1A1 with the following sequence features. In some embodiments, the molecules provided herein have an antigen binding fragment that has (a) a heavy chain variable (VH) region including: (1) a VH CDR1 having an amino acid sequence of SEQ ID NOS: 281, 284, 287, or 290; (2) a VH CDR2 having an amino acid sequence SEQ ID NOS: 282, 285, 288, or 291; and (3) a VH CDR3 having an amino acid sequence of SEQ ID NOS: 283, 286, 289, or 292; and/or (b) a light chain variable (VL) region including: (1) a VL CDR1 having an amino acid sequence of SEQ ID NOS: 293, 296, 299, or 302; (2) a VL CDR2 having an amino acid sequence of SEQ ID NOS: 294, 297, 300, or 303; and (3) a VL CDR3 having an amino acid sequence of SEQ ID NOS: 295, 298, 301, or 304.

In some embodiments, provided herein are antibodies having (a) a heavy chain variable (VH) region including: (1) a VH CDR1 having an amino acid sequence of SEQ ID NOS: 281, 284, 287, or 290; (2) a VH CDR2 having an amino acid sequence SEQ ID NOS: 282, 285, 288, or 291; and (3) a VH CDR3 having an amino acid sequence of SEQ ID NOS: 283, 286, 289, or 292; and (b) a light chain variable (VL) region including: (1) a VL CDR1 having an amino acid sequence of SEQ ID NOS: 293, 296, 299, or 302; (2) a VL CDR2 having an amino acid sequence of SEQ ID NOS: 294, 297, 300, or 303; and (3) a VL CDR3 having an amino acid sequence of SEQ ID NOS: 295, 298, 301, or 304. The antibody can be a monoclonal antibody. The antibody can be a humanized antibody.

Accordingly, provided herein are molecules having an antigen binding fragment that immunospecifically binds to BTN1A1 or glycosylated BTN1A1 with the following sequence features. In some embodiments, the molecules provided herein have an antigen binding fragment that has (a) a heavy chain variable (VH) region including: (1) a VH CDR1 having an amino acid sequence of SEQ ID NOS: 309, 312, 315, or 318; (2) a VH CDR2 having an amino acid sequence SEQ ID NOS: 310, 313, 316, or 319; and (3) a VH CDR3 having an amino acid sequence of SEQ ID NOS: 311, 314, 317, or 320; and/or (b) a light chain variable (VL) region including: (1) a VL CDR1 having an amino acid sequence of SEQ ID NOS: 321, 324, 327, or 330; (2) a VL CDR2 having an amino acid sequence of SEQ ID NOS: 322, 325, 328, or 331; and (3) a VL CDR3 having an amino acid sequence of SEQ ID NOS: 323, 326, 329, or 332.

In some embodiments, provided herein are antibodies having (a) a heavy chain variable (VH) region including: (1) a VH CDR1 having an amino acid sequence of SEQ ID NOS: 309, 312, 315, or 318; (2) a VH CDR2 having an amino acid sequence SEQ ID NOS: 310, 313, 316, or 319; and (3) a VH CDR3 having an amino acid sequence of SEQ ID NOS: 311, 314, 317, or 320; and (b) a light chain variable (VL) region including: (1) a VL CDR1 having an amino acid sequence of SEQ ID NOS: 321, 324, 327, or 330; (2) a VL CDR2 having an amino acid sequence of SEQ ID NOS: 322, 325, 328, or 331; and (3) a VL CDR3 having an amino acid sequence of SEQ ID NOS: 323, 326, 329, or 332. The antibody can be a monoclonal antibody. The antibody can be a humanized antibody.

In some embodiments, the molecules provided herein have an antigen binding fragment that has a heavy chain variable (VH) region including: (1) a VH CDR1 having an amino acid sequence of SEQ ID NOS: 7, 10, 13, 16, 35, 38, 41, 44, 63, 66, 69, or 72; (2) a VH CDR2 having an amino acid sequence of SEQ ID NOS: 8, 11, 14, 17, 36, 39, 42, 45, 64, 67, 70, or 73; and/or (3) a VH CDR3 having an amino acid sequence of SEQ ID NOS: 9, 12, 15, 18, 37, 40, 43, 46, 65, 68, 71, or 74. In some embodiments, the heavy chain variable (VH) region includes (1) a VH CDR1 having an amino acid sequence of SEQ ID NOS: 7, 10, 13, 16, 35, 38, 41, 44, 63, 66, 69, or 72; and (2) a VH CDR2 having an amino acid sequence of SEQ ID NOS: 8, 11, 14, 17, 36, 39, 42, 45, 64, 67, 70, or 73. In some embodiments, the heavy chain variable (VH) region includes (1) a VH CDR1 having an amino acid sequence of SEQ ID NOS: 7, 10, 13, 16, 35, 38, 41, 44, 63, 66, 69, or 72; and (3) a VH CDR3 having an amino acid sequence of SEQ ID NOS: 9, 12, 15, 18, 37, 40, 43, 46, 65, 68, 71, or 74. In some embodiments, the molecules provided herein have an antigen binding fragment that has a heavy chain variable (VH) region including: (2) a VH CDR2 having an amino acid sequence of SEQ ID NOS: 8, 11, 14, 17, 36, 39, 42, 45, 64, 67, 70, or 73; and (3) a VH CDR3 having an amino acid sequence of SEQ ID NOS: 9, 12, 15, 18, 37, 40, 43, 46, 65, 68, 71, or 74.

In some embodiments, the molecules provided herein have an antigen binding fragment that has a heavy chain variable (VH) region including: (1) a VH CDR1 having an amino acid sequence of SEQ ID NOS: 91, 94, 97, 100, 119, 122, 125, 128, 147, 150, 153, or 156; (2) a VH CDR2 having an amino acid sequence of SEQ ID NOS: 92, 95, 98, 101, 120, 123, 126, 129, 148, 151, 154, or 157; and/or (3) a VH CDR3 having an amino acid sequence of SEQ ID NOS: 93, 96, 99, 102, 121, 124, 127, 130, 149, 152, 155, or 158. In some embodiments, the heavy chain variable (VH) region includes (1) a VH CDR1 having an amino acid sequence of SEQ ID NOS: 91, 94, 97, 100, 119, 122, 125, 128, 147, 150, 153, or 156; and (2) a VH CDR2 having an amino acid sequence of SEQ ID NOS: 92, 95, 98, 101, 120, 123, 126, 129, 148, 151, 154, or 157. In some embodiments, the heavy chain variable (VH) region includes (1) a VH CDR1 having an amino acid sequence of SEQ ID NOS: 91, 94, 97, 100, 119, 122, 125, 128, 147, 150, 153, or 156; and (3) a VH CDR3 having an amino acid sequence of SEQ ID NOS: 93, 96, 99, 102, 121, 124, 127, 130, 149, 152, 155, or 158. In some embodiments, the molecules provided herein have an antigen binding fragment that has a heavy chain variable (VH) region including: (2) a VH CDR2 having an amino acid sequence of SEQ ID NOS: 92, 95, 98, 101, 120, 123, 126, 129, 148, 151, 154, or 157; and (3) a VH CDR3 having an amino acid sequence of SEQ ID NOS: 93, 96, 99, 102, 121, 124, 127, 130, 149, 152, 155, or 158.

In some embodiments, the molecules provided herein have an antigen binding fragment that has a heavy chain variable (VH) region including: (1) a VH CDR1 having an amino acid sequence of SEQ ID NOS: 197, 200, 203, or 206; (2) a VH CDR2 having an amino acid sequence of SEQ ID NOS: 198, 201, 204, or 207; and/or (3) a VH CDR3 having an amino acid sequence of SEQ ID NOS: 199, 202, 205, or 208. In some embodiments, the heavy chain variable (VH) region includes (1) a VH CDR1 having an amino acid sequence of SEQ ID NOS: 197, 200, 203, or 206; and (2) a VH CDR2 having an amino acid sequence of SEQ ID NOS: 198, 201, 204, or 207. In some embodiments, the heavy chain variable (VH) region includes (1) a VH CDR1 having an amino acid sequence of SEQ ID NOS: 197, 200, 203, or 206; and (3) a VH CDR3 having an amino acid sequence of SEQ ID NOS: 199, 202, 205, or 208. In some embodiments, the molecules provided herein have an antigen binding fragment that has a heavy chain variable (VH) region including: (2) a VH CDR2 having an amino acid sequence of SEQ ID NOS: 198, 201, 204, or 207; and (3) a VH CDR3 having an amino acid sequence of SEQ ID NOS: 199, 202, 205, or 208.

In some embodiments, the molecules provided herein have an antigen binding fragment that has a heavy chain variable (VH) region including: (1) a VH CDR1 having an amino acid sequence of SEQ ID NOS: 225, 228, 231, or 234; (2) a VH CDR2 having an amino acid sequence of SEQ ID NOS: 226, 229, 232, or 235; and/or (3) a VH CDR3 having an amino acid sequence of SEQ ID NOS: 227, 230, 233, or 236. In some embodiments, the heavy chain variable (VH) region includes (1) a VH CDR1 having an amino acid sequence of SEQ ID NOS: 225, 228, 231, or 234; and (2) a VH CDR2 having an amino acid sequence of SEQ ID NOS: 226, 229, 232, or 235. In some embodiments, the heavy chain variable (VH) region includes (1) a VH CDR1 having an amino acid sequence of SEQ ID NOS: 225, 228, 231, or 234; and (3) a VH CDR3 having an amino acid sequence of SEQ ID NOS: 227, 230, 233, or 236. In some embodiments, the molecules provided herein have an antigen binding fragment that has a heavy chain variable (VH) region including: (2) a VH CDR2 having an amino acid sequence of SEQ ID NOS: 226, 229, 232, or 235; and (3) a VH CDR3 having an amino acid sequence of SEQ ID NOS: 227, 230, 233, or 236.

In some embodiments, the molecules provided herein have an antigen binding fragment that has a heavy chain variable (VH) region including: (1) a VH CDR1 having an amino acid sequence of SEQ ID NOS: 253, 256, 259, or 262; (2) a VH CDR2 having an amino acid sequence of SEQ ID NOS: 254, 257, 260, or 263; and/or (3) a VH CDR3 having an amino acid sequence of SEQ ID NOS: 255, 258, 261, or 264. In some embodiments, the heavy chain variable (VH) region includes (1) a VH CDR1 having an amino acid sequence of SEQ ID NOS: 253, 256, 259, or 262; and (2) a VH CDR2 having an amino acid sequence of SEQ ID NOS: 254, 257, 260, or 263. In some embodiments, the heavy chain variable (VH) region includes (1) a VH CDR1 having an amino acid sequence of SEQ ID NOS: 253, 256, 259, or 262; and (3) a VH CDR3 having an amino acid sequence of SEQ ID NOS: 255, 258, 261, or 264. In some embodiments, the molecules provided herein have an antigen binding fragment that has a heavy chain variable (VH) region including: (2) a VH CDR2 having an amino acid sequence of SEQ ID NOS: 254, 257, 260, or 263; and (3) a VH CDR3 having an amino acid sequence of SEQ ID NOS: 255, 258, 261, or 264.

In some embodiments, the molecules provided herein have an antigen binding fragment that has a heavy chain variable (VH) region including: (1) a VH CDR1 having an amino acid sequence of SEQ ID NOS: 281, 284, 287, or 290; (2) a VH CDR2 having an amino acid sequence of SEQ ID NOS: 282, 285, 288, or 291; and/or (3) a VH CDR3 having an amino acid sequence of SEQ ID NOS: 283, 286, 289, or 292. In some embodiments, the heavy chain variable (VH) region includes (1) a VH CDR1 having an amino acid sequence of SEQ ID NOS: 281, 284, 287, or 290; and (2) a VH CDR2 having an amino acid sequence of SEQ ID NOS: 282, 285, 288, or 291. In some embodiments, the heavy chain variable (VH) region includes (1) a VH CDR1 having an amino acid sequence of SEQ ID NOS: 281, 284, 287, or 290; and (3) a VH CDR3 having an amino acid sequence of SEQ ID NOS: 283, 286, 289, or 292. In some embodiments, the molecules provided herein have an antigen binding fragment that has a heavy chain variable (VH) region including: (2) a VH CDR2 having an amino acid sequence of SEQ ID NOS: 282, 285, 288, or 291; and (3) a VH CDR3 having an amino acid sequence of SEQ ID NOS: 283, 286, 289, or 292.

In some embodiments, the molecules provided herein have an antigen binding fragment that has a heavy chain variable (VH) region including: (1) a VH CDR1 having an amino acid sequence of SEQ ID NOS: 309, 312, 315, or 318; (2) a VH CDR2 having an amino acid sequence of SEQ ID NOS: 310, 313, 316, or 319; and/or (3) a VH CDR3 having an amino acid sequence of SEQ ID NOS: 311, 314, 317, or 320. In some embodiments, the heavy chain variable (VH) region includes (1) a VH CDR1 having an amino acid sequence of SEQ ID NOS: 309, 312, 315, or 318; and (2) a VH CDR2 having an amino acid sequence of SEQ ID NOS: 310, 313, 316, or 319. In some embodiments, the heavy chain variable (VH) region includes (1) a VH CDR1 having an amino acid sequence of SEQ ID NOS: 309, 312, 315, or 318; and (3) a VH CDR3 having an amino acid sequence of SEQ ID NOS: 311, 314, 317, or 320. In some embodiments, the molecules provided herein have an antigen binding fragment that has a heavy chain variable (VH) region including: (2) a VH CDR2 having an amino acid sequence of SEQ ID NOS: 310, 313, 316, or 319; and (3) a VH CDR3 having an amino acid sequence of SEQ ID NOS: 311, 314, 317, or 320.

In some embodiments, the molecules provided herein have an antigen binding fragment that has a heavy chain variable (VH) region including a VH CDR1 having an amino acid sequence of SEQ ID NOS: 7, 10, 13, 16, 35, 38, 41, 44, 63, 66, 69, 72, 91, 94, 97, 100, 119, 122, 125, 128, 147, 150, 153, 156, 197, 200, 203, 206, 225, 228, 231, 234, 253, 256, 259, 262, 281, 284, 287, 290, 309, 312, 315, or 318. The VH CDR1 can have an amino acid sequence of SEQ ID NO: 7. The VH CDR1 can have an amino acid sequence of SEQ ID NO: 10. The VH CDR1 can have an amino acid sequence of SEQ ID NO: 13. The VH CDR1 can have an amino acid sequence of SEQ ID NO: 16. The VH CDR1 can have an amino acid sequence of SEQ ID NO: 35. The VH CDR1 can have an amino acid sequence of SEQ ID NO: 38. The VH CDR1 can have an amino acid sequence of SEQ ID NO: 41. The VH CDR1 can have an amino acid sequence of SEQ ID NO: 44. The VH CDR1 can have an amino acid sequence of SEQ ID NO: 63. The VH CDR1 can have an amino acid sequence of SEQ ID NO: 66. The VH CDR1 can have an amino acid sequence of SEQ ID NO: 69. The VH CDR1 can have an amino acid sequence of SEQ ID NO: 72. The VH CDR1 can have an amino acid sequence of SEQ ID NO: 91. The VH CDR1 can have an amino acid sequence of SEQ ID NO: 94. The VH CDR1 can have an amino acid sequence of SEQ ID NO: 97. The VH CDR1 can have an amino acid sequence of SEQ ID NO: 100. The VH CDR1 can have an amino acid sequence of SEQ ID NO: 119. The VH CDR1 can have an amino acid sequence of SEQ ID NO: 122. The VH CDR1 can have an amino acid sequence of SEQ ID NO: 125. The VH CDR1 can have an amino acid sequence of SEQ ID NO: 128. The VH CDR1 can have an amino acid sequence of SEQ ID NO: 147. The VH CDR1 can have an amino acid sequence of SEQ ID NO: 150. The VH CDR1 can have an amino acid sequence of SEQ ID NO: 153. The VH CDR1 can have an amino acid sequence of SEQ ID NO: 156. The VH CDR1 can have an amino acid sequence of SEQ ID NO: 197. The VH CDR1 can have an amino acid sequence of SEQ ID NO: 200. The VH CDR1 can have an amino acid sequence of SEQ ID NO: 203. The VH CDR1 can have an amino acid sequence of SEQ ID NO: 206. The VH CDR1 can have an amino acid sequence of SEQ ID NO: 225. The VH CDR1 can have an amino acid sequence of SEQ ID NO: 228. The VH CDR1 can have an amino acid sequence of SEQ ID NO: 231. The VH CDR1 can have an amino acid sequence of SEQ ID NO: 234. The VH CDR1 can have an amino acid sequence of SEQ ID NO: 253. The VH CDR1 can have an amino acid sequence of SEQ ID NO: 256. The VH CDR1 can have an amino acid sequence of SEQ ID NO: 259. The VH CDR1 can have an amino acid sequence of SEQ ID NO: 262. The VH CDR1 can have an amino acid sequence of SEQ ID NO: 281. The VH CDR1 can have an amino acid sequence of SEQ ID NO: 284. The VH CDR1 can have an amino acid sequence of SEQ ID NO: 287. The VH CDR1 can have an amino acid sequence of SEQ ID NO: 290. The VH CDR1 can have an amino acid sequence of SEQ ID NO: 309. The VH CDR1 can have an amino acid sequence of SEQ ID NO: 312. The VH CDR1 can have an amino acid sequence of SEQ ID NO: 315. The VH CDR1 can have an amino acid sequence of SEQ ID NO: 318.

In some embodiments, the molecules provided herein have an antigen binding fragment that has a heavy chain variable (VH) region including a VH CDR2 having an amino acid sequence of SEQ ID NOS: 8, 11, 14, 17, 36, 39, 42, 45, 64, 67, 70, 73, 92, 95, 98, 101, 120, 123, 126, 129, 148, 151, 154, 157, 198, 201, 204, 207, 226, 229, 232, 235, 254, 257, 260, 263, 282, 285, 288, 291, 310, 313, 316, or 319. The VH CDR2 can have an amino acid sequence of SEQ ID NO: 8. The VH CDR2 can have an amino acid sequence of SEQ ID NO: 11. The VH CDR2 can have an amino acid sequence of SEQ ID NO: 14. The VH CDR2 can have an amino acid sequence of SEQ ID NO: 17. The VH CDR2 can have an amino acid sequence of SEQ ID NO: 36. The VH CDR2 can have an amino acid sequence of SEQ ID NO: 39. The VH CDR2 can have an amino acid sequence of SEQ ID NO: 42. The VH CDR2 can have an amino acid sequence of SEQ ID NO: 45. The VH CDR2 can have an amino acid sequence of SEQ ID NO: 64. The VH CDR2 can have an amino acid sequence of SEQ ID NO: 67. The VH CDR2 can have an amino acid sequence of SEQ ID NO: 70. The VH CDR2 can have an amino acid sequence of SEQ ID NO: 73. The VH CDR2 can have an amino acid sequence of SEQ ID NO: 92. The VH CDR2 can have an amino acid sequence of SEQ ID NO: 95. The VH CDR2 can have an amino acid sequence of SEQ ID NO: 98. The VH CDR2 can have an amino acid sequence of SEQ ID NO: 101. The VH CDR2 can have an amino acid sequence of SEQ ID NO: 120. The VH CDR2 can have an amino acid sequence of SEQ ID NO: 123. The VH CDR2 can have an amino acid sequence of SEQ ID NO: 126. The VH CDR2 can have an amino acid sequence of SEQ ID NO: 129. The VH CDR2 can have an amino acid sequence of SEQ ID NO: 148. The VH CDR2 can have an amino acid sequence of SEQ ID NO: 151. The VH CDR2 can have an amino acid sequence of SEQ ID NO: 154. The VH CDR2 can have an amino acid sequence of SEQ ID NO: 157. The VH CDR2 can have an amino acid sequence of SEQ ID NO: 198. The VH CDR2 can have an amino acid sequence of SEQ ID NO: 201. The VH CDR2 can have an amino acid sequence of SEQ ID NO: 204. The VH CDR2 can have an amino acid sequence of SEQ ID NO: 207. The VH CDR2 can have an amino acid sequence of SEQ ID NO: 226. The VH CDR2 can have an amino acid sequence of SEQ ID NO: 229. The VH CDR2 can have an amino acid sequence of SEQ ID NO: 232. The VH CDR2 can have an amino acid sequence of SEQ ID NO: 235. The VH CDR2 can have an amino acid sequence of SEQ ID NO: 254. The VH CDR2 can have an amino acid sequence of SEQ ID NO: 257. The VH CDR2 can have an amino acid sequence of SEQ ID NO: 260. The VH CDR2 can have an amino acid sequence of SEQ ID NO: 263. The VH CDR2 can have an amino acid sequence of SEQ ID NO: 282. The VH CDR2 can have an amino acid sequence of SEQ ID NO: 285. The VH CDR2 can have an amino acid sequence of SEQ ID NO: 288. The VH CDR2 can have an amino acid sequence of SEQ ID NO: 291. The VH CDR2 can have an amino acid sequence of SEQ ID NO: 310. The VH CDR2 can have an amino acid sequence of SEQ ID NO: 313. The VH CDR2 can have an amino acid sequence of SEQ ID NO: 316. The VH CDR2 can have an amino acid sequence of SEQ ID NO: 319.

In some embodiments, the molecules provided herein have an antigen binding fragment that has a heavy chain variable (VH) region including a VH CDR3 having an amino acid sequence of SEQ ID NOS: 9, 12, 15, 18, 37, 40, 43, 46, 65, 68, 71, 74, 93, 96, 99, 102, 121, 124, 127, 130, 149, 152, 155, 158, 199, 202, 205, 208, 227, 230, 233, 236, 255, 258, 261, 264, 283, 286, 289, 292, 311, 314, 317, or 320. The VH CDR3 can have an amino acid sequence of SEQ ID NO: 9. The VH CDR3 can have an amino acid sequence of SEQ ID NO: 12. The VH CDR3 can have an amino acid sequence of SEQ ID NO: 15. The VH CDR3 can have an amino acid sequence of SEQ ID NO: 20. The VH CDR3 can have an amino acid sequence of SEQ ID NO: 37. The VH CDR3 can have an amino acid sequence of SEQ ID NO: 40. The VH CDR3 can have an amino acid sequence of SEQ ID NO: 43. The VH CDR3 can have an amino acid sequence of SEQ ID NO: 46. The VH CDR3 can have an amino acid sequence of SEQ ID NO: 65. The VH CDR3 can have an amino acid sequence of SEQ ID NO: 68. The VH CDR3 can have an amino acid sequence of SEQ ID NO: 71. The VH CDR3 can have an amino acid sequence of SEQ ID NO: 74. The VH CDR3 can have an amino acid sequence of SEQ ID NO: 93. The VH CDR3 can have an amino acid sequence of SEQ ID NO: 96. The VH CDR3 can have an amino acid sequence of SEQ ID NO: 99. The VH CDR3 can have an amino acid sequence of SEQ ID NO: 102. The VH CDR3 can have an amino acid sequence of SEQ ID NO: 121. The VH CDR3 can have an amino acid sequence of SEQ ID NO: 124. The VH CDR3 can have an amino acid sequence of SEQ ID NO: 127. The VH CDR3 can have an amino acid sequence of SEQ ID NO: 130. The VH CDR3 can have an amino acid sequence of SEQ ID NO: 149. The VH CDR3 can have an amino acid sequence of SEQ ID NO: 152. The VH CDR3 can have an amino acid sequence of SEQ ID NO: 155. The VH CDR3 can have an amino acid sequence of SEQ ID NO: 158. The VH CDR3 can have an amino acid sequence of SEQ ID NO: 199. The VH CDR3 can have an amino acid sequence of SEQ ID NO: 202. The VH CDR3 can have an amino acid sequence of SEQ ID NO: 205. The VH CDR3 can have an amino acid sequence of SEQ ID NO: 208. The VH CDR3 can have an amino acid sequence of SEQ ID NO: 227. The VH CDR3 can have an amino acid sequence of SEQ ID NO: 230. The VH CDR3 can have an amino acid sequence of SEQ ID NO: 233. The VH CDR3 can have an amino acid sequence of SEQ ID NO: 236. The VH CDR3 can have an amino acid sequence of SEQ ID NO: 255. The VH CDR3 can have an amino acid sequence of SEQ ID NO: 258. The VH CDR3 can have an amino acid sequence of SEQ ID NO: 261. The VH CDR3 can have an amino acid sequence of SEQ ID NO: 264. The VH CDR3 can have an amino acid sequence of SEQ ID NO: 283. The VH CDR3 can have an amino acid sequence of SEQ ID NO: 286. The VH CDR3 can have an amino acid sequence of SEQ ID NO: 289. The VH CDR3 can have an amino acid sequence of SEQ ID NO: 292. The VH CDR3 can have an amino acid sequence of SEQ ID NO: 311. The VH CDR3 can have an amino acid sequence of SEQ ID NO: 314. The VH CDR3 can have an amino acid sequence of SEQ ID NO: 317. The VH CDR3 can have an amino acid sequence of SEQ ID NO: 320.

In some embodiments, the molecules provided herein have an antigen binding fragment that has a heavy chain variable (VH) region including: (1) a VH CDR1 having an amino acid sequence of SEQ ID NO: 7; (2) a VH CDR2 having an amino acid sequence of SEQ ID NO: 8; and/or (3) a VH CDR3 having an amino acid sequence of SEQ ID NO: 9.

In some embodiments, the molecules provided herein have an antigen binding fragment that has a heavy chain variable (VH) region including: (1) a VH CDR1 having an amino acid sequence of SEQ ID NO: 10; (2) a VH CDR2 having an amino acid sequence of SEQ ID NO: 11; and/or (3) a VH CDR3 having an amino acid sequence of SEQ ID NO: 12.

In some embodiments, the molecules provided herein have an antigen binding fragment that has a heavy chain variable (VH) region including: (1) a VH CDR1 having an amino acid sequence of SEQ ID NO: 13; (2) a VH CDR2 having an amino acid sequence of SEQ ID NO: 14; and/or (3) a VH CDR3 having an amino acid sequence of SEQ ID NO: 15.

In some embodiments, the molecules provided herein have an antigen binding fragment that has a heavy chain variable (VH) region including: (1) a VH CDR1 having an amino acid sequence of SEQ ID NO: 16; (2) a VH CDR2 having an amino acid sequence of SEQ ID NO: 17; and/or (3) a VH CDR3 having an amino acid sequence of SEQ ID NO: 18.

In some embodiments, the molecules provided herein have an antigen binding fragment that has a heavy chain variable (VH) region including: (1) a VH CDR1 having an amino acid sequence of SEQ ID NO: 35; (2) a VH CDR2 having an amino acid sequence of SEQ ID NO: 36; and/or (3) a VH CDR3 having an amino acid sequence of SEQ ID NO: 37.

In some embodiments, the molecules provided herein have an antigen binding fragment that has a heavy chain variable (VH) region including: (1) a VH CDR1 having an amino acid sequence of SEQ ID NO: 38; (2) a VH CDR2 having an amino acid sequence of SEQ ID NO: 39; and/or (3) a VH CDR3 having an amino acid sequence of SEQ ID NO: 40.

In some embodiments, the molecules provided herein have an antigen binding fragment that has a heavy chain variable (VH) region including: (1) a VH CDR1 having an amino acid sequence of SEQ ID NO: 41; (2) a VH CDR2 having an amino acid sequence of SEQ ID NO: 42; and/or (3) a VH CDR3 having an amino acid sequence of SEQ ID NO: 43.

In some embodiments, the molecules provided herein have an antigen binding fragment that has a heavy chain variable (VH) region including: (1) a VH CDR1 having an amino acid sequence of SEQ ID NO: 44; (2) a VH CDR2 having an amino acid sequence of SEQ ID NO: 45; and/or (3) a VH CDR3 having an amino acid sequence of SEQ ID NO: 46.

In some embodiments, the molecules provided herein have an antigen binding fragment that has a heavy chain variable (VH) region including: (1) a VH CDR1 having an amino acid sequence of SEQ ID NO: 63; (2) a VH CDR2 having an amino acid sequence of SEQ ID NO: 64; and/or (3) a VH CDR3 having an amino acid sequence of SEQ ID NO: 65.

In some embodiments, the molecules provided herein have an antigen binding fragment that has a heavy chain variable (VH) region including: (1) a VH CDR1 having an amino acid sequence of SEQ ID NO: 66; (2) a VH CDR2 having an amino acid sequence of SEQ ID NO: 67; and/or (3) a VH CDR3 having an amino acid sequence of SEQ ID NO: 68.

In some embodiments, the molecules provided herein have an antigen binding fragment that has a heavy chain variable (VH) region including: (1) a VH CDR1 having an amino acid sequence of SEQ ID NO: 69; (2) a VH CDR2 having an amino acid sequence of SEQ ID NO: 70; and/or (3) a VH CDR3 having an amino acid sequence of SEQ ID NO: 71.

In some embodiments, the molecules provided herein have an antigen binding fragment that has a heavy chain variable (VH) region including: (1) a VH CDR1 having an amino acid sequence of SEQ ID NO: 72; (2) a VH CDR2 having an amino acid sequence of SEQ ID NO: 73; and/or (3) a VH CDR3 having an amino acid sequence of SEQ ID NO: 74.

In some embodiments, the molecules provided herein have an antigen binding fragment that has a heavy chain variable (VH) region including: (1) a VH CDR1 having an amino acid sequence of SEQ ID NO: 91; (2) a VH CDR2 having an amino acid sequence of SEQ ID NO: 92; and/or (3) a VH CDR3 having an amino acid sequence of SEQ ID NO: 93.

In some embodiments, the molecules provided herein have an antigen binding fragment that has a heavy chain variable (VH) region including: (1) a VH CDR1 having an amino acid sequence of SEQ ID NO: 94; (2) a VH CDR2 having an amino acid sequence of SEQ ID NO: 95; and/or (3) a VH CDR3 having an amino acid sequence of SEQ ID NO: 96.

In some embodiments, the molecules provided herein have an antigen binding fragment that has a heavy chain variable (VH) region including: (1) a VH CDR1 having an amino acid sequence of SEQ ID NO: 97; (2) a VH CDR2 having an amino acid sequence of SEQ ID NO: 98; and/or (3) a VH CDR3 having an amino acid sequence of SEQ ID NO: 99.

In some embodiments, the molecules provided herein have an antigen binding fragment that has a heavy chain variable (VH) region including: (1) a VH CDR1 having an amino acid sequence of SEQ ID NO: 100; (2) a VH CDR2 having an amino acid sequence of SEQ ID NO: 101; and/or (3) a VH CDR3 having an amino acid sequence of SEQ ID NO: 102.

In some embodiments, the molecules provided herein have an antigen binding fragment that has a heavy chain variable (VH) region including: (1) a VH CDR1 having an amino acid sequence of SEQ ID NO: 119; (2) a VH CDR2 having an amino acid sequence of SEQ ID NO: 120; and/or (3) a VH CDR3 having an amino acid sequence of SEQ ID NO: 121.

In some embodiments, the molecules provided herein have an antigen binding fragment that has a heavy chain variable (VH) region including: (1) a VH CDR1 having an amino acid sequence of SEQ ID NO: 122; (2) a VH CDR2 having an amino acid sequence of SEQ ID NO: 123; and/or (3) a VH CDR3 having an amino acid sequence of SEQ ID NO: 124.

In some embodiments, the molecules provided herein have an antigen binding fragment that has a heavy chain variable (VH) region including: (1) a VH CDR1 having an amino acid sequence of SEQ ID NO: 125; (2) a VH CDR2 having an amino acid sequence of SEQ ID NO: 126; and/or (3) a VH CDR3 having an amino acid sequence of SEQ ID NO: 127.

In some embodiments, the molecules provided herein have an antigen binding fragment that has a heavy chain variable (VH) region including: (1) a VH CDR1 having an amino acid sequence of SEQ ID NO: 128; (2) a VH CDR2 having an amino acid sequence of SEQ ID NO: 129; and/or (3) a VH CDR3 having an amino acid sequence of SEQ ID NO: 130.

In some embodiments, the molecules provided herein have an antigen binding fragment that has a heavy chain variable (VH) region including: (1) a VH CDR1 having an amino acid sequence of SEQ ID NO: 147; (2) a VH CDR2 having an amino acid sequence of SEQ ID NO: 148; and/or (3) a VH CDR3 having an amino acid sequence of SEQ ID NO: 149.

In some embodiments, the molecules provided herein have an antigen binding fragment that has a heavy chain variable (VH) region including: (1) a VH CDR1 having an amino acid sequence of SEQ ID NO: 150; (2) a VH CDR2 having an amino acid sequence of SEQ ID NO: 151; and/or (3) a VH CDR3 having an amino acid sequence of SEQ ID NO: 152.

In some embodiments, the molecules provided herein have an antigen binding fragment that has a heavy chain variable (VH) region including: (1) a VH CDR1 having an amino acid sequence of SEQ ID NO: 153; (2) a VH CDR2 having an amino acid sequence of SEQ ID NO: 154; and/or (3) a VH CDR3 having an amino acid sequence of SEQ ID NO: 155.

In some embodiments, the molecules provided herein have an antigen binding fragment that has a heavy chain variable (VH) region including: (1) a VH CDR1 having an amino acid sequence of SEQ ID NO: 156; (2) a VH CDR2 having an amino acid sequence of SEQ ID NO: 157; and/or (3) a VH CDR3 having an amino acid sequence of SEQ ID NO: 158.

In some embodiments, the molecules provided herein have an antigen binding fragment that has a heavy chain variable (VH) region including: (1) a VH CDR1 having an amino acid sequence of SEQ ID NO: 197; (2) a VH CDR2 having an amino acid sequence of SEQ ID NO: 198; and/or (3) a VH CDR3 having an amino acid sequence of SEQ ID NO: 199.

In some embodiments, the molecules provided herein have an antigen binding fragment that has a heavy chain variable (VH) region including: (1) a VH CDR1 having an amino acid sequence of SEQ ID NO: 200; (2) a VH CDR2 having an amino acid sequence of SEQ ID NO: 201; and/or (3) a VH CDR3 having an amino acid sequence of SEQ ID NO: 202.

In some embodiments, the molecules provided herein have an antigen binding fragment that has a heavy chain variable (VH) region including: (1) a VH CDR1 having an amino acid sequence of SEQ ID NO: 203; (2) a VH CDR2 having an amino acid sequence of SEQ ID NO: 204; and/or (3) a VH CDR3 having an amino acid sequence of SEQ ID NO: 205.

In some embodiments, the molecules provided herein have an antigen binding fragment that has a heavy chain variable (VH) region including: (1) a VH CDR1 having an amino acid sequence of SEQ ID NO: 206; (2) a VH CDR2 having an amino acid sequence of SEQ ID NO: 207; and/or (3) a VH CDR3 having an amino acid sequence of SEQ ID NO: 208.

In some embodiments, the molecules provided herein have an antigen binding fragment that has a heavy chain variable (VH) region including: (1) a VH CDR1 having an amino acid sequence of SEQ ID NO: 225; (2) a VH CDR2 having an amino acid sequence of SEQ ID NO: 226; and/or (3) a VH CDR3 having an amino acid sequence of SEQ ID NO: 227.

In some embodiments, the molecules provided herein have an antigen binding fragment that has a heavy chain variable (VH) region including: (1) a VH CDR1 having an amino acid sequence of SEQ ID NO: 228; (2) a VH CDR2 having an amino acid sequence of SEQ ID NO: 229; and/or (3) a VH CDR3 having an amino acid sequence of SEQ ID NO: 230.

In some embodiments, the molecules provided herein have an antigen binding fragment that has a heavy chain variable (VH) region including: (1) a VH CDR1 having an amino acid sequence of SEQ ID NO: 231; (2) a VH CDR2 having an amino acid sequence of SEQ ID NO: 232; and/or (3) a VH CDR3 having an amino acid sequence of SEQ ID NO: 233.

In some embodiments, the molecules provided herein have an antigen binding fragment that has a heavy chain variable (VH) region including: (1) a VH CDR1 having an amino acid sequence of SEQ ID NO: 234; (2) a VH CDR2 having an amino acid sequence of SEQ ID NO: 235; and/or (3) a VH CDR3 having an amino acid sequence of SEQ ID NO: 236.

In some embodiments, the molecules provided herein have an antigen binding fragment that has a heavy chain variable (VH) region including: (1) a VH CDR1 having an amino acid sequence of SEQ ID NO: 253; (2) a VH CDR2 having an amino acid sequence of SEQ ID NO: 254; and/or (3) a VH CDR3 having an amino acid sequence of SEQ ID NO: 255.

In some embodiments, the molecules provided herein have an antigen binding fragment that has a heavy chain variable (VH) region including: (1) a VH CDR1 having an amino acid sequence of SEQ ID NO: 256; (2) a VH CDR2 having an amino acid sequence of SEQ ID NO: 257; and/or (3) a VH CDR3 having an amino acid sequence of SEQ ID NO: 258.

In some embodiments, the molecules provided herein have an antigen binding fragment that has a heavy chain variable (VH) region including: (1) a VH CDR1 having an amino acid sequence of SEQ ID NO: 259; (2) a VH CDR2 having an amino acid sequence of SEQ ID NO: 260; and/or (3) a VH CDR3 having an amino acid sequence of SEQ ID NO: 261.

In some embodiments, the molecules provided herein have an antigen binding fragment that has a heavy chain variable (VH) region including: (1) a VH CDR1 having an amino acid sequence of SEQ ID NO: 262; (2) a VH CDR2 having an amino acid sequence of SEQ ID NO: 263; and/or (3) a VH CDR3 having an amino acid sequence of SEQ ID NO: 264.

In some embodiments, the molecules provided herein have an antigen binding fragment that has a heavy chain variable (VH) region including: (1) a VH CDR1 having an amino acid sequence of SEQ ID NO: 281; (2) a VH CDR2 having an amino acid sequence of SEQ ID NO: 282; and/or (3) a VH CDR3 having an amino acid sequence of SEQ ID NO: 283.

In some embodiments, the molecules provided herein have an antigen binding fragment that has a heavy chain variable (VH) region including: (1) a VH CDR1 having an amino acid sequence of SEQ ID NO: 284; (2) a VH CDR2 having an amino acid sequence of SEQ ID NO: 285; and/or (3) a VH CDR3 having an amino acid sequence of SEQ ID NO: 286.

In some embodiments, the molecules provided herein have an antigen binding fragment that has a heavy chain variable (VH) region including: (1) a VH CDR1 having an amino acid sequence of SEQ ID NO: 287; (2) a VH CDR2 having an amino acid sequence of SEQ ID NO: 288; and/or (3) a VH CDR3 having an amino acid sequence of SEQ ID NO: 289.

In some embodiments, the molecules provided herein have an antigen binding fragment that has a heavy chain variable (VH) region including: (1) a VH CDR1 having an amino acid sequence of SEQ ID NO: 290; (2) a VH CDR2 having an amino acid sequence of SEQ ID NO: 291; and/or (3) a VH CDR3 having an amino acid sequence of SEQ ID NO: 292.

In some embodiments, the molecules provided herein have an antigen binding fragment that has a heavy chain variable (VH) region including: (1) a VH CDR1 having an amino acid sequence of SEQ ID NO: 309; (2) a VH CDR2 having an amino acid sequence of SEQ ID NO: 310; and/or (3) a VH CDR3 having an amino acid sequence of SEQ ID NO: 311.

In some embodiments, the molecules provided herein have an antigen binding fragment that has a heavy chain variable (VH) region including: (1) a VH CDR1 having an amino acid sequence of SEQ ID NO: 312; (2) a VH CDR2 having an amino acid sequence of SEQ ID NO: 313; and/or (3) a VH CDR3 having an amino acid sequence of SEQ ID NO: 314.

In some embodiments, the molecules provided herein have an antigen binding fragment that has a heavy chain variable (VH) region including: (1) a VH CDR1 having an amino acid sequence of SEQ ID NO: 315; (2) a VH CDR2 having an amino acid sequence of SEQ ID NO: 316; and/or (3) a VH CDR3 having an amino acid sequence of SEQ ID NO: 317.

In some embodiments, the molecules provided herein have an antigen binding fragment that has a heavy chain variable (VH) region including: (1) a VH CDR1 having an amino acid sequence of SEQ ID NO: 318; (2) a VH CDR2 having an amino acid sequence of SEQ ID NO: 319; and/or (3) a VH CDR3 having an amino acid sequence of SEQ ID NO: 320.

In some embodiments, the molecules provided herein have an antigen binding fragment that has a heavy chain variable (VH) region that has the amino acid sequence of SEQ ID NO: 3. The molecule can be an antibody. The antibody can be a monoclonal antibody. The antibody can be a humanized antibody.

In some embodiments, the molecules provided herein have an antigen binding fragment that has a heavy chain variable (VH) region that has the amino acid sequence of SEQ ID NO: 31. The molecule can be an antibody. The antibody can be a monoclonal antibody. The antibody can be a humanized antibody.

In some embodiments, the molecules provided herein have an antigen binding fragment that has a heavy chain variable (VH) region that has the amino acid sequence of SEQ ID NO: 59. The molecule can be an antibody. The antibody can be a monoclonal antibody. The antibody can be a humanized antibody.

In some embodiments, the molecules provided herein have an antigen binding fragment that has a heavy chain variable (VH) region that has the amino acid sequence of SEQ ID NO: 87. The molecule can be an antibody. The antibody can be a monoclonal antibody. The antibody can be a humanized antibody.

In some embodiments, the molecules provided herein have an antigen binding fragment that has a heavy chain variable (VH) region that has the amino acid sequence of SEQ ID NO: 115. The molecule can be an antibody. The antibody can be a monoclonal antibody. The antibody can be a humanized antibody.

In some embodiments, the molecules provided herein have an antigen binding fragment that has a heavy chain variable (VH) region that has the amino acid sequence of SEQ ID NO: 143. The molecule can be an antibody. The antibody can be a monoclonal antibody. The antibody can be a humanized antibody.

In some embodiments, the molecules provided herein have an antigen binding fragment that has a heavy chain variable (VH) region that has the amino acid sequence of SEQ ID NO: 193. The molecule can be an antibody. The antibody can be a monoclonal antibody. The antibody can be a humanized antibody.

In some embodiments, the molecules provided herein have an antigen binding fragment that has a heavy chain variable (VH) region that has the amino acid sequence of SEQ ID NO: 221. The molecule can be an antibody. The antibody can be a monoclonal antibody. The antibody can be a humanized antibody.

In some embodiments, the molecules provided herein have an antigen binding fragment that has a heavy chain variable (VH) region that has the amino acid sequence of SEQ ID NO: 249. The molecule can be an antibody. The antibody can be a monoclonal antibody. The antibody can be a humanized antibody.

In some embodiments, the molecules provided herein have an antigen binding fragment that has a heavy chain variable (VH) region that has the amino acid sequence of SEQ ID NO: 277. The molecule can be an antibody. The antibody can be a monoclonal antibody. The antibody can be a humanized antibody.

In some embodiments, the molecules provided herein have an antigen binding fragment that has a heavy chain variable (VH) region that has the amino acid sequence of SEQ ID NO: 305. The molecule can be an antibody. The antibody can be a monoclonal antibody. The antibody can be a humanized antibody.

In some embodiments, the molecules provided herein have an antigen binding fragment that has a light chain variable (VL) region including: (1) a VL CDR1 having an amino acid sequence of SEQ ID NOS: 19, 22, 25, 28, 47, 50, 53, 56, 75, 78, 81, or 84; (2) a VL CDR2 having an amino acid sequence of SEQ ID NOS: 20, 23, 26, 29, 48, 51, 54, 57, 76, 79, 82, or 85; and/or (3) a VL CDR3 having an amino acid sequence of SEQ ID NOS: 21, 24, 27, 30, 49, 52, 55, 58, 77, 80, 83, or 86.

In some embodiments, the molecules provided herein have an antigen binding fragment that has a light chain variable (VL) region including: (1) a VL CDR1 having an amino acid sequence of SEQ ID NOS: 103, 106, 109, 112, 131, 134, 137, 140, 159, 162, 165, or 168; (2) a VL CDR2 having an amino acid sequence of SEQ ID NOS: 104, 107, 110, 113, 132, 135, 138, 141, 160, 163, 166, or 169; and/or (3) a VL CDR3 having an amino acid sequence of SEQ ID NOS: 105, 108, 111, 114, 133, 136, 139, 142, 161, 164, 167, or 170.

In some embodiments, the molecules provided herein have an antigen binding fragment that has a light chain variable (VL) region including: (1) a VL CDR1 having an amino acid sequence of SEQ ID NOS: 209, 212, 215, or 218; (2) a VL CDR2 having an amino acid sequence of SEQ ID NOS: 210, 213, 216, or 219; and/or (3) a VL CDR3 having an amino acid sequence of SEQ ID NOS: 211, 214, 217, or 220.

In some embodiments, the molecules provided herein have an antigen binding fragment that has a light chain variable (VL) region including: (1) a VL CDR1 having an amino acid sequence of SEQ ID NOS: 237, 240, 243, or 246; (2) a VL CDR2 having an amino acid sequence of SEQ ID NOS: 238, 241, 244, or 247; and/or (3) a VL CDR3 having an amino acid sequence of SEQ ID NOS: 239, 242, 245, or 248.

In some embodiments, the molecules provided herein have an antigen binding fragment that has a light chain variable (VL) region including: (1) a VL CDR1 having an amino acid sequence of SEQ ID NOS: 265, 268, 271, or 274; (2) a VL CDR2 having an amino acid sequence of SEQ ID NOS: 266, 269, 272, or 275; and/or (3) a VL CDR3 having an amino acid sequence of SEQ ID NOS: 267, 270, 273, or 276.

In some embodiments, the molecules provided herein have an antigen binding fragment that has a light chain variable (VL) region including: (1) a VL CDR1 having an amino acid sequence of SEQ ID NOS: 293, 296, 299, or 302; (2) a VL CDR2 having an amino acid sequence of SEQ ID NOS: 294, 297, 300, or 303; and/or (3) a VL CDR3 having an amino acid sequence of SEQ ID NOS: 295, 298, 301, or 304.

In some embodiments, the molecules provided herein have an antigen binding fragment that has a light chain variable (VL) region including: (1) a VL CDR1 having an amino acid sequence of SEQ ID NOS: 321, 324, 327, or 330; (2) a VL CDR2 having an amino acid sequence of SEQ ID NOS: 322, 325, 328, or 331; and/or (3) a VL CDR3 having an amino acid sequence of SEQ ID NOS: 323, 326, 329, or 332.

In some embodiments, the molecules provided herein have an antigen binding fragment that has a light chain variable (VL) region including: (1) a VL CDR1 having an amino acid sequence of SEQ ID NOS: 19, 22, 25, 28, 47, 50, 53, 56, 75, 78, 81, or 84; and (2) a VL CDR2 having an amino acid sequence of SEQ ID NOS: 20, 23, 26, 29, 48, 51, 54, 57, 76, 79, 82, or 85. In some embodiments, the molecules provided herein have an antigen binding fragment that has a light chain variable (VL) region including: (1) a VL CDR1 having an amino acid sequence of SEQ ID NOS: 19, 22, 25, 28, 47, 50, 53, 56, 75, 78, 81, or 84; and (3) a VL CDR3 having an amino acid sequence of SEQ ID NOS: 21, 24, 27, 30, 49, 52, 55, 58, 77, 80, 83, or 86. In some embodiments, the molecules provided herein have an antigen binding fragment that has a light chain variable (VL) region including: (2) a VL CDR2 having an amino acid sequence of SEQ ID NOS: 20, 23, 26, 29, 48, 51, 54, 57, 76, 79, 82, or 85; and (3) a VL CDR3 having an amino acid sequence of SEQ ID NOS: 21, 24, 27, 30, 49, 52, 55, 58, 77, 80, 83, or 86.

In some embodiments, the molecules provided herein have an antigen binding fragment that has a light chain variable (VL) region including: (1) a VL CDR1 having an amino acid sequence of SEQ ID NOS: 103, 106, 109, 112, 131, 134, 137, 140, 159, 162, 165, or 168; and (2) a VL CDR2 having an amino acid sequence of SEQ ID NOS: 104, 107, 110, 113, 132, 135, 138, 141, 160, 163, 166, or 169. In some embodiments, the molecules provided herein have an antigen binding fragment that has a light chain variable (VL) region including: (1) a VL CDR1 having an amino acid sequence of SEQ ID NOS: 103, 106, 109, 112, 131, 134, 137, 140, 159, 162, 165, or 168; and (3) a VL CDR3 having an amino acid sequence of SEQ ID NOS: 105, 108, 111, 114, 133, 136, 139, 142, 161, 164, 167, or 170. In some embodiments, the molecules provided herein have an antigen binding fragment that has a light chain variable (VL) region including: (2) a VL CDR2 having an amino acid sequence of SEQ ID NOS: 104, 107, 110, 113, 132, 135, 138, 141, 160, 163, 166, or 169; and (3) a VL CDR3 having an amino acid sequence of SEQ ID NOS: 105, 108, 111, 114, 133, 136, 139, 142, 161, 164, 167, or 170.

In some embodiments, the molecules provided herein have an antigen binding fragment that has a light chain variable (VL) region including: (1) a VL CDR1 having an amino acid sequence of SEQ ID NOS: 209, 212, 215, or 21; and (2) a VL CDR2 having an amino acid sequence of SEQ ID NOS: 210, 213, 216, or 219. In some embodiments, the molecules provided herein have an antigen binding fragment that has a light chain variable (VL) region including: (1) a VL CDR1 having an amino acid sequence of SEQ ID NOS: 209, 212, 215, or 21; and (3) a VL CDR3 having an amino acid sequence of SEQ ID NOS: 211, 214, 217, or 220. In some embodiments, the molecules provided herein have an antigen binding fragment that has a light chain variable (VL) region including: (2) a VL CDR2 having an amino acid sequence of SEQ ID NOS: 210, 213, 216, or 219; and (3) a VL CDR3 having an amino acid sequence of SEQ ID NOS: 211, 214, 217, or 220.

In some embodiments, the molecules provided herein have an antigen binding fragment that has a light chain variable (VL) region including: (1) a VL CDR1 having an amino acid sequence of SEQ ID NOS: 237, 240, 243, or 246; and (2) a VL CDR2 having an amino acid sequence of SEQ ID NOS: 238, 241, 244, or 247. In some embodiments, the molecules provided herein have an antigen binding fragment that has a light chain variable (VL) region including: (1) a VL CDR1 having an amino acid sequence of SEQ ID NOS: 237, 240, 243, or 246; and (3) a VL CDR3 having an amino acid sequence of SEQ ID NOS: 239, 242, 245, or 248. In some embodiments, the molecules provided herein have an antigen binding fragment that has a light chain variable (VL) region including: (2) a VL CDR2 having an amino acid sequence of SEQ ID NOS: 238, 241, 244, or 247; and (3) a VL CDR3 having an amino acid sequence of SEQ ID NOS: 239, 242, 245, or 248.

In some embodiments, the molecules provided herein have an antigen binding fragment that has a light chain variable (VL) region including: (1) a VL CDR1 having an amino acid sequence of SEQ ID NOS: 265, 268, 271, or 274; and (2) a VL CDR2 having an amino acid sequence of SEQ ID NOS: 266, 269, 272, or 275. In some embodiments, the molecules provided herein have an antigen binding fragment that has a light chain variable (VL) region including: (1) a VL CDR1 having an amino acid sequence of SEQ ID NOS: 265, 268, 271, or 274; and (3) a VL CDR3 having an amino acid sequence of SEQ ID NOS: 267, 270, 273, or 276. In some embodiments, the molecules provided herein have an antigen binding fragment that has a light chain variable (VL) region including: (2) a VL CDR2 having an amino acid sequence of SEQ ID NOS: 266, 269, 272, or 275; and (3) a VL CDR3 having an amino acid sequence of SEQ ID NOS: 267, 270, 273, or 276.

In some embodiments, the molecules provided herein have an antigen binding fragment that has a light chain variable (VL) region including: (1) a VL CDR1 having an amino acid sequence of SEQ ID NOS: 293, 296, 299, or 302; and (2) a VL CDR2 having an amino acid sequence of SEQ ID NOS: 294, 297, 300, or 303. In some embodiments, the molecules provided herein have an antigen binding fragment that has a light chain variable (VL) region including: (1) a VL CDR1 having an amino acid sequence of SEQ ID NOS: 293, 296, 299, or 302; and (3) a VL CDR3 having an amino acid sequence of SEQ ID NOS: 295, 298, 301, or 304. In some embodiments, the molecules provided herein have an antigen binding fragment that has a light chain variable (VL) region including: (2) a VL CDR2 having an amino acid sequence of SEQ ID NOS: 294, 297, 300, or 303; and (3) a VL CDR3 having an amino acid sequence of SEQ ID NOS: 295, 298, 301, or 304.

In some embodiments, the molecules provided herein have an antigen binding fragment that has a light chain variable (VL) region including: (1) a VL CDR1 having an amino acid sequence of SEQ ID NOS: 321, 324, 327, or 330; and (2) a VL CDR2 having an amino acid sequence of SEQ ID NOS: 322, 325, 328, or 331. In some embodiments, the molecules provided herein have an antigen binding fragment that has a light chain variable (VL) region including: (1) a VL CDR1 having an amino acid sequence of SEQ ID NOS: 321, 324, 327, or 330; and (3) a VL CDR3 having an amino acid sequence of SEQ ID NOS: 323, 326, 329, or 332. In some embodiments, the molecules provided herein have an antigen binding fragment that has a light chain variable (VL) region including: (2) a VL CDR2 having an amino acid sequence of SEQ ID NOS: 322, 325, 328, or 331; and (3) a VL CDR3 having an amino acid sequence of SEQ ID NOS: 323, 326, 329, or 332.

In some embodiments, the molecules provided herein have an antigen binding fragment that has a light chain variable (VL) region including a VL CDR1 having an amino acid sequence of SEQ ID NOS: 19, 22, 25, 28, 47, 50, 53, 56, 75, 78, 81, 84, 103, 106, 109, 112, 131, 134, 137, 140, 159, 162, 165, 168, 209, 212, 215, 218, 237, 240, 243, 246, 265, 268, 271, 274, 293, 296, 299, 302, 321, 324, 327, or 330. The VL CDR1 can have an amino acid sequence of SEQ ID NO: 19. The VL CDR1 can have an amino acid sequence of SEQ ID NO: 22. The VL CDR1 can have an amino acid sequence of SEQ ID NO: 25. The VL CDR1 can have an amino acid sequence of SEQ ID NO: 28. The VL CDR1 can have an amino acid sequence of SEQ ID NO: 47. The VL CDR1 can have an amino acid sequence of SEQ ID NO: 50. The VL CDR1 can have an amino acid sequence of SEQ ID NO: 53. The VL CDR1 can have an amino acid sequence of SEQ ID NO: 56. The VL CDR1 can have an amino acid sequence of SEQ ID NO: 75. The VL CDR1 can have an amino acid sequence of SEQ ID NO: 78. The VL CDR1 can have an amino acid sequence of SEQ ID NO: 81. The VL CDR1 can have an amino acid sequence of SEQ ID NO: 84. The VL CDR1 can have an amino acid sequence of SEQ ID NO: 103. The VL CDR1 can have an amino acid sequence of SEQ ID NO: 106. The VL CDR1 can have an amino acid sequence of SEQ ID NO: 109. The VL CDR1 can have an amino acid sequence of SEQ ID NO: 112. The VL CDR1 can have an amino acid sequence of SEQ ID NO: 131. The VL CDR1 can have an amino acid sequence of SEQ ID NO: 134. The VL CDR1 can have an amino acid sequence of SEQ ID NO: 137. The VL CDR1 can have an amino acid sequence of SEQ ID NO: 140. The VL CDR1 can have an amino acid sequence of SEQ ID NO: 159. The VL CDR1 can have an amino acid sequence of SEQ ID NO: 162. The VL CDR1 can have an amino acid sequence of SEQ ID NO: 165. The VL CDR1 can have an amino acid sequence of SEQ ID NO: 168. The VL CDR1 can have an amino acid sequence of SEQ ID NO: 209. The VL CDR1 can have an amino acid sequence of SEQ ID NO: 212. The VL CDR1 can have an amino acid sequence of SEQ ID NO: 215. The VL CDR1 can have an amino acid sequence of SEQ ID NO: 218. The VL CDR1 can have an amino acid sequence of SEQ ID NO: 237. The VL CDR1 can have an amino acid sequence of SEQ ID NO: 162408. The VL CDR1 can have an amino acid sequence of SEQ ID NO: 243. The VL CDR1 can have an amino acid sequence of SEQ ID NO: 246. The VL CDR1 can have an amino acid sequence of SEQ ID NO: 265. The VL CDR1 can have an amino acid sequence of SEQ ID NO: 268. The VL CDR1 can have an amino acid sequence of SEQ ID NO: 271. The VL CDR1 can have an amino acid sequence of SEQ ID NO: 274. The VL CDR1 can have an amino acid sequence of SEQ ID NO: 293. The VL CDR1 can have an amino acid sequence of SEQ ID NO: 296. The VL CDR1 can have an amino acid sequence of SEQ ID NO: 299. The VL CDR1 can have an amino acid sequence of SEQ ID NO: 302. The VL CDR1 can have an amino acid sequence of SEQ ID NO: 321. The VL CDR1 can have an amino acid sequence of SEQ ID NO: 324. The VL CDR1 can have an amino acid sequence of SEQ ID NO: 327. The VL CDR1 can have an amino acid sequence of SEQ ID NO: 330.

In some embodiments, the molecules provided herein have an antigen binding fragment that has a light chain variable (VL) region including a VL CDR2 having an amino acid sequence of SEQ ID NOS: 20, 23, 26, 29, 48, 51, 54, 57, 76, 79, 82, 85, 104, 107, 110, 113, 132, 135, 138, 141, 160, 163, 166, 169, 210, 213, 216, 219, 238, 241, 244, 247, 266, 269, 272, 275, 294, 297, 300, 303, 322, 325, 328, or 331. The VL CDR2 can have an amino acid sequence of SEQ ID NO:20. The VL CDR2 can have an amino acid sequence of SEQ ID NO: 23. The VL CDR2 can have an amino acid sequence of SEQ ID NO: 26. The VL CDR2 can have an amino acid sequence of SEQ ID NO: 29. The VL CDR2 can have an amino acid sequence of SEQ ID NO: 48. The VL CDR2 can have an amino acid sequence of SEQ ID NO: 51. The VL CDR2 can have an amino acid sequence of SEQ ID NO: 54. The VL CDR2 can have an amino acid sequence of SEQ ID NO: 57. The VL CDR2 can have an amino acid sequence of SEQ ID NO: 76. The VL CDR2 can have an amino acid sequence of SEQ ID NO: 79. The VL CDR2 can have an amino acid sequence of SEQ ID NO: 82. The VL CDR2 can have an amino acid sequence of SEQ ID NO: 85. The VL CDR2 can have an amino acid sequence of SEQ ID NO: 104. The VL CDR2 can have an amino acid sequence of SEQ ID NO: 107. The VL CDR2 can have an amino acid sequence of SEQ ID NO: 110. The VL CDR2 can have an amino acid sequence of SEQ ID NO: 113. The VL CDR2 can have an amino acid sequence of SEQ ID NO: 132. The VL CDR2 can have an amino acid sequence of SEQ ID NO: 135. The VL CDR2 can have an amino acid sequence of SEQ ID NO: 138. The VL CDR2 can have an amino acid sequence of SEQ ID NO: 141. The VL CDR2 can have an amino acid sequence of SEQ ID NO: 160. The VL CDR2 can have an amino acid sequence of SEQ ID NO: 163. The VL CDR2 can have an amino acid sequence of SEQ ID NO: 166. The VL CDR2 can have an amino acid sequence of SEQ ID NO: 169. The VL CDR2 can have an amino acid sequence of SEQ ID NO: 210. The VL CDR2 can have an amino acid sequence of SEQ ID NO: 213. The VL CDR2 can have an amino acid sequence of SEQ ID NO: 216. The VL CDR2 can have an amino acid sequence of SEQ ID NO: 219. The VL CDR2 can have an amino acid sequence of SEQ ID NO: 238. The VL CDR2 can have an amino acid sequence of SEQ ID NO: 241. The VL CDR2 can have an amino acid sequence of SEQ ID NO: 244. The VL CDR2 can have an amino acid sequence of SEQ ID NO: 247. The VL CDR2 can have an amino acid sequence of SEQ ID NO: 266. The VL CDR2 can have an amino acid sequence of SEQ ID NO: 269. The VL CDR2 can have an amino acid sequence of SEQ ID NO: 272. The VL CDR2 can have an amino acid sequence of SEQ ID NO: 275. The VL CDR2 can have an amino acid sequence of SEQ ID NO: 294. The VL CDR2 can have an amino acid sequence of SEQ ID NO: 297. The VL CDR2 can have an amino acid sequence of SEQ ID NO: 300. The VL CDR2 can have an amino acid sequence of SEQ ID NO: 303. The VL CDR2 can have an amino acid sequence of SEQ ID NO: 322. The VL CDR2 can have an amino acid sequence of SEQ ID NO: 325. The VL CDR2 can have an amino acid sequence of SEQ ID NO: 328. The VL CDR2 can have an amino acid sequence of SEQ ID NO: 331.

In some embodiments, the molecules provided herein have an antigen binding fragment that has a light chain variable (VL) region including a VL CDR3 having an amino acid sequence of SEQ ID NOS: 21, 24, 27, 30, 49, 52, 55, 58, 77, 80, 83, 86, 105, 108, 111, 114, 133, 136, 139, 142, 161, 164, 167, 170, 211, 214, 217, 220, 239, 242, 245, 248, 267, 270, 273, 276, 295, 298, 301, 304, 323, 326, 329, or 332. The VL CDR3 can have an amino acid sequence of SEQ ID NO: 21. The VL CDR3 can have an amino acid sequence of SEQ ID NO: 24. The VL CDR3 can have an amino acid sequence of SEQ ID NO: 27. The VL CDR3 can have an amino acid sequence of SEQ ID NO: 30. The VL CDR3 can have an amino acid sequence of SEQ ID NO: 49. The VL CDR3 can have an amino acid sequence of SEQ ID NO: 52. The VL CDR3 can have an amino acid sequence of SEQ ID NO: 55. The VL CDR3 can have an amino acid sequence of SEQ ID NO: 58. The VL CDR3 can have an amino acid sequence of SEQ ID NO: 77. The VL CDR3 can have an amino acid sequence of SEQ ID NO: 80. The VL CDR3 can have an amino acid sequence of SEQ ID NO: 83. The VL CDR3 can have an amino acid sequence of SEQ ID NO: 86. The VL CDR3 can have an amino acid sequence of SEQ ID NO: 105. The VL CDR3 can have an amino acid sequence of SEQ ID NO: 108. The VL CDR3 can have an amino acid sequence of SEQ ID NO: 111. The VL CDR3 can have an amino acid sequence of SEQ ID NO: 114. The VL CDR3 can have an amino acid sequence of SEQ ID NO: 133. The VL CDR3 can have an amino acid sequence of SEQ ID NO: 136. The VL CDR3 can have an amino acid sequence of SEQ ID NO: 139. The VL CDR3 can have an amino acid sequence of SEQ ID NO: 142. The VL CDR3 can have an amino acid sequence of SEQ ID NO: 161. The VL CDR3 can have an amino acid sequence of SEQ ID NO: 164. The VL CDR3 can have an amino acid sequence of SEQ ID NO: 167. The VL CDR3 can have an amino acid sequence of SEQ ID NO: 170. The VL CDR3 can have an amino acid sequence of SEQ ID NO: 211. The VL CDR3 can have an amino acid sequence of SEQ ID NO: 214. The VL CDR3 can have an amino acid sequence of SEQ ID NO: 217. The VL CDR3 can have an amino acid sequence of SEQ ID NO: 220. The VL CDR3 can have an amino acid sequence of SEQ ID NO: 239. The VL CDR3 can have an amino acid sequence of SEQ ID NO: 242. The VL CDR3 can have an amino acid sequence of SEQ ID NO: 245. The VL CDR3 can have an amino acid sequence of SEQ ID NO: 248. The VL CDR3 can have an amino acid sequence of SEQ ID NO: 267. The VL CDR3 can have an amino acid sequence of SEQ ID NO: 270. The VL CDR3 can have an amino acid sequence of SEQ ID NO: 273. The VL CDR3 can have an amino acid sequence of SEQ ID NO: 276. The VL CDR3 can have an amino acid sequence of SEQ ID NO: 295. The VL CDR3 can have an amino acid sequence of SEQ ID NO: 298. The VL CDR3 can have an amino acid sequence of SEQ ID NO: 301. The VL CDR3 can have an amino acid sequence of SEQ ID NO: 304. The VL CDR3 can have an amino acid sequence of SEQ ID NO: 323. The VL CDR3 can have an amino acid sequence of SEQ ID NO: 326. The VL CDR3 can have an amino acid sequence of SEQ ID NO: 329. The VL CDR3 can have an amino acid sequence of SEQ ID NO: 332.

In some embodiments, the molecules provided herein have an antigen binding fragment that has a light chain variable (VL) region that has (1) a VL CDR1 having an amino acid sequence of SEQ ID NO: 19; (2) a VL CDR2 having an amino acid sequence of SEQ ID NO: 20; and/or (3) a VL CDR3 having an amino acid sequence of SEQ ID NO: 21.

In some embodiments, the molecules provided herein have an antigen binding fragment that has a light chain variable (VL) region that has (1) a VL CDR1 having an amino acid sequence of SEQ ID NO: 22; (2) a VL CDR2 having an amino acid sequence of SEQ ID NO: 23; and/or (3) a VL CDR3 having an amino acid sequence of SEQ ID NO: 24.

In some embodiments, the molecules provided herein have an antigen binding fragment that has a light chain variable (VL) region that has (1) a VL CDR1 having an amino acid sequence of SEQ ID NO: 25; (2) a VL CDR2 having an amino acid sequence of SEQ ID NO: 26; and/or (3) a VL CDR3 having an amino acid sequence of SEQ ID NO: 27.

In some embodiments, the molecules provided herein have an antigen binding fragment that has a light chain variable (VL) region that has (1) a VL CDR1 having an amino acid sequence of SEQ ID NO: 28; (2) a VL CDR2 having an amino acid sequence of SEQ ID NO: 29; and/or (3) a VL CDR3 having an amino acid sequence of SEQ ID NO: 30.

In some embodiments, the molecules provided herein have an antigen binding fragment that has a light chain variable (VL) region that has (1) a VL CDR1 having an amino acid sequence of SEQ ID NO: 47; (2) a VL CDR2 having an amino acid sequence of SEQ ID NO: 48; and/or (3) a VL CDR3 having an amino acid sequence of SEQ ID NO: 49.

In some embodiments, the molecules provided herein have an antigen binding fragment that has a light chain variable (VL) region that has (1) a VL CDR1 having an amino acid sequence of SEQ ID NO: 50; (2) a VL CDR2 having an amino acid sequence of SEQ ID NO: 51; and/or (3) a VL CDR3 having an amino acid sequence of SEQ ID NO: 52.

In some embodiments, the molecules provided herein have an antigen binding fragment that has a light chain variable (VL) region that has (1) a VL CDR1 having an amino acid sequence of SEQ ID NO: 53; (2) a VL CDR2 having an amino acid sequence of SEQ ID NO: 54; and/or (3) a VL CDR3 having an amino acid sequence of SEQ ID NO: 55.

In some embodiments, the molecules provided herein have an antigen binding fragment that has a light chain variable (VL) region that has (1) a VL CDR1 having an amino acid sequence of SEQ ID NO: 56; (2) a VL CDR2 having an amino acid sequence of SEQ ID NO: 57; and/or (3) a VL CDR3 having an amino acid sequence of SEQ ID NO: 58.

In some embodiments, the molecules provided herein have an antigen binding fragment that has a light chain variable (VL) region that has (1) a VL CDR1 having an amino acid sequence of SEQ ID NO: 75; (2) a VL CDR2 having an amino acid sequence of SEQ ID NO: 76; and/or (3) a VL CDR3 having an amino acid sequence of SEQ ID NO: 77.

In some embodiments, the molecules provided herein have an antigen binding fragment that has a light chain variable (VL) region that has (1) a VL CDR1 having an amino acid sequence of SEQ ID NO: 78; (2) a VL CDR2 having an amino acid sequence of SEQ ID NO: 79; and/or (3) a VL CDR3 having an amino acid sequence of SEQ ID NO: 80.

In some embodiments, the molecules provided herein have an antigen binding fragment that has a light chain variable (VL) region that has (1) a VL CDR1 having an amino acid sequence of SEQ ID NO: 81; (2) a VL CDR2 having an amino acid sequence of SEQ ID NO: 82; and/or (3) a VL CDR3 having an amino acid sequence of SEQ ID NO: 83.

In some embodiments, the molecules provided herein have an antigen binding fragment that has a light chain variable (VL) region that has (1) a VL CDR1 having an amino acid sequence of SEQ ID NO: 84; (2) a VL CDR2 having an amino acid sequence of SEQ ID NO: 85; and/or (3) a VL CDR3 having an amino acid sequence of SEQ ID NO: 86.

In some embodiments, the molecules provided herein have an antigen binding fragment that has a light chain variable (VL) region that has (1) a VL CDR1 having an amino acid sequence of SEQ ID NO: 103; (2) a VL CDR2 having an amino acid sequence of SEQ ID NO: 104; and/or (3) a VL CDR3 having an amino acid sequence of SEQ ID NO: 105.

In some embodiments, the molecules provided herein have an antigen binding fragment that has a light chain variable (VL) region that has (1) a VL CDR1 having an amino acid sequence of SEQ ID NO: 106; (2) a VL CDR2 having an amino acid sequence of SEQ ID NO: 107; and/or (3) a VL CDR3 having an amino acid sequence of SEQ ID NO: 108.

In some embodiments, the molecules provided herein have an antigen binding fragment that has a light chain variable (VL) region that has (1) a VL CDR1 having an amino acid sequence of SEQ ID NO: 109; (2) a VL CDR2 having an amino acid sequence of SEQ ID NO: 110; and/or (3) a VL CDR3 having an amino acid sequence of SEQ ID NO: 111.

In some embodiments, the molecules provided herein have an antigen binding fragment that has a light chain variable (VL) region that has (1) a VL CDR1 having an amino acid sequence of SEQ ID NO: 112; (2) a VL CDR2 having an amino acid sequence of SEQ ID NO: 113; and/or (3) a VL CDR3 having an amino acid sequence of SEQ ID NO: 114.

In some embodiments, the molecules provided herein have an antigen binding fragment that has a light chain variable (VL) region that has (1) a VL CDR1 having an amino acid sequence of SEQ ID NO: 131; (2) a VL CDR2 having an amino acid sequence of SEQ ID NO: 132; and/or (3) a VL CDR3 having an amino acid sequence of SEQ ID NO: 133.

In some embodiments, the molecules provided herein have an antigen binding fragment that has a light chain variable (VL) region that has (1) a VL CDR1 having an amino acid sequence of SEQ ID NO: 134; (2) a VL CDR2 having an amino acid sequence of SEQ ID NO: 135; and/or (3) a VL CDR3 having an amino acid sequence of SEQ ID NO: 136.

In some embodiments, the molecules provided herein have an antigen binding fragment that has a light chain variable (VL) region that has (1) a VL CDR1 having an amino acid sequence of SEQ ID NO: 137; (2) a VL CDR2 having an amino acid sequence of SEQ ID NO: 138; and/or (3) a VL CDR3 having an amino acid sequence of SEQ ID NO: 139.

In some embodiments, the molecules provided herein have an antigen binding fragment that has a light chain variable (VL) region that has (1) a VL CDR1 having an amino acid sequence of SEQ ID NO: 140; (2) a VL CDR2 having an amino acid sequence of SEQ ID NO: 141; and/or (3) a VL CDR3 having an amino acid sequence of SEQ ID NO: 142.

In some embodiments, the molecules provided herein have an antigen binding fragment that has a light chain variable (VL) region that has (1) a VL CDR1 having an amino acid sequence of SEQ ID NO: 159; (2) a VL CDR2 having an amino acid sequence of SEQ ID NO: 160; and/or (3) a VL CDR3 having an amino acid sequence of SEQ ID NO: 161.

In some embodiments, the molecules provided herein have an antigen binding fragment that has a light chain variable (VL) region that has (1) a VL CDR1 having an amino acid sequence of SEQ ID NO: 162; (2) a VL CDR2 having an amino acid sequence of SEQ ID NO: 163; and/or (3) a VL CDR3 having an amino acid sequence of SEQ ID NO: 164.

In some embodiments, the molecules provided herein have an antigen binding fragment that has a light chain variable (VL) region that has (1) a VL CDR1 having an amino acid sequence of SEQ ID NO: 165; (2) a VL CDR2 having an amino acid sequence of SEQ ID NO: 166; and/or (3) a VL CDR3 having an amino acid sequence of SEQ ID NO: 167.

In some embodiments, the molecules provided herein have an antigen binding fragment that has a light chain variable (VL) region that has (1) a VL CDR1 having an amino acid sequence of SEQ ID NO: 168; (2) a VL CDR2 having an amino acid sequence of SEQ ID NO: 169; and/or (3) a VL CDR3 having an amino acid sequence of SEQ ID NO: 170.

In some embodiments, the molecules provided herein have an antigen binding fragment that has a light chain variable (VL) region that has (1) a VL CDR1 having an amino acid sequence of SEQ ID NO: 209; (2) a VL CDR2 having an amino acid sequence of SEQ ID NO: 210; and/or (3) a VL CDR3 having an amino acid sequence of SEQ ID NO: 211.

In some embodiments, the molecules provided herein have an antigen binding fragment that has a light chain variable (VL) region that has (1) a VL CDR1 having an amino acid sequence of SEQ ID NO: 212; (2) a VL CDR2 having an amino acid sequence of SEQ ID NO: 213; and/or (3) a VL CDR3 having an amino acid sequence of SEQ ID NO: 214.

In some embodiments, the molecules provided herein have an antigen binding fragment that has a light chain variable (VL) region that has (1) a VL CDR1 having an amino acid sequence of SEQ ID NO: 215; (2) a VL CDR2 having an amino acid sequence of SEQ ID NO: 216; and/or (3) a VL CDR3 having an amino acid sequence of SEQ ID NO: 217.

In some embodiments, the molecules provided herein have an antigen binding fragment that has a light chain variable (VL) region that has (1) a VL CDR1 having an amino acid sequence of SEQ ID NO: 218; (2) a VL CDR2 having an amino acid sequence of SEQ ID NO: 219; and/or (3) a VL CDR3 having an amino acid sequence of SEQ ID NO: 220.

In some embodiments, the molecules provided herein have an antigen binding fragment that has a light chain variable (VL) region that has (1) a VL CDR1 having an amino acid sequence of SEQ ID NO: 237; (2) a VL CDR2 having an amino acid sequence of SEQ ID NO: 238; and/or (3) a VL CDR3 having an amino acid sequence of SEQ ID NO: 239.

In some embodiments, the molecules provided herein have an antigen binding fragment that has a light chain variable (VL) region that has (1) a VL CDR1 having an amino acid sequence of SEQ ID NO: 240; (2) a VL CDR2 having an amino acid sequence of SEQ ID NO: 241; and/or (3) a VL CDR3 having an amino acid sequence of SEQ ID NO: 242.

In some embodiments, the molecules provided herein have an antigen binding fragment that has a light chain variable (VL) region that has (1) a VL CDR1 having an amino acid sequence of SEQ ID NO: 243; (2) a VL CDR2 having an amino acid sequence of SEQ ID NO: 244; and/or (3) a VL CDR3 having an amino acid sequence of SEQ ID NO: 245.

In some embodiments, the molecules provided herein have an antigen binding fragment that has a light chain variable (VL) region that has (1) a VL CDR1 having an amino acid sequence of SEQ ID NO: 246; (2) a VL CDR2 having an amino acid sequence of SEQ ID NO: 247; and/or (3) a VL CDR3 having an amino acid sequence of SEQ ID NO: 248.

In some embodiments, the molecules provided herein have an antigen binding fragment that has a light chain variable (VL) region that has (1) a VL CDR1 having an amino acid sequence of SEQ ID NO: 265; (2) a VL CDR2 having an amino acid sequence of SEQ ID NO: 266; and/or (3) a VL CDR3 having an amino acid sequence of SEQ ID NO: 267.

In some embodiments, the molecules provided herein have an antigen binding fragment that has a light chain variable (VL) region that has (1) a VL CDR1 having an amino acid sequence of SEQ ID NO: 268; (2) a VL CDR2 having an amino acid sequence of SEQ ID NO: 269; and/or (3) a VL CDR3 having an amino acid sequence of SEQ ID NO: 270.

In some embodiments, the molecules provided herein have an antigen binding fragment that has a light chain variable (VL) region that has (1) a VL CDR1 having an amino acid sequence of SEQ ID NO: 271; (2) a VL CDR2 having an amino acid sequence of SEQ ID NO: 272; and/or (3) a VL CDR3 having an amino acid sequence of SEQ ID NO: 273.

In some embodiments, the molecules provided herein have an antigen binding fragment that has a light chain variable (VL) region that has (1) a VL CDR1 having an amino acid sequence of SEQ ID NO: 274; (2) a VL CDR2 having an amino acid sequence of SEQ ID NO: 275; and/or (3) a VL CDR3 having an amino acid sequence of SEQ ID NO: 276.

In some embodiments, the molecules provided herein have an antigen binding fragment that has a light chain variable (VL) region that has (1) a VL CDR1 having an amino acid sequence of SEQ ID NO: 293; (2) a VL CDR2 having an amino acid sequence of SEQ ID NO: 294; and/or (3) a VL CDR3 having an amino acid sequence of SEQ ID NO: 295.

In some embodiments, the molecules provided herein have an antigen binding fragment that has a light chain variable (VL) region that has (1) a VL CDR1 having an amino acid sequence of SEQ ID NO: 296; (2) a VL CDR2 having an amino acid sequence of SEQ ID NO: 297; and/or (3) a VL CDR3 having an amino acid sequence of SEQ ID NO: 298.

In some embodiments, the molecules provided herein have an antigen binding fragment that has a light chain variable (VL) region that has (1) a VL CDR1 having an amino acid sequence of SEQ ID NO: 299; (2) a VL CDR2 having an amino acid sequence of SEQ ID NO: 300; and/or (3) a VL CDR3 having an amino acid sequence of SEQ ID NO: 301.

In some embodiments, the molecules provided herein have an antigen binding fragment that has a light chain variable (VL) region that has (1) a VL CDR1 having an amino acid sequence of SEQ ID NO: 302; (2) a VL CDR2 having an amino acid sequence of SEQ ID NO: 303; and/or (3) a VL CDR3 having an amino acid sequence of SEQ ID NO: 304.

In some embodiments, the molecules provided herein have an antigen binding fragment that has a light chain variable (VL) region that has (1) a VL CDR1 having an amino acid sequence of SEQ ID NO: 321; (2) a VL CDR2 having an amino acid sequence of SEQ ID NO: 322; and/or (3) a VL CDR3 having an amino acid sequence of SEQ ID NO: 323.

In some embodiments, the molecules provided herein have an antigen binding fragment that has a light chain variable (VL) region that has (1) a VL CDR1 having an amino acid sequence of SEQ ID NO: 324; (2) a VL CDR2 having an amino acid sequence of SEQ ID NO: 325; and/or (3) a VL CDR3 having an amino acid sequence of SEQ ID NO: 326.

In some embodiments, the molecules provided herein have an antigen binding fragment that has a light chain variable (VL) region that has (1) a VL CDR1 having an amino acid sequence of SEQ ID NO: 327; (2) a VL CDR2 having an amino acid sequence of SEQ ID NO: 328; and/or (3) a VL CDR3 having an amino acid sequence of SEQ ID NO: 329.

In some embodiments, the molecules provided herein have an antigen binding fragment that has a light chain variable (VL) region that has (1) a VL CDR1 having an amino acid sequence of SEQ ID NO: 330; (2) a VL CDR2 having an amino acid sequence of SEQ ID NO: 331; and/or (3) a VL CDR3 having an amino acid sequence of SEQ ID NO: 332.

In some embodiments, the molecules provided herein have an antigen binding fragment that has a light chain variable (VL) region that has the amino acid sequence of SEQ ID NO: 5. The molecule can be an antibody. The antibody can be a monoclonal antibody. The antibody can be a humanized antibody.

In some embodiments, the molecules provided herein have an antigen binding fragment that has a light chain variable (VL) region that has the amino acid sequence of SEQ ID NO: 33. The molecule can be an antibody. The antibody can be a monoclonal antibody. The antibody can be a humanized antibody.

In some embodiments, the molecules provided herein have an antigen binding fragment that has a light chain variable (VL) region that has the amino acid sequence of SEQ ID NO: 61. The molecule can be an antibody. The antibody can be a monoclonal antibody. The antibody can be a humanized antibody.

In some embodiments, the molecules provided herein have an antigen binding fragment that has a light chain variable (VL) region that has the amino acid sequence of SEQ ID NO: 89. The molecule can be an antibody. The antibody can be a monoclonal antibody. The antibody can be a humanized antibody.

In some embodiments, the molecules provided herein have an antigen binding fragment that has a light chain variable (VL) region that has the amino acid sequence of SEQ ID NO: 117. The molecule can be an antibody. The antibody can be a monoclonal antibody. The antibody can be a humanized antibody.

In some embodiments, the molecules provided herein have an antigen binding fragment that has a light chain variable (VL) region that has the amino acid sequence of SEQ ID NO: 145. The molecule can be an antibody. The antibody can be a monoclonal antibody. The antibody can be a humanized antibody.

In some embodiments, the molecules provided herein have an antigen binding fragment that has a light chain variable (VL) region that has the amino acid sequence of SEQ ID NO: 195. The molecule can be an antibody. The antibody can be a monoclonal antibody. The antibody can be a humanized antibody.

In some embodiments, the molecules provided herein have an antigen binding fragment that has a light chain variable (VL) region that has the amino acid sequence of SEQ ID NO: 223. The molecule can be an antibody. The antibody can be a monoclonal antibody. The antibody can be a humanized antibody.

In some embodiments, the molecules provided herein have an antigen binding fragment that has a light chain variable (VL) region that has the amino acid sequence of SEQ ID NO: 251. The molecule can be an antibody. The antibody can be a monoclonal antibody. The antibody can be a humanized antibody.

In some embodiments, the molecules provided herein have an antigen binding fragment that has a light chain variable (VL) region that has the amino acid sequence of SEQ ID NO: 279. The molecule can be an antibody. The antibody can be a monoclonal antibody. The antibody can be a humanized antibody.

In some embodiments, the molecules provided herein have an antigen binding fragment that has a light chain variable (VL) region that has the amino acid sequence of SEQ ID NO: 307. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NOS: 7, 10, 13, 16, 35, 38, 41, 44, 63, 66, 69, or 72; (2) a VH CDR2 having an amino acid sequence of SEQ ID NOS: 8, 11, 14, 17, 36, 39, 42, 45, 64, 67, 70, or 73; and/or (3) a VH CDR3 having an amino acid sequence of SEQ ID NOS: 9, 12, 15, 18, 37, 40, 43, 46, 65, 68, 71, or 74; and (b) a light chain variable (VL) region including: (1) a VL CDR1 having an amino acid sequence of SEQ ID NOS: 19, 22, 25, 28, 47, 50, 53, 56, 75, 78, 81, or 84; (2) a VL CDR2 having an amino acid sequence of SEQ ID NOS: 20, 23, 26, 29, 48, 51, 54, 57, 76, 79, 82, or 85; and/or (3) a VL CDR3 having an amino acid sequence of SEQ ID NOS: 21, 24, 27, 30, 49, 52, 55, 58, 77, 80, 83, or 86. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NOS: 91, 94, 97, 100, 119, 122, 125, 128, 147, 150, 153, or 156; (2) a VH CDR2 having an amino acid sequence of SEQ ID NOS: 92, 95, 98, 101, 120, 123, 126, 129, 148, 151, 154, or 157; and/or (3) a VH CDR3 having an amino acid sequence of SEQ ID NOS: 93, 96, 99, 102, 121, 124, 127, 130, 149, 152, 155, or 158; and (b) a light chain variable (VL) region including: (1) a VL CDR1 having an amino acid sequence of SEQ ID NOS: 103, 106, 109, 112, 131, 134, 137, 140, 159, 162, 165, or 168; (2) a VL CDR2 having an amino acid sequence of SEQ ID NOS: 104, 107, 110, 113, 132, 135, 138, 141, 160, 163, 166, or 169; and/or (3) a VL CDR3 having an amino acid sequence of SEQ ID NOS: 105, 108, 111, 114, 133, 136, 139, 142, 161, 164, 167, or 170. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NOS: 197, 200, 203, or 206; (2) a VH CDR2 having an amino acid sequence of SEQ ID NOS: 198, 201, 204, or 207; and/or (3) a VH CDR3 having an amino acid sequence of SEQ ID NOS: 199, 202, 205, or 208; and (b) a light chain variable (VL) region including: (1) a VL CDR1 having an amino acid sequence of SEQ ID NOS: 209, 212, 215, or 218; (2) a VL CDR2 having an amino acid sequence of SEQ ID NOS: 210, 213, 216, or 219; and/or (3) a VL CDR3 having an amino acid sequence of SEQ ID NOS: 211, 214, 217, or 220. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NOS: 225, 228, 231, or 234; (2) a VH CDR2 having an amino acid sequence of SEQ ID NOS: 226, 229, 232, or 235; and/or (3) a VH CDR3 having an amino acid sequence of SEQ ID NOS: 227, 230, 233, or 236; and (b) a light chain variable (VL) region including: (1) a VL CDR1 having an amino acid sequence of SEQ ID NOS: 237, 240, 243, or 246; (2) a VL CDR2 having an amino acid sequence of SEQ ID NOS: 238, 241, 244, or 247; and/or (3) a VL CDR3 having an amino acid sequence of SEQ ID NOS: 239, 242, 245, or 248. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NOS: 253, 256, 259, or 262; (2) a VH CDR2 having an amino acid sequence of SEQ ID NOS: 254, 257, 260, or 263; and/or (3) a VH CDR3 having an amino acid sequence of SEQ ID NOS: 255, 258, 261, or 264; and (b) a light chain variable (VL) region including: (1) a VL CDR1 having an amino acid sequence of SEQ ID NOS: 265, 268, 271, or 274; (2) a VL CDR2 having an amino acid sequence of SEQ ID NOS: 266, 269, 272, or 275; and/or (3) a VL CDR3 having an amino acid sequence of SEQ ID NOS: 267, 270, 273, or 276. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NOS: 281, 284, 287, or 290; (2) a VH CDR2 having an amino acid sequence of SEQ ID NOS: 282, 285, 288, or 291; and/or (3) a VH CDR3 having an amino acid sequence of SEQ ID NOS: 283, 286, 289, or 292; and (b) a light chain variable (VL) region including: (1) a VL CDR1 having an amino acid sequence of SEQ ID NOS: 293, 296, 299, or 302; (2) a VL CDR2 having an amino acid sequence of SEQ ID NOS: 294, 297, 300, or 303; and/or (3) a VL CDR3 having an amino acid sequence of SEQ ID NOS: 295, 298, 301, or 304. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NOS: 309, 312, 315, or 318; (2) a VH CDR2 having an amino acid sequence of SEQ ID NOS: 310, 313, 316, or 319; and/or (3) a VH CDR3 having an amino acid sequence of SEQ ID NOS: 311, 314, 317, or 320; and (b) a light chain variable (VL) region including: (1) a VL CDR1 having an amino acid sequence of SEQ ID NOS: 321, 324, 327, or 330; (2) a VL CDR2 having an amino acid sequence of SEQ ID NOS: 322, 325, 328, or 331; and/or (3) a VL CDR3 having an amino acid sequence of SEQ ID NOS: 323, 326, 329, or 332. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 7; (2) a VH CDR2 having an amino acid sequence of SEQ ID NO 8; and/or (3) a VH CDR3 having an amino acid sequence of SEQ ID NO: 9; and (b) a light chain variable (VL) region including: (1) a VL CDR1 having an amino acid sequence of SEQ ID NO: 19; (2) a VL CDR2 having an amino acid sequence of SEQ ID NO: 20; and/or (3) a VL CDR3 having an amino acid sequence of SEQ ID NO: 21. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 10; (2) a VH CDR2 having an amino acid sequence of SEQ ID NO: 11; and/or (3) a VH CDR3 having an amino acid sequence of SEQ ID NO 12; and (b) a light chain variable (VL) region including: (1) a VL CDR1 having an amino acid sequence of SEQ ID NO: 22; (2) a VL CDR2 having an amino acid sequence of SEQ ID NO: 23; and/or (3) a VL CDR3 having an amino acid sequence of SEQ ID NO: 24. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 13; (2) a VH CDR2 having an amino acid sequence of SEQ ID NO: 14; and/or (3) a VH CDR3 having an amino acid sequence of SEQ ID NO 15; and (b) a light chain variable (VL) region including: (1) a VL CDR1 having an amino acid sequence of SEQ ID NO: 25; (2) a VL CDR2 having an amino acid sequence of SEQ ID NO: 26; and/or (3) a VL CDR3 having an amino acid sequence of SEQ ID NO: 27. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 16; (2) a VH CDR2 having an amino acid sequence of SEQ ID NO: 17; and (3) a VH CDR3 having an amino acid sequence of SEQ ID NO: 18; and (b) a light chain variable (VL) region including: (1) a VL CDR1 having an amino acid sequence of SEQ ID NO: 28; (2) a VL CDR2 having an amino acid sequence of SEQ ID NO: 29; and (3) a VL CDR3 having an amino acid sequence of SEQ ID NO: 30. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 35; (2) a VH CDR2 having an amino acid sequence of SEQ ID NO: 36; and (3) a VH CDR3 having an amino acid sequence of SEQ ID NO: 37; and (b) a light chain variable (VL) region including: (1) a VL CDR1 having an amino acid sequence of SEQ ID NO: 47; (2) a VL CDR2 having an amino acid sequence of SEQ ID NO: 48; and (3) a VL CDR3 having an amino acid sequence of SEQ ID NO: 49. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 38; (2) a VH CDR2 having an amino acid sequence of SEQ ID NO: 39; and (3) a VH CDR3 having an amino acid sequence of SEQ ID NO: 40; and (b) a light chain variable (VL) region including: (1) a VL CDR1 having an amino acid sequence of SEQ ID NO: 50; (2) a VL CDR2 having an amino acid sequence of SEQ ID NO: 51; and (3) a VL CDR3 having an amino acid sequence of SEQ ID NO: 52. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 41; (2) a VH CDR2 having an amino acid sequence of SEQ ID NO: 42; and (3) a VH CDR3 having an amino acid sequence of SEQ ID NO: 43; and (b) a light chain variable (VL) region including: (1) a VL CDR1 having an amino acid sequence of SEQ ID NO: 53; (2) a VL CDR2 having an amino acid sequence of SEQ ID NO: 54; and (3) a VL CDR3 having an amino acid sequence of SEQ ID NO: 55. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 44; (2) a VH CDR2 having an amino acid sequence of SEQ ID NO: 45; and (3) a VH CDR3 having an amino acid sequence of SEQ ID NO: 46; and (b) a light chain variable (VL) region including: (1) a VL CDR1 having an amino acid sequence of SEQ ID NO: 56; (2) a VL CDR2 having an amino acid sequence of SEQ ID NO: 57; and (3) a VL CDR3 having an amino acid sequence of SEQ ID NO: 58. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 63; (2) a VH CDR2 having an amino acid sequence of SEQ ID NO: 64; and (3) a VH CDR3 having an amino acid sequence of SEQ ID NO: 65; and (b) a light chain variable (VL) region including: (1) a VL CDR1 having an amino acid sequence of SEQ ID NO: 75; (2) a VL CDR2 having an amino acid sequence of SEQ ID NO: 76; and (3) a VL CDR3 having an amino acid sequence of SEQ ID NO: 77. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 66; (2) a VH CDR2 having an amino acid sequence of SEQ ID NO: 67; and (3) a VH CDR3 having an amino acid sequence of SEQ ID NO: 68; and (b) a light chain variable (VL) region including: (1) a VL CDR1 having an amino acid sequence of SEQ ID NO: 78; (2) a VL CDR2 having an amino acid sequence of SEQ ID NO: 79; and (3) a VL CDR3 having an amino acid sequence of SEQ ID NO: 80. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 69; (2) a VH CDR2 having an amino acid sequence of SEQ ID NO: 70; and (3) a VH CDR3 having an amino acid sequence of SEQ ID NO: 71; and (b) a light chain variable (VL) region including: (1) a VL CDR1 having an amino acid sequence of SEQ ID NO: 81; (2) a VL CDR2 having an amino acid sequence of SEQ ID NO: 82; and (3) a VL CDR3 having an amino acid sequence of SEQ ID NO: 83. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 72; (2) a VH CDR2 having an amino acid sequence of SEQ ID NO: 73; and (3) a VH CDR3 having an amino acid sequence of SEQ ID NO: 74; and (b) a light chain variable (VL) region including: (1) a VL CDR1 having an amino acid sequence of SEQ ID NO: 84; (2) a VL CDR2 having an amino acid sequence of SEQ ID NO: 85; and (3) a VL CDR3 having an amino acid sequence of SEQ ID NO: 86. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 91; (2) a VH CDR2 having an amino acid sequence of SEQ ID NO: 92; and (3) a VH CDR3 having an amino acid sequence of SEQ ID NO: 93; and (b) a light chain variable (VL) region including: (1) a VL CDR1 having an amino acid sequence of SEQ ID NO: 103; (2) a VL CDR2 having an amino acid sequence of SEQ ID NO: 104; and (3) a VL CDR3 having an amino acid sequence of SEQ ID NO: 105. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 94; (2) a VH CDR2 having an amino acid sequence of SEQ ID NO: 95; and (3) a VH CDR3 having an amino acid sequence of SEQ ID NO: 96; and (b) a light chain variable (VL) region including: (1) a VL CDR1 having an amino acid sequence of SEQ ID NO: 106; (2) a VL CDR2 having an amino acid sequence of SEQ ID NO: 107; and (3) a VL CDR3 having an amino acid sequence of SEQ ID NO: 108. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 97; (2) a VH CDR2 having an amino acid sequence of SEQ ID NO: 98; and (3) a VH CDR3 having an amino acid sequence of SEQ ID NO: 99; and (b) a light chain variable (VL) region including: (1) a VL CDR1 having an amino acid sequence of SEQ ID NO: 109; (2) a VL CDR2 having an amino acid sequence of SEQ ID NO: 110; and (3) a VL CDR3 having an amino acid sequence of SEQ ID NO: 111. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 100; (2) a VH CDR2 having an amino acid sequence of SEQ ID NO: 101; and (3) a VH CDR3 having an amino acid sequence of SEQ ID NO: 102; and (b) a light chain variable (VL) region including: (1) a VL CDR1 having an amino acid sequence of SEQ ID NO: 112; (2) a VL CDR2 having an amino acid sequence of SEQ ID NO: 113; and (3) a VL CDR3 having an amino acid sequence of SEQ ID NO: 114. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 119; (2) a VH CDR2 having an amino acid sequence of SEQ ID NO: 120; and (3) a VH CDR3 having an amino acid sequence of SEQ ID NO:

121; and (b) a light chain variable (VL) region including: (1) a VL CDR1 having an amino acid sequence of SEQ ID NO: 131; (2) a VL CDR2 having an amino acid sequence of SEQ ID NO: 132; and (3) a VL CDR3 having an amino acid sequence of SEQ ID NO: 133. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 122; (2) a VH CDR2 having an amino acid sequence of SEQ ID NO: 123; and (3) a VH CDR3 having an amino acid sequence of SEQ ID NO: 124; and (b) a light chain variable (VL) region including: (1) a VL CDR1 having an amino acid sequence of SEQ ID NO: 134; (2) a VL CDR2 having an amino acid sequence of SEQ ID NO: 135; and (3) a VL CDR3 having an amino acid sequence of SEQ ID NO: 136. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 125; (2) a VH CDR2 having an amino acid sequence of SEQ ID NO: 126; and (3) a VH CDR3 having an amino acid sequence of SEQ ID NO: 127; and (b) a light chain variable (VL) region including: (1) a VL CDR1 having an amino acid sequence of SEQ ID NO: 137; (2) a VL CDR2 having an amino acid sequence of SEQ ID NO: 138; and (3) a VL CDR3 having an amino acid sequence of SEQ ID NO: 139. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 128; (2) a VH CDR2 having an amino acid sequence of SEQ ID NO: 129; and (3) a VH CDR3 having an amino acid sequence of SEQ ID NO: 130; and (b) a light chain variable (VL) region including: (1) a VL CDR1 having an amino acid sequence of SEQ ID NO: 140; (2) a VL CDR2 having an amino acid sequence of SEQ ID NO: 141; and (3) a VL CDR3 having an amino acid sequence of SEQ ID NO: 142. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 147; (2) a VH CDR2 having an amino acid sequence of SEQ ID NO: 148; and (3) a VH CDR3 having an amino acid sequence of SEQ ID NO: 149; and (b) a light chain variable (VL) region including: (1) a VL CDR1 having an amino acid sequence of SEQ ID NO: 159; (2) a VL CDR2 having an amino acid sequence of SEQ ID NO: 160; and (3) a VL CDR3 having an amino acid sequence of SEQ ID NO: 161. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 150; (2) a VH CDR2 having an amino acid sequence of SEQ ID NO: 151; and (3) a VH CDR3 having an amino acid sequence of SEQ ID NO: 152; and (b) a light chain variable (VL) region including: (1) a VL CDR1 having an amino acid sequence of SEQ ID NO:

162; (2) a VL CDR2 having an amino acid sequence of SEQ ID NO: 163; and (3) a VL CDR3 having an amino acid sequence of SEQ ID NO: 164. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 153; (2) a VH CDR2 having an amino acid sequence of SEQ ID NO: 154; and (3) a VH CDR3 having an amino acid sequence of SEQ ID NO: 155; and (b) a light chain variable (VL) region including: (1) a VL CDR1 having an amino acid sequence of SEQ ID NO: 165; (2) a VL CDR2 having an amino acid sequence of SEQ ID NO: 166; and (3) a VL CDR3 having an amino acid sequence of SEQ ID NO: 167. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 156; (2) a VH CDR2 having an amino acid sequence of SEQ ID NO: 157; and (3) a VH CDR3 having an amino acid sequence of SEQ ID NO: 158; and (b) a light chain variable (VL) region including: (1) a VL CDR1 having an amino acid sequence of SEQ ID NO: 168; (2) a VL CDR2 having an amino acid sequence of SEQ ID NO: 169; and (3) a VL CDR3 having an amino acid sequence of SEQ ID NO: 170. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 197; (2) a VH CDR2 having an amino acid sequence of SEQ ID NO: 198; and/or (3) a VH CDR3 having an amino acid sequence of SEQ ID NO: 199; and (b) a light chain variable (VL) region including: (1) a VL CDR1 having an amino acid sequence of SEQ ID NO: 209; (2) a VL CDR2 having an amino acid sequence of SEQ ID NO: 210; and/or (3) a VL CDR3 having an amino acid sequence of SEQ ID NO: 211. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 200; (2) a VH CDR2 having an amino acid sequence of SEQ ID NO: 201; and/or (3) a VH CDR3 having an amino acid sequence of SEQ ID NO 202; and (b) a light chain variable (VL) region including: (1) a VL CDR1 having an amino acid sequence of SEQ ID NO: 212; (2) a VL CDR2 having an amino acid sequence of SEQ ID NO: 213; and/or (3) a VL CDR3 having an amino acid sequence of SEQ ID NO: 214. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 203; (2) a VH CDR2 having an amino acid sequence of SEQ ID NO: 204; and/or (3) a VH CDR3 having an amino acid sequence of SEQ ID NO 205; and (b) a light chain variable (VL) region including: (1) a VL CDR1 having an amino acid sequence of SEQ ID NO: 215; (2) a VL CDR2 having an amino acid sequence of SEQ ID NO: 216; and/or (3) a VL CDR3 having an amino acid sequence of SEQ ID NO: 217. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 206; (2) a VH CDR2 having an amino acid sequence of SEQ ID NO: 207; and (3) a VH CDR3 having an amino acid sequence of SEQ ID NO: 208; and (b) a light chain variable (VL) region including: (1) a VL CDR1 having an amino acid sequence of SEQ ID NO: 218; (2) a VL CDR2 having an amino acid sequence of SEQ ID NO: 219; and (3) a VL CDR3 having an amino acid sequence of SEQ ID NO: 220. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 225; (2) a VH CDR2 having an amino acid sequence of SEQ ID NO 226; and/or (3) a VH CDR3 having an amino acid sequence of SEQ ID NO: 227; and (b) a light chain variable (VL) region including: (1) a VL CDR1 having an amino acid sequence of SEQ ID NO: 237; (2) a VL CDR2 having an amino acid sequence of SEQ ID NO: 238; and/or (3) a VL CDR3 having an amino acid sequence of SEQ ID NO: 239. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 228; (2) a VH CDR2 having an amino acid sequence of SEQ ID NO: 229; and (3) a VH CDR3 having an amino acid sequence of SEQ ID NO: 230; and (b) a light chain variable (VL) region including: (1) a VL CDR1 having an amino acid sequence of SEQ ID NO: 240; (2) a VL CDR2 having an amino acid sequence of SEQ ID NO: 241; and (3) a VL CDR3 having an amino acid sequence of SEQ ID NO: 242. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 231; (2) a VH CDR2 having an amino acid sequence of SEQ ID NO: 232; and/or (3) a VH CDR3 having an amino acid sequence of SEQ ID NO 233; and (b) a light chain variable (VL) region including: (1) a VL CDR1 having an amino acid sequence of SEQ ID NO: 243; (2) a VL CDR2 having an amino acid sequence of SEQ ID NO: 244; and/or (3) a VL CDR3 having an amino acid sequence of SEQ ID NO: 245. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 234; (2) a VH CDR2 having an amino acid sequence of SEQ ID NO: 235; and/or (3) a VH CDR3 having an amino acid sequence of SEQ ID NO 236; and (b) a light chain variable (VL) region including: (1) a VL CDR1 having an amino acid sequence of SEQ ID NO: 246; (2) a VL CDR2 having an amino acid sequence of SEQ ID NO: 247; and/or (3) a VL CDR3 having an amino acid sequence of SEQ ID NO: 248. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 253; (2) a VH CDR2 having an amino acid sequence of SEQ ID NO: 254; and/or (3) a VH CDR3 having an amino acid sequence of SEQ ID NO: 255; and (b) a light chain variable (VL) region including: (1) a VL CDR1 having an amino acid sequence of SEQ ID NO: 265; (2) a VL CDR2 having an amino acid sequence of SEQ ID NO: 266; and/or (3) a VL CDR3 having an amino acid sequence of SEQ ID NO: 267. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 256; (2) a VH CDR2 having an amino acid sequence of SEQ ID NO: 257; and/or (3) a VH CDR3 having an amino acid sequence of SEQ ID NO 258; and (b) a light chain variable (VL) region including: (1) a VL CDR1 having an amino acid sequence of SEQ ID NO: 268; (2) a VL CDR2 having an amino acid sequence of SEQ ID NO: 269; and/or (3) a VL CDR3 having an amino acid sequence of SEQ ID NO: 270. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 259; (2) a VH CDR2 having an amino acid sequence of SEQ ID NO: 260; and/or (3) a VH CDR3 having an amino acid sequence of SEQ ID NO 261; and (b) a light chain variable (VL) region including: (1) a VL CDR1 having an amino acid sequence of SEQ ID NO: 271; (2) a VL CDR2 having an amino acid sequence of SEQ ID NO: 272; and/or (3) a VL CDR3 having an amino acid sequence of SEQ ID NO: 273. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 262; (2) a VH CDR2 having an amino acid sequence of SEQ ID NO: 263; and (3) a VH CDR3 having an amino acid sequence of SEQ ID NO: 264; and (b) a light chain variable (VL) region including: (1) a VL CDR1 having an amino acid sequence of SEQ ID NO: 274; (2) a VL CDR2 having an amino acid sequence of SEQ ID NO: 275; and (3) a VL CDR3 having an amino acid sequence of SEQ ID NO: 276. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 281; (2) a VH CDR2 having an amino acid sequence of SEQ ID NO: 282; and/or (3) a VH CDR3 having an amino acid sequence of SEQ ID NO: 283; and (b) a light chain variable (VL) region including: (1) a VL CDR1 having an amino acid sequence of SEQ ID NO: 293; (2) a VL CDR2 having an amino acid sequence of SEQ ID NO: 294; and/or (3) a VL CDR3 having an amino acid sequence of SEQ ID NO: 295. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 284; (2) a VH CDR2 having an amino acid sequence of SEQ ID NO: 285; and/or (3) a VH CDR3 having an amino acid sequence of SEQ ID NO 286; and (b) a light chain variable (VL) region including: (1) a VL CDR1 having an amino acid sequence of SEQ ID NO: 296; (2) a VL CDR2 having an amino acid sequence of SEQ ID NO: 297; and/or (3) a VL CDR3 having an amino acid sequence of SEQ ID NO: 298. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 287; (2) a VH CDR2 having an amino acid sequence of SEQ ID NO: 288; and/or (3) a VH CDR3 having an amino acid sequence of SEQ ID NO 289; and (b) a light chain variable (VL) region including: (1) a VL CDR1 having an amino acid sequence of SEQ ID NO: 299; (2) a VL CDR2 having an amino acid sequence of SEQ ID NO: 300; and/or (3) a VL CDR3 having an amino acid sequence of SEQ ID NO: 301. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 290; (2) a VH CDR2 having an amino acid sequence of SEQ ID NO: 291; and (3) a VH CDR3 having an amino acid sequence of SEQ ID NO: 292; and (b) a light chain variable (VL) region including: (1) a VL CDR1 having an amino acid sequence of SEQ ID NO: 302; (2) a VL CDR2 having an amino acid sequence of SEQ ID NO: 303; and (3) a VL CDR3 having an amino acid sequence of SEQ ID NO: 304. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 309; (2) a VH CDR2 having an amino acid sequence of SEQ ID NO: 310; and/or (3) a VH CDR3 having an amino acid sequence of SEQ ID NO: 311; and (b) a light chain variable (VL) region including: (1) a VL CDR1 having an amino acid sequence of SEQ ID NO: 321; (2) a VL CDR2 having an amino acid sequence of SEQ ID NO: 322; and/or (3) a VL CDR3 having an amino acid sequence of SEQ ID NO: 323. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 312; (2) a VH CDR2 having an amino acid sequence of SEQ ID NO: 313; and/or (3) a VH CDR3 having an amino acid sequence of SEQ ID NO 314; and (b) a light chain variable (VL) region including: (1) a VL CDR1 having an amino acid sequence of SEQ ID NO: 324; (2) a VL CDR2 having an amino acid sequence of SEQ ID NO: 325; and/or (3) a VL CDR3 having an amino acid sequence of SEQ ID NO: 326. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 315; (2) a VH CDR2 having an amino acid sequence of SEQ ID NO: 316; and/or (3) a VH CDR3 having an amino acid sequence of SEQ ID NO 317; and (b) a light chain variable (VL) region including: (1) a VL CDR1 having an amino acid sequence of SEQ ID NO: 327; (2) a VL CDR2 having an amino acid sequence of SEQ ID NO: 328; and/or (3) a VL CDR3 having an amino acid sequence of SEQ ID NO: 329. The molecule can be an antibody. The antibody can be a monoclonal antibody. The antibody can be a humanized antibody.

In some embodiments, the molecules provided herein have an antigen binding fragment that has (a) a heavy chain variable (VH) region including: (1) a VH CDR1 having an amino acid sequence of SEQ ID NO: 318; (2) a VH CDR2 having an amino acid sequence of SEQ ID NO: 319; and (3) a VH CDR3 having an amino acid sequence of SEQ ID NO: 320; and (b) a light chain variable (VL) region including: (1) a VL CDR1 having an amino acid sequence of SEQ ID NO: 330; (2) a VL CDR2 having an amino acid sequence of SEQ ID NO: 331; and (3) a VL CDR3 having an amino acid sequence of SEQ ID NO: 332. The molecule can be an antibody. The antibody can be a monoclonal antibody. The antibody can be a humanized antibody.

In some embodiments, the molecules provided herein have an antigen binding fragment that has a VH region that has the amino acid sequence of SEQ ID NO: 3 and the VL region that has the amino acid sequence of SEQ ID NO: 5. The molecule can be an antibody. The antibody can be a monoclonal antibody. The antibody can be a humanized antibody.

In some embodiments, the molecules provided herein have an antigen binding fragment that has a VH region that has the amino acid sequence of SEQ ID NO: 31 and the VL region that has the amino acid sequence of SEQ ID NO: 33. The molecule can be an antibody. The antibody can be a monoclonal antibody. The antibody can be a humanized antibody.

In some embodiments, the molecules provided herein have an antigen binding fragment that has a VH region that has the amino acid sequence of SEQ ID NO: 59 and the VL region that has the amino acid sequence of SEQ ID NO: 61. The molecule can be an antibody. The antibody can be a monoclonal antibody. The antibody can be a humanized antibody.

In some embodiments, the molecules provided herein have an antigen binding fragment that has a VH region that has the amino acid sequence of SEQ ID NO: 87 and the VL region that has the amino acid sequence of SEQ ID NO: 89. The molecule can be an antibody. The antibody can be a monoclonal antibody. The antibody can be a humanized antibody.

In some embodiments, the molecules provided herein have an antigen binding fragment that has a VH region that has the amino acid sequence of SEQ ID NO: 115 and the VL region that has the amino acid sequence of SEQ ID NO: 117. The molecule can be an antibody. The antibody can be a monoclonal antibody. The antibody can be a humanized antibody.

In some embodiments, the molecules provided herein have an antigen binding fragment that has a VH region that has the amino acid sequence of SEQ ID NO: 143 and the VL region that has the amino acid sequence of SEQ ID NO: 145. The molecule can be an antibody. The antibody can be a monoclonal antibody. The antibody can be a humanized antibody.

In some embodiments, the molecules provided herein have an antigen binding fragment that has a VH region that has the amino acid sequence of SEQ ID NO: 193 and the VL region that has the amino acid sequence of SEQ ID NO: 195. The molecule can be an antibody. The antibody can be a monoclonal antibody. The antibody can be a humanized antibody.

In some embodiments, the molecules provided herein have an antigen binding fragment that has a VH region that has the amino acid sequence of SEQ ID NO: 221 and the VL region that has the amino acid sequence of SEQ ID NO: 223. The molecule can be an antibody. The antibody can be a monoclonal antibody. The antibody can be a humanized antibody.

In some embodiments, the molecules provided herein have an antigen binding fragment that has a VH region that has the amino acid sequence of SEQ ID NO: 249 and the VL region that has the amino acid sequence of SEQ ID NO: 251. The molecule can be an antibody. The antibody can be a monoclonal antibody. The antibody can be a humanized antibody.

In some embodiments, the molecules provided herein have an antigen binding fragment that has a VH region that has the amino acid sequence of SEQ ID NO: 277 and the VL region that has the amino acid sequence of SEQ ID NO: 279. The molecule can be an antibody. The antibody can be a monoclonal antibody. The antibody can be a humanized antibody.

In some embodiments, the molecules provided herein have an antigen binding fragment that has a VH region that has the amino acid sequence of SEQ ID NO: 305 and the VL region that has the amino acid sequence of SEQ ID NO: 307. The molecule can be an antibody. The antibody can be a monoclonal antibody. The antibody can be a humanized antibody.

In some embodiments, the molecules provided herein is the mouse monoclonal antibody designated as STC703, or a humanized antibody version thereof. A humanized STC703 antibody can have the VH region, the VL region, or both the VH and VL region of STC703 as described herein. A humanized STC703 antibody can also have six CDR regions (VH CDR1, VH CDR2, VH CDR3, VL CDR1, VL CDR2 and VL CDR3) of STC703 as described herein. The humanized STC703 antibody can also have less than the six CDR regions of STC703. In some embodiments, the humanized STC703 antibody can also have one, two, three, four, or five CDR regions (VH CDR1, VH CDR2, VH CDR3, VL CDR1, VL CDR2 and VL CDR3) of STC703.

In some embodiments, the molecules provided herein is the mouse monoclonal antibody designated as STC810, or a humanized antibody version thereof. A humanized STC810 antibody can have the VH region, the VL region, or both the VH and VL region of STC810 as described herein. A humanized STC810 antibody can also have six CDR regions (VH CDR1, VH CDR2, VH CDR3, VL CDR1, VL CDR2 and VL CDR3) of STC810 as described herein. The humanized STC810 antibody can also have less than the six CDR regions of STC810. In some embodiments, the humanized STC810 antibody can also have one, two, three, four, or five CDR regions (VH CDR1, VH CDR2, VH CDR3, VL CDR1, VL CDR2 and VL CDR3) of STC810.

In some embodiments, the molecules provided herein is the mouse monoclonal antibody designated as STC820, or a humanized antibody version thereof. A humanized STC820 antibody can have the VH region, the VL region, or both the VH and VL region of STC820 as described herein. A humanized STC820 antibody can also have six CDR regions (VH CDR1, VH CDR2, VH CDR3, VL CDR1, VL CDR2 and VL CDR3) of STC820 as described herein. The humanized STC820 antibody can also have less than the six CDR regions of STC820. In some embodiments, the humanized STC820 antibody can also have one, two, three, four, or five CDR regions (VH CDR1, VH CDR2, VH CDR3, VL CDR1, VL CDR2 and VL CDR3) of STC820.

In some embodiments, the molecules provided herein is the mouse monoclonal antibody designated as STC1011, or a humanized antibody version thereof. A humanized STC1011 antibody can have the VH region, the VL region, or both the VH and VL region of STC1012 as described herein. A humanized STC1011 antibody can also have six CDR regions (VH CDR1, VH CDR2, VH CDR3, VL CDR1, VL CDR2 and VL CDR3) of STC1011 as described herein. The humanized STC1011 antibody can also have less than the six CDR regions of STC1011. In some embodiments, the humanized STC1011 antibody can also have one, two, three, four, or five CDR regions (VH CDR1, VH CDR2, VH CDR3, VL CDR1, VL CDR2 and VL CDR3) of STC1011.

In some embodiments, the molecules provided herein is the mouse monoclonal antibody designated as STC1012, or a humanized antibody version thereof. A humanized STC1012 antibody can have the VH region, the VL region, or both the VH and VL region of STC1012 as described herein. A humanized STC1012 antibody can also have six CDR regions (VH CDR1, VH CDR2, VH CDR3, VL CDR1, VL CDR2 and VL CDR3) of STC1012 as described herein. The humanized STC1012 antibody can also have less than the six CDR regions of STC1012. In some embodiments, the humanized STC1012 antibody can also have one, two, three, four, or five CDR regions (VH CDR1, VH CDR2, VH CDR3, VL CDR1, VL CDR2 and VL CDR3) of STC1012.

In some embodiments, the molecules provided herein is the mouse monoclonal antibody designated as STC1029, or a humanized antibody version thereof. A humanized STC1029 antibody can have the VH region, the VL region, or both the VH and VL region of STC1029 as described herein. A humanized STC1029 antibody can also have six CDR regions (VH CDR1, VH CDR2, VH CDR3, VL CDR1, VL CDR2 and VL CDR3) of STC1012 as described herein. The humanized STC1029 antibody can also have less than the six CDR regions of STC1029. In some embodiments, the humanized STC1029 antibody can also have one, two, three, four, or five CDR regions (VH CDR1, VH CDR2, VH CDR3, VL CDR1, VL CDR2 and VL CDR3) of STC1029.

In some embodiments, the molecules provided herein is the mouse monoclonal antibody designated as STC2602, or a humanized antibody version thereof. A humanized STC2602 antibody can have the VH region, the VL region, or both the VH and VL region of STC2602 as described herein. A humanized STC2602 antibody can also have six CDR regions (VH CDR1, VH CDR2, VH CDR3, VL CDR1, VL CDR2 and VL CDR3) of STC2602 as described herein. The humanized STC2602 antibody can also have less than the six CDR regions of STC2602. In some embodiments, the humanized STC2602 antibody can also have one, two, three, four, or five CDR regions (VH CDR1, VH CDR2, VH CDR3, VL CDR1, VL CDR2 and VL CDR3) of STC2602.

In some embodiments, the molecules provided herein is the mouse monoclonal antibody designated as STC2714, or a humanized antibody version thereof. A humanized STC2714 antibody can have the VH region, the VL region, or both the VH and VL region of STC2714 as described herein. A humanized STC2714 antibody can also have six CDR regions (VH CDR1, VH CDR2, VH CDR3, VL CDR1, VL CDR2 and VL CDR3) of STC2714 as described herein.

The humanized STC2714 antibody can also have less than the six CDR regions of STC2602. In some embodiments, the humanized STC2714 antibody can also have one, two, three, four, or five CDR regions (VH CDR1, VH CDR2, VH CDR3, VL CDR1, VL CDR2 and VL CDR3) of STC2714.

In some embodiments, the molecules provided herein is the mouse monoclonal antibody designated as STC2739, or a humanized antibody version thereof. A humanized STC2739 antibody can have the VH region, the VL region, or both the VH and VL region of STC2739 as described herein. A humanized STC2739 antibody can also have six CDR regions (VH CDR1, VH CDR2, VH CDR3, VL CDR1, VL CDR2 and VL CDR3) of STC2739 as described herein. The humanized STC2739 antibody can also have less than the six CDR regions of STC2739. In some embodiments, the humanized STC2739 antibody can also have one, two, three, four, or five CDR regions (VH CDR1, VH CDR2, VH CDR3, VL CDR1, VL CDR2 and VL CDR3) of STC2739.

In some embodiments, the molecules provided herein is the mouse monoclonal antibody designated as STC2778, or a humanized antibody version thereof. A humanized STC2778 antibody can have the VH region, the VL region, or both the VH and VL region of STC2778 as described herein. A humanized STC2778 antibody can also have six CDR regions (VH CDR1, VH CDR2, VH CDR3, VL CDR1, VL CDR2 and VL CDR3) of STC2778 as described herein. The humanized STC2778 antibody can also have less than the six CDR regions of STC2778. In some embodiments, the humanized STC2778 antibody can also have one, two, three, four, or five CDR regions (VH CDR1, VH CDR2, VH CDR3, VL CDR1, VL CDR2 and VL CDR3) of STC2778.

In some embodiments, the molecules provided herein is the mouse monoclonal antibody designated as STC2781, or a humanized antibody version thereof. A humanized STC2781 antibody can have the VH region, the VL region, or both the VH and VL region of STC2781 as described herein. A humanized STC2781 antibody can also have six CDR regions (VH CDR1, VH CDR2, VH CDR3, VL CDR1, VL CDR2 and VL CDR3) of STC2781 as described herein. The humanized STC2781 antibody can also have less than the six CDR regions of STC2781. In some embodiments, the humanized STC2781 antibody can also have one, two, three, four, or five CDR regions (VH CDR1, VH CDR2, VH CDR3, VL CDR1, VL CDR2 and VL CDR3) of STC2781.

Standard techniques known to those of skill in the art can be used to introduce mutations in the nucleotide sequence encoding an antigen binding fragment, or an antibody, provided herein, including, for example, site-directed mutagenesis and PCR-mediated mutagenesis which results in amino acid substitutions. In certain embodiments, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a specific embodiment, the derivatives have conservative amino acid substitutions are made at one or more predicted non-essential amino acid residues. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

In some embodiments, the molecules provided herein having an antigen binding fragment that immunospecifically binds to BTN1A1 or glycosylated BTN1A1 can have an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of the murine monoclonal antibody STC703, STC810, STC820, STC1011, STC1012, STC1029, STC2602, STC2714, STC2739, STC2778, or STC2781, or an antigen-binding fragment thereof, such as a VH domain or VL domain. In one embodiment, the molecules provided herein can have an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to an amino acid sequence depicted in SEQ ID NOS: 3, 5, 31, 33, 59, 61, 87, 89, 115, 117, 143, 145, 193, 195, 221, 223, 249, 251, 277, 279, 305 or 307. In yet another embodiment, the molecules provided herein can have a VH CDR and/or a VL CDR amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to a VH CDR amino acid sequence and/or a VL CDR amino acid sequence depicted in any one of Tables 2a-12b above.

In some embodiments, the molecules provided herein can have an amino acid sequence of a VH domain and/or an amino acid sequence a VL domain encoded by a nucleotide sequence that hybridizes to the complement of a nucleotide sequence encoding any one of the VH and/or VL domains depicted in any one of Tables 2a-12b under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3).

In another embodiment, the molecules provided herein can have an amino acid sequence of a VH CDR or an amino acid sequence of a VL CDR encoded by a nucleotide sequence that hybridizes to the complement of a nucleotide sequence encoding any one of the VH CDRs and/or VL CDRs depicted in any one of Tables 2a-12b under stringent conditions (e.g., hybridization to filter-bound DNA in 6×SSC at about 45° C. followed by one or more washes in 0.2×SSC/0.1% SDS at about 50-65° C.), under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3)

In some embodiments, provided herein are also isolated nucleic acid that encode an amino acid sequence f a VH CDR or an amino acid sequence of a VL CDR depicted in any one of Tables 2a-12b, or that hybridizes to the complement of a nucleic acid sequence encoding any one of the VH CDRs and/or VL CDRs depicted in any one of Tables 2a-12b under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, provided herein are also isolated nucleic acid that encode an amino acid sequence of a VH domain and/or an amino acid sequence a VL domain depicted in any one of Tables 2a-12b, or that hybridizes to the complement of a nucleotide sequence encoding any one of the VH and/or VL domains depicted in any one of Tables 2a-12b under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 4 or that hybridizes to the complement of a nucleotide sequence of SEQ ID NO: 4 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 6 or that hybridizes to the complement of a nucleotide sequence of SEQ ID NO: 6 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 32 or that hybridizes to the complement of a nucleotide sequence of SEQ ID NO: 32 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 36 or that hybridizes to the complement of a nucleotide sequence of SEQ ID NO: 34 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 60 or that hybridizes to the complement of a nucleotide sequence of SEQ ID NO: 60 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 62 or that hybridizes to the complement of a nucleotide sequence of SEQ ID NO: 62 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 88 or that hybridizes to the complement of a nucleotide sequence of SEQ ID NO: 88 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 90 or that hybridizes to the complement of a nucleotide sequence of SEQ ID NO: 90 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 116 or that hybridizes to the complement of a nucleotide sequence of SEQ ID NO: 116 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 118 or that hybridizes to the complement of a nucleotide sequence of SEQ ID NO: 118 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 144 or that hybridizes to the complement of a nucleotide sequence of SEQ ID NO: 144 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 146 or that hybridizes to the complement of a nucleotide sequence of SEQ ID NO: 146 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 194 or that hybridizes to the complement of a nucleotide sequence of SEQ ID NO: 194 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 196 or that hybridizes to the complement of a nucleotide sequence of SEQ ID NO: 196 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 222 or that hybridizes to the complement of a nucleotide sequence of SEQ ID NO: 222 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 224 or that hybridizes to the complement of a nucleotide sequence of SEQ ID NO: 224 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 250 or that hybridizes to the complement of a nucleotide sequence of SEQ ID NO: 250 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 252 or that hybridizes to the complement of a nucleotide sequence of SEQ ID NO: 252 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 278 or that hybridizes to the complement of a nucleotide sequence of SEQ ID NO: 278 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 280 or that hybridizes to the complement of a nucleotide sequence of SEQ ID NO: 280 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 306 or that hybridizes to the complement of a nucleotide sequence of SEQ ID NO: 306 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

In some embodiments, the isolated nucleic acid can have a sequence of SEQ ID NO: 308 or that hybridizes to the complement of a nucleotide sequence of SEQ ID NO: 308 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art.

The BTN1A1 epitopes of STC810 were mapped by cross-link analysis. Table 13 summarizes the cross-linked peptides of BTN1A1-Fc and STC810, which represent BTN1A1 epitopes of STC810 (SEQ ID NOS: 171-173). FIG. 13A shows a synthesized epitope of BTN1A1(ECD)-Fc antigen for STC810:

(SEQ ID NO: 174)
LELRWFRKKVSPA (SEQ ID NO: 175)
EEGLFTVAASVIIRDTSAKNV

Table 14 summarizes the the cross-linked peptides of BTN1A1-His and STC810, which represent BTN1A1 epitopes of STC810 (SEQ ID NOS: 176-179). FIG. 13B shows a synthesized epitope of BTN1A1(ECD)-His antigen for STC810.

(SEQ ID NO: 180)
GRATLVQDGIAKGRV (SEQ ID NO: 181)
EEGLFTVAASVIIRDTSAKNV

TABLE 13

Cross-linked peptides of BTN1A1-Fc with STC810 analyzed by nLC-orbitrap MS/MS.

| Proteolysis | Sequence | Protein 1 | Protein 2 | Sequence protein 1 | Sequence protein 2 |
|---|---|---|---|---|---|
| Chymotrypsin | RKKVSPAVL (SEQ ID NO: 171)-YCARGAY (SEQ ID NO: 182)-a1-b1 | BTN1A1-FC | STC810 HC | 41-49 | 95-101 |
| | RKKVSPAVL(SEQ ID NO: 171)-YCARGAY(SEQ ID NO: 182)-a2-b1 | BTN1A1-FC | STC810 HC | 41-49 | 95-101 |
| | RKKVSPAVL(SEQ ID NO: 171)-YCARGAY(SEQ ID NO: 182)-a3-b1 | BTN1A1-FC | STC810 HC | 41-49 | 95-101 |
| | TVAASVIIRDTSAKNV SCY (SEQ ID NO: 172)-TFTHY (SEQ ID NO: 183)-a11-b3 | BTN1A1-FC | STC810 HC | 175-193 | 28-32 |
| | TVAASVIIRDTSAKNV SCY (SEQ ID NO: 172)-TFTHY (SEQ ID NO: 183)-a11-b4 | BTN1A1-FC | STC810 HC | 175-193 | 28-32 |
| | TVAASVIIRDTSAKNV SCY (SEQ ID NO: 172)-TFTHY (SEQ ID NO: 183)-a14-b4 | BTN1A1-FC | STC810 HC | 175-193 | 28-32 |
| Thermolysin | IRDTSAKN (SEQ ID NO: 173)-FTFGSGTE (SEQ ID NO: 184)-a4-b7 | BTN1A1-FC | STC810LC | 182-189 | 96-105 |

TABLE 14

Cross-linked peptides of BTN1A1-His with STC810 analyzed by nLC-orbitrap MS/MS.

| Proteolysis | Sequence | Protein 1 | Protein 2 | Sequence protein 1 | Sequence protein 2 |
|---|---|---|---|---|---|
| Trypsin | ATLVQDGIAKGR (SEQ ID NO: 176)-SLEWIGYIYPSNGGTG YNQKFKSR (SEQ ID NO: 185)-a10-b11 | BTN1A1-His | STC810 HC | 69-80 | 44-67 |
| | NPDEEGLFTVAASVIIR DTSAK (SEQ ID NO: 177)-LLISYTSSLHSGVPSR (SEQ ID NO: 186)-a13-b6 | BTN1A1-His | STC810 LC | 167-188 | 46-61 |
| | NPDEEGLFTVAASVIIR DTSAK (SEQ ID NO: 177)-LLISYTSSLHSGVPSR (SEQ ID NO: 186)-a9-b6 | BTN1A1-His | STC810 LC | 167-188 | 46-61 |
| Chymotrypsin | TVAASVIIRDTSAKNV SCY (SEQ ID NO: 178)-TFTHY (SEQ ID NO: 187)-a11-b3 | BTN1A1-His | STC810 HC | 175-193 | 28-32 |
| | TVAASVIIRDTSAKNV SCY (SEQ ID NO: 178)-TFTHY (SEQ ID NO: 187)-a5-b3 | BTN1A1-His | STC810 HC | 175-193 | 28-32 |
| Thermolysin | AEQXPEYRGRAT (SEQ ID NO: 179)-LHSGVPSR (SEQ ID NO: 188)-a10-b2 | BTN1A1-His | STC810 LC | 59-70 | 54-61 |

Accordingly, also provided herein are the molecule is an molecules having an antigen binding fragment that competitively blocks (e.g., in a dose-dependent manner) a BTN1A1 epitope described herein. In some embodiments, provided herein are molecules having an antigen binding fragment that competitively block (e.g., in a dose-dependent manner) an BTN1A1 epitope of STC703, STC810, STC820, STC1011, STC1012, STC1029, STC2602, STC2714, STC2739, STC2778, or STC2781. In some embodiments, provided herein are molecules having an antigen binding fragment that competitively block (e.g., in a dose-dependent manner) an BTN1A1 epitope of STC1011, STC1012, or STC1029. In some embodiments, provided herein are molecules having an antigen binding fragment that competitively block (e.g., in a dose-dependent manner) an BTN1A1 epitope of STC703, STC810, or STC820. In some embodiments, provided herein are molecules having an antigen binding fragment that competitively block (e.g., in a dose-dependent manner) an BTN1A1 epitope of STC703 or STC810. In some embodiments, provided herein are molecules having an antigen binding fragment that competitively block (e.g., in a dose-dependent manner) an BTN1A1 epitope of STC810. In some embodiments, provided herein are molecules having an antigen binding fragment that competitively block (e.g., in a dose-dependent manner) an BTN1A1 epitope of STC2602, STC2714, STC2739, STC2778, STC2781. In some embodiments, provided herein are molecules having an antigen binding fragment that competitively block (e.g., in a dose-dependent manner) an BTN1A1 epitope of STC2714 or STC2778. In some embodiments, provided herein are molecules having an antigen binding fragment that competitively block (e.g., in a dose-dependent manner) an BTN1A1 epitope of STC2714. In some embodiments, the molecules provided herein have an antigen binding fragment that immunospecifically binds to an epitope of BTN1A1 as described herein. In some embodiments, the molecules provided herein have an antigen binding fragment that immunospecifically binds to an BTN1A1 epitope of STC703, STC810, STC820, STC1011, STC1012, STC1029, STC2602, STC2714, STC2739, STC2778, or STC2781. In some embodiments, the molecules provided herein have an antigen binding fragment that immunospecifically binds to an BTN1A1 epitope of STC1011, STC1012, or STC1029. In some embodiments, the molecules provided herein have an antigen binding fragment that immunospecifically binds to an BTN1A1 epitope of STC703, STC810, or STC820. In some embodiments, the molecules provided herein have an antigen binding fragment that immunospecifically binds to an BTN1A1 epitope of STC703 or STC810. In some embodiments, the molecules provided herein have an antigen binding fragment that immunospecifically binds to an BTN1A1 epitope of STC810. The molecule can be an antibody. In some embodiments, the molecules provided herein have an antigen binding fragment that immunospecifically binds to an BTN1A1 epitope of STC2602, STC2714, STC2739, STC2778, STC2781. In some embodiments, the molecules provided herein have an antigen binding fragment that immunospecifically binds to an BTN1A1 epitope of STC2714. The molecule can be an antibody. The antibody can be a monoclonal antibody. The antibody can be a humanized antibody.

In some embodiments, provided herein are anti-BTN1A1 antibodies that competitively block (e.g., in a dose-dependent manner) a BTN1A1 epitope described herein. In some embodiments, provided herein are anti-BTN1A1 antibodies that competitively block (e.g., in a dose-dependent manner) a BTN1A1 epitope of STC703, STC810, STC820, STC1011, STC1012, STC1029, STC2602, STC2714, STC2739, STC2778, or STC2781 as described herein. In some embodiments, provided herein are anti-BTN1A1 antibodies that competitively block (e.g., in a dose-dependent manner) a BTN1A1 epitope described herein. In some embodiments, provided herein are anti-BTN1A1 antibodies that competitively block (e.g., in a dose-dependent manner) a BTN1A1 epitope described herein. In some embodiments, provided herein are anti-BTN1A1 antibodies that competitively block (e.g., in a dose-dependent manner) a BTN1A1 epitope of STC1011, STC1012, or STC1029 as described herein. In some embodiments, provided herein are anti-BTN1A1 antibodies that competitively block (e.g., in a dose-dependent manner) a BTN1A1 epitope of STC703, STC810, or STC820 as described herein. In some embodiments, provided herein are anti-BTN1A1 antibodies that competitively block (e.g., in a dose-dependent manner) a BTN1A1 epitope of STC703 or STC810 as described herein. In some embodiments, provided herein are anti-BTN1A1 antibodies that competitively block (e.g., in a dose-dependent manner) a BTN1A1 epitope of STC810 as described herein. In some embodiments, provided herein are anti-BTN1A1 antibodies that competitively block (e.g., in a dose-dependent manner) a BTN1A1 epitope of STC2602, STC2714, STC2739, STC2778, STC2781 as described herein. In some embodiments, provided herein are anti-BTN1A1 antibodies that competitively block (e.g., in a dose-dependent manner) a BTN1A1 epitope of STC2714 as described herein. In some embodiments, the anti-BTN1A1 antibodies provided herein immunospecifically bind to an epitope of BTN1A1 as described herein. In some embodiments, the anti-BTN1A1 antibodies provided herein immunospecifically bind to an BTN1A1 epitope of STC703, STC810, STC820, STC1011, STC1012, STC1029, STC2602, STC2714, STC2739, STC2778, or STC2781. In some embodiments, the anti-BTN1A1 antibodies provided herein immunospecifically bind to an BTN1A1 epitope of STC1011, STC1012, or STC1029. In some embodiments, the anti-BTN1A1 antibodies provided herein immunospecifically bind to an BTN1A1 epitope of STC703, STC810, or STC820. In some embodiments, the anti-BTN1A1 antibodies provided herein immunospecifically bind to an BTN1A1 epitope of STC703 or STC810. In some embodiments, the anti-BTN1A1 antibodies provided herein immunospecifically bind to an BTN1A1 epitope of STC810. In some embodiments, the anti-BTN1A1 antibodies provided herein immunospecifically bind to an BTN1A1 epitope of STC2602, STC2714, STC2739, STC2778, or STC2781. In some embodiments, the anti-BTN1A1 antibodies provided herein immunospecifically bind to an BTN1A1 epitope of STC2714.

In some embodiments, the molecules having an antigen binding fragment that competitively block (e.g., in a dose-dependent manner) a BTN1A1 epitope, whereby the BTN1A1 epitope has at least five consecutive amino acids of an amino acid sequence of SEQ ID NOS: 171-181. In some embodiments, the molecules provided herein have an antigen binding fragment that immunospecifically binds to an epitope of BTN1A1, whereby the BTN1A1 epitope has at least five consecutive amino acids of an amino acid sequence of SEQ ID NOS: 171-181. The epitope of BTN1A1 can have at least six, at least seven, at least eight, at least nine, at least ten, at least eleven, at least twelve, at least thirteen, at least fourteen, or at least fifteen, consecutive amino acids of an amino acid sequence of SEQ ID NOS: 171-181. The epitope of BTN1A1 can have at least six consecutive amino acids of an amino acid sequence of SEQ ID NOS: 171-181. The epitope of BTN1A1 can have at least seven consecutive amino acids of an amino acid sequence of SEQ ID NOS: 171-181. The epitope of BTN1A1 can have at least eight consecutive amino acids of an amino acid sequence of SEQ ID NOS: 171-181. The epitope of BTN1A1 can have at least nine consecutive amino acids of an amino acid sequence of SEQ ID NOS: 171-181. The epitope of BTN1A1 can have at least ten consecutive amino acids of an amino acid sequence of SEQ ID NOS: 171-181. The epitope of BTN1A1 can have at least eleven consecutive amino acids of an amino acid sequence of SEQ ID NOS: 171-181. The epitope of BTN1A1 can have at least twelve consecutive amino acids of an amino acid sequence of SEQ ID NOS: 171-181. The epitope of BTN1A1 can have at least thirteen consecutive amino acids of an amino acid sequence of SEQ ID NOS: 171-181. The epitope of BTN1A1 can have at least fourteen consecutive amino acids of an amino acid sequence of SEQ ID NOS: 171-181. The epitope of BTN1A1 can have at least fifteen consecutive amino acids of an amino acid sequence of SEQ ID NOS: 171-181. The molecule can be an antibody. The antibody can be a monoclonal antibody. The antibody can be a humanized antibody.

In some embodiments, the molecules having an antigen binding fragment that competitively block (e.g., in a dose-dependent manner) a BTN1A1 epitope, whereby the BTN1A1 epitope has an amino acid sequence of SEQ ID NOS: 171-181. In some embodiments, the molecules provided herein have an antigen binding fragment that immunospecifically binds to an epitope of BTN1A1, whereby the BTN1A1 epitope has an amino acid sequence of SEQ ID NOS: 171, 172, 173, 174, 175, 176, 177, 178, 179, 180, or 181. The epitope of BTN1A1 can have an amino acid sequence of SEQ ID NO: 171. The epitope of BTN1A1 can have an amino acid sequence of SEQ ID NO: 172. The epitope of BTN1A1 can have an amino acid sequence of SEQ ID NO: 173. The epitope of BTN1A1 can have an amino acid sequence of SEQ ID NO: 174. The epitope of BTN1A1 can have an amino acid sequence of SEQ ID NO: 175. The epitope of BTN1A1 can have an amino acid sequence of SEQ ID NO: 176. The epitope of BTN1A1 can have an amino acid sequence of SEQ ID NO: 177. The epitope of BTN1A1 can have an amino acid sequence of SEQ ID NO: 178. The epitope of BTN1A1 can have an amino acid sequence of SEQ ID NO: 179. The epitope of BTN1A1 can have an amino acid sequence of SEQ ID NO: 180. The epitope of BTN1A1 can have an amino acid sequence of SEQ ID NO: 181.

In some embodiments, the molecules provided herein can be chemically modified, e.g., by the covalent attachment of any type of molecule to the antibody. For example, but not by way of limitation, the antibody derivatives include antibodies that have been chemically modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formulation, metabolic synthesis of tunicamycin, etc. Additionally, the antibody may contain one or more non-classical amino acids.

The molecules provided herein can have a framework region known to those of skill in the art (e.g., a human or non-human fragment). The framework region can, for example, be naturally occurring or consensus framework regions. In specific embodiments, the framework region of an antibody provided herein is human (see, e.g., Chothia et al., 1998, *J. Mol. Biol.* 278:457-479 for a listing of human framework regions, which is incorporated by reference herein in its entirety). See also Kabat et al. (1991) *Sequences of Proteins of Immunological Interest* (U.S. Department of Health and Human Services, Washington, D.C.) 5th ed.

In another aspect, provided herein are molecules having an antigen binding fragment that competitively blocks (e.g., in a dose-dependent manner) a BTN1A1 epitope of an anti-BTN1A1 antibody described herein. In some embodiments, provided herein are molecules having an antigen binding fragment that competitively block (e.g., in a dose-dependent manner) an BTN1A1 epitope of STC703, STC810, STC820, STC1011, STC1012, STC1029, STC2602, STC2714, STC2739, STC2778, or STC2781. In some embodiments, the molecules provided herein have an antigen binding fragment that immunospecifically binds to an epitope of BTN1A1 as described herein. In some embodiments, the molecules provided herein have an antigen binding fragment that immunospecifically binds to an BTN1A1 epitope of STC703, STC810, STC820, STC1011, STC1012, STC1029, STC2602, STC2714, STC2739, STC2778, or STC2781. The molecule can be an antibody. The antibody can be a monoclonal antibody. The antibody can be a humanized antibody.

In some embodiments, provided herein are anti-BTN1A1 antibodies that competitively block (e.g., in a dose-dependent manner) a BTN1A1 epitope described herein. In some embodiments, provided herein are anti-BTN1A1 antibodies that competitively block (e.g., in a dose-dependent manner) a BTN1A1 epitope of an anti-BTN1A1 antibody, such as STC703, STC810, STC820, STC1011, STC1012, STC1029, STC2602, STC2714, STC2739, STC2778, or STC2781. In some embodiments, the anti-BTN1A1 antibodies provided herein immunospecifically bind to an epitope of an anti-BTN1A1 antibody, such as STC703, STC810, STC820, STC1011, STC1012, STC1029, STC2602, STC2714, STC2739, STC2778, or STC2781. In some embodiments, the anti-BTN1A1 antibodies provided herein immunospecifically bind to an BTN1A1 epitope of STC703, STC810, STC820, STC1011, STC1012, STC1029, STC2602, STC2714, STC2739, STC2778, or STC2781.

In certain embodiments, the molecules provided herein have a high affinity for BTN1A1, glycosylated BTN1A1, a BTN1A1 dimer (e.g., a glycosylated BTN1A1 dimer) or a polypeptide, or polypeptide fragment or epitope thereof. In one embodiment, the molecules provided herein can be anti-BTN1A1 antibodies that have a higher affinity for a BTN1A1 antibody than known antibodies (e.g., commercially available monoclonal antibodies discussed elsewhere herein). In a specific embodiment, the molecules provided herein can be anti-BTN1A1 antibodies can have a 2- to 10-fold (or more) higher affinity for a BTN1A1 antigen than a known anti-BTN1A1 antibody as assessed by techniques described herein or known to one of skill in the art (e.g., a BIAcore assay). In accordance with these embodiments, the affinity of the antibodies are, in one embodiment, assessed by a BIAcore assay.

In certain embodiments, molecules provided herein can have an antigen binding fragment that binds to BTN1A1, glycosylated BTN1A1, a BTN1A1 dimer (e.g., a glycosylated BTN1A1 dimer) or a polypeptide, or polypeptide fragment or epitope thereof with a dissociation constant ($K_D$) of no more than 1 μM, no more than 100 nM, no more than 10 nM, no more than 1 nM, or no more than 0.1 nM. In some embodiments, molecules provided herein can be anti-BTN1A1 antibodies having a $K_D$ of no more than 500 nM. In some embodiments, molecules provided herein can be anti-BTN1A1 antibodies having a $K_D$ of no more than 200 nM. In some embodiments, molecules provided herein can be anti-BTN1A1 antibodies having a $K_D$ of no more than 100 nM. In some embodiments, molecules provided herein can be anti-BTN1A1 antibodies having a Kd of no more than 50 nM. In some embodiments, molecules provided herein can be anti-BTN1A1 antibodies having a $K_D$ of no more than 20 nM. In some embodiments, molecules provided herein can be anti-BTN1A1 antibodies having a $K_D$ of no more than 10 nM. In some embodiments, molecules provided herein can be anti-BTN1A1 antibodies having a $K_D$ of no more than 5 nM. In some embodiments, molecules provided herein can be anti-BTN1A1 antibodies having a $K_D$ of no more than 2 nM. In some embodiments, molecules provided herein can be anti-BTN1A1 antibodies having a $K_D$ of no more than 1 nM. In some embodiments, molecules provided herein can be anti-BTN1A1 antibodies having a $K_D$ of no more than 0.5 nM. In some embodiments, molecules provided herein can be anti-BTN1A1 antibodies having a $K_D$ of no more than 0.1 nM.

In certain embodiments, molecules provided herein can block or neutralize the activities of BTN1A1. The molecule can be a neutralizing antibody. The neutralizing antibody can block the binding the BTN1A1 with its natural ligands and inhibit the signaling pathways mediated by BTN1A1 and/or its other physiological activities. The IC50 of a neutralizing antibody can range between 0.01-10 μg/ml in the neutralization assay. The IC50 of a neutralizing antibody can be no more than 10 μg/ml. The IC50 of a neutralizing antibody can be no more than 8 μg/ml. The IC50 of a neutralizing antibody can be no more than 6 μg/ml. The IC50 of a neutralizing antibody can be no more than 4 μg/ml. The IC50 of a neutralizing antibody can be no more than 2 μg/ml. The IC50 of a neutralizing antibody can be no more than 1 μg/ml. The IC50 of a neutralizing antibody can be no more than 0.8 μg/ml. The IC50 of a neutralizing antibody can be no more than 0.6 μg/ml. The IC50 of a neutralizing antibody can be no more than 0.4 μg/ml. The IC50 of a neutralizing antibody can be no more than 0.2 μg/ml. The IC50 of a neutralizing antibody can be no more than 0.1 μg/ml. The IC50 of a neutralizing antibody can be no more than 0.08 μg/ml. The IC50 of a neutralizing antibody can be no more than 0.06 μg/ml. The IC50 of a neutralizing antibody can be no more than 0.04 μg/ml. The IC50 of a neutralizing antibody can be no more than 0.02 μg/ml. The IC50 of a neutralizing antibody can be no more than 0.01 μg/ml.

The molecules provided herein having an antigen binding fragment that immunospecifically binds to BTN1A1 or glycosylated BTN1A1 or a BTN1A1 dimer (e.g., a glycosylated BTN1A1 dimer) can be anti-BTN1A1 antibodies. Antibodies provided herein include, but are not limited to, synthetic antibodies, monoclonal antibodies, recombinantly produced antibodies, multispecific antibodies (including bispecific antibodies), human antibodies, humanized antibodies, camelized antibodies, chimeric antibodies, intrabodies, anti-idiotypic (anti-Id) antibodies, and functional fragments of any of the above. Non-limiting examples of functional fragments include single-chain Fvs (scFv) (e.g., including monospecific, bispecific, etc.), Fab fragments, F(ab') fragments, $F(ab)_2$ fragments, $F(ab')_2$ fragments, disulfide-linked Fvs (sdFv), Fd fragments, Fv fragments, diabody, triabody, tetrabody and minibody.

In particular, molecules provided herein include immunoglobulin molecules and immunologically active portions of immunoglobulin molecules, e.g., molecules that contain an antigen binding fragment that immunospecifically binds to BTN1A1 or glycosylated BTN1A1 or a BTN1A1 dimer (e.g., a glycosylated BTN1A1 dimer). The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule.

The molecules provided herein can be monospecific, bispecific, trispecific antibodies or antibodies of greater multispecificity. Multispecific antibodies may be specific for different epitopes of a BTN1A1 as described here, or can be specific for both a BTN1A1 polypeptide as well as for a heterologous epitope, such as a heterologous polypeptide or solid support material. In specific embodiments, the antibodies provided herein are monospecific for a given epitope of a BTN1A1 polypeptide and do not bind to other epitopes.

5.2.3. Modifications and Derivatives

The binding properties of any of the above molecules having an antigen binding fragment that immunospecifically binds to BTN1A1 or glycosylated BTN1A1 or a BTN1A1 dimer (e.g., a glycosylated BTN1A1 dimer) can be further improved by screening for variants that exhibit desired properties. For example, such improvement can be done using various phage display methods known in the art. In phage display methods, functional antibody domains are displayed on the surface of phage particles which carry the polynucleotide sequences encoding them. In a particular embodiment, such phage can be utilized to display antigen binding fragments, such as Fab and Fv or disulfide-bond stabilized Fv, expressed from a repertoire or combinatorial antibody library (e.g., human or murine). Phage expressing an antigen binding fragment that binds the antigen of interest can be selected or identified with antigen, e.g., using labeled antigen or antigen bound or captured to a solid surface or bead. Phage used in these methods are typically filamentous phage, including fd and M13. The antigen binding fragments are expressed as a recombinantly fused protein to either the phage gene III or gene VIII protein. Examples of phage display methods that can be used to make the antibodies or other molecules having an antigen binding fragment as described herein include those disclosed in Brinkman et al., *J Immunol Methods,* 182:41-50 (1995); Ames et al., *J Immunol. Methods,* 184:177-186 (1995); Kettleborough et al., *Eur. J. Immunol.,* 24:952-958(1994); Persic et al., *Gene,* 187:9-18 (1997); Burton et al., *Adv. Immunol.* 57:191-280 (1994); PCT Publications WO 92/001047; WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; all of which are hereby incorporated by references in their entireties.

As described in the above references, after phage selection, the antibody coding regions from the phage can be isolated and used to generate whole antibodies, including humanized antibodies, or any other desired fragments, and expressed in any desired host, including mammalian cells, insect cells, plant cells, yeast, and bacteria, e.g., as described in detail below. For example, techniques to recombinantly produce Fab, Fab' and $F(ab')_2$ fragments can also be employed using methods known in the art such as those disclosed in PCT Publication WO 92/22324; Mullinax, R. L. et al., *BioTechniques,* 12(6):864-869 (1992); and Sawai et al., *Am. J. Reprod. Immunol.* 34:26-34 (1995); and Better, M. et al. *Science* 240:1041-1043(1988); all of which are hereby incorporated by references in their entireties. Examples of techniques which can be used to produce single-chain Fvs and antibodies include those described in U.S. Pat. Nos. 4,946,778 and 5,258,498; Huston, J. S. et al., *Methods in Enzymology* 203:46-88(1991); Shu, L. et al., *Proc. Natl. Acad. Sci.* (USA) 90:7995-7999; and Skerra. A. et al., *Science* 240:1038-1040 (1988); all of which are hereby incorporated by references in their entireties.

Phage display technology can be used to increase the affinity of an anti-BTN1A1 antibody of or anti-glycosylated BTN1A1 antibodies or of BTN1A1 dimer antibodies, or other molecules having an antigen binding fragment that immunospecifically binds BTN1A1 or glycosylated BTN1A1 or a BTN1A1 dimer (e.g., a glycosylated BTN1A1 dimer) as described herein. This technique can be used in obtaining high affinity antibodies that could be used in the combinatorial methods described herein. This technology, referred to as affinity maturation, employs mutagenesis or CDR walking and re-selection using such receptors or ligands (or their extracellular domains) or an antigenic fragment thereof to identify antibodies that bind with higher affinity to the antigen when compared with the initial or parental antibody (See, e.g., Glaser, S. M. et al., *J. Immunol.* 149:3903-3913(1992)). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen. Any screening method known in the art can be used to identify mutant antibodies with increased avidity to the antigen (e.g., ELISA) (see, e.g., Wu, H. et al., *Proc. Natl. Acad. Sci.* (USA) 95(11):6037-6042(1998); Yelton, D. E. et al., *J. Immunol.* 155:1994-2004 (1995). CDR walking which randomizes the light chain can also be used. (see Schier et al., *J. Mol. Biol.* 263:551-567(1996)).

Random mutagenesis can be used in concert with methods of phage display to identify improved CDRs and/or variable regions. Phage display technology can alternatively be used to increase (or decrease) CDR affinity by directed mutagenesis (e.g., affinity maturation or "CDR-walking"). This technique uses the target antigen or an antigenic fragment thereof to identify antibodies having CDRs that bind with higher (or lower) affinity to the antigen when compared with the initial or parental antibody (see, e.g., Glaser, S. M. et al., *J. Immunol.* 149:3903-3913(1992)).

Methods for accomplishing such affinity maturation are described for example in: Krause, J. C. et al., Maio. 2(1) pii: e00345-10. doi: 10.1128/mBio.00345-10(2011); Kuan, C. T. et al., *Int. J. Cancer* 10.1002/ijc.25645; Hackel, B. J. et al., *J. Mol. Biol.* 401(1):84-96(2010); Montgomery, D. L. et al., MAbs 1(5):462-474(2009); Gustchina, E. et al., *Virology* 393(1):112-119 (2009); Finlay, W. J. et al., *J. Mol. Biol.* 388(3):541-558 (2009); Bostrom, J. et al., *Methods Mol. Biol.* 525:353-376 (2009); Steidl, S. et al., *Mol. Immunol.* 46(1):135-144 (2008); and Barderas, R. et al., *Proc. Natl. Acad. Sci.* (USA) 105(26):9029-9034 (2008); all of which are hereby incorporated by references in their entireties.

Provided herein are also derivatives of any of the above-described molecules having an antigen binding fragment that immunospecifically binds to BTN1A1 or glycosylated BTN1A1 or a BTN1A1 dimer, which can be an anti-BTN1A1 antibody or anti-glycosylated BTN1A1 antibody or an anti-BTN1A1 dimer antibody, but which has one, two, three, four, five or more amino acid substitutions, additions, deletions or modifications relative to a "parental" (or wild-type) molecule. Such amino acid substitutions or additions can introduce naturally occurring (i.e., DNA-encoded) or non-naturally occurring amino acid residues. Such amino acids can be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In some embodiments, the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al., *J. Biol. Chem.* 277(30): 26733-26740 (2002); Davies J. et al. *Biotechnology & Bioengineering* 74(4): 288-294(2001); all of which are hereby incorporated by references in their entireties). Methods of altering carbohydrate contents are known to those skilled in the art, see, e.g., Wallick, S. C. et al., *J. Exp. Med.* 168(3): 1099-1109(1988); Tao, M. H. et al., *J. Immunol.* 143(8): 2595-2601 (1989); Routledge, E. G. et al., *Transplantation* 60(8):847-53 (1995); Elliott, S. et al., *Nature Biotechnol.* 21:414-21(2003); Shields, R. L. et al., *J. Biol. Chem.* 277(30): 26733-26740 (2002); all of which are hereby incorporated by references in their entireties.

In some embodiments, a humanized antibody is a derivative antibody. Such a humanized antibody includes amino acid residue substitutions, deletions or additions in one or more non-human CDRs. The humanized antibody derivative can have substantially the same binding, better binding, or worse binding when compared to a non-derivative humanized antibody. In some embodiments, one, two, three, four, or five amino acid residues of the CDR have been mutated, such as substituted, deleted or added.

The molecules and antibodies as described herein can be modified by chemical modifications using techniques known to those of skill in the art, including, but not limited to, specific chemical cleavage, acetylation, formulation, metabolic synthesis of tunicamycin, etc. In one embodiment, a derivative molecule or a derivative antibody possesses a similar or identical function as the parental molecule or antibody. In another embodiment, a derivative molecule or a derivative antibody exhibits an altered activity relative to the parent molecule or parental antibody. For example, a derivative antibody (or fragment thereof) can bind to its epitope more tightly or be more resistant to proteolysis than the parental antibody.

Substitutions, additions or deletions in the derivatized antibodies can be in the Fc region of the antibody and can thereby serve to modify the binding affinity of the antibody to one or more FcγR. Methods for modifying antibodies with modified binding to one or more FcγR are known in the art, see, e.g., PCT Publication Nos. WO 04/029207, WO 04/029092, WO 04/028564, WO 99/58572, WO 99/51642, WO 98/23289, WO 89/07142, WO 88/07089, and U.S. Pat. Nos. 5,843,597 and 5,642,821; all of which are hereby incorporated by references in their entireties. In some embodiments, the antibodies or other molecules can have altered affinity for an activating FcγR, e.g., FcγRIIIA Preferably such modifications also have an altered Fc-mediated effector function. Modifications that affect Fc-mediated effector function are well known in the art (see U.S. Pat. No. 6,194,551, and WO 00/42072). In some embodiments, the modification of the Fc region results in an antibody with an altered antibody-mediated effector function, an altered binding to other Fc receptors (e.g., Fc activation receptors), an altered antibody-dependent cell-mediated cytotoxicity (ADCC) activity, an altered C1q binding activity, an altered complement-dependent cytotoxicity activity (CDC), a phagocytic activity, or any combination thereof.

ADCC is a cell-mediated reaction in which antigen-nonspecific cytotoxic cells that express FcRs (e.g., natural killer (NK) cells, neutrophils, and macrophages) recognize antibody bound to the surface of a target cell and subsequently cause lysis of (i.e., "kill") the target cell. The primary mediator cells are NK cells. NK cells express FcγRIII only, with FcγRIIIA being an activating receptor and FcγRIIIB an inhibiting one; monocytes express FcγRI, FcγRII and FcγRIII (Ravetch et al. (1991) *Annu. Rev. Immunol.,* 9:457-92). ADCC activity can be expressed as a concentration of antibody or Fc fusion protein at which the lysis of target cells is half-maximal. Accordingly, in some embodiments, the concentration of an antibody or Fc fusion protein of the invention, at which the lysis level is the same as the half-maximal lysis level by the wild-type control, is at least 2-, 3-, 5-, 10-, 20-, 50-, 100-fold lower than the concentration of the wild-type control itself. Additionally, in some embodiments, the antibody or Fc fusion protein of the invention can exhibit a higher maximal target cell lysis as compared to the wild-type control. For example, the maximal target cell lysis of an antibody or Fc fusion protein can be 10%, 15%, 20%, 25% or more higher than that of the wild-type control.

The molecules and antibodies as described herein can be modified to have enhanced potency. In some embodiments, the molecules and antibodies are modified with respect to effector function, e.g., so as to enhance ADCC and/or complement dependent cytotoxicity (CDC). In some embodiments, these therapeutic molecules or antibodies have enhanced interaction with killer cells bearing Fc receptors. Enhancement of effector functions, such as ADCC, can be achieved by various means, including introducing one or more amino acid substitutions in an Fc region. Also, cysteine residue(s) can be introduced in the Fc region, allowing interchain disulfide bond formation in this region. The homodimeric antibody can also have improved internalization capability and/or increased CDC and ADCC. Caron et al., *J. Exp Med.,* 176:1191-95 (1992) and Shopes, B. *J Immunol.,* 148:2918-22 (1992). Homodimeric antibodies with enhanced anti-cancer activity can also be prepared using heterobifunctional cross-linkers. Wolff et al., *Cancer Research,* 53:2560-65 (1993). Additionally, an antibody or molecule can be engineered which has dual Fc regions and can thereby have enhanced CDC and ADCC capabilities. Stevenson et al., *Anti-Cancer Drug Design* 3:219-30 (1989).

The glycosylation pattern of the Fc region can also be engineered. A number of antibody glycosylation forms have been reported as having a positive impact on effector function, including ADCC. Thus, engineering of the carbohydrate component of the Fc region, particularly reducing core fucosylation, can also have enhanced therapeutic potency. Shinkawa T, et al., *J Biol. Chem.,* 278:3466-73 (2003); Niwa R, et al., *Cancer Res.,* 64:2127-33 (2004); Okazaki A, et al., *J Mol. Biol.* 336:1239ˆ19 (2004); and Shields R L, et al., *J Biol. Chem.* 277:26733-40 (2002). Antibodies or molecules described herein with select glycoforms can be produced by a number of means, including the use of glycosylation pathway inhibitors, mutant cell lines that have absent or reduced activity of particular enzymes in the glycosylation pathway, engineered cells with gene expression in the glycosylation pathway either enhanced or knocked out, and in vitro remodeling with glycosidases and glycosyltransferases. Methods to modify the glycosylation of Fc region and enhance the therapeutic potency of antibodies or other molecules having an antigen binding fragment are known in the art. Rothman et al., *Molecular Immunology* 26: 1113-1123 (1989); Umana et al., *Nature Biotechnology* 17: 176-180 (1999); Shields et al., JBC 277:26733-26740 (2002); Shinkawa et al., JBC 278: 3466-3473 (2003); Bischoff et al., *J. Biol. Chem.* 265(26):15599-15605 (1990); U.S. Pat. Nos. 6,861,242 and 7,138,262, as well as US Publication No. 2003/0124652; all of which are hereby incorporated by reference in their entireties. A person of ordinary skill in the art would understand that the antibodies and molecules provided herein can be modified by any methods known in the art to have enhanced therapeutic potency.

Derivative molecules or antibodies can also have altered half-lives (e.g., serum half-lives) of parental molecules or antibodies in a mammal, preferably a human. In some embodiments, such alteration results in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of humanized antibodies or other molecules in a mammal, preferably a human, results in a higher serum titer of said antibodies or other molecules in the mammal, and thus, reduces the frequency of the administration of said antibodies or other molecules and/or reduces the concentration of said antibodies or other molecules to be administered. Molecules or antibodies having increased in vivo half-lives can be generated by techniques known to those of skill in the art. For example, molecules or antibodies with increased in vivo half-lives can be generated by modifying (e.g., substituting, deleting or adding) amino acid residues identified as involved in the interaction between the Fc domain and the FcRn receptor. The humanized antibodies as described herein can be engineered to increase biological half-lives (see, e.g. U.S. Pat. No. 6,277,375). For example, humanized antibodies as described herein can be engineered in the Fc-hinge domain to have increased in vivo or serum half-lives.

Molecules or antibodies as described herein with increased in vivo half-lives can be generated by attaching to said antibodies or antibody fragments polymer molecules such as high molecular weight polyethyleneglycol (PEG). PEG can be attached to the molecules or antibodies with or without a multifunctional linker either through site-specific conjugation of the PEG to the N- or C-terminus of said molecules or antibodies or via epsilon-amino groups present on lysine residues. Linear or branched polymer derivatization that results in minimal loss of biological activity can be used. The degree of conjugation can be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

The molecules or antibodies as described herein can also be modified by the methods and coupling agents described by Davis et al. (See U.S. Pat. No. 4,179,337) in order to provide compositions that can be injected into the mammalian circulatory system with substantially no immunogenic response. Removal of the Fc portion can reduce the likelihood that the antibody fragment elicits an undesirable immunological response and, thus, antibodies without Fc can be used for prophylactic or therapeutic treatments. As described above, antibodies can also be constructed so as to be chimeric, partially or fully human, so as to reduce or eliminate the adverse immunological consequences resulting from administering to an animal an antibody that has been produced in, or has sequences from, other species.

5.2.4. Fusions and Conjugates

Provided herein are molecules having an antigen binding fragment that immunospecifically binds to BTN1A1 or glycosylated BTN1A1 or a BTN1A1 dimer, including anti-BTN1A1 antibodies, anti-glycosylated BTN1A1 antibodies, and anti-BTN1A1 dimer antibodies. In some embodiments, such molecules are expressed as a fusion protein with other proteins or chemically conjugated to another moiety.

In some embodiments, the molecule is a fusion protein having an Fc portion, whereby the Fc portion can be varied by isotype or subclass, can be a chimeric or hybrid, and/or can be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, J. P. et al., *Mol. Immun.* 34(6):441-452 (1997), Swann, P. G., *Curr. Opin. Immun.* 20:493-499 (2008), and Presta, L. G., *Curr. Opin. Immun.* 20:460-470 (2008). In some embodiments the Fc region is the native IgG1, IgG2, or IgG4 Fc region. In some embodiments the Fc region is a hybrid, for example a chimeric having of IgG2/IgG4 Fc constant regions. Modications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host), and IgG1 with altered pH-dependent binding to FcRn. The Fc region can include the entire hinge region, or less than the entire hinge region.

Another embodiment includes IgG2-4 hybrids and IgG4 mutants that have reduce binding to FcR which increase their half-life. Representative IG2-4 hybrids and IgG4 mutants are described in Angal et al., *Molec. Immunol.* 30(1):105-108 (1993); Mueller et al., *Mol. Immun.* 34(6): 441-452 (1997); and U.S. Pat. No. 6,982,323; all of which are hereby incorporated by references in their entireties. In some embodiments the IgG1 and/or IgG2 domain is deleted for example, Angal et al. describe IgG1 and IgG2 having serine 241 replaced with a proline.

In some embodiments, the molecules are polypeptides having at least 10, at least 20, at least 30, at least 40, at least 50, at least 60, at least 70, at least 80, at least 90 or at least 100 amino acids.

In some embodiments, provided herein are molecules that have an antigen binding fragment that immunospecifically binds to BTN1A1, glycosylated BTN1A1 or a BTN1A1 dimer, which link to or covalently bind or form into a complex with at least one moiety. Such a moiety can be, but is not limited to, one that increases the efficacy of molecules as diagnostic or therapeutic agents. In some embodiments, the moiety can be image agents, toxins, therapeutic enzymes, antibiotics, radio-labeled nucleotides and the like.

Molecules provided herein can include a therapeutic moiety (or one or more therapeutic moieties). Molecules provided herein can be an antibody conjugated or recombinantly fused to a therapeutic moiety, such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Therapeutic moieties include, but are not limited to, antimetabolites (e.g., methotrexate, 6-mercaptopurine, 6-thioguanine, cytarabine, 5-fluorouracil decarbazine); alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP), and cisplatin); anthracyclines (e.g., daunorubicin (formerly daunomycin) and doxorubicin); antibiotics (e.g., d actinomycin (formerly actinomycin), bleomycin, mithramycin, and anthramycin (AMC)); Auristatin molecules (e.g., auristatin PHE, auristatin F, monomethyl auristatin E, bryostatin 1, and solastatin 10; see Woyke et al., Antimicrob. Agents Chemother. 46:3802-8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun. 266:76-80 (1999), Mohammad et al., Int. J. Oncol. 15:367-72 (1999), all of which are incorporated herein by reference); hormones (e.g., glucocorticoids, progestins, androgens, and estrogens), DNA-repair enzyme inhibitors (e.g., etoposide or topotecan), kinase inhibitors (e.g., compound ST1571, imatinib mesylate (Kantarjian et al., Clin Cancer Res. 8(7):2167-76 (2002)); cytotoxic agents (e.g., paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucorticoids, procaine, tetracaine, lidocaine, propranolol, and puromycin and analogs or homologs thereof and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459); farnesyl transferase inhibitors (e.g., R115777, BMS-214662, and those disclosed by, for example, U.S. Pat. Nos. 6,458, 935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305); topoisomerase inhibitors (e.g., camptothecin; irinotecan; SN-38; topotecan; 9-aminocamptothecin; GG-211 (GI 147211); DX-8951f; 1ST-622; rubitecan; pyrazoloacridine; XR-5000; saintopin; UCE6; UCE1022; TAN-1518A; TAN 1518B; KT6006; KT6528; ED-110; NB-506; ED-110; NB-506; and rebeccamycin); bulgarein; DNA minor groove binders such as Hoescht dye 33342 and Hoechst dye 33258; nitidine; fagaronine; epiberberine; coralyne; beta-lapachone; BC-4-1; bisphosphonates (e.g., alendronate, cimadronte, clodronate, tiludronate, etidronate, ibandronate, neridronate, olpandronate, risedronate, piridronate, pamidronate, zolendronate) HMG-CoA reductase inhibitors, (e.g., lovastatin, simvastatin, atorvastatin, pravastatin, fluvastatin, statin, cerivastatin, lescol, lupitor, rosuvastatin and atorvastatin); antisense oligonucleotides (e.g., those disclosed in the U.S. Pat. Nos. 6,277,832, 5,998,596, 5,885,834, 5,734,033, and 5,618,709); adenosine deaminase inhibitors (e.g., Fludarabine phosphate and 2-Chlorodeoxyadenosine); ibritumomab tiuxetan (Zevalin®); tositumomab (Bexxar®)) and pharmaceutically acceptable salts, solvates, clathrates, and prodrugs thereof.

Further, molecules provided herein be antibodies conjugated or recombinantly fused to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, γ-interferon, α-interferon, nerve growth factor, platelet derived growth factor, tissue plasminogen activator, an apoptotic agent, e.g., TNF-γ, TNF-γ, AIM I (see, International Publication No. WO 97/33899), AIM II (see, International Publication No. WO 97/34911), Fas Ligand (Takahashi et al., 1994, J. Immunol., 6:1567-1574), and VEGF (see, International Publication No. WO 99/23105), an anti-angiogenic agent, e.g., angiostatin, endostatin or a component of the coagulation pathway (e.g., tissue factor); or, a biological response modifier such as, for example, a lymphokine (e.g., interferon gamma, interleukin-1 ("IL-1"), interleukin-2 ("IL-2"), interleukin-5 ("IL-5"), interleukin-6 ("IL-6"), interleukin-7 ("IL-7"), interleukin 9 ("IL-9"), interleukin-10 ("IL-10"), interleukin-12 ("IL-12"), interleukin-15 ("IL-15"), interleukin-23 ("IL-23"), granulocyte macrophage colony stimulating factor ("GM-CSF"), and granulocyte colony stimulating factor ("G-CSF")), or a growth factor (e.g., growth hormone ("GH")), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (prothrombin), factor V, XIIa, VIII, XIIIa, XI, XIa, IX, IXa, X, phospholipid, and fibrin monomer).

In addition, an antibody provided herein can be conjugated to therapeutic moieties such as a radioactive metal ion, such as alpha-emitters such as $^{213}$Bi or macrocyclic chelators useful for conjugating radiometal ions, including but not limited to, $^{131}$In, $^{131}$LU, $^{131}$Y, $^{131}$Ho, $^{131}$Sm, to polypeptides. In certain embodiments, the macrocyclic chelator is 1,4,7,10-tetraazacyclododecane-N,N',N",N"'-tetraacetic acid (DOTA) which can be attached to the antibody via a linker molecule. Such linker molecules are commonly known in the art and described in Denardo et al., 1998, *Clin Cancer Res.* 4(10):2483-90; Peterson et al., 1999, *Bioconjug. Chem.* 10(4):553-7; and Zimmerman et al., 1999, *Nucl. Med. Biol.* 26(8):943-50, each incorporated by reference in their entireties.

The therapeutic moiety or drug conjugated or recombinantly fused to an antibody provided herein that immunospecifically binds to BTN1A1, glycosylated BTN1A1 or a BTN1A1 dimer (e.g., a glycosylated BTN1A1 dimer) should be chosen to achieve the desired prophylactic or therapeutic effect(s). In certain embodiments, the antibody is a modified antibody. A clinician or other medical personnel should consider the following when deciding on which therapeutic moiety or drug to conjugate or recombinantly fuse to an antibody provided herein: the nature of the disease, the severity of the disease, and the condition of the subject.

In some embodiments, the moiety can be enzymes, hormones, cell surface receptors, toxins (such as abrin, ricin A, *pseudomonas* exotoxin (i.e., PE-40), diphtheria toxin, ricin, gelonin, or pokeweed antiviral protein), proteins (such as tumor necrosis factor, interferon (e.g., α-interferon, β-interferon), nerve growth factor, platelet derived growth factor, tissue plasminogen activator, or an apoptotic agent (e.g., tumor necrosis factor-α, tumor necrosis factor-β)), biological response modifiers (such as, for example, a lymphokine (e.g., interleukin-1 ("IL-1"), interleukin-2 ("IL-2"), interleukin-6 ("IL-6")), granulocyte macrophage colony stimulating factor ("GM-CSF"), granulocyte colony stimulating factor ("G-CSF"), or macrophage colony stimulating factor, ("M-CSF")), or growth factors (e.g., growth hormone ("GH"))), cytotoxins (e.g., a cytostatic or cytocidal agent, such as paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, monomethyl auristatin F (MMAF), monomethyl auristatin E (MMAE; e.g., vedotin) and puromycin and analogs or homologs thereof), antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, BiCNU® (carmustine; BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), or anti-mitotic agents (e.g., vincristine and vinblastine).

Techniques for conjugating such therapeutic moieties to antibodies are well known; see, e.g., Amon et al., "*Monoclonal Antibodies For Immunotargeting Of Drugs In Cancer Therapy*", in MONOCLONAL ANTIBODIES AND CANCER THERAPY, Reisfeld et al. (eds.), 1985, pp. 243-56, Alan R. Liss, Inc.); Hellstrom et al., "*Antibodies For Drug Delivery*", in CONTROLLED DRUG DELIVERY (2nd Ed.), Robinson et al. (eds.), 1987, pp. 623-53, Marcel Dekker, Inc.); Thorpe, "*Antibody Carriers Of Cytotoxic Agents In Cancer Therapy: A Review*", in MONOCLONAL ANTIBODIES '84: BIOLOGICAL AND CLINICAL APPLICATIONS, Pinchera et al. (eds.), 1985, pp. 475-506); "*Analysis, Results, And Future Prospective Of The Therapeutic Use Of Radiolabeled Antibody In Cancer Therapy*", in MONOCLONAL ANTIBODIES FOR CANCER DETECTION AND THERAPY, Baldwin et al. (eds.), 1985, pp. 303-16, Academic Press; Thorpe et al., *Immunol. Rev.* 62:119-158 (1982); Carter et al., *Cancer J.* 14(3):154-169 (2008); Alley et al., *Curr. Opin. Chem. Biol.* 14(4):529-537 (2010); Carter et al., *Amer. Assoc. Cancer Res. Educ. Book.* 2005(1):147-154 (2005); Carter et al., *Cancer J.* 14(3):154-169(2008); Chari, *Acc. Chem Res.* 41(1):98-107 (2008); Doronina et al., Nat. Biotechnol. 21(7):778-784(2003); Ducry et al., *Bioconjug Chem.* 21(1):5-13(2010); Senter, *Curr. Opin. Chem. Biol.* 13(3):235-244 (2009); and Teicher, *Curr Cancer Drug Targets.* 9(8):982-1004 (2009).

In some embodiments, molecules as described herein can be conjugated to a marker, such as a peptide, to facilitate purification. In some embodiments, the marker is a hexahistidine peptide, the hemagglutinin "HA" tag, which corresponds to an epitope derived from the influenza hemagglutinin protein (Wilson, I. A. et al., *Cell,* 37:767-778 (1984)), or the "flag" tag (Knappik, A. et al., *Biotechniques* 17(4):754-761 (1994)).

In some embodiments, the moiety can be an image agent that can be detected in an assay. Such image agent can be enzymes, prosthetic groups, radiolabels, nonradioactive paramagnetic metal ions, haptens, fluorescent labels, phosphorescent molecules, chemiluminescent molecules, chromophores, luminescent molecules, bioluminescent molecules, photoaffinity molecules, colored particles or ligands, such as biotin.

In some embodiments, the enzymes include, but not limited to, horseradish peroxidase, alkaline phosphatase, beta-galactosidase, or acetylcholinesterase; the prosthetic group complexes include, but not limited to, streptavidin/biotin and avidin/biotin; the fluorescent materials include, but not limited to, umbelliferone, fluorescein, fluorescein isothiocyanate, rhodamine, dichlorotriazinylamine fluorescein, dansyl chloride or phycoerythrin; the luminescent material such as, but not limited to, luminol; the bioluminescent materials include, but not limited to, luciferase, luciferin, and aequorin; the radioactive material include, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanium ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re, rhodium ($^{105}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb), yttrium ($^{90}$Y), zinc ($^{65}$Zn); positron emitting metals using various positron emission tomographies, and nonradioactive paramagnetic metal ions.

The image agent can be conjugated to the molecule having an antigen binding fragment either directly, or indirectly through an intermediate (such as, for example, a linker known in the art) using techniques known in the art. See, for example, U.S. Pat. No. 4,741,900 for metal ions which can be conjugated to antibodies and other molecules as described herein for use as diagnostics. Some conjugation methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6α-diphenylglycouril-3 attached to the antibody. Monoclonal antibodies can also be reacted with an enzyme in the presence of a coupling agent such as glutaraldehyde or periodate. Conjugates with fluorescein markers can be prepared in the presence of these coupling agents or by reaction with an isothiocyanate.

The molecules as described herein can be conjugated to a second antibody to form an antibody heteroconjugate as described by Segal in U.S. Pat. No. 4,676,980. Such heteroconjugate antibodies can additionally bind to haptens (e.g., fluorescein), or to cellular markers (e.g., 4-1-BB, B7-H4, CD4, CD8, CD14, CD25, CD27, CD40, CD68, CD163, CTLA4, GITR, LAG-3, OX40, TIM3, TIM4, TLR2, LIGHT, ICOS, B7-H3, B7-H7, B7-H7CR, CD70, CD47) or to cytokines (e.g., IL-7, IL-15, IL-12, IL-4 TGF-beta, IL-10, IL-17, IFNγ, Flt3, BLys) or chemokines (e.g., CCL21).

The molecules as described herein can be attached to solid supports, which can be useful for immunoassays or purification of the target antigen or of other molecules that are capable of binding to target antigen that has been immobilized to the support via binding to an antibody or antigen binding fragment as described herein. Such solid supports include, but are not limited to, glass, cellulose, polyacrylamide, nylon, polystyrene, polyvinyl chloride or polypropylene.

Provided herein are also nucleic acid molecules (DNA or RNA) that encode any such antibodies, antigen binding fragments, and molecules having the antigen binding fragment that immunospecifically binds to BTN1A1 glycosylated BTN1A1 or a BTN1A1 dimer (e.g., a glycosylated BTN1A1 dimer). Provided herein are also vector molecules (such as plasmids) that are capable of transmitting or of replication such nucleic acid molecules. The nucleic acids can be single-stranded, double-stranded, and can contain both single-stranded and double-stranded portions.

Antibody-Drug Conjugates (ADCs)

As the molecules provided herein can result in internalization of BTN1A1 into the cells. Provided herein are also Antibody-Drug Conjugates (ADCs) that include any anti-BTN1A1 antibody described herein. In a specific embodiment, provided herein are ADCs having STC703, STC810, STC820, STC1011, STC1012, STC1029, STC2602, STC2714, STC2739, STC2778, or STC2781 or a humanized variant thereof as the antibody.

In some embodiments, provided herein are antibody-drug conjugates, including an antibody-drug conjugate of the following formulas (Ia) and (Ib):

(Ia)

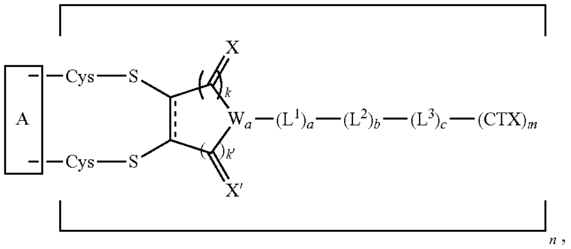

(Ib)

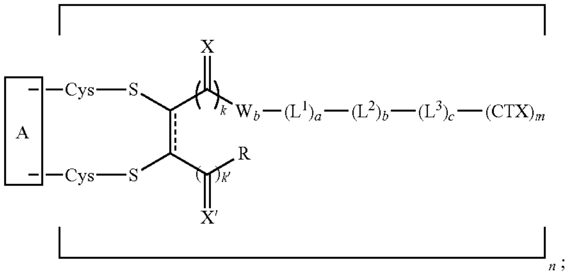

or a pharmaceutically acceptable salt thereof;

wherein:

A is a molecule that have an antigen binding fragment;

the two depicted cysteine residues are from an opened cysteine-cysteine disulfide bond in A;

each X and X' is independently O, S, NH, or $NR^1$ wherein $R^1$ is $C_{1-6}$ alkyl;

$W_a$ is $=N-$, $=CH-$, $=CHCH_2-$, $=C(R^2)-$, or $=CHCH(R^2)-$; $W_b$ $-NH-$, $-N(R^1)-$, $-CH_2-$, $-CH_2-NH-$, $-CH_2-N(R^1)-$, $-CH_2CH_2-$, $-CH(R^2)-$, or $-CH_2CH(R^2)-$; wherein $R^1$ and $R^2$ are independently $C_{1-6}$ alkyl;

CTX is a cytotoxin;

R is any chemical group; or R is absent;

each $L^1$, $L^2$ and $L^3$ is independently a linker selected from the group consisting of $-O-$, $-C(O)-$, $-S-$, $-S(O)-$, $-S(O)_2-$, $-NH-$, $-NCH_3-$, $-(CH_2)_q-$, $-NH(CH_2)_2NH-$, $-OC(O)-$, $-CO_2-$, $-NHCH_2CH_2C(O)-$, $-C(O)NHCH_2CH_2NH-$, $-NHCH_2C(O)-$, $-NHC(O)-$, $-C(O)NH-$, $-NCH_3C(O)-$, $-C(O)NCH_3-$, $-(CH_2CH_2O)_p-$, $-(CH_2CH_2O)_pCH_2CH_2-$, $-CH_2CH_2-(CH_2CH_2O)_p-$, $-OCH(CH_2O-)_2$, $-(AA)_r-$, cyclopentanyl, cyclohexanyl, unsubstituted phenylenyl, and phenylenyl substituted by 1 or 2 substituents selected from the group consisting of halo, $CF_3-$, $CF_3O-$, $CH_3O-$, $-C(O)OH$, $-C(O)OC_{1-3}$ alkyl, $-C(O)CH_3$, $-CN$, $-NH-$, $-NH_2$, $-O-$, $-OH$, $-NHCH_3$, $-N(CH_3)_2$, and $C_{1-3}$ alkyl;

a, b and c are each independently an integer of 0, 1, 2 or 3, provided that at least one of a, b or c is 1;

each k and k' is independently an integer of 0 or 1;

each p is independently an integer of 1 to 14;

each q is independently an integer from 1 to 12;

each AA is independently an amino acid;

each r is 1 to 12;

m is an integer of 1 to 4;

n is an integer of 1 to 4; and the ------ bond represents a single or a double bond.

In certain embodiments of the antibody-drug conjugate (ADC) of formula (Ib), R is selected from the group consisting of W, $(L^1)_a$, $(L^2)_b$, $(L^3)_c$, Z, W-$(L^1)_a$-$(L^2)_b$-$(L^3)_c$, $(L^1)_a$-$(L^2)_b$-$(L^3)_c$-Z, and W-$(L^1)_a$-$(L^2)_b$-$(L^3)_c$-Z, as defined herein. In certain embodiments, R is selected from the group consisting of W, $(L^1)_a$, $(L^2)_b$, $(L^3)_c$, and W-$(L^1)_a$-$(L^2)_b$-$(L^3)_c$. In certain embodiments, R is selected from the group consisting of Z, $(L^1)_a$-$(L^2)_b$-$(L^3)_c$-Z, and W-$(L^1)_a$-$(L^2)_b$-$(L^3)_c$-Z.

In certain embodiments of the antibody-drug conjugate (ADC) of formula (Ib), R is a detectable probe. In certain embodiments, R is a fluorophore, chromophore, radiolabel, enzyme, ligand, antibody or antibody fragment. In certain embodiments, R is a ligand (e.g., a ligand specific for a receptor on a tumor cell, such as a prostate specific membrane antigen, or a virally infected cell, such as an HIV infected cell).

In certain embodiments of the antibody-drug conjugate (ADC) of formula (Ib), R is bonded to the rest of the linker molecule via an amide, an N—($C_{1-6}$ alkyl)amide, a carbamate, an N—($C_{1-6}$ alkyl)carbamate, an amine, an N—($C_{1-6}$ alkyl)amine, an ether, a thioether, an urea, an N—($C_{1-6}$ alkyl)urea, or an N,N-di($C_{1-6}$ alkyl)urea bond.

In certain embodiments of the antibody-drug conjugate (ADC) of formula (Ia) or (Ib), each $L^1$, $L^2$ and $L^3$ is independently selected from the group consisting of $-NHC(O)-$, $-C(O)NH-$, $-(CH_2CH_2O)_p-$, $-(CH_2CH_2O)_pCH_2CH_2-$, $-CH_2CH_2-(CH_2CH_2O)_p-$, $-OCH(CH_2O-)_2$, $-(AA)_r-$, unsubstituted phenylenyl, and phenylenyl substituted by 1 or 2 substituents selected from the group consisting of halo, $CF_3-$, $CF_3O-$, $CH_3O-$, $-C(O)OH$, $-C(O)OC_{1-3}$ alkyl, $-C(O)CH_3$, $-CN$, $-NH-$, $-NH_2$, $-O-$, $-OH$, $-NHCH_3$, $-N(CH_3)_2$, and $C_{1-3}$ alkyl; where a, b and c are each independently 0 or 1; and each p and r is independently 1, 2 or 3. In certain embodiments, one or more of the $L^1$, $L^2$ and $L^3$ is $-(AA)_r-$, wherein $-(AA)_r-$ is ValCit (e.g., the first amino acid is Valine, the second amino acid is Citrulline, and r is 1). In certain embodiments, one or more of the $L^1$, $L^2$ and $L^3$ is $-(AA)_r-$, wherein $-(AA)_r-$ is ValAla (e.g., the first amino acid is Valine, the second amino acid is Alanine, and r is 1). In certain embodiments, one or more of the $L^1$, $L^2$ and $L^3$ is phenylenyl substituted by $-C(O)OH$ and $-NH_2$. In certain embodiments, one or more of the $L^1$, $L^2$ and $L^3$ is phenylenyl substituted by $-C(O)O-$ and $-NH-$. In certain embodiments, one or more of the $L^1$, $L^2$ and $L^3$ is phenylenyl substituted by $-OC(O)-$ and $-NH-$. In certain embodiments, one or more of the $L^1$, $L^2$ and $L^3$ is phenylenyl substituted by —O— and —NH—. In certain embodiments, one or more of the $L^1$, $L^2$ and $L^3$ is para aminobenzyl (PAB), which is optionally substituted with —C(O)O—, —OC(O)— or —O—. In certain embodiments, $L^1$ is $—(CH_2)_q—$, $L^2$ is absent, $L^3$ is absent, and the CTX is bonded to $(L^1)_a$-$(L^2)_b$-$(L^3)_c$ via an amide bond. In certain embodiments, $L^1$ is $—(CH_2)_q—$, $L^2$ is $—(OCH_2CH_2)_p—$, $L^3$ is absent, and the CTX is bonded to $(L^1)_a$-$(L^2)_b$-$(L^3)_c$ via an amide bond. In certain embodiments, $L^1$ is $—(CH_2CH_2O)_p—$, $L^2$ is $—(CH_2)_q—$, $L^3$ is absent, and the CTX is bonded to $(L^1)_a$-$(L^2)_b$-$(L^3)_c$ via an amide bond. In certain embodiments, each $L^1$ is independently selected from the group consisting of $—(CH_2CH_2O)_pCH_2CH_2—$ and $—CH_2CH_2—(CH_2CH_2O)_p—$, $L^2$ is absent, $L^3$ is absent, and the CTX is bonded to $(L^1)_a$-$(L^2)_b$-$(L^3)_c$ via an amide bond. In certain embodiments, each $L^1$ is independently selected from the group consisting of $—(CH_2)_q—$, $—(CH_2CH_2O)_p$, $—(CH_2CH_2O)_pCH_2CH_2—$, $—CH_2CH_2—(CH_2CH_2O)_p—$, and —C(O)—, $L^2$ is Val-Cit, $L^3$ is PAB, and the CTX is bonded to $(L^1)_a$-$(L^2)_b$-$(L^3)_c$ via an amide bond. In certain embodiments, each $L^1$ is independently selected from the group consisting of $—(CH_2)_q—$, $—(CH_2CH_2O)_p$, $—(CH_2CH_2O)_pCH_2CH_2—$, $—CH_2CH_2—(CH_2CH_2O)_p—$, and —C(O)—, $L^2$ is Val-Cit, $L^3$ is PAB, and the CTX is bonded to $(L^1)_a$-$(L^2)_b$-$(L^3)_c$ via an amide bond. In certain embodiments, each $L^1$ is independently selected from the group consisting of $—(CH_2)_q—$, $—(CH_2CH_2O)_p$, $—(CH_2CH_2O)_pCH_2CH_2—$, $—CH_2CH_2—(CH_2CH_2O)_p—$, and —C(O)—, $L^2$ is Val-Ala, $L^3$ is PAB, and the CTX is bonded to $(L^1)_a$-$(L^2)_b$-$(L^3)_c$ via an amide bond.

In certain embodiments of the antibody-drug conjugate (ADC) of formula (Ia) or (Ib), CTX is selected from a from the group consisting of a tubulin stabilizer, a tubulin destabilizer, a DNA alkylator, a DNA minor groove binder, a DNA intercalator, a topoisomerase I inhibitor, a topoisomerase II inhibitor, a gyrase inhibitor, a protein synthesis inhibitor, a proteosome inhibitor, and an anti-metabolite.

In certain embodiments of the antibody-drug conjugate (ADC) of formula (Ia) or (Ib), the CTX is a chemotherapeutic agent. Those of ordinary skill in the art will be aware of appropriate chemotherapeutic agents as disclosed, for example, in Chu, E., DeVite, V. T., 2012, Physicians' Cancer Chemotherapy Drug Manual 2012 (Jones & Bartlett Learning Oncology), and similar documents.

In certain embodiments, the CTX may be any FDA-approved chemotherapeutic agent. In certain embodiments, the CTX may be any FDA-approved chemotherapeutic agent available for cancer treatment.

In certain embodiments, the CTX is selected from the group consisting of an alkylating agents, an anthracyclines, a cytoskeletal disruptors (taxanes), an epothilones, an histone deacetylase Inhibitor (HDAC), an inhibitor of Topoisomerase I, an Inhibitor of Topoisomerase II, a kinase inhibitor, a monoclonal antibodies, a nucleotide analog, a peptide antibiotic, a platinum-based agent, a retinoids, a Vinca alkaloid or a derivative thereof, and radioisotope.

In certain embodiments, the CTX is selected from the group consising of Actinomycin, all-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine.

In certain embodiments, the CTX is selected from the group consisting of a tubulin stabilizer, a tubulin destabilizer, a DNA alkylator, a DNA minor groove binder, a DNA intercalator, a topoisomerase I inhibitor, a topoisomerase II inhibitor, a gyrase inhibitor, a protein synthesis inhibitor, a proteosome inhibitor, and an anti-metabolite.

In certain embodiments, the CTX is selected from the group consisting of Actinomycin D, Amonafide, an auristatin, benzophenone, benzothiazole, a calicheamicin, Camptothecin, CC-1065 (NSC 298223), Cemadotin, Colchicine, Combretastatin A4, Dolastatin, Doxorubicin, Elinafide, Emtansine (DM1), Etoposide, KF-12347 (Leinamycin), a maytansinoid, Methotrexate, Mitoxantrone, Nocodazole, Proteosome Inhibitor 1 (PSI 1), Roridin A, T-2 Toxin (trichothecene analog), Taxol, a tubulysin, Velcade®, and Vincristine. In certain embodiments, the CTX is an auristatin, a calicheamicin, a maytansinoid, or a tubulysin.

In certain embodiments, the CTX is monomethylauristatin E (MMAE), monomethylauristatin F (MMAF), a pyrrolobenzodiazepine (PDB), calicheamicin γ, mertansine, or tubulysin T2. In certain embodiments, the CTX is MMAE or MMAF. In certain embodiments, the CTX is a PDB. In certain embodiments, the CTX is tubulysin T2. In certain embodiments, the CTX is tubulysin T3, or tubulysin T4, the structures for which are provided below:

T3

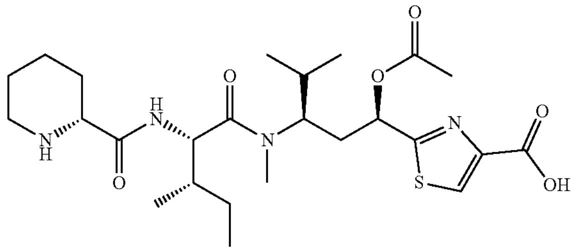

T4

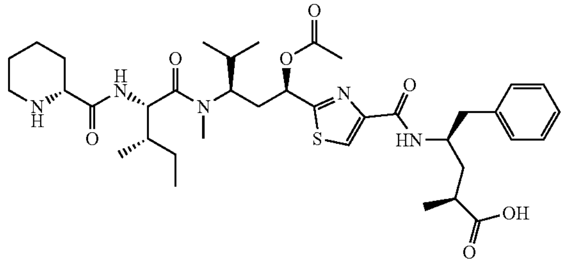

Thus, the conjugated or fusion proteins provided herein can include any anti-BTN1A1 antibody or antigen binding fragments described herein. In one embodiment, a conjugated or fusion protein provided herein includes the VH or VL domain of the murine monoclonal antibody STC703, STC810, STC820, STC1011, STC1012, STC1029, STC2602, STC2714, STC2739, STC2778, or STC2781, as depicted in any one of Tables 2a-12b. In one embodiment, a conjugated or fusion protein provided herein includes both the VH and VL domain of the murine monoclonal antibody STC703, STC810, STC820, STC1011, STC1012, STC1029, STC2602, STC2714, STC2739, STC2778, or STC2781, as depicted in any one of Tables 2a-12b. In another embodiment, a conjugated or fusion protein provided herein includes one or more VH CDRs having the amino acid sequence of any one of the VH CDRs of the murine monoclonal antibody STC703, STC810, STC820, STC1011, STC1012, STC1029, STC2602, STC2714, STC2739, STC2778, or STC2781, as depicted in any one of Tables 2a-12b. In another embodiment, a conjugated or fusion protein includes one or more VL CDRs having the amino acid sequence of any one of the VL CDRs of the murine monoclonal antibody STC703, STC810, STC820, STC1011, STC1012, STC1029, STC2602, STC2714, STC2739, STC2778, or STC2781, as depicted in any one of Tables 2a-12b. In yet another embodiment, a conjugated or fusion protein provided herein includes at least one VH CDR and at least one VL CDR of the murine monoclonal antibody STC703, STC810, STC820, STC1011, STC1012, STC1029, STC2602, STC2714, STC2739, STC2778, or STC2781, as depicted in any one of Tables 2a-12b.

In some embodiments, a conjugated or fusion protein provided can include an antigen binding fragment that competitively blocks (e.g., in a dose-dependent manner) a BTN1A1 epitope described herein. The BTN1A1 epitope can be an epitope of STC703, STC810, STC820, STC1011, STC1012, STC1029, STC2602, STC2714, STC2739, STC2778, or STC2781. In some embodiments, a conjugated or fusion protein provided can include an antigen binding fragment that immunospecifically binds to an epitope of a BTN1A1 antibody as described herein. The BTN1A1 epitope can be an epitope of STC703, STC810, STC820, STC1011, STC1012, STC1029, STC2602, STC2714, STC2739, STC2778, or STC2781.

5.3 Compositions

Provided herein are also compositions having molecules that have an antigen binding fragment that immunospecifically binds to BTN1A1 (including glycosylated BTN1A1 and BTN1A1 dimers). In some embodiments, the compositions have anti-BTN1A1 antibodies (including anti-glycosylated BTN1A1 antibodies and anti-BTN1A1 dimer antibodies). In some embodiments, the antigen binding fragment immunospecifically binds to BTN1A1 glycosylated at positions N55, N215, and/or N449. In some embodiments, the antigen binding fragment immunospecifically binds to BTN1A1 glycosylated at position N55. In some embodiments, the antigen binding fragment immunospecifically binds to BTN1A1 glycosylated at position N215. In some embodiments, the antigen binding fragment immunospecifically binds to BTN1A1 glycosylated at position N449. In some embodiments, the antigen binding fragment immunospecifically binds to one or more glycosylation motifs. In some embodiments, the antigen binding fragment immunospecifically binds to BTN1A1 glycosylated at positions N55 and N215. In some embodiments, the antigen binding fragment immunospecifically binds to BTN1A1 glycosylated at positions N215 and N449. In some embodiments, the antigen binding fragment immunospecifically binds to BTN1A1 glycosylated at positions N55 and N449. In some embodiments, the antigen binding fragment immunospecifically binds to BTN1A1 glycosylated at positions N55, N215 and N449. In some embodiments, the antigen binding fragment immunospecifically binds to a BTN1A1 dimer, e.g., a BTN1A1 dimer glycosylated at one or more of positions N55, N215 and N449 of one or more of the BTN1A1 monomers in the BTN1A1 dimer.

In some embodiments, provided herein are compositions having molecules that have an antigen binding fragment that immunospecifically binds to BTN1A1, wherein the antigen binding fragment preferentially binds glycosylated BTN1A1 over non-glycosylated BTN1A1. In some embodiments, the glycosylated BTN1A1 is a BTN1A1 dimer. In some embodiments, the antigen binding fragments preferentially bind to BTN1A1 glycosylated at positions N55, N215, and/or N449 over non-glycosylated BTN1A1. In some embodiments, the antigen binding fragments preferentially bind to BTN1A1 glycosylated at position N55 over non-glycosylated BTN1A1. In some embodiments, the antigen binding fragments preferentially bind to BTN1A1 glycosylated at position N215 over non-glycosylated BTN1A1. In some embodiments, the antigen binding fragments preferentially bind to BTN1A1 glycosylated at position N449 over non-glycosylated BTN1A1. In some embodiments, the antigen binding fragments preferentially bind to one or more glycosylation motifs. In some embodiments, the antigen binding fragments preferentially binds BTN1A1 glycosylated at positions N55 and N215 over non-glycosylated BTN1A1. In some embodiments, the antigen binding fragments preferentially bind to BTN1A1 glycosylated at positions N215 and N449 over non-glycosylated BTN1A1. In some embodiments, the antigen binding fragments preferentially bind to BTN1A1 glycosylated at positions N55 and N449 over non-glycosylated BTN1A1. In some embodiments, the antigen binding fragments preferentially bind to BTN1A1 glycosylated at positions N55, N215 and N449 over non-glycosylated BTN1A1.

In some embodiments, the compositions provided herein include a molecule that has an antigen binding fragment that immunospecifically binds to BTN1A1, whereby the antigen binding fragment preferentially binds a BTN1A1 dimer over a BTN1A1 monomer. In some embodiments, the BTN1A1 dimer is glycosylated at one or more of positions N55, N215 and N449 of one or more of the BTN1A1 monomers in the BTN1A1 dimer.

In some embodiments, the antigen binding fragment binds to glycosylated BTN1A1 with $K_D$ less than half of the $K_D$ exhibited relative to unglycosylated BTN1A1. In some embodiments, the antigen binding fragment binds to glycosylated BTN1A1 with $K_D$ at least 2 times less than the $K_D$ exhibited relative to unglycosylated BTN1A1. In some embodiments, the antigen binding fragment binds to glycosylated BTN1A1 with $K_D$ at least 5 times less than the $K_D$ exhibited relative to unglycosylated BTN1A1. In some embodiments, the antigen binding fragment binds to glycosylated BTN1A1 with $K_D$ at least 10 times less than the $K_D$ exhibited relative to unglycosylated BTN1A1. In some embodiments, the antigen binding fragment binds to glycosylated BTN1A1 with $K_D$ at least 15 times less than the $K_D$ exhibited relative to unglycosylated BTN1A1. In some embodiments, the antigen binding fragment binds to glycosylated BTN1A1 with $K_D$ at least 20 times less than the $K_D$ exhibited relative to unglycosylated BTN1A1. In some embodiments, the antigen binding fragment binds to glycosylated BTN1A1 with $K_D$ at least 25 times less than the $K_D$ exhibited relative to unglycosylated BTN1A1. In some embodiments, the antigen binding fragment binds to glycosylated BTN1A1 with $K_D$ at least 30 times less than the $K_D$ exhibited relative to unglycosylated BTN1A1. In some embodiments, the antigen binding fragment binds to glycosylated BTN1A1 with $K_D$ at least 40 times less than the $K_D$ exhibited relative to unglycosylated BTN1A1. In some embodiments, the antigen binding fragment binds to glycosylated BTN1A1 with $K_D$ at least 50 times less than the $K_D$ exhibited relative to unglycosylated BTN1A1.

In some embodiments, the antigen binding fragment binds to a BTN1A1 dimer (e.g., a glycosylated BTN1A1 dimer) with $K_D$ less than half of the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ at least 2 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ at least 5 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ at least 10 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ at least 15 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ at least 20 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ at least 25 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ at least 30 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ at least 40 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ at least 50 times less than the $K_D$ exhibited relative to a BTN1A1 monomer (e.g., a glycosylated BTN1A1 monomer).

In some embodiments, the antigen binding fragment binds to glycosylated BTN1A1 with an MFI that is at least twice as high as the MFI as exhibited relative to unglycosylated BTN1A1. In some embodiments, the antigen binding fragment binds to glycosylated BTN1A1 with an MFI that is at least five times as high as the MFI as exhibited relative to unglycosylated BTN1A1. In some embodiments, the antigen binding fragment binds to glycosylated BTN1A1 with an MFI that is at least 10 times as high as the MFI as exhibited relative to unglycosylated BTN1A1. In some embodiments, the antigen binding fragment binds to glycosylated BTN1A1 with an MFI that is at least 15 times as high as the MFI as exhibited relative to unglycosylated BTN1A1. In some embodiments, the antigen binding fragment binds to glycosylated BTN1A1 with an MFI that is at least 20 times as high as the MFI as exhibited relative to unglycosylated BTN1A1. In some embodiments, the antigen binding fragment binds to glycosylated BTN1A1 with an MFI that is at least 25 times as high as the MFI as exhibited relative to unglycosylated BTN1A1. In some embodiments, the antigen binding fragment binds to glycosylated BTN1A1 with an MFI that is at least 30 times as high as the MFI as exhibited relative to unglycosylated BTN1A1. In some embodiments, the antigen binding fragment binds to glycosylated BTN1A1 with an MFI that is at least 40 times as high as the MFI as exhibited relative to unglycosylated BTN1A1. In some embodiments, the antigen binding fragment binds to glycosylated BTN1A1 with an MFI that is at least 50 times as high as the MFI as exhibited relative to unglycosylated BTN1A1.

In some embodiments, the antigen binding fragment binds to a BTN1A1 dimer (e.g., a glycosylated BTN1A1 dimer) with an MFI that is at least twice as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least five times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 10 times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 15 times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 20 times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 25 times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 30 times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 35 times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 40 times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 50 times as high as the MFI as exhibited relative to a BTN1A1 monomer (e.g., a glycosylated BTN1A1 monomer).

In another aspect, provided herein are compositions having molecules that have an antigen binding fragment that immunospecifically masks BTN1A1 glycosylation at positions N55, N215, and/or N449. In some embodiments, the antigen binding fragments immunospecifically mask BTN1A1 glycosylation at position N55. In some embodiments, the antigen binding fragments immunospecifically mask BTN1A1 glycosylation at position N215. In some embodiments, the antigen binding fragments immunospecifically mask BTN1A1 glycosylation at position N449. In some embodiments, the antigen binding fragments immunospecifically mask one or more glycosylation motifs of BTN1A1. In some embodiments, the antigen binding fragments immunospecifically mask BTN1A1 glycosylation at positions N55 and N215. In some embodiments, the antigen binding fragments immunospecifically mask BTN1A1 glycosylation at positions N215 and N449. In some embodiments, the antigen binding fragments immunospecifically mask BTN1A1 glycosylation at positions N55 and N449. In some embodiments, the antigen binding fragments immunospecifically mask BTN1A1 glycosylation at positions N55, N215 and N449.

In some embodiments, the compositions can have a molecule having antigen binding fragment that includes the VH or VL domain of the murine monoclonal antibody STC703, STC810, STC820, STC1011, STC1012, STC1029, STC2602, STC2714, STC2739, STC2778, or STC2781, as depicted in Tables 2a-12b. In some embodiments, the compositions can have a molecule having antigen binding fragment that includes both the VH and VL domain of the murine monoclonal antibody STC703, STC810, STC820, STC1011, STC1012, STC1029, STC2602, STC2714, STC2739, STC2778, or STC2781, as depicted in Tables 2a-12b. In some embodiments, the compositions can have a molecule having antigen binding fragment that includes one or more VH CDRs having the amino acid sequence of any one of the VH CDRs of the murine monoclonal antibody STC703, STC810, STC820, STC1011, STC1012, STC1029, STC2602, STC2714, STC2739, STC2778, or STC2781, as depicted in Tables 2a-12b. In another embodiment, the compositions can have a molecule having antigen binding fragment that includes one or more VL CDRs having the amino acid sequence of any one of the VL CDRs of the murine monoclonal antibody STC703, STC810, STC820, STC1011, STC1012, STC1029, STC2602, STC2714, STC2739, STC2778, or STC2781, as depicted in Tables 2a-12b. In yet another embodiment, the compositions can have a molecule having antigen binding fragment that includes at least one VH CDR and at least one VL CDR of the murine monoclonal antibody STC703, STC810, STC820, STC1011, STC1012, STC1029, STC2602, STC2714, STC2739, STC2778, or STC2781, as depicted in Tables 2a-12b.

In some embodiments, the compositions can have a molecule having antigen binding fragment that competitively blocks (e.g., in a dose-dependent manner) the BTN1A1 epitope of an anti-BTN1A1 antibody described herein, such as STC703, STC810, STC820, STC1011, STC1012, STC1029, STC2602, STC2714, STC2739, STC2778, or STC2781. In some embodiments, the compositions can have a molecule having an antigen binding fragment that immunospecifically binds to an epitope of an anti-BTN1A1 antibody described herein, such as STC703, STC810, STC820, STC1011, STC1012, STC1029, STC2602, STC2714, STC2739, STC2778, or STC2781.

In some embodiments, the composition can have at least 0.1% by weight the antibodies or other molecules as described herein. In some embodiments, the composition can have at least 0.5%, 1%, 2%, 3%, 4%, 5%, 6%, 7% 8%, 9%, 10%, 15%, 20%, 25%, 30%, 35%, 40%, 45%, 50%, 55%, 60%, 65%, 70%, 75%, 80%, 85%, 90%, or more by weight of the anti-BTN1A1 antibodies or other molecules having an antigen binding fragment that immunospecifically binds to BTN1A1. In other embodiments, for example, the anti-BTN1A1 antibodies or other molecules having an antigen binding fragment that immunospecifically binds to BTN1A1 can constitute between about 2% to about 75% of the weight of the composition, between about 25% to about 60%, between about 30% to about 50%, or any range therein.

The composition can be a pharmaceutical composition having anti-BTN1A1 antibodies or other molecules having an antigen binding fragment that immunospecifically binds to BTN1A1 as the active ingredient as well as a pharmaceutically acceptable carrier. The pharmaceutical composition can further include one or more additional active ingredient. A pharmaceutically acceptable carrier can be a carrier approved by a regulatory agency of the Federal or a state government, or listed in the U.S. Pharmacopeia, European Pharmacopeia or other generally recognized Pharmacopeia for use in animals, and more particularly in humans.

The preparation of a pharmaceutical composition having the antibodies or other molecules as described herein as active ingredient are known to those of skill in the art in light of the present disclosure, as exemplified by Remington's Pharmaceutical Sciences, 18th Ed., 1990, incorporated herein by reference. Moreover, for animal (including human) administration, it is understood that preparations should meet sterility, pyrogenicity, general safety, and purity standards as required by FDA Office of Biological Standards.

The pharmaceutically acceptable carriers include liquid, semi-solid, i.e., pastes, or solid carriers. Examples of carriers or diluents include fats, oils, water, saline solutions, lipids, liposomes, resins, binders, fillers, and the like, or combinations thereof. The pharmaceutically acceptable carrier can include aqueous solvents (e.g., water, alcoholic/aqueous solutions, ethanol, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings (e.g., lecithin), surfactants, antioxidants, preservatives (e.g., antibacterial or antifungal agents, anti-oxidants, chelating agents, inert gases, parabens (e.g., methylparabens, propylparabens), chlorobutanol, phenol, sorbic acid, thimerosal), isotonic agents (e.g., sugars, sodium chloride), absorption delaying agents (e.g., aluminum monostearate, gelatin), salts, drugs, drug stabilizers (e.g., buffers, amino acids, such as glycine and lysine, carbohydrates, such as dextrose, mannose, galactose, fructose, lactose, sucrose, maltose, sorbitol, mannitol, etc), gels, binders, excipients, disintegration agents, lubricants, sweetening agents, flavoring agents, dyes, fluid and nutrient replenishers, such like materials and combinations thereof, as would be known to one of ordinary skill in the art. Except insofar as any conventional media, agent, diluent, or carrier is detrimental to the recipient or to the therapeutic effectiveness of the composition contained therein, its use in administrable composition for use in practicing the methods is appropriate. The pH and exact concentration of the various components in a pharmaceutical composition are adjusted according to well-known parameters. In accordance with certain aspects of the present disclosure, the composition can be combined with the carrier in any convenient and practical manner, i.e., by solution, suspension, emulsification, admixture, encapsulation, absorption, grinding, and the like. Such procedures are routine for those skilled in the art.

In some embodiments, a pharmaceutically acceptable carrier can be an aqueous pH buffered solution. Examples include buffers such as phosphate, citrate, and other organic acids; antioxidants including ascorbic acid; low molecular weight ((e.g., less than about 10 amino acid residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

In some embodiments, pharmaceutically acceptable carriers can be sterile liquids, such as water and oils, including those of petroleum, animal, vegetable or synthetic origin, such as peanut oil, soybean oil, mineral oil, sesame oil and the like. Water can be a carrier, particularly when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, polysorbate-80 and the like. The composition can also contain minor amounts of wetting or emulsifying agents, or pH buffering agents. These compositions can take the form of solutions, suspensions, emulsion, tablets, pills, capsules, powders, sustained-release formulations and the like.

Certain embodiments of the present disclosure can have different types of carriers depending on whether it is to be administered in solid, liquid, or aerosol form, and whether it needs to be sterile for the route of administration, such as injection. The compositions can be formulated for administration intravenously, intradermally, transdermally, intrathecally, intraarterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference). Typically, such compositions can be prepared as either liquid solutions or suspensions; solid forms suitable for use to prepare solutions or suspensions upon the addition of a liquid prior to injection can also be prepared; and, the preparations can also be emulsified.

The anti-BTN1A1 antibodies or other molecules having an antigen binding fragment that immunospecifically binds to BTN1A1 can be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups can also be derived from inorganic bases, such as, for example, sodium, potassium, ammonium, calcium, or ferric hydroxides; or such organic bases as isopropylamine, trimethylamine, 2-ethylamino ethanol, histidine, or procaine.

In further embodiments, provided herein are pharmaceutical compositions having a lipid. A lipid can broadly include a class of substances that are characteristically insoluble in water and extractable with an organic solvent. Examples include compounds that contain long-chain aliphatic hydrocarbons and their derivatives. A lipid can be naturally occurring or synthetic (i.e., designed or produced by man). A lipid can be a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Compounds other than those specifically described herein that are understood by one of skill in the art as lipids can also be used.

One of ordinary skill in the art would be familiar with the range of techniques that can be employed for dispersing a composition in a lipid vehicle. For example, antibodies can be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of active ingredient in each therapeutically useful composition can be prepared in such a way that a suitable dosage will be obtained in any given unit dose of the compound. Factors, such as solubility, bioavailability, biological half-life, route of administration, product shelf life, as well as other pharmacological considerations, can be contemplated by one skilled in the art of preparing such pharmaceutical formulations, and as such, a variety of dosages and treatment regimens may be desirable.

A unit dose or dosage refers to physically discrete units suitable for use in a subject, each unit containing a predetermined quantity of the pharmaceutical composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. In other non-limiting examples, a dose can have from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above. The practitioner responsible for administration will, in any event, determine the concentration of active ingredient(s) in a composition and appropriate dose(s) for the individual subject.

As a person of ordinary skill in the art would understand, the compositions described herein are not limited by the particular nature of the therapeutic preparation. For example, such compositions can be provided in formulations together with physiologically tolerable liquid, gel, or solid carriers, diluents, and excipients. These therapeutic preparations can be administered to mammals for veterinary use, such as with domestic animals, and clinical use in humans in a manner similar to other therapeutic agents. In general, the dosage required for therapeutic efficacy varies according to the type of use and mode of administration, as well as the particularized requirements of individual subjects. The actual dosage amount of a composition administered to an animal patient, including a human patient, can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount can vary according to the response of the subject. The practitioner responsible for administration will, in any event, determine the concentration of active ingredient(s) in a composition and appropriate dose(s) for the individual subject.

5.4 Therapeutic Uses and Methods of Treatments

BTN1A1 is specifically and highly expressed in cancer cells. In some embodiments, provided herein are therapeutic uses of molecules having an antigen binding fragment that immunospecifically binds to BTN1A1, glycosylated BTN1A1, or a BTN1A1 dimer (e.g., a glycosylated BTN1A1 dimer) in cancer treatments. In some embodiments, these molecules bind to BTN1A1-expressing cancer cells and induce an immune response resulting in destruction these cancer cells. The molecules provided herein, including anti-BTN1A1 antibodies (e.g., STC703, STC810, STC820, STC1011, STC1012, STC1029, STC2602, STC2714, STC2739, STC2778, or STC2781, or a humanized variant thereof) can enhance T-cell dependent apoptisis of cancer cells and inhibit proliferation of cancer cells.

This disclosure is based, in part on the surprising finding that expression of BTN1A1 and PD-L1 are mutually exclusive in certain cancers, such as lung squamous cell carcinoma, prostate adenocarcinoma, pancreatic adenocarcinoma, and hepatocellular carcinoma. See, e.g., Example 2, FIGS. 3A-D and FIGS. 4A-D.

This disclosure is further based, in part on the surprising finding that anti-BTN1A1 antibodies can be efficacious in the treatment of cancer that is resistant or refractory to anti-PD-1 or anti-PD-L1 therapy. See, e.g., Example 5, FIGS. 7-10.

In some embodiments, the anti-PD-1 therapy or the anti-PD-L1 therapy includes an anti-PD-1 or anti-PD-L1 antibody or antibody fragment, or a soluble PD-1 or PD-L1 ligand, or Fc-fusion protein thereof (e.g., AMP-224, a PD-L2 Fc fusion soluble receptor).

In some embodiments, the anti-PD-1 therapy includes nivolumab (Opdivo), pembrolizumab (Keytruda®), pidilizumab, AMP-514, or AMP-224.

In some embodiments, the anti-PD-1 therapy includes an anti-PD-1 antibody provided in International Application No. PCT/US2016/64394.

In some embodiments, the anti-PD-L1 therapy includes YW243.55.570, MPDL3280A, MEDI-4736, MSB-0010718C, or MDX-1105.

In some embodiments, the anti-PD-L1 therapy includes an antibody provided in International Application No. PCT/US2016/024691, published as WO 2016/160792 A1, and International Application No. PCT/US2017/024027.

Accordingly, in one aspect, provided herein is a method of treating an anti-PD-1 therapy or anti-PD-L1 therapy resistant or refractory cancer in a subject, including administering to the subject a therapeutically effective amount of a molecule including an antigen binding fragment that immunospecifically binds to BTN1A1.

In some embodiments, the subject has an anti-PD-1 therapy or anti-PD-L1 therapy resistant cancer. In some embodiments, the subject has an anti-PD-1 therapy resistant cancer. In some embodiments, the subject has an anti-PD-L1 therapy resistant cancer.

In some embodiments, the subject has an anti-PD-1 therapy or anti-PD-L1 therapy refractory cancer. In some embodiments, the subject has an anti-PD-1 therapy refractory cancer. In some embodiment, the subject has an anti-PD-L1 therapy refractory cancer.

In some embodiments, the subject is treatment naïve (e.g., the subject has not received any anti-cancer treatment) prior to treatment with the molecule including an antigen binding fragment that immunospecifically binds to BTN1A1. In some embodiments, the subject has received one or more anti-cancer treatments other than an anti-PD-1 therapy or anti-PD-L1 therapy (e.g., a chemotherapy, radiation therapy, surgery, or treatment with another targeted anticancer drug, such as Herceptin® (trastuzumab)) prior to treatment with the molecule including an antigen binding fragment that immunospecifically binds to BTN1A1. In some embodiments, the subject has received one or more anti-PD1 therapies or anti-PD-L1 therapies prior to treatment with the molecule including an antigen binding fragment that immunospecifically binds to BTN1A1.

In some embodiments, the anti-PD-1 therapy or anti-PD-L1 therapy resistant or refractory cancer is a lung cancer or a breast cancer. In some embodiments, the anti-PD-1 therapy or anti-PD-L1 therapy resistant or refractory cancer is a lung cancer. In some embodiments, the anti-PD-1 therapy or anti-PD-L1 therapy resistant or refractory cancer is a a breast cancer. In some embodiments, the lung cancer is a Lewis lung carcinoma. In some embodiments, the breast cancer is a mammary carcinoma.

In some embodiments, the molecule including an antigen binding fragment that immunospecifically binds to BTN1A1 is administered parenterally. In some embodiments, the molecule includes an anti-BTN1A1 dimer antibody or antigen binding fragment thereof.

In some embodiment the treatment produces at least one therapeutic effect, such as a reduction in size of a tumor, a reduction in number of metastatic lesions over time, a complete response, a partial response, or a stable disease.

The molecules provided herein having an antigen binding fragment that immunospecifically binds to BTN1A1, including anti-BTN1A1 antibodies (e.g., STC703, STC810, STC820, STC1011, STC1012, STC1029, STC2602, STC2714, STC2739, STC2778, or STC2781, or a humanized variant thereof) can cause the internalization of BTN1A1 into lysosomes. Thus, also provided herein are methods of using molecules provided herein to deliver a compound to a cell expressing BTN1A1 by contacting the cell with molecules provided herein conjugated with the compound. The compound can be an imaging agent, a therapeutic agent, a toxin or a radionuclide as described herein. The compound can be conjugated with anti-BTN1A1 antibody. The conjugate can be any conjugate as described herein, such as an ADC. The cell can be a cancer cell. The cell can also be a population of cells that include both cancer cells and normal cells. Because cancer cells specifically and highly express BTN1A1, the molecules described herein can be used to achieve specific drug delivery to cancer cells but not normal cells.

The molecules provided herein having an antigen binding fragment that immunospecifically binds to BTN1A1, including anti-BTN1A1 antibodies (e.g., STC703, STC810, STC820, STC1011, STC1012, STC1029, STC2602, STC2714, STC2739, STC2778, or STC2781, or a humanized variant thereof) can modulating an immune response in a subject. The molecules provided herein can promote T-cell activation. The molecules provided herein can promote T-cell proliferation. The molecules provided herein can increase cytokine production. The molecules provided herein can also enhance T-cell dependent apoptosis of a cell expressing BTN1A1 or inhibit the proliferation of cells expressing BTN1A1.

Accordingly, provided herein are methods of modulating an immune response in a subject by administering an effective amount of the molecules described herein that have an antigen binding fragment that immunospecifically binds to BTN1A1, including anti-BTN1A1 antibodies (e.g., STC703, STC810, STC820, STC1011, STC1012, STC1029, STC2602, STC2714, STC2739, STC2778, or STC2781, or a humanized variant thereof). Modulating an immune response can include (a) increasing T-cell activation (e.g., $CD8^+$ T-cell activation); (b) increasing T-cell proliferation; and/or (c) increasing cytokine production. In some embodiments, the methods further include administering an anti-PD1 therapy or an anti-PD-L1 therapy.

Also provided herein are methods of enhancing T-cell dependent apoptosis of a cell expressing BTN1A1 by contacting the cell with an effective amount of molecules described herein that have an antigen binding fragment that immunospecifically binds to BTN1A1, including anti-BTN1A1 antibodies (e.g., STC703, STC810, STC820, STC1011, STC1012, STC1029, STC2602, STC2714, STC2739, STC2778, or STC2781, or a humanized variant thereof). Provided herein are also methods of inhibiting the proliferation of cells expressing BTN1A1 by contacting the cell with an effective amount of molecules described herein that have an antigen binding fragment that immunospecifically binds to BTN1A1, including anti-BTN1A1 antibodies (e.g., STC703, STC810, STC820, STC1011, STC1012, STC1029, STC2602, STC2714, STC2739, STC2778, or STC2781, or a humanized variant thereof). The cells can be cancer cells. In some embodiments, the methods further include administering an anti-PD1 therapy or an anti-PD-L1 therapy.

In some embodiments, these molecules can be used to treat cancer by inhibiting the suppressive activity of BTN1A1 in T-cell activation or proliferation. Accordingly, provided herein are uses of these molecules in up-modulating the immune system of a subject by inhibiting or blocking the BTN1A1 signaling. In some embodiments, provided herein are uses of these molecules to block BTN1A1 from binding T cells.

In some embodiments, these molecules result in the destruction of cancer cells through ADCC or CDC mechanism. In some embodiments, these molecules are engineered to have enhanced ADCC activity. In some embodiments, these molecules are engineered to have enhanced CDC activity. For example, these molecules can be engineered to have enhanced interaction with killer cells bearing Fc receptors. Methods to produce such engineered molecules, including engineered antibodies or Fc-fusion proteins, are described herein and also known in the art.

In another aspect, provided herein is a method of killing or inhibiting the proliferation of a cancer cell resistant to an anti-PD-1 therapy or an anti-PD-L1 therapy, including contacting the cell with an effective amount of a molecule including an antigen binding fragment that immunospecifically binds to BTN1A1.

In some embodiments, provided herein are uses of molecules having an antigen binding fragment that immunospecifically binds to BTN1A1, glycosylated BTN1A1, or a BTN1A1 dimer (e.g., a glycosylated BTN1A1 dimer), including anti-BTN1A1 antibodies, anti-glycosylated BTN1A1 antibodies, and anti-BTN1A1 dimer antibodies to treat a disease or disorder in a subject who overexpresses BTN1A1. In some embodiments, the expression level of BTN1A1 in the subject is higher than a reference level. The reference level can be the average or medium expression level of BTN1A1 in a population of healthy individuals. The reference level can also be determined by statistic analysis of the expression level of a sample population.

In another aspect, provided herein is a method of treating cancer, including (i) obtaining a sample including cancer cells from the subject having the cancer; (ii) determining the level of BTN1A1 in the sample; (iii) diagnosing the subject as being likely to be responsive to a molecule including an antigen binding fragment that immunospecifically binds to BTN1A1, if the level of BTN1A1 in the sample is higher than or equal to a BTN1A1 reference level, and (iv) administering to the subject a therapeutically effective amount of the molecule including an antigen binding fragment that immunospecifically binds to BTN1A1.

In another aspect, provided herein is a method of treating cancer, including (i) obtaining a sample including cancer cells from the subject having the cancer; (ii) determining the level of PD-L1 in the sample; (iii) diagnosing the subject as being likely to be responsive to a molecule including an antigen binding fragment that immunospecifically binds to BTN1A1, if the level of PD-L1 in the sample is lower than or equal to a PD-L1 reference level, and (iv) administering to the subject a therapeutically effective amount of the molecule including an antigen binding fragment that immunospecifically binds to BTN1A1.

In another aspect, provided herein is a method of treating an anti-PD1 therapy or anti-PD-L1 therapy resistant or refractory cancer, including (i) obtaining a sample including cancer cells from the subject having the anti-PD1 therapy or anti-PD-L1 therapy resistant or refractory cancer; (ii) determining the level of BTN1A1 in the sample; (iii) diagnosing the subject as being likely to be responsive to a molecule including an antigen binding fragment that immunospecifically binds to BTN1A1, if the level of BTN1A1 in the sample is higher than or equal to a BTN1A1 reference level, and (iv) administering to the subject a therapeutically effective amount of the molecule including an antigen binding fragment that immunospecifically binds to BTN1A1.

In another aspect, provided herein is a method of treating an anti-PD1 therapy or anti-PD-L1 therapy resistant or refractory cancer, including (i) obtaining a sample including cancer cells from the subject having the anti-PD1 therapy or anti-PD-L1 therapy resistant or refractory cancer cancer; (ii) determining the level of BTN1A1 and/or PD-L1 in the sample; (iii) diagnosing the subject as being likely to be responsive to a molecule including an antigen binding fragment that immunospecifically binds to BTN1A1, if the level of BTN1A1 in the sample is higher than or equal to a BTN1A1 reference level and/or if the level of PD-L1 in the sample is equal to or lower than a PD-L1 reference level, and (iv) administering to the subject a therapeutically effective amount of the molecule including an antigen binding fragment that immunospecifically binds to BTN1A1.

In another aspect, provided herein is a method of treating cancer, including (i) obtaining a sample including cancer cells from the subject having the cancer; (ii) determining the level of BTN1A1 and/or PD-L1 in the sample; (iii) diagnosing the subject as being likely to be responsive to a molecule including an antigen binding fragment that immunospecifically binds to BTN1A1, if the level of BTN1A1 in the sample is higher than or equal to a BTN1A1 reference level and/or if the level of PD-L1 in the sample is equal to or lower than a PD-L1 reference level, and (iv) administering to the subject a therapeutically effective amount of the molecule including an antigen binding fragment that immunospecifically binds to BTN1A1.

In some embodiments, the subject has an anti-PD-1 therapy or anti-PD-L1 therapy resistant or refractory cancer. In some embodiments, the subject has an anti-PD-1 therapy or anti-PD-L1 therapy resistant cancer. In some embodiments, the subject has an anti-PD-1 therapy resistant cancer. In some embodiments, the subject has an anti-PD-L1 therapy resistant cancer. In some embodiments, the subject has an anti-PD-1 therapy or anti-PD-L1 therapy refractory cancer. In some embodiments, the subject has an anti-PD-1 therapy refractory cancer. In some embodiment, the subject has an anti-PD-L1 therapy refractory cancer.

In some embodiments, the anti-PD-1 therapy or anti-PD-L1 therapy resistant or refractory cancer is a lung cancer or a breast cancer. In some embodiments, the anti-PD-1 therapy or anti-PD-L1 therapy resistant or refractory cancer is a lung cancer. In some embodiments, the anti-PD-1 therapy or anti-PD-L1 therapy resistant or refractory cancer is a a breast cancer. In some embodiments, the lung cancer is a Lewis lung carcinoma. In some embodiments, the breast cancer is a mammary carcinoma.

In some embodiments, the subject has a cancer that is, at least partially, responsive to an anti-PD-1 therapy or anti-PD-L1 therapy.

In some embodiment, the BTN1A1 is expressed in the cancer, In some embodiments, the BTN1A1 expressing cancer includes, e.g., breast cancer, neuroendocrine prostate cancer (NEPC), diffuse large B-cell lymphoma, melanoma, a cancer from the National Cancer Institute cancer panel (NCI 60), uveal melanoma, pancreas cancer, ovarian cancer, uterine cancer, lung adenocarcinoma, desmoplastic small-round-cell tumor, bladder cancer, colorectal cancer, lung squamous cell carcinoma, liver cancer, lung cancer, stomach cancer, cholangiocarcinoma, esophagus squamous cell carcinoma, head and neck cancer, sarcoma, prostate cancer, liver cancer, pancreas cancer, pheochromocytoma or paraganglioma (PCPG), cervical cancer, glioma, or acute myeloid leukemia (AML).

In some embodiments, the method includes determining the level of BTN1A1 in the sample. In some embodiment, the method includes determining the level of PD-L1 in the sample. In some embodiments, the method includes determining the level of BTN1A1 and PD-L1 in the sample.

In some embodiments, the subject is diagnosted as being likely to be responsive to a molecule including an antigen binding fragment that immunospecifically binds to BTN1A1, if the level of BTN1A1 in the sample is higher than or equal to a BTN1A1 reference level. In some embodiments, the subject is diagnosed as being likely to be responsive to a molecule including an antigen binding fragment that immunospecifically binds to BTN1A1, if the level of BTN1A1 in the sample is higher than a BTN1A1 reference level.

In some embodiments, the subject is diagnosted as being likely to be responsive to a molecule including an antigen binding fragment that immunospecifically binds to BTN1A1, if the level of PD-L1 in the sample is lower than or equal to a PD-L1 reference level. In some embodiments, the subject is diagnosed as being likely to be responsive to a molecule including an antigen binding fragment that immunospecifically binds to BTN1A1, if the level of PD-L1 in the sample is lower than a PD-L1 reference level.

In some embodiments, the subject is diagnosed as being likely to be responsive to a molecule including an antigen binding fragment that immunospecifically binds to BTN1A1, if the level of BTN1A1 is equal to or higher than a BTN1A1 reference level and if the level of PD-L1 is lower than or equal to a PD-L1 reference level. In some embodiments, the subject is diagnosed as being likely to be responsive to a molecule including an antigen binding fragment that immunospecifically binds to BTN1A1, if the level of BTN1A1 is higher than or equal to a BTN1A1 reference level and if the level of PD-L1 is lower than a PD-L1 reference level. In some embodiments, the subject is diagnosed as being likely to be responsive to a molecule including an antigen binding fragment that immunospecifically binds to BTN1A1, if the level of BTN1A1 is higher than a BTN1A1 reference level and if the level of PD-L1 is lower than a PD-L1 reference level.

The sample can be any solid or liquid sample from the subject.

In some embodiments, the sample is a liquid biopsy sample. In some embodiments, the sample used in the methods provided herein includes body fluids from a subject. Non-limiting examples of body fluids include blood (e.g., whole blood), blood plasma, amniotic fluid, aqueous humor, bile, cerumen, cowper's fluid, pre-ejaculatory fluid, chyle, chyme, female ejaculate, interstitial fluid, lymph, menses, breast milk, mucus, pleural fluid, pus, saliva, sebum, semen, serum, sweat, tears, urine, vaginal lubrication, vomit, water, feces, internal body fluids (including cerebrospinal fluid surrounding the brain and the spinal cord), synovial fluid, intracellular fluid (the fluid inside cells), and vitreous humour (the fluid in the eyeball). In some embodiments, the sample is a blood sample. The blood sample can be obtained using conventional techniques as described in, e.g., Innis et al, eds., PCR Protocols (Academic Press, 1990). White blood cells can be separated from blood samples using conventional techniques or commercially available kits, e.g., RosetteSep kit (Stein Cell Technologies, Vancouver, Canada). Sub-populations of white blood cells, e.g., mononuclear cells, B cells, T cells, monocytes, granulocytes, or lymphocytes, can be further isolated using conventional techniques, e.g., magnetically activated cell sorting (MACS) (Miltenyi Biotec, Auburn, California) or fluorescently activated cell sorting (FACS) (Becton Dickinson, San Jose, California).

In some embodiments, the sample is a solid biopsy sample. In some embodiments, the sample used in the present methods includes a biopsy (e.g., a tumor biopsy). The biopsy can be from any organ or tissue, for example, skin, liver, lung, heart, colon, kidney, bone marrow, teeth, lymph node, hair, spleen, brain, breast, or other organs. Any biopsy technique known by those skilled in the art can be used for isolating a sample from a subject, for instance, open biopsy, close biopsy, core biopsy, incisional biopsy, excisional biopsy, or fine needle aspiration biopsy.

In some embodiments, the sample is a paraffin embedded formaldehyde fixed tissue sample. In some embodiments, the sample is a tissue slice. In some embodiments, the sample is provided on a tissue array.

In some embodiments the level of the biomarkers is measured by determining the protein level of the biomarker.

The level of BTN1A1 or PD-L1 in the sample can be analyzed using any method known in the art. See, e.g., Section 5.6 (Companion Diagnostics). In some embodiments, determining the level of BTN1A1 or PD-L1 in the sample can include analyzing the level of a BTN1A1 or PD-L1 nucleic acid or a BTN1A1 or PD-L1 protein. BTN1A1 or PD-L1 nucleic acid levels can, e.g., be analyzed using a polymerase chain reaction (PCR) method (e.g., RT-PCR or Q-PCR), a nucleic acid array based method (e.g., a genchip), or a nucleic acid sequencing method, such as a next-generation sequencing method. BTN1A1 or PD-L1 protein levels can be determined using, e.g., a western-blot, ELISA, FACS, immunohistochemistry method. BTN1A1 or PD-L1 levels can be determined in absolute quantitative terms (e.g., weight BTN1A1 or PD-L1 per weight of tissue, or molar amounts per tissue volume or per liquid sample volume). In some embodiments, BTN1A1 or PD-L1 levels are determined in relative or semi-quantitative terms (e.g., relative intensities of BTN1A1 or PD-L1 specific staining in different regions of a tissue sample). BTN1A1 or PD-L1 levels can be determined independently using the same method or different methods. In some embodiments, relative BTN1A1 or PD-L1 levels are determined in a tissue slice of a solid tumor sample using immunohistochemistry combined with fluorescence microscopy or bright field microscopy.

In some embodiments, determining the level of BTN1A1 and/or PD-L1 in the sample includes analyzing the cell surface expression of BTN1A1 and/or PD-L1, e.g., using a FACS assay or immunocytochemistry.

In some embodiment the treatment produces at least one therapeutic effect, such as a reduction in size of a tumor, a reduction in number of metastatic lesions over time, a complete response, a partial response, or a stable disease.

In some embodiments the reference is prepared by using a control sample obtained from the subject prior to administering the molecule including an antigen binding fragment that immunospecifically binds to BTN1A1 to the subject, and the control sample is from the same source as the sample. In some embodiments the reference is prepared by using a control sample obtained from a healthy subject not having cancer, and the control sample is from the same source as the sample. In some embodiments the reference is prepared by using a control sample obtained from a group of healthy subjects not having cancer, and the control sample is from the same source as the sample. In some embodiments the reference is prepared by using a control sample obtained from a second subject having cancer, and the control sample is from the same source as the sample. In some embodiments the reference is prepared by using a control sample obtained from a group of subjects having cancer, and the control sample is from the same source as the sample.

Also provided herein are therapeutic uses of molecules having an antigen binding fragment that immunospecifically binds to BTN1A1, glycosylated BTN1A1, or a BTN1A1 dimer, which include anti-BTN1A1 antibodies, anti-glycosylated BTN1A1 antibodies, and anti-BTN1A1 dimer antibodies. In some embodiments, the molecules have an antigen binding fragment that immunospecifically binds to glycosylated BTN1A1. In some embodiments, the antigen binding fragment immunospecifically binds to BTN1A1 glycosylated at positions N55, N215, and/or N449. In some embodiments, the antigen binding fragment immunospecifically binds to BTN1A1 glycosylated at position N55. In some embodiments, the antigen binding fragment immunospecifically binds to BTN1A1 glycosylated at position N215. In some embodiments, the antigen binding fragment immunospecifically binds to BTN1A1 glycosylated at position N449. In some embodiments, the antigen binding fragment immunospecifically binds to one or more glycosylation motifs. In some embodiments, the antigen binding fragment immunospecifically binds to BTN1A1 glycosylated at positions N55 and N215. In some embodiments, the antigen binding fragments immunospecifically binds to BTN1A1 glycosylated at positions N215 and N449. In some embodiments, the antigen binding fragments immunospecifically binds to BTN1A1 glycosylated at positions N55 and N449. In some embodiments, the antigen binding fragments immunospecifically binds to BTN1A1 glycosylated at positions N55, N215 and N449. In some embodiments, the antigen binding fragment immunospecifically binds to a BTN1A1 dimer, e.g., a BTN1A1 dimer glycosylated at one or more of positions N55, N215 and N449 of one or more of the BTN1A1 monomers in the BTN1A1 dimer.

In some embodiments, provided herein are therapeutic uses of molecules having an antigen binding fragment that preferentially binds glycosylated BTN1A1 over non-glycosylated BTN1A1. In some embodiments, the antigen binding fragments preferentially bind to BTN1A1 glycosylated at positions N55, N215, and/or N449 over non-glycosylated BTN1A1. In some embodiments, the antigen binding fragments preferentially bind to BTN1A1 glycosylated at position N55 over non-glycosylated BTN1A1. In some embodiments, the antigen binding fragments preferentially bind to BTN1A1 glycosylated at position N215 over non-glycosylated BTN1A1. In some embodiments, the antigen binding fragments preferentially bind to BTN1A1 glycosylated at position N449 over non-glycosylated BTN1A1. In some embodiments, the antigen binding fragments preferentially bind to one or more glycosylation motifs. In some embodiments, the antigen binding fragments preferentially binds BTN1A1 glycosylated at positions N55 and N215 over non-glycosylated BTN1A1. In some embodiments, the antigen binding fragments preferentially bind to BTN1A1 glycosylated at positions N215 and N449 over non-glycosylated BTN1A1. In some embodiments, the antigen binding fragments preferentially bind to BTN1A1 glycosylated at positions N55 and N449 over non-glycosylated BTN1A1. In some embodiments, the antigen binding fragments preferentially binds BTN1A1 glycosylated at positions N55, N215 and N449 over non-glycosylated BTN1A1. In some embodiments, the glycosylated BTN1A1 is a BTN1A1 dimer.

In some embodiments, provided herein are therapeutic uses of molecules having an antigen binding fragment that preferentially binds a BTN1A1 dimer over a BTN1A1 monomer. In some embodiments, the BTN1A1 dimer is glycosylated at one or more of positions N55, N215 and N449 of one or more of the BTN1A1 monomers in the BTN1A1 dimer.

In some embodiments, the antigen binding fragment binds to glycosylated BTN1A1 with a $K_D$ less than half of the $K_D$ exhibited relative to unglycosylated BTN1A1. In some embodiments, the antigen binding fragment binds to glycosylated BTN1A1 with a $K_D$ at least 2 times less than the $K_D$ exhibited relative to unglycosylated BTN1A1. In some embodiments, the antigen binding fragment binds to glycosylated BTN1A1 with a $K_D$ at least 5 times less than the $K_D$ exhibited relative to unglycosylated BTN1A1. In some embodiments, the antigen binding fragment binds to glycosylated BTN1A1 with a $K_D$ at least 10 times less than the $K_D$ exhibited relative to unglycosylated BTN1A1. In some embodiments, the antigen binding fragment binds to glycosylated BTN1A1 with a $K_D$ at least 15 times less than the $K_D$ exhibited relative to unglycosylated BTN1A1. In some embodiments, the antigen binding fragment binds to glycosylated BTN1A1 with a $K_D$ at least 20 times less than the $K_D$ exhibited relative to unglycosylated BTN1A1. In some embodiments, the antigen binding fragment binds to glycosylated BTN1A1 with a $K_D$ at least 25 times less than the $K_D$ exhibited relative to unglycosylated BTN1A1. In some embodiments, the antigen binding fragment binds to glycosylated BTN1A1 with a $K_D$ at least 30 times less than the $K_D$ exhibited relative to unglycosylated BTN1A1. In some embodiments, the antigen binding fragment binds to glycosylated BTN1A1 with a $K_D$ at least 35 times less than the $K_D$ exhibited relative to unglycosylated BTN1A1. In some embodiments, the antigen binding fragment binds to glycosylated BTN1A1 with a $K_D$ at least 40 times less than the $K_D$ exhibited relative to unglycosylated BTN1A1. In some embodiments, the antigen binding fragment binds to glycosylated BTN1A1 with a $K_D$ at least 50 times less than the $K_D$ exhibited relative to unglycosylated BTN1A1.

In some embodiments, the antigen binding fragment binds to a BTN1A1 dimer (e.g., a glycosylated BTN1A1 dimer) with a $K_D$ less than half of the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with a $K_D$ at least 2 times less than the $K_D$ exhibited relative to the BTN1A1 monomer (e.g., a glycosylated BTN1A1 monomer). In some embodiments, the antigen binding fragment binds to a BTN1A1 dimer (e.g., a glycosylated BTN1A1 dimer) with a $K_D$ at least 5 times less than the $K_D$ exhibited relative to the BTN1A1 monomer (e.g., a glycosylated BTN1A1 monomer). In some embodiments, the antigen binding fragment binds to a BTN1A1 dimer (e.g., a glycosylated BTN1A1 dimer) with a $K_D$ at least 10 times less than the $K_D$ exhibited relative to the BTN1A1 monomer (e.g., a glycosylated BTN1A1 monomer). In some embodiments, the antigen binding fragment binds to a BTN1A1 dimer (e.g., a glycosylated BTN1A1 dimer) with a $K_D$ at least 15 times less than the $K_D$ exhibited relative to the BTN1A1 monomer (e.g., a glycosylated BTN1A1 monomer). In some embodiments, the antigen binding fragment binds to a BTN1A1 dimer (e.g., a glycosylated BTN1A1 dimer) with a $K_D$ at least 20 times less than the $K_D$ exhibited relative to the BTN1A1 monomer (e.g., a glycosylated BTN1A1 monomer). In some embodiments, the antigen binding fragment binds to a BTN1A1 dimer (e.g., a glycosylated BTN1A1 dimer) with a $K_D$ at least 25 times less than the $K_D$ exhibited relative to the BTN1A1 monomer (e.g., a glycosylated BTN1A1 monomer). In some embodiments, the antigen binding fragment binds to a BTN1A1 dimer (e.g., a glycosylated BTN1A1 dimer) with a $K_D$ at least 30 times less than the $K_D$ exhibited relative to the BTN1A1 monomer (e.g., a glycosylated BTN1A1 monomer). In some embodiments, the antigen binding fragment binds to a BTN1A1 dimer (e.g., a glycosylated BTN1A1 dimer) with a $K_D$ at least 35 times less than the $K_D$ exhibited relative to the BTN1A1 monomer (e.g., a glycosylated BTN1A1 monomer). In some embodiments, the antigen binding fragment binds to a BTN1A1 dimer (e.g., a glycosylated BTN1A1 dimer) with a $K_D$ at least 40 times less than the $K_D$ exhibited relative to the BTN1A1 monomer (e.g., a glycosylated BTN1A1 monomer). In some embodiments, the antigen binding fragment binds to a BTN1A1 dimer (e.g., a glycosylated BTN1A1 dimer) with a $K_D$ at least 50 times less than the $K_D$ exhibited relative to the BTN1A1 monomer (e.g., a glycosylated BTN1A1 monomer).

In some embodiments, the antigen binding fragment binds to glycosylated BTN1A1 with an MFI that is at least twice as high as the MFI as exhibited relative to unglycosylated BTN1A1. In some embodiments, the antigen binding fragment binds to glycosylated BTN1A1 with an MFI that is at least five times as high as the MFI as exhibited relative to unglycosylated BTN1A1. In some embodiments, the antigen binding fragment binds to glycosylated BTN1A1 with an MFI that is at least 10 times as high as the MFI as exhibited relative to unglycosylated BTN1A1. In some embodiments, the antigen binding fragment binds to glycosylated BTN1A1 with an MFI that is at least 15 times as high as the MFI as exhibited relative to unglycosylated BTN1A1. In some embodiments, the antigen binding fragment binds to glycosylated BTN1A1 with an MFI that is at least 20 times as high as the MFI as exhibited relative to unglycosylated BTN1A1. In some embodiments, the antigen binding fragment binds to glycosylated BTN1A1 with an MFI that is at least 25 times as high as the MFI as exhibited relative to unglycosylated BTN1A1. In some embodiments, the antigen binding fragment binds to glycosylated BTN1A1 with an MFI that is at least 30 times as high as the MFI as exhibited relative to unglycosylated BTN1A1. In some embodiments, the antigen binding fragment binds to glycosylated BTN1A1 with an MFI that is at least 40 times as high as the MFI as exhibited relative to unglycosylated BTN1A1. In some embodiments, the antigen binding fragment binds to glycosylated BTN1A1 with an MFI that is at least 50 times as high as the MFI as exhibited relative to unglycosylated BTN1A1.

In some embodiments, the antigen binding fragment binds to a BTN1A1 dimer (e.g., a glycosylated BTN1A1 dimer) with an MFI that is at least twice as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least five times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 10 times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 15 times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 20 times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 30 times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 40 times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 50 times as high as the MFI as exhibited relative to a BTN1A1 monomer (e.g., a glycosylated BTN1A1 monomer).

In some embodiments, provided herein are therapeutic uses of molecules having an antigen binding fragment that immunospecifically masks BTN1A1 glycosylation at positions N55, N215, and/or N449. In some embodiments, the antigen binding fragments immunospecifically mask BTN1A1 glycosylation at position N55. In some embodiments, the antigen binding fragments immunospecifically mask BTN1A1 glycosylation at position N215. In some embodiments, the antigen binding fragments immunospecifically mask BTN1A1 glycosylation at position N449. In some embodiments, the antigen binding fragments immunospecifically mask one or more glycosylation motifs of BTN1A1. In some embodiments, the antigen binding fragments immunospecifically mask BTN1A1 glycosylation at positions N55 and N215. In some embodiments, the antigen binding fragments immunospecifically mask BTN1A1 glycosylation at positions N215 and N449. In some embodiments, the antigen binding fragments immunospecifically mask BTN1A1 glycosylation at positions N55 and N449. In some embodiments, the antigen binding fragments immunospecifically mask BTN1A1 glycosylation at positions N55, N215 and N449.

In some embodiments, provided herein are therapeutic uses of molecules having antigen binding fragment that includes the VH or VL domain of the murine monoclonal antibody STC703, STC810, STC820, STC1011, STC1012, STC1029, STC2602, STC2714, STC2739, STC2778, or STC2781, as depicted in Tables 2a-12b. In one embodiment, the molecules can have an antigen binding fragment that includes both the VH and VL domain of the murine monoclonal antibody STC703, STC810, STC820, STC1011, STC1012, STC1029, STC2602, STC2714, STC2739, STC2778, or STC2781, as depicted in Tables 2a-12b. In another embodiment, provided herein are therapeutic uses of molecules having antigen binding fragment that includes one or more VH CDRs having the amino acid sequence of any one of the VH CDRs of the murine monoclonal antibody STC703, STC810, STC820, STC1011, STC1012, STC1029, STC2602, STC2714, STC2739, STC2778, or STC2781, as depicted in Tables 2a-12b. In another embodiment, the molecules can have an antigen binding fragment that includes one or more VL CDRs having the amino acid sequence of any one of the VL CDRs of the murine monoclonal antibody STC703, STC810, STC820, STC1011, STC1012, STC1029, STC2602, STC2714, STC2739, STC2778, or STC2781, as depicted in Tables 2a-12b. In yet another embodiment, the molecules can have an antigen binding fragment that includes at least one VH CDR and at least one VL CDR of the murine monoclonal antibody STC703, STC810, STC820, STC1011, STC1012, STC1029, STC2602, STC2714, STC2739, STC2778, or STC2781, as depicted in Tables 2a-12b.

In some embodiments, provided herein are therapeutic uses of molecules having antigen binding fragment that competitively blocks (e.g., in a dose-dependent manner) a BTN1A1 epitope described herein. The BTN1A1 epitope can be an epitope of STC703, STC810, STC820, STC1011, STC1012, STC1029, STC2602, STC2714, STC2739, STC2778, or STC2781. In some embodiments, provided herein are therapeutic uses of molecules having an antigen binding fragment that immunospecifically binds to a BTN1A1 epitope of a BTN1A1 antibody described herein. The BTN1A1 epitope can be an epitope of STC703, STC810, STC820, STC1011, STC1012, STC1029, STC2602, STC2714, STC2739, STC2778, or STC2781.

5.4.1. Diseases and Disorders

In some embodiments, provided herein are uses of the antibodies or other molecules to mediate increased production of cytokines, such as IFN-γ. Thus, provided herein are uses of such antibodies or other molecules in the treatment of diseases and conditions that can be treated with cytokines, such as ovarian and other forms of cancer. In some embodiments, provided herein are uses of the antibodies and other molecules in mediating increased T-cell (e.g., $CD8^+$ T-cell) activity or proliferation. Thus, provided in some embodiments are the use of such antibodies and other molecules in the treatment of diseases and conditions that are treatable by increasing T-cell activity or proliferation, such as cancer. In some embodiments, provided herein are uses of the antibodies or other molecules as described herein to mediate both increased T-cell activity and increased T-cell proliferation.

Up-modulation of the immune system is particularly desirable in the treatment of cancers. Additionally, BTN1A1 is specifically and highly expressed in cancer cells. Molecules described herein can also bind to cancer cells and cause their destruction by either direct cytotoxicity, or through ADCC or CDC mechanism. Thus, provided herein are methods of cancer treatment. A cancer refers to a neoplasm or tumor resulting from abnormal uncontrolled growth of cells. A cancer can be a primary cancer or a metastatic cancer.

In some embodiments, provided herein are methods to treat a cancer in a subject by administering a molecule having an antigen binding fragment that immunospecifically binds to BTN1A1, glycosylated BTN1A1, or a BTN1A1 dimer (e.g., a glycosylated BTN1A1 dimer). Cancers for which the treatment methods can be useful include any malignant cell type, such as those found in a solid tumor or a hematological cancer. Exemplary solid tumors include, but are not limited to, a tumor of an organ selected from the group consisting of pancreas, colon, cecum, esophagus, stomach, brain, head, neck, thyroid, thymus, ovary, kidney, larynx, sarcoma, lung, bladder, melanoma, prostate, and breast. Exemplary hematological cancers include, but not limited to, tumors of the bone marrow, T or B cell malignancies, leukemias, lymphomas, blastomas, myelomas, and the like. In some embodiments, the methods further include administering an anti-PD1 therapy or an anti-PD-L1 therapy.

In some embodiments, provided herein are methods to treat a cancer in a subject by administering the molecule described herein having an antigen binding fragment that immunospecifically binds to BTN1A1, glycosylated BTN1A1, or a BTN1A1 dimer (e.g., a glycosylated BTN1A1 dimer), whereby the cancer can be breast cancer, neuroendocrine prostate cancer (NEPC), diffuse large B-cell lymphoma, melanoma, cancer from the National Cancer Institute cancer panel (NCI 60), uveal melanoma, pancreas cancer, ovarian cancer, uterine cancer, lung adenocarcinoma, desmoplastic small-round-cell tumor, bladder cancer, colorectal cancer, lung squamous cell carcinoma, liver cancer, lung cancer, stomach cancer, cholangiocarcinoma, esophagus squamous cell carcinoma, head and neck cancer, sarcoma, prostate cancer, liver cancer, pancreas cancer, pheochromocytoma or paraganglioma (PCPG), cervical cancer, glioma, or acute myeloid leukemia (AML). The molecules used for treating the cancer can be any molecules described herein having an antigen binding fragment that immunospecifically binds to BTN1A1, glycosylated BTN1A1, or a BTN1A1 dimer (e.g., a glycosylated BTN1A1 dimer). In some embodiments, the antigen binding fragment preferentially binds glycosylated BTN1A1 over non-glycosylated BTN1A1. In some embodiments, the antigen binding fragment preferentially binds a BTN1A1 dimer (e.g., a glycosylated BTN1A1 dimer) over a BTN1A1 monomer (e.g., a glycosylated BTN1A1 monomer). In some embodiments, the antigen binding fragments immunospecifically mask BTN1A1 glycosylation at positions N55, N215, N449, or any combination thereof. In some embodiments, the molecule used for treating the cancer includes STC703, STC810, STC820, STC1011, STC1012, STC1029, STC2602, STC2714, STC2739, STC2778, or STC2781. In some embodiments, the methods further include administering an anti-PD1 therapy or an anti-PD-L1 therapy.

In some embodiments, provided herein are methods to treat a cancer in a subject by administering the molecule described herein having an antigen binding fragment that immunospecifically binds to BTN1A1, glycosylated BTN1A1, or a BTN1A1 dimer (e.g., a glycosylated BTN1A1 dimer), whereby the cancer can be lung squamous carcinoma, prostate adenocarcinoma, pancreatic adenocarcinoma, or hepatocellular carcinoma. The molecules used for treating lung squamous carcinoma, prostate adenocarcinoma, pancreatic adenocarcinoma, or hepatocellular carcinoma can be any molecules described herein having an antigen binding fragment that immunospecifically binds to BTN1A1, glycosylated BTN1A1, or a BTN1A1 dimer (e.g., a glycosylated BTN1A1 dimer). In some embodiments, the antigen binding fragment preferentially binds glycosylated BTN1A1 over non-glycosylated BTN1A1. In some embodiments, the antigen binding fragment preferentially binds a BTN1A1 dimer (e.g., a glycosylated BTN1A1 dimer) over a BTN1A1 monomer (e.g., a glycosylated BTN1A1 monomer). In some embodiments, the antigen binding fragments immunospecifically mask BTN1A1 glycosylation at positions N55, N215, N449, or any combination thereof. In some embodiments, the molecule used for treating lung squamous carcinoma, prostate adenocarcinoma, pancreatic adenocarcinoma, or hepatocellular carcinoma includes STC703, STC810, STC820, STC1011, STC1012, STC1029, STC2602, STC2714, STC2739, STC2778, or STC2781. In some embodiments, the methods further include administering an anti-PD1 therapy or an anti-PD-L1 therapy.

In some embodiments, provided herein are methods to treat a cancer in a subject by administering the molecule described herein having an antigen binding fragment that immunospecifically binds to BTN1A1, glycosylated BTN1A1, or a BTN1A1 dimer (e.g., a glycosylated BTN1A1 dimer) whereby the cancer is an anti-PD-1 therapy or an anti-PD-L1 therapy resistant or refractory cancer. The molecules used for treating is an anti-PD-1 therapy or an anti-PD-L1 therapy resistant or refractory cancer can be any molecules described herein having an antigen binding fragment that immunospecifically binds to BTN1A1, glycosylated BTN1A1, or a BTN1A1 dimer. In some embodiments, the antigen binding fragment preferentially binds glycosylated BTN1A1 over non-glycosylated BTN1A1. In some embodiments, the antigen binding fragment preferentially binds a BTN1A1 dimer (e.g., a glycosylated BTN1A1 dimer) over a BTN1A1 monomer (e.g., a glycosylated BTN1A1 monomer). In some embodiments, the antigen binding fragments immunospecifically mask BTN1A1 glycosylation at positions N55, N215, N449, or any combination thereof. In some embodiments, the molecule used for treating an anti-PD-1 therapy or an anti-PD-L1 therapy resistant or refractory cancer includes STC703, STC810, STC820, STC1011, STC1012, STC1029, STC2602, STC2714, STC2739, STC2778, or STC2781. In some embodiments, the cancer is an anti-PD-1 therapy resistant or refractory cancer. In some embodiments, the cancer is an anti-PD-L1 therapy resistant or refractory cancer. In some embodiments, the anti-PD-1 therapy resistant or refractory cancer is a breast cancer or a lung cancer. In some embodiments, the anti-PD-1 therapy resistant or refractory cancer is a mammary carcinoma or a Lewis lung carcinoma. In some embodiments, the anti-PD-1 therapy resistant or refractory cancer is a mammary carcinoma. In some embodiments, the anti-PD-1 therapy resistant or refractory cancer is a Lewis lung carcinoma.

Further examples of cancers that can be treated using the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung, mesothelioma), cancer of the peritoneum, hepatocellular cancer, gastric or stomach cancer (including gastrointestinal cancer and gastrointestinal stromal cancer), esophageal cancer, pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulvar cancer, thyroid cancer, various types of head and neck cancer, melanoma, superficial spreading melanoma, lentigo malignant melanoma, acral lentiginous melanomas, nodular melanomas, uveal melanomas, germ cell tumors (yolk sac tumors, testicular cancer, choriocarcinoma), as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia), chronic lymphocytic leukemia (CLL), acute lymphoblastic leukemia (ALL), Hairy cell leukemia, multiple myeloma, acute myeloid leukemia (AML) and chronic myeloblastic leukemia.

The cancer can also be of any of the following histological types: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, provided herein are methods to treat a cancer in a subject by administering the molecule described herein having an antigen binding fragment that immunospecifically binds to BTN1A1, glycosylated BTN1A1, or a BTN1A1 dimer (e.g., a glycosylated BTN1A1 dimer), whereby the cancer is lung cancer, prostate cancer, pancreas cancer, ovarian cancer, liver cancer, head & neck cancer, breast cancer, or stomach cancer. In some embodiments, provided herein are methods to treat a cancer in a subject by administering the molecule described herein having an antigen binding fragment that immunospecifically binds to BTN1A1, glycosylated BTN1A1, or a BTN1A1 dimer (e.g., a glycosylated BTN1A1 dimer), whereby the cancer can be lung cancer. The lung cancer can be non-small cell lung cancer (NSCLC). The lung cancer can be small cell lung cancer (SCLC). The NSCLC can be squamous NSCLC. The molecules used for treating lung cancer can be any molecules described herein having an antigen binding fragment that immunospecifically binds to BTN1A1 or glycosylated BTN1A1. In some embodiments, the antigen binding fragment preferentially binds glycosylated BTN1A1 over non-glycosylated BTN1A1. In some embodiments, the antigen binding fragments immunospecifically mask BTN1A1 glycosylation at positions N55, N215, N449, or any combination thereof. In some embodiments, the molecule used for treating lung cancer is STC703, STC810, STC820, STC1011, STC1012, STC1029, STC2602, STC2714, STC2739, STC2778, or STC2781. In some embodiments, the molecule used for treating NSCLC includes STC703, STC810, STC820, STC1011, STC1012, STC1029, STC2602, STC2714, STC2739, STC2778, or STC2781. In some embodiments, the molecule used for treating squamous NSCLC includes STC703, STC810, STC820, STC1011, STC1012, STC1029, STC2602, STC2714, STC2739, STC2778, or STC2781. In some embodiments, the methods further include administering an anti-PD1 therapy or an anti-PD-L1 therapy.

In some embodiments, provided herein are methods to treat a cancer in a subject by administering the molecule described herein having an antigen binding fragment that immunospecifically binds to BTN1A1, glycosylated BTN1A1, or a BTN1A1 dimer (e.g., a glycosylated BTN1A1 dimer) whereby the cancer can be prostate cancer. The molecules used for treating prostate cancer can be any molecules described herein having an antigen binding fragment that immunospecifically binds to BTN1A1, glycosylated BTN1A1, or a BTN1A1 dimer. In some embodiments, the antigen binding fragment preferentially binds glycosylated BTN1A1 over non-glycosylated BTN1A1. In some embodiments, the antigen binding fragment preferentially binds a BTN1A1 dimer (e.g., a glycosylated BTN1A1 dimer) over a BTN1A1 monomer (e.g., a glycosylated BTN1A1 monomer). In some embodiments, the antigen binding fragments immunospecifically mask BTN1A1 glycosylation at positions N55, N215, N449, or any combination thereof. In some embodiments, the molecule used for treating prostate cancer includes STC703, STC810, STC820, STC1011, STC1012, STC1029, STC2602, STC2714, STC2739, STC2778, or STC2781. In some embodiments, the methods further include administering an anti-PD1 therapy or an anti-PD-L1 therapy.

In some embodiments, provided herein are methods to treat a cancer in a subject by administering the molecule described herein having an antigen binding fragment that immunospecifically binds to BTN1A1, glycosylated BTN1A1, or a BTN1A1 dimer (e.g., a glycosylated BTN1A1 dimer) whereby the cancer can be pancreas cancer. The molecules used for treating pancreas cancer can be any molecules described herein having an antigen binding fragment that immunospecifically binds to BTN1A1, glycosylated BTN1A1, or a BTN1A1 dimer. In some embodiments, the antigen binding fragment preferentially binds glycosylated BTN1A1 over non-glycosylated BTN1A1. In some embodiments, the antigen binding fragment preferentially binds a BTN1A1 dimer (e.g., a glycosylated BTN1A1 dimer) over a BTN1A1 monomer (e.g., a glycosylated BTN1A1 monomer). In some embodiments, the antigen binding fragments immunospecifically mask BTN1A1 glycosylation at positions N55, N215, N449, or any combination thereof. In some embodiments, the molecule used for treating pancreas cancer includes STC703, STC810, STC820, STC1011, STC1012, or STC1029, STC2602, STC2714, STC2739, STC2778, or STC2781. In some embodiments, the methods further include administering an anti-PD1 therapy or an anti-PD-L1 therapy.

In some embodiments, provided herein are methods to treat a cancer in a subject by administering the molecule described herein having an antigen binding fragment that immunospecifically binds to BTN1A1, glycosylated BTN1A1, or a BTN1A1 dimer (e.g., a glycosylated BTN1A1 dimer), whereby the cancer can be ovarian cancer. The molecules used for treating ovarian cancer can be any molecules described herein having an antigen binding fragment that immunospecifically binds to BTN1A1, glycosylated BTN1A1, or a BTN1A1 dimer (e.g., a glycosylated BTN1A1 dimer). In some embodiments, the antigen binding fragment preferentially binds glycosylated BTN1A1 over non-glycosylated BTN1A1. In some embodiments, the antigen binding fragment preferentially binds a BTN1A1 dimer (e.g., a glycosylated BTN1A1 dimer) over a BTN1A1 monomer (e.g., a glycosylated BTN1A1 monomer). In some embodiments, the antigen binding fragments immunospecifically mask BTN1A1 glycosylation at positions N55, N215, N449, or any combination thereof. In some embodiments, the molecule used for treating ovarian cancer includes STC703, STC810, STC820, STC1011, STC1012, STC1029, STC2602, STC2714, STC2739, STC2778, or STC2781. In some embodiments, the methods further include administering an anti-PD1 therapy or an anti-PD-L1 therapy.

In some embodiments, provided herein are methods to treat a cancer in a subject by administering the molecule described herein having an antigen binding fragment that immunospecifically binds to BTN1A1, glycosylated BTN1A1, or a BTN1A1 dimer (e.g., a glycosylated BTN1A1 dimer), whereby the cancer can be liver cancer. The molecules used for treating liver cancer can be any molecules described herein having an antigen binding fragment that immunospecifically binds to BTN1A1, glycosylated BTN1A1, or a BTN1A1 dimer (e.g., a glycosylated BTN1A1 dimer). In some embodiments, the antigen binding fragment preferentially binds glycosylated BTN1A1 over non-glycosylated BTN1A1. In some embodiments, the antigen binding fragment preferentially binds a BTN1A1 dimer (e.g., a glycosylated BTN1A1 dimer) over a BTN1A1 monomer (e.g., a glycosylated BTN1A1 monomer). In some embodiments, the antigen binding fragments immunospecifically mask BTN1A1 glycosylation at positions N55, N215, N449, or any combination thereof. In some embodiments, the molecules used for treating liver cancer includes STC703, STC810, STC820, STC1011, STC1012, STC1029, STC2602, STC2714, STC2739, STC2778, or STC2781. In some embodiments, the methods further include administering an anti-PD1 therapy or an anti-PD-L1 therapy.

In some embodiments, provided herein are methods to treat a cancer in a subject by administering the molecule described herein having an antigen binding fragment that immunospecifically binds to BTN1A1, glycosylated BTN1A1, or a BTN1A1 dimer (e.g., a glycosylated BTN1A1 dimer), whereby the cancer can be head & neck cancer. The molecules used for treating head & neck cancer can be any molecules described herein having an antigen binding fragment that immunospecifically binds to BTN1A1, glycosylated BTN1A1, or a BTN1A1 dimer (e.g., a glycosylated BTN1A1 dimer). In some embodiments, the antigen binding fragment preferentially binds glycosylated BTN1A1 over non-glycosylated BTN1A1. In some embodiments, the antigen binding fragment preferentially binds a BTN1A1 dimer (e.g., a glycosylated BTN1A1 dimer) over a BTN1A1 monomer (e.g., a glycosylated BTN1A1 monomer). In some embodiments, the antigen binding fragments immunospecifically mask BTN1A1 glycosylation at positions N55, N215, N449, or any combination thereof. In some embodiments, the molecule used for treating head & neck cancer includes STC703, STC810, STC820, STC1011, STC1012, STC1029, STC2602, STC2714, STC2739, STC2778, or STC2781. In some embodiments, the methods further include administering an anti-PD1 therapy or an anti-PD-L1 therapy.

In some embodiments, provided herein are methods to treat a cancer in a subject by administering the molecule described herein having an antigen binding fragment that immunospecifically binds to BTN1A1, glycosylated BTN1A1, or a BTN1A1 dimer (e.g., a glycosylated BTN1A1 dimer), whereby the cancer can be breast cancer. The molecules used for treating breast cancer can be any molecules described herein having an antigen binding fragment that immunospecifically binds to BTN1A1, glycosylated BTN1A1, or a BTN1A1 dimer (e.g., a glycosylated BTN1A1 dimer). In some embodiments, the antigen binding fragment preferentially binds glycosylated BTN1A1 over non-glycosylated BTN1A1. In some embodiments, the antigen binding fragment preferentially binds a BTN1A1 dimer (e.g., a glycosylated BTN1A1 dimer) over a BTN1A1 monomer (e.g., a glycosylated BTN1A1 monomer). In some embodiments, the antigen binding fragments immunospecifically mask BTN1A1 glycosylation at positions N55, N215, N449, or any combination thereof. In some embodiments, the molecule used for treating breast cancer includes STC703, STC810, STC820, STC1011, STC1012, STC1029, STC2602, STC2714, STC2739, STC2778, or STC2781. In some embodiments, the methods further include administering an anti-PD1 therapy or an anti-PD-L1 therapy.

In some embodiments, provided herein are methods to treat a cancer in a subject by administering the molecule described herein having an antigen binding fragment that immunospecifically binds to BTN1A1, glycosylated BTN1A1, or a BTN1A1 dimer (e.g., a glycosylated BTN1A1 dimer), whereby the cancer can be stomach cancer. The molecules used for treating stomach cancer can be any molecules described herein having an antigen binding fragment that immunospecifically binds to BTN1A1, glycosylated BTN1A1, or a BTN1A1 dimer (e.g., a glycosylated BTN1A1 dimer). In some embodiments, the antigen binding fragment preferentially binds glycosylated BTN1A1 over non-glycosylated BTN1A1. In some embodiments, the antigen binding fragment preferentially binds a BTN1A1 dimer (e.g., a glycosylated BTN1A1 dimer) over a BTN1A1 monomer (e.g., a glycosylated BTN1A1 monomer). In some embodiments, the antigen binding fragments immunospecifically mask BTN1A1 glycosylation at positions N55, N215, N449, or any combination thereof. In some embodiments, the molecules used for treating stomach cancer includes STC703, STC810, STC820, STC1011, STC1012, STC1029, STC2602, STC2714, STC2739, STC2778, or STC2781. In some embodiments, the methods further include administering an anti-PD1 therapy or an anti-PD-L1 therapy.

The molecules used for treating cancer can be any molecules described herein having an antigen binding fragment that immunospecifically binds to BTN1A1, glycosylated BTN1A1, or a BTN1A1 dimer (e.g., a glycosylated BTN1A1 dimer). In some embodiments, the antigen binding fragment preferentially binds glycosylated BTN1A1 over non-glycosylated BTN1A1. In some embodiments, the antigen binding fragment binds to glycosylated BTN1A1 with $K_D$ less than half of the $K_D$ exhibited relative to unglycosylated BTN1A1. In some embodiments, the antigen binding fragment binds to glycosylated BTN1A1 with $K_D$ at least 2 times less than the $K_D$ exhibited relative to unglycosylated BTN1A1. In some embodiments, the antigen binding fragment binds to glycosylated BTN1A1 with $K_D$ at least 5 times less than the $K_D$ exhibited relative to unglycosylated BTN1A1. In some embodiments, the antigen binding fragment binds to glycosylated BTN1A1 with $K_D$ at least 10 times less than the $K_D$ exhibited relative to unglycosylated BTN1A1. In some embodiments, the antigen binding fragment binds to glycosylated BTN1A1 with $K_D$ at least 15 times less than the $K_D$ exhibited relative to unglycosylated BTN1A1. In some embodiments, the antigen binding fragment binds to glycosylated BTN1A1 with $K_D$ at least 20 times less than the $K_D$ exhibited relative to unglycosylated BTN1A1. In some embodiments, the antigen binding fragment binds to glycosylated BTN1A1 with $K_D$ at least 30 times less than the $K_D$ exhibited relative to unglycosylated BTN1A1. In some embodiments, the antigen binding fragment binds to glycosylated BTN1A1 with $K_D$ at least 40 times less than the $K_D$ exhibited relative to unglycosylated BTN1A1. In some embodiments, the antigen binding fragment binds to glycosylated BTN1A1 with $K_D$ at least 50 times less than the $K_D$ exhibited relative to unglycosylated BTN1A1. In some embodiments, the antigen binding fragment binds to glycosylated BTN1A1 with an MFI that is at least twice as high as the MFI as exhibited relative to unglycosylated BTN1A1. In some embodiments, the antigen binding fragment binds to glycosylated BTN1A1 with an MFI that is at least five times as high as the MFI as exhibited relative to unglycosylated BTN1A1. In some embodiments, the antigen binding fragment binds to glycosylated BTN1A1 with an MFI that is at least 10 times as high as the MFI as exhibited relative to unglycosylated BTN1A1. In some embodiments, the antigen binding fragment binds to glycosylated BTN1A1 with an MFI that is at least 15 times as high as the MFI as exhibited relative to unglycosylated BTN1A1. In some embodiments, the antigen binding fragment binds to glycosylated BTN1A1 with an MFI that is at least 20 times as high as the MFI as exhibited relative to unglycosylated BTN1A1. In some embodiments, the antigen binding fragment binds to glycosylated BTN1A1 with an MFI that is at least 30 times as high as the MFI as exhibited relative to unglycosylated BTN1A1. In some embodiments, the antigen binding fragment binds to glycosylated BTN1A1 with an MFI that is at least 40 times as high as the MFI as exhibited relative to unglycosylated BTN1A1. In some embodiments, the antigen binding fragment binds to glycosylated BTN1A1 with an MFI that is at least 50 times as high as the MFI as exhibited relative to unglycosylated BTN1A1. In some embodiments, the antigen binding fragment preferentially binds a BTN1A1 dimer (e.g., a glycosylated BTN1A1 dimer) over a BTN1A1 monomer (e.g., a glycosylated BTN1A1 monomer). In some embodiments, the antigen binding fragment binds to a BTN1A1 dimer (e.g., a glycosylated BTN1A1 dimer) with a $K_D$ less than half of the Kd exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with a $K_D$ at least 2 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with a $K_D$ at least 5 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with a $K_D$ at least 10 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with a $K_D$ at least 15 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with a $K_D$ at least 20 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with a $K_D$ at least 30 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with a $K_D$ at least 40 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with a $K_D$ at least 50 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least twice as high as the MFI as exhibited relative to a BTN1A1 dimer (e.g., a glycosylated BTN1A1 dimer). In some embodiments, the antigen binding fragment binds to a BTN1A1 dimer (e.g., a glycosylated BTN1A1 dimer) with an MFI that is at least five times as high as the MFI as exhibited relative to a BTN1A1 monomer (e.g. a glycosylated BTN1A1 monomer). In some embodiments, the antigen binding fragment binds to a BTN1A1 dimer (e.g., a glycosylated BTN1A1 dimer) with an MFI that is at least 10 times as high as the MFI as exhibited relative to a BTN1A1 monomer (e.g. a glycosylated BTN1A1 monomer). In some embodiments, the antigen binding fragment binds to a BTN1A1 dimer (e.g., a glycosylated BTN1A1 dimer) with an MFI that is at least 15 times as high as the MFI as exhibited relative to a BTN1A1 monomer (e.g. a glycosylated BTN1A1 monomer). In some embodiments, the antigen binding fragment binds to a BTN1A1 dimer (e.g., a glycosylated BTN1A1 dimer) with an MFI that is at least 20 times as high as the MFI as exhibited relative to a BTN1A1 monomer (e.g. a glycosylated BTN1A1 monomer). In some embodiments, the antigen binding fragment binds to a BTN1A1 dimer (e.g., a glycosylated BTN1A1 dimer) with an MFI that is at least 30 times as high as the MFI as exhibited relative to a BTN1A1 monomer (e.g. a glycosylated BTN1A1 monomer). In some embodiments, the antigen binding fragment binds to a BTN1A1 dimer (e.g., a glycosylated BTN1A1 dimer) with an MFI that is at least 40 times as high as the MFI as exhibited relative to a BTN1A1 monomer (e.g. a glycosylated BTN1A1 monomer). In some embodiments, the antigen binding fragment binds to a BTN1A1 dimer (e.g., a glycosylated BTN1A1 dimer) with an MFI that is at least 50 times as high as the MFI as exhibited relative to a BTN1A1 monomer (e.g. a glycosylated BTN1A1 monomer).

In some embodiments, the antigen binding fragments immunospecifically mask BTN1A1 glycosylation at positions N55, N215, N449, or any combination thereof.

In some embodiments, the molecule useful for cancer treatment is STC703, STC810, STC820, STC1011, STC1012, STC1029, STC2602, STC2714, STC2739, STC2778, or STC2781.

In some embodiments, the methods further include administering an anti-PD1 therapy or an anti-PD-L1 therapy.

5.4.2. Methods of Administration

Provided herein are also methods of using the anti-BTN1A1 antibodies or other molecules having an antigen binding fragment that immunospecifically binds to BTN1A1, glycosylated BTN1A1, or a BTN1A1 dimer (e.g., a glycosylated BTN1A1 dimer) as an antitumor agent by administering a therapeutically effective amount of the antibodies or molecules provided herein to a patient in need thereof. In some embodiments, the patient is a cancer patient.

Various delivery systems are also known and can be used to administer the anti-BTN1A1 antibodies or other molecules having an antigen binding fragment that immunospecifically binds to BTN1A1, glycosylated BTN1A1, or a BTN1A1 dimer (e.g., a glycosylated BTN1A1 dimer), or related pharmaceutical compositions, such as encapsulation in liposomes, microparticles, microcapsules, recombinant cells capable of expressing the antibody or fusion protein, receptor-mediated endocytosis (see, e.g., Wu and Wu, 1987, 1 *Biol. Chem.* 262:4429-4432), construction of a nucleic acid as part of a retroviral or other vector, etc.

The methods of administration as provided herein include, but are not limited to, injection, as by parenteral administration (e.g., intradermal, intramuscular, intraperitoneal, intravenous and subcutaneous), epidural, and mucosal (e.g., intranasal and oral routes). In some embodiments, the antibodies, other molecules, or pharmaceutical compositions provided herein are administered intramuscularly, intravenously, subcutaneously, intravenously, intraperitoneally, orally, intramuscularly, subcutaneously, intracavity, transdermally, or dermally. The compositions can be administered by any convenient route, for example, by infusion or bolus injection, by absorption through epithelial or mucocutaneous linings (e.g., oral mucosa, rectal and intestinal mucosa, etc.) and can be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,20; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903; all of which are hereby incorporated by reference in their entireties. In some embodiments, the antibodies, other molecules, or pharmaceutical compositions provided herein are administered locally to the area in need of treatment, which can be achieved by, for example, local infusion, by injection, or by means of an implant, said implant being of a porous, non-porous, or gelatinous material, including membranes, such as sialastic membranes, or fibers. In some embodiments, when administering antibodies or other molecules as described herein, care is taken to use materials to which the antibodies or other molecules do not absorb.

In some embodiments, the humanized or chimeric antibodies provided herein are formulated in liposomes for targeted delivery. Liposomes are vesicles comprised of concentrically ordered phopsholipid bilayers which encapsulate an aqueous phase. Liposomes typically have various types of lipids, phospholipids, and/or surfactants. The components of liposomes are arranged in a bilayer configuration, similar to the lipid arrangement of biological membranes. Liposomes can be useful delivery vehicles due, in part, to their biocompatibility, low immunogenicity, and low toxicity. Methods for preparation of liposomes are known in the art and are provided herein, see, e.g., Epstein et al., 1985, *Proc. Natl. Acad. Sci. USA,* 82: 3688; Hwang et al., 1980 *Proc. Natl. Acad. Sci. USA,* 77: 4030-4; U.S. Pat. Nos. 4,485,045 and 4,544,545; all of which are hereby incorporated by reference in their entireties.

Provided herein are also methods of preparing liposomes with a prolonged serum half-life, i.e., enhanced circulation time, such as those disclosed in U.S. Pat. No. 5,013,556. In some embodiments, liposomes used in the methods provided herein are not rapidly cleared from circulation, i.e., are not taken up into the mononuclear phagocyte system (MPS). Provided herein are also sterically stabilized liposomes which are prepared using common methods known to one skilled in the art. Sterically stabilized liposomes can contain lipid components with bulky and highly flexible hydrophilic moieties, which reduces the unwanted reaction of liposomes with serum proteins, reduces oposonization with serum components and reduces recognition by MPS. Sterically stabilized liposomes can be prepared using polyethylene glycol. For preparation of liposomes and sterically stabilized liposome, see, e.g., Bendas et al., 2001 *BioDrugs,* 15(4): 215-224; Allen et al., 1987 *FEBS Lett.* 223: 42-6; Klibanov et al., 1990 *FEBS Lett.,* 268: 235-7; Blum et al., 1990, *Biochim. Biophys. Acta.,* 1029: 91-7; Torchilin et al., 1996, *J. Liposome Res.* 6: 99-116; Litzinger et al., 1994, *Biochim. Biophys. Acta,* 1190: 99-107; Maruyama et al., 1991, *Chem. Pharm. Bull.,* 39: 1620-2; Klibanov et al., 1991, *Biochim Biophys Acta,* 1062; 142-8; Allen et al., 1994, *Adv. Drug Deliv. Rev,* 13: 285-309, which are hereby incorporated by reference in their entireties.

Provided herein are also liposomes that are adapted for specific organ targeting, see, e.g., U.S. Pat. No. 4,544,545, or specific cell targeting, see, e.g., U.S. Patent Application Publication No. 2005/0074403, which are hereby incorporated by reference in their entireties. Particularly useful liposomes for use in the compositions and methods provided herein can be generated by reverse phase evaporation method with a lipid composition including phosphatidylcholine, cholesterol, and PEG derivatized phosphatidylethanolamine (PEG-PE). Liposomes can be extruded through filters of defined pore size to yield liposomes with the desired diameter. In some embodiments, a molecule having an antigen binding fragment, e.g., F(ab'), can be conjugated to the liposomes using previously described methods, see, e.g., Martin et al., 1982, *J. Biol. Chem.* 257: 286-288, which is hereby incorporated by reference in its entirety.

The humanized or chimeric antibodies as described herein can also be formulated as immunoliposomes. Immunoliposomes refer to a liposomal composition, whereby an antibody or a fragment thereof is linked, covalently or non-covalently to the liposomal surface. The chemistry of linking an antibody to the liposomal surface is known in the art, see, e.g., U.S. Pat. No. 6,787,153; Allen et al., 1995, *Stealth Liposomes, Boca Rotan*: CRC Press, 233-44; Hansen et al., 1995, *Biochim. Biophys. Acta,* 1239: 133-144, which are hereby incorporated by reference in their entireties. In some embodiments, immunoliposomes for use in the methods and compositions provided herein are further sterically stabilized. In some embodiments, the humanized antibodies as described herein are linked covalently or non-covalently to a hydrophobic anchor, which is stably rooted in the lipid bilayer of the liposome. Examples of hydrophobic anchors include, but are not limited to, phospholipids, e.g., phosoatidylethanolamine (PE), phospahtidylinositol (PI). To achieve a covalent linkage between an antibody and a hydrophobic anchor, any of the known biochemical strategies in the art can be used, see, e.g., J. Thomas August ed., 1997, *Gene Therapy: Advances in Pharmacology*, Volume 40, Academic Press, San Diego, Calif., p. 399-435, which are hereby incorporated by reference in their entireties. For example, a functional group on an antibody molecule can react with an active group on a liposome associated hydrophobic anchor, e.g., an amino group of a lysine side chain on an antibody may be coupled to liposome associated N-glutaryl-phosphatidylethanolamine activated with water-soluble carbodiimide; or a thiol group of a reduced antibody can be coupled to liposomes via thiol reactive anchors, such as pyridylthiopropionylphosphatidylethanolamine. See, e.g., Dietrich et al., 1996, *Biochemistry,* 35: 1100-1105; Loughrey et al., 1987, *Biochim. Biophys. Acta,* 901: 157-160; Martin et al., 1982, *J. Biol. Chem.* 257: 286-288; Martin et al., 1981, *Biochemistry,* 20: 4429-38, which are hereby incorporated by reference in their entireties. The immunoliposomal formulations having the anti-BTN1A1 antibodies or other molecules having an antigen binding fragment that immunospecifically binds to BTN1A1 or glycosylated BTN1A1 can be particularly effective as therapeutic agents, since they deliver the active ingredient to the cytoplasm of the target cell, i.e., the cell including the receptor to which the antibody binds. In some embodiments, the immunoliposomes can have an increased half-life in blood, specifically target cells, and can be internalized into the cytoplasm of the target cells thereby avoiding loss of the therapeutic agent or degradation by the endolysosomal pathway.

The immunoliposomal compositions provided herein can have one or more vesicle forming lipids, an antibody or other molecule of the invention or a fragment or derivative thereof, and, optionally, a hydrophilic polymer. A vesicle forming lipid can be a lipid with two hydrocarbon chains, such as acyl chains and a polar head group. Examples of vesicle forming lipids include phospholipids, e.g., phosphatidylcholine, phosphatidylethanolamine, phosphatidic acid, phosphatidylinositol, sphingomyelin, and glycolipids, e.g., cerebrosides, gangliosides. Additional lipids useful in the formulations provided herein are known to one skilled in the art and encompassed within the description. In some embodiments, the immunoliposomal compositions further include a hydrophilic polymer, e.g., polyethylene glycol, and ganglioside GM1, which increases the serum half-life of the liposome. Methods of conjugating hydrophilic polymers to liposomes are well known in the art and encompassed within the description. Additional exemplary immunoliposomes and methods of preparing them can be find in, e.g., U.S. Patent Application Publication No. 2003/0044407; PCT International Publication No. WO 97/38731, Vingerhoeads et al., 1994, *Immunomethods,* 4: 259-72; Maruyama, 2000, *Biol. Pharm. Bull.* 23(7): 791-799; Abra et al., 2002, *Journal of Liposome Research,* 12(1&2): 1-3; Park, 2002, *Bioscience Reports,* 22(2): 267-281; Bendas et al., 2001 *BioDrugs,* 14(4): 215-224, J. Thomas August ed., 1997, *Gene Therapy: Advances in Pharmacology*, Volume 40, Academic Press, San Diego, Calif., p. 399-435; all of which are hereby incorporated by reference in their entireties.

Provided herein are also methods of treating a cancer patient by administering a unit dose to the patient the anti-BTN1A1 antibodies or other molecules having an antigen binding fragment that immunospecifically binds to BTN1A, specifically glycosylated BTN1A1, or a BTN1A1 dimer (e.g., a glycosylated BTN1A1 dimer). A unit dose refers to physically discrete units suitable as unitary dosage for the subject, each unit containing a predetermined quantity of active material calculated to produce the desired therapeutic effect in association with the required diluent, i.e., carrier, or vehicle.

The antibodies, molecules, or compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual subject. However, suitable dosage ranges for systemic application are disclosed herein and depend on the route of administration. Suitable regimes for initial and booster administration are also contemplated and typically include by an initial administration followed by repeated doses at one or more hour intervals by a subsequent injection or other administration. Exemplary multiple administrations are described herein and are useful to maintain continuously high serum and tissue levels of polypeptide or antibody. Alternatively, continuous intravenous infusion sufficient to maintain concentrations in the blood in the ranges specified for in vivo therapies are contemplated.

A therapeutically effective amount is a predetermined amount calculated to achieve the desired effect. Generally, the dosage will vary with age of, condition of, sex of, and extent of the disease in the patient and can be determined by one of skill in the art. The dosage can be adjusted by the individual physician in the event of any complication.

In some embodiments, the antibodies, molecules, or pharmaceutical compositions provided herein are packaged in a hermetically sealed container, such as an ampoule or sachette. In one embodiment, the antibodies, molecules, or pharmaceutical compositions provided herein are supplied as a dry sterilized lyophilized powder or water free concentrate in a hermetically sealed container and can be reconstituted, e.g., with water or saline to the appropriate concentration for administration to a subject. In some embodiments, the antibodies, molecules, or pharmaceutical compositions provided herein are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized antibodies, molecules, or pharmaceutical compositions provided herein should be stored at between 2 and 8° C. in their original container and should be administered within 12 hours, preferably within 6 hours, within 5 hours, within 3 hours, or within 1 hour after being reconstituted. In an alternative embodiment, the antibodies, molecules, or pharmaceutical compositions provided herein are supplied in liquid form in a hermetically sealed container indicating the quantity and concentration of the antibodies, molecules, or pharmaceutical compositions. In some embodiments, the liquid form of the antibodies, molecules, or pharmaceutical compositions provided herein are supplied in a hermetically sealed container at least 1 mg/ml, more preferably at least 2.5 mg/ml, at least 5 mg/ml, at least 8 mg/ml, at least 10 mg/ml, at least 15 mg/ml, at least 25 mg/ml, at least 50 mg/ml, at least 100 mg/ml, at least 150 mg/ml, at least 200 mg/ml.

The precise dose to be employed in the formulation will also depend on the route of administration, and the seriousness of the condition, and should be decided according to the judgment of the practitioner and each patient's circumstances. Effective doses can be extrapolated from dose-response curves derived from in vitro or animal model test systems. For the anti-BTN1A1 antibodies or other molecules having an antigen binding fragment that immunospecifically binds to BTN1A1, glycosylated BTN1A1, or a BTN1A1 dimer (e.g., a glycosylated BTN1A1 dimer), the dosage administered to a patient is typically 0.01 mg/kg to 100 mg/kg of the patient's body weight. In some embodiments, the dosage administered to a patient is between 0.01 mg/kg and 20 mg/kg, 0.01 mg/kg and 10 mg/kg, 0.01 mg/kg and 5 mg/kg, 0.01 and 2 mg/kg, 0.01 and 1 mg/kg, 0.01 mg/kg and 0.75 mg/kg, 0.01 mg/kg and 0.5 mg/kg, 0.01 mg/kg to 0.25 mg/kg, 0.01 to 0.15 mg/kg, 0.01 to 0.10 mg/kg, 0.01 to 0.05 mg/kg, or 0.01 to 0.025 mg/kg of the patient's body weight. In particular, the dosage administered to a patient can be 0.2 mg/kg, 0.3 mg/kg, 1 mg/kg, 3 mg/kg, 6 mg/kg or 10 mg/kg. A dose as low as 0.01 mg/kg is predicted to show appreciable pharmacodynamic effects. Dose levels of 0.10-1 mg/kg are predicted to be most appropriate. Higher doses (e.g., 1-30 mg/kg) can also be expected to be active. Generally, human antibodies have a longer half-life within the human body than antibodies from other species due to the immune response to the foreign polypeptides. Thus, lower dosages of human antibodies and less frequent administration can be practiced. Further, the dosage and frequency of administration of antibodies or other molecules provided herein can be reduced by enhancing uptake and tissue penetration of the antibodies by modifications such as, for example, lipidation.

In yet another embodiment, the compositions can be delivered in a controlled release or sustained release system. Any technique known to one of skill in the art can be used to produce sustained release formulations having one or more antibodies, molecules, or pharmaceutical compositions provided herein. See, e.g., U.S. Pat. No. 4,526,938; PCT publication WO 91/05548; PCT publication WO 96/20698; Ning et al., *Radiotherapy & Oncology* 39:179-189 (1996), Song et al., *PDA Journal of Pharmaceutical Science & Technology* 50:372-397 (1995); Cleek et al., *Pro. Intl. Symp. Control. Rel. Bioact. Mater.* 24:853-854 (1997); and Lam et al., *Proc. Intl. Symp. Control Rel. Bioact. Mater.* 24:759-760(1997); all of which are hereby incorporated by reference in their entireties. In one embodiment, a pump can be used in a controlled release system (See Langer, supra; Sefton, 1987, *CRC Crit. Ref Biomed. Eng.* 14:20; Buchwald et al., 1980, *Surgery* 88:507; and Saudek et al., 1989, *N. Engl. J. Med.* 321:574). In another embodiment, polymeric materials can be used to achieve controlled release of antibodies (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J., Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 7 1:105); U.S. Pat. Nos. 5,679,377; 5,916,597; 5,912,015; 5,989,463; 5,128,326; PCT Publication No. WO 99/15154; and PCT Publication No. WO 99/20253); all of which are hereby incorporated by references in their entireties.

Examples of polymers that can be used in sustained release formulations include, but are not limited to, poly(-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in Medical Applications of Controlled Release, supra, vol. 2, pp. 115-138 (1984)). In another embodiment, polymeric compositions useful as controlled release implants are used according to Dunn et al. (see U.S. Pat. No. 5,945,155), which is hereby incorporated by references in its entirety. Based upon the therapeutic effect of the in situ controlled release of the bioactive material from the polymer system, the implantation can generally occur anywhere within the body of the patient in need of therapeutic treatment.

In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (see U.S. Pat. No. 5,888,533). Controlled release systems are also discussed in the review by Langer (1990, *Science* 249:1527-1533). Any technique known to one of skill in the art can be used to produce sustained release formulations including one or more therapeutic agents provided herein. See, e.g., U.S. Pat. No. 4,526,938; International Publication Nos. WO 91/05548 and WO 96/20698; Ning et al., 1996, *Radiotherapy & Oncology* 39:179-189; Song et al., 1995, *PDA Journal of Pharmaceutical Science & Technology* 50:372-397; Cleek et al., 1997, *Pro. Int'l. Symp. Control. Rel. Bioact. Mater.* 24:853-854; and Lam et al., 1997, *Proc. Int'l. Symp. Control Rel. Bioact. Mater.* 24:759-760; all of which are hereby incorporated by references in their entireties.

Provided herein are also embodiment whereby the composition has nucleic acids encoding antibodies or other molecules as provided herein, whereby the nucleic acid can be administered in vivo to promote expression of its encoded antibody or other molecule, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al., 1991, *Proc. Natl. Acad. Sci. USA* 88:1864-1868). Alternatively, a nucleic acid can be introduced intracellularly and incorporated within host cell DNA for expression by homologous recombination.

Treatment of a subject with a therapeutically effective amount of antibodies, other molecules or pharmaceutical composition provided herein can include a single treatment or a series of treatments. It is contemplated that the antibodies, molecules, or pharmaceutical compositions provided herein can be administered systemically or locally to treat disease, such as to inhibit tumor cell growth or to kill cancer cells in cancer patients with locally advanced or metastatic cancers. They can be administered intravenously, intrathecally, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g., cancer that the surgery failed to eliminate) does not survive. In some embodiments, they can be administered after the regression of primary cancer to prevent metastasis.

5.5 Combination Therapies

Also provided herein are compositions and methods that include administration of the anti-BTN1A1 antibodies (including anti-glycosylated BTN1A1 antibodies and anti-BTN1A1 dimer antibodies) or other molecules having an antigen binding fragment that immunospecifically binds to BTN1A1, glycosylated BTN1A1, or a BTN1A1 dimer (e.g., a glycosylated BTN1A1 dimer) to a subject in need thereof, in combination with a second therapy. In some embodiments, the subject is a cancer patient and the second therapy is an anti-cancer or anti-hyperproliferative therapy.

In some embodiments, the compositions and methods that include administration of the antibodies or other molecules provided herein, when used in combination with another anti-cancer or anti-hyperproliferative therapy, can enhance the therapeutic potency of the other anti-cancer or anti-hyperproliferative therapy. Accordingly, methods and compositions described herein can be provided in combination with a second therapy to achieve the desired effect, such as killing of a cancer cell, inhibition of cellular hyperproliferation, and/or inhibition of cancer metastasis.

In some embodiments, the second therapy has a direct cytotoxic effect, such as a chemotherapy, a targeted therapy, a cryotherapy, a hyperthermia therapy, a photodynamic therapy, a high intensity focused ultrasound (HIFU) therapy, a radiotherapy, or a surgical therapy. The targeted therapy can be a biological targeted therapy or a small molecule targeted therapy. In other embodiments, the second therapy does not have a direct cytotoxic effect. For example, the second therapy may be an agent that upregulates the immune system without having a direct cytotoxic effect.

The second therapy can be an anti-PD1 therapy or an anti-PD-L1 therapy.

Accordingly, in another aspect, provided herein is a method of treating cancer in a subject, including administering to the subject a therapeutically effective amount of a molecule including an antigen binding fragment that immunospecifically binds to BTN1A1 and a therapeutically effective amount of an anti-PD-1 therapy and/or an anti-PD-L1 therapy.

In some embodiments, the method includes administering an anti-PD-1 therapy. In some embodiments, the method includes administering an anti-PD-L1 therapy. In some embodiments, the method includes administering an anti-PD-1 therapy and an anti-PD-L1 therapy.

In some embodiments, the anti-PD-1 therapy or the anti-PD-L1 therapy includes an anti-PD-1 or anti-PD-L1 antibody or antibody fragment, or a soluble PD-1 or PD-L1 ligand, or Fc-fusion protein thereof.

In some embodiments, the anti-PD-1 therapy includes nivolumab (Opdivo), pembrolizumab (Keytruda), pidilizumab, AMP-514, AMP-224, or a combination thereof.

In some embodiments, the anti-PD-1 therapy includes an anti-PD-1 antibody provided in International Application No. PCT/US2016/64394.

In some embodiments, the anti-PD-L1 therapy includes YW243.55.S70, MPDL3280A, MEDI-4736, MSB-0010718C, MDX-1105 or a combination thereof.

In some embodiments, the anti-PD-L1 therapy includes an antibody provided in International Application No. PCT/US2016/024691, published as WO 2016/160792 A1, and International Application No. PCT/US2017/024027.

In some embodiments, the molecule including the antigen binding fragment that immunospecifically binds to BTN1A1 and the anti-PD-1 therapy and/or an anti-PD-L1 therapy are formulated together.

In some embodiments, the molecule including the antigen binding fragment that immunospecifically binds to BTN1A1 and the anti-PD-1 therapy and/or an anti-PD-L1 therapy are formulated separately.

In some embodiments, the molecule including the antigen binding fragment that immunospecifically binds to BTN1A1 and the anti-PD-1 therapy or an anti-PD-L1 therapy are administered independently at the same time or separately within time intervals, optionally followed by one or more cycles of repeat dosing.

In some embodiments, the treatment produces at least one therapeutic effect selected from a group consisting of a reduction in size of a tumor, a reduction in number of metastatic lesions over time, a complete response, a partial response, and a stable disease.

Provided herein are methods that include administration of the anti-BTN1A1 antibodies or other molecules having an antigen binding fragment that immunospecifically binds to BTN1A1, glycosylated BTN1A1, or a BTN1A1 dimer (e.g., a glycosylated BTN1A1 dimer) to a subject in need thereof, in combination with a second or additional therapy (e.g., an anti-PD-1 therapy or an anti-PD-L1 therapy). The antibodies, other molecules, or pharmaceutical compositions provided herein can be administered before, during, after, or in various combinations relative to the second anti-cancer therapy. The administrations can be in intervals ranging from concurrently to minutes to days to weeks. In some embodiments where the antibodies or other molecules described herein are provided to a patient separately from a second anti-cancer agent, one would generally ensure that a significant period of time did not expire between the time of each delivery, such that the two compounds would still be able to exert an advantageously combined effect on the patient. In such instances, it is contemplated that one can provide a patient with the antibodies or other molecules provided herein, and the second anti-cancer therapy within about 12 to 24 or 72 h of each other and, more particularly, within about 6-12 h of each other. In some situations the time period for treatment can be extended significantly where several days (2, 3, 4, 5, 6, or 7) to several weeks (1, 2, 3, 4, 5, 6, 7, or 8) lapse between respective administrations.

In some embodiments, a course of treatment will last 1-90 days or more (this such range includes intervening days). It is contemplated that one agent can be given on any day of day 1 to day 90 (this such range includes intervening days) or any combination thereof, and another agent is given on any day of day 1 to day 90 (this such range includes intervening days) or any combination thereof. Within a single day (24-hour period), the patient can be given one or multiple administrations of the agent(s). Moreover, after a course of treatment, it is contemplated that there is a period of time at which no anti-cancer treatment is administered. This time period can last 1-7 days, and/or 1-5 weeks, and/or 1-12 months or more (this such range includes intervening days), depending on the condition of the patient, such as their prognosis, strength, health, etc. The treatment cycles can be repeated as necessary.

Various combinations can be employed. Listed below are some examples with the treatment with the anti-BTN1A1 antibody or other molecules described herein as "A" and a second anti-cancer therapy (e.g., an anti-PD-1 therapy or an anti-PD-L1 therapy) as "B":

A/B/A B/A/B B/B/A A/A/B A/B/B B/A/A A/B/B/B B/A/B/B B/B/B/A B/B/A/B A/A/B/B A/B/A/B A/B/B/A B/B/A/A B/A/B/A B/A/A/B A/A/A/B B/A/A/A A/B/A/A A/A/B/A

Administration of any antibodies, molecules, or pharmaceutical compositions provided herein, in combination of a second therapy (e.g., an anti-PD-1 therapy or an anti-PD-L1 therapy) to a patient will follow general protocols for the administration of such second therapy, taking into account the toxicity, if any, of the second therapy. Therefore, in some embodiments there is a step of monitoring toxicity that is attributable to combination therapy.

Chemotherapy

A wide variety of chemotherapeutic agents can be used in accordance with the present embodiments as the second therapy. A chemotherapeutic can be a compound or composition that is administered in the treatment of cancer. These agents or drugs can be categorized by their mode of activity within a cell, for example, whether and at what stage they affect the cell cycle. Alternatively, an agent can be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammalI and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; antimetabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

Radiotherapy

Another conventional anticancer therapy that can be used in combination with the methods and compositions described herein is radiotherapy, or radiation therapy. Radiotherapy include using γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287; all of which are hereby incorporated by references in their entireties), and UV-irradiation. It is most likely that all of these factors affect a broad range of damage on DNA, on the precursors of DNA, on the replication and repair of DNA, and on the assembly and maintenance of chromosomes.

Tumor microenvironment is intrinsically inhibitory due to the presence of myeloid-derived suppressor cells and regulatory T cells that infiltrate the tumor and function to suppress immune responses. In addition, the expression of certain inhibitory molecules on T cells and antigen presenting cells (APCs) can limit effective immune responses. Radiation mediates anti-tumor effects through the induction of tumor cell apoptosis, senescence, autophagy, and in some situations, can stimulate more effective immune responses.

In some embodiments, the molecules or compositions provided herein are administered in combination with high-dose radiation (HDR) therapy. In some embodiments, HDR therapy is administered to a subject by placing a radioactive implant, such as a pellet, close to, or inside, a tumor in the subject's body (brachytherapy). In some embodiments, HDR therapy is administered in combination with external beam radiation.

Radiation can be a means to place tumor cells under a stressed condition so that the tumor cells can activate mechanisms to survive the stress. Molecules activated under such stressed conditions can be served as targets for therapies used in combination of radiation. BTN1A1 was identified as a potential target that overexpresses under such conditions.

The molecules as described herein that have an antigen binding fragment that immunospecifically binds BTN1A1, glycosylated BTN1A1, or a BTN1A1 dimer (e.g., a glycosylated BTN1A1 dimer) can stimulate local and systemic immune response. In some embodiments, a therapeutically effective amount of the antibodies, other molecules, or pharmaceutical compositions as described herein are administered before, at the same time with, or after a radiotherapy to achieve a synergistic effect.

In some embodiments, a therapeutically effective amount of the antibodies, other molecules, or pharmaceutical compositions described herein are administered that effectively sensitizes a tumor in a host to irradiation. Irradiation can be ionizing radiation and in particular gamma radiation. In some embodiments, the gamma radiation is emitted by linear accelerators or by radionuclides. The irradiation of the tumor by radionuclides can be external or internal.

In some embodiments, the administration of the antibodies, other molecules, or pharmaceutical compositions described herein commences up to one month, in particular up to 10 days or a week, before the irradiation of the tumor. Additionally, irradiation of the tumor is fractionated the administration of the antibodies, other molecules, or pharmaceutical compositions described herein is maintained in the interval between the first and the last irradiation session.

Irradiation can also be X-ray radiation, gamma ray radiation, or charged particle radiation (proton beam, carbon beam, helium beam) (or "radiation" in general). Dosage ranges for radiation range from daily doses of 50 to 600 roentgens for some interval periods of time (2 or more days to several weeks), to single doses of 800 to 6000 roentgens. Radiation can be administered once daily, twice daily, three times daily, or four times daily. Dosage ranges for radioisotopes vary widely, and depend on the half-life of the isotope, the strength and type of radiation emitted, and the uptake by the neoplastic cells.

Targeted Therapy

Targeted cancer therapies are drugs or other substances that block the growth and spread of cancer by interfering with specific molecules ("molecular targets") that are involved in the growth, progression, and spread of cancer. Targeted cancer therapies are also referred to as "molecularly targeted drugs," "molecularly targeted therapies," "precision medicines," or similar names. Differing from standard chemotherapy, targeted therapies act on specific molecular targets that are associated with cancer, whereas standard chemotherapies usually act on all rapidly dividing normal and cancerous cells.

Targeted therapies include both small molecules targeted therapies and biologic targeted therapies, such as monoclonal antibodies. Small-molecule compounds are typically developed for targets that are located inside the cell because such agents are able to enter cells relatively easily. Biologic targeted therapies such as monoclonal antibodies are commonly used for targets that are outside cells or on the cell surface.

A number of different targeted therapies have been approved for use in cancer treatment. These therapies include hormone therapies, signal transduction inhibitors, gene expression modulator, apoptosis inducer, angiogenesis inhibitor, immunotherapies, and toxin delivery molecules.

Hormone therapies slow or stop the growth of hormone-sensitive tumors, which require certain hormones to grow. Hormone therapies act by preventing the body from producing the hormones or by interfering with the action of the hormones. Hormone therapies have been approved for both breast cancer and prostate cancer.

Signal transduction inhibitors block the activities of molecules that participate in signal transduction, the process by which a cell responds to signals from its environment. During this process, once a cell has received a specific signal, the signal is relayed within the cell through a series of biochemical reactions that ultimately produce the appropriate response(s). In some cancers, the malignant cells are stimulated to divide continuously without being prompted to do so by external growth factors. Signal transduction inhibitors interfere with this inappropriate signaling.

Gene expression modulators modify the function of proteins that play a role in controlling gene expression. Apoptosis inducers cause cancer cells to undergo a process of controlled cell death called apoptosis. Apoptosis is one method the body uses to get rid of unneeded or abnormal cells, but cancer cells have strategies to avoid apoptosis. Apoptosis inducers can get around these strategies to cause the death of cancer cells.

Angiogenesis inhibitors block the growth of new blood vessels to tumors (a process called tumor angiogenesis). A blood supply is necessary for tumors to grow beyond a certain size because blood provides the oxygen and nutrients that tumors need for continued growth. Treatments that interfere with angiogenesis can block tumor growth. Some targeted therapies that inhibit angiogenesis interfere with the action of vascular endothelial growth factor (VEGF), a substance that stimulates new blood vessel formation. Other angiogenesis inhibitors target other molecules that stimulate new blood vessel growth.

Immunotherapies trigger the immune system to destroy cancer cells. Some immunotherapies are monoclonal antibodies that recognize specific molecules on the surface of cancer cells. Binding of the monoclonal antibody to the target molecule results in the immune destruction of cells that express that target molecule. Other monoclonal antibodies bind to certain immune cells to help these cells better kill cancer cells.

Monoclonal antibodies that deliver toxic molecules can cause the death of cancer cells specifically. Once the antibody has bound to its target cell, the toxic molecule that is linked to the antibody—such as a radioactive substance or a poisonous chemical—is taken up by the cell, ultimately killing that cell. The toxin will not affect cells that lack the target for the antibody—i.e., the vast majority of cells in the body.

Cancer vaccines and gene therapy are also considered targeted therapies because they interfere with the growth of specific cancer cells.

For illustration, provided below is a list of FDA approved targeted therapies that can be used in accordance with the present embodiments as the second therapy.

- Adenocarcinoma of the stomach or gastroesophageal junction: Trastuzumab (Herceptin®), ramucirumab (Cyramza®)
- Basal cell carcinoma: Vismodegib (Erivedge™), sonidegib (Odomzo®)
- Brain cancer: Bevacizumab (Avastin®), everolimus (Afinitor®)
- Breast cancer: Everolimus (Afinitor®), tamoxifen, toremifene (Fareston®), Trastuzumab (Herceptin®), fulvestrant (Faslodex®), anastrozole (Arimidex®), exemestane (Aromasin®), lapatinib (Tykerb®), letrozole (Femara®), pertuzumab (Perjeta®), ado-trastuzumab emtansine (Kadcyla™), palbociclib (Ibrance®)

Cervical cancer: Bevacizumab (Avastin®)

Colorectal cancer: Cetuximab (Erbitux®), panitumumab (Vectibix®), bevacizumab (Avastin®), ziv-aflibercept (Zaltrap®), regorafenib (Stivarga®), ramucirumab (Cyramza®)

Dermatofibrosarcoma protuberans: Imatinib mesylate (Gleevec®)

Endocrine/neuroendocrine tumors: Lanreotide acetate (Somatuline® Depot)

Head and neck cancer: Cetuximab (Erbitux®)

Gastrointestinal stromal tumor: Imatinib mesylate (Gleevec®), sunitinib (Sutent®), regorafenib (Stivarga®)

Giant cell tumor of the bone: Denosumab (Xgeva®)

Kaposi sarcoma: Alitretinoin (Panretin®)

Kidney cancer: Bevacizumab (Avastin®), sorafenib (Nexavar®), sunitinib (Sutent®), pazopanib (Votrient®), temsirolimus (Torisel®), everolimus (Afinitor®), axitinib (Inlyta®)

Leukemia: Tretinoin (Vesanoid®), imatinib mesylate (Gleevec®), dasatinib (Sprycel®), nilotinib (Tasigna®), bosutinib (Bosulif®), rituximab (Rituxan®), alemtuzumab (Campath®), ofatumumab (Arzerra®), obinutuzumab (Gazyva™) ibrutinib (Imbruvica™), idelalisib (Zydelig®), blinatumomab (Blincyto™)

Liver cancer: Sorafenib (Nexavar®)

Lung cancer: Bevacizumab (Avastin®), crizotinib (Xalkori®), erlotinib (Tarceva®), gefitinib (Iressa®), afatinib dimaleate (Gilotrif®), ceritinib (LDK378/Zykadia), ramucirumab (Cyramza®), nivolumab (Opdivo®), pembrolizumab (Keytruda®)

Lymphoma: Ibritumomab tiuxetan (Zevalin®), denileukin diftitox (Ontak®), brentuximab vedotin (Adcetris®), rituximab (Rituxan®), vorinostat (Zolinza®), romidepsin (Istodax®), bexarotene (Targretin®), bortezomib (Velcade®), pralatrexate (Folotyn®), lenaliomide (Revlimid®), ibrutinib (Imbruvica™) siltuximab (Sylvant™), idelalisib (Zydelig®), belinostat (Beleodag™)

Melanoma: Ipilimumab (Yervoy®), vemurafenib (Zelboraf®), trametinib (Mekinist®), dabrafenib (Tafinlar®), pembrolizumab (Keytruda®), nivolumab (Opdivo®)

Multiple myeloma: Bortezomib (Velcade®), carfilzomib (Kyprolis®), lenaliomide (Revlimid®), pomalidomide (Pomalyst®), panobinostat (Farydak®)

Myelodysplastic/myeloproliferative disorders: Imatinib mesylate (Gleevec®), ruxolitinib phosphate (Jakafi™)

Neuroblastoma: Dinutuximab (Unituxin™)

Ovarian epithelial/fallopian tube/primary peritoneal cancers: Bevacizumab (Avastin®), olaparib (Lynparza™)

Pancreatic cancer: Erlotinib (Tarceva®), everolimus (Afinitor®), sunitinib (Sutent®)

Prostate cancer: Cabazitaxel (Jevtana®), enzalutamide (Xtandi®), abiraterone acetate (Zytiga®), radium 223 chloride (Xofigo®)

Soft tissue sarcoma: Pazopanib (Votrient®)

Systemic mastocytosis: Imatinib mesylate (Gleevec®)

Thyroid cancer: Cabozantinib (Cometriq™), vandetanib (Caprelsa®), sorafenib (Nexavar®), lenvatinib mesylate (Lenvima™)

Immunotherapy

The skilled artisan will understand that immunotherapies can be used in combination or in conjunction with methods of the embodiments. In the context of cancer treatment, immunotherapeutics generally rely on the use of immune effector cells and molecules to target and destroy cancer cells. Rituximab (RITUXAN®) is such an example. Checkpoint inhibitors, such as, for example, ipilumimab, are another such example. The immune effector can be, for example, an antibody specific for some marker on the surface of a tumor cell. The antibody alone can serve as an effector of therapy or it can recruit other cells to actually affect cell killing. The antibody also can be conjugated to a drug or toxin (e.g., chemotherapeutic, radionuclide, ricin A chain, cholera toxin, pertussis toxin) and serve merely as a targeting agent. Alternatively, the effector can be a lymphocyte carrying a surface molecule that interacts, either directly or indirectly, with a tumor cell target. Various effector cells include cytotoxic T cells and NK cells.

In some embodiments, the immunotherapy is an an anti-PD-1 therapy or an anti-PD-L1 therapy).

An anti-PD-1 therapy can include any inhibitor of PD-1. In some embodiments, an anti-PD-1 therapy can include an anti-PD-1 antibody or antigen binding fragment thereof, an inhibitory nucleic acid, or a soluble PD-1 ligand (e.g., a soluble PD-L1), or a fusion-protein thereof (e.g., an Fc-fusion protein). In some embodiments, the anti-PD-1 therapy includes nivolumab (Opdivo), pembrolizumab (Keytruda), pidilizumab, AMP-514, or AMP-224.

In some embodiments, the anti-PD-1 therapy includes Nivolumab (CAS Registry Number: 946414-94-4). Nivolumab is also known as MDX-1 106, MDX-1 106-04, ONO-4538, or BMS-936558. Nivolumab is a fully human IgG4 monoclonal antibody that specifically blocks PD-1. Nivolumab (clone 5C4) and other human monoclonal antibodies that specifically bind to PD-1 are disclosed in U.S. Pat. No. 8,008,449 and WO2006/121 168.

In some embodiments, the anti-PD-1 therapy includes Pembrolizumab. Pembrolizumab is also known as KEYTRUDA®, lambrolizumab, Merck 3745, MK-3475 or SCH-900475. Pembrolizumab is a humanized IgG4 monoclonal antibody that binds to PD-1. Pembrolizumab is disclosed, e.g., in Hamid, O. et al. (2013) New England Journal of Medicine 369 (2): 134-44, WO2009/1 14335, and U.S. Pat. No. 8,354,509.

In some embodiments, the anti-PD-1 therapy is Pidilizumab. Pidilizumab, also known as CT-011 (CureTech), is a humanized IgG1 monoclonal antibody that binds to PD-1. Pidilizumab and other humanized anti-PD-1 monoclonal antibodies are disclosed in WO2009/101611.

In some embodiments, the anti-PD-1 therapy includes an anti-PD-1 antibody provided in International Application No. PCT/US2016/64394.

Additional anti-PD 1 antibodies that can be useful as anti-PD1 therapies are disclosed in U.S. Pat. No. 8,609,089, US 2010028330, and/or US 201201 14649.

In some embodiments, the anti-PD-1 therapy includes the fusion protein AMP 514 (Amplimmune). AMP-224, also known as B7-DCIg is, e.g., disclosed in WO2010/027827 and WO201 1/066342. AMP-224 is a PD-L2 Fc fusion soluble receptor that blocks the interaction between PD1 and B7-H1.

In some embodiments, the anti-PD-1 therapy includes an immunoadhesin (e.g., an immunoadhesin including an extracellular or PD-1 binding portion of PD-L1 or PD-L2 fused to a constant region (e.g., an Fc region of an immunoglobulin sequence)). In some embodiments, the anti-PD-1 therapy includes the fusion protein AMP-224 (Fc-fusion of PD-L2).

An anti-PD-L1 therapy can include any inhibitor of PD-L1. In some embodiments, an anti-PD-1 therapy can include an anti-PD-L1 antibody or antigen binding fragment thereof, an inhibitory nucleic acid, or a soluble PD-L1 ligand (e.g., a soluble PD-1), or a fusion-protein thereof (e.g., an Fc-fusion protein). In some embodiments, the anti-PD-L1 therapy includes YW243.55.S70, MPDL3280A, MEDI-4736, MSB-0010718C, or MDX-1105.

In some embodiments, the anti-PD-L1 therapy includes MDX-1105. MDX-1105, is also known as BMS-936559. See, e.g., WO2007/005874.

In some embodiments, the PD-L1 therapy includes the antibody YW243.55.570, as described, e.g., in WO 2010/077634 (heavy and light chain variable region sequences shown in SEQ ID NOS: 20 and 21, respectively).

In some embodiments, the PD-L1 therapy includes MDPL3280A (Genentech/Roche). MDPL3280A is a human Fc optimized IgG1 monoclonal antibody that binds to PD-L1. MDPL3280A and other human monoclonal antibodies to PD-L1 are disclosed, e.g., in U.S. Pat. No. 7,943,743 and U.S. Publication No.: 20120039906.

In some embodiments, the anti-PD-L1 therapy includes the antibody MSB0010718C (Merck Serono). MSB0010718C is also known as A09-246-2.

In some embodiments, the anti-PD-L1 therapy includes MDPL3280A (Genentech/Roche), a human Fc optimized IgG1 monoclonal antibody that binds to PD-L1. MDPL3280A and other human monoclonal antibodies to PD-L1 are disclosed in U.S. Pat. No. 7,943,743 and U.S. Publication No.: 20120039906.

In some embodiments, the anti-PD-L1 therapy includes an antibody provided in International Application No. PCT/US2016/024691, published as WO 2016/160792 A1, and International Application No. PCT/US2017/024027.

In one aspect of immunotherapy, the tumor cell bear some marker that is amenable to targeting, i.e., is not present on the majority of other cells. Many tumor markers exist and any of these can be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, *Infect Immun.,* 66(11):5329-36 (1998); Christodoulides et al., *Microbiology,* 66(11):5329-36(1998)); cytokine therapy, e.g., interferons α, β, and γ, IL-1, GM-CSF, and TNF (Bukowski et al., *Clin Cancer Res.,* 4(10):2337-47 (1998); Davidson et al., *J Immunother.,* 21(5):389-98(1998); Hellstrand et al., *Acta Oncol.* 37(4):347-53(1998)); gene therapy, e.g., TNF, IL-1, IL-2, and p53 (Qin et al., *Proc Natl Acad Sci USA,* 95(24):14411-6(1998); Austin-Ward and Villaseca, *Rev Med Chil,* 126(7):838-45 (1998); U.S. Pat. Nos. 5,830,880 and 5,846,945); and monoclonal antibodies, e.g., anti-PD1, anti-PDL1, anti-CD20, anti-ganglioside GM2, and anti-p185 (Topalian et al., *The New England journal of medicine,* 366:2443-2454 (2012); Brahmer et al., *The New England journal of medicine* 366:2455-2465 (2012); Hollander, *Front Immunol* (2012): 3:3. doi: 10.3389/fimmu.2012.00003; Hanibuchi et al., *Int J Cancer,* 78(4):480-5(1998); U.S. Pat. No. 5,824,311); all of which are hereby incorporated by reference in their entireties. It is contemplated that one or more anti-cancer therapies can be employed with the therapies described herein that involve the use the molecules having an antigen binding fragment that immunospecifically binds to BTN1A1 or glycosylated BTN1A1.

Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment can be accomplished by perfusion, direct injection, or local application of the area with an additional anti-cancer therapy. Such treatment can be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments can be of varying dosages as well.

Additional Types of Therapies

Additional types of cancer therapies known in the art can be used in combination or in conjunction with methods and compositions provided herein, including but not limited to a cryotherapy, a hyperthermia therapy, a photodynamic therapy, and a high intensity focused ultrasound (HIFU) therapy.

Cryotherapy (also called cryosurgery) is the use of extreme cold produced by liquid nitrogen (or argon gas) to destroy abnormal tissue. Cryosurgery is used to treat external tumors, such as those on the skin. For external tumors, liquid nitrogen is applied directly to the cancer cells with a cotton swab or spraying device. Cryosurgery can also be used to treat tumors inside the body (internal tumors and tumors in the bone). For internal tumors, liquid nitrogen or argon gas is circulated through a hollow instrument called a cryoprobe, which is placed in contact with the tumor. The probes can be put into the tumor during surgery or through the skin (percutaneously). After cryosurgery, the frozen tissue thaws and is either naturally absorbed by the body (for internal tumors), or it dissolves and forms a scab (for external tumors).

A hyperthermia therapy (also called thermal therapy or thermotherapy) is a type of cancer treatment in which body tissue is exposed to high temperatures (up to 113° F.). There are several methods of hyperthermia, including local, regional, and whole-body hyperthermia.

In local hyperthermia, heat is applied to a small area, such as a tumor, using various techniques that deliver energy to heat the tumor. Different types of energy can be used to apply heat, including microwave, radiofrequency, and ultrasound. Depending on the tumor location, there are several approaches to local hyperthermia, including external approaches, intraluminal or endocavitary methods, and interstitial techniques.

In regional hyperthermia, various approaches can be used to heat large areas of tissue, such as a body cavity, organ, or limb, including deep tissue approaches, regional perfusion techniques, and continuous hyperthermic peritoneal perfusion (CHPP).

Whole-body hyperthermia can be used to treat metastatic cancer that has spread throughout the body, which can be accomplished by several techniques that raise the body temperature to 107-108° F., including the use of thermal chambers (similar to large incubators) or hot water blankets.

A photodynamic therapy (PDT) is a treatment that uses a drug, called a photosensitizer or photosensitizing agent, and a particular type of light. When photosensitizers are exposed to a specific wavelength of light, they produce a form of oxygen that kills nearby cells. In the first step of PDT for cancer treatment, a photosensitizing agent is injected into the bloodstream. The agent is absorbed by cells all over the body but stays in cancer cells longer than it does in normal cells. Approximately 24 to 72 hours after injection, when most of the agent has left normal cells but remains in cancer cells, the tumor is exposed to light. The photosensitizer in the tumor absorbs the light and produces an active form of oxygen that destroys nearby cancer cells.

The light used for PDT can come from a laser or other sources. Laser light can be directed through fiber optic cables (thin fibers that transmit light) to deliver light to areas inside the body. Other light sources include light-emitting diodes (LEDs), which can be used for surface tumors, such as skin cancer. Extracorporeal photopheresis (ECP) is a type of PDT in which a machine is used to collect the patient's blood cells, treat them outside the body with a photosensitizing agent, expose them to light, and then return them to the patient.

A high intensity focused ultrasound therapy (or HIFU) is a type of cancer treatment. Doctors give the HIFU treatment using a machine that gives off high frequency sound waves that deliver a strong beam to a specific part of a cancer and kill the cancer cells.

Other Agents

It is contemplated that other agents can be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions can increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, can be used in combination with certain aspects of the present embodiments to improve the treatment efficacy.

5.6 Companion Diagnostics

This disclosure is based, at least in part, on the recognition that the expression of BTN1A1 and PD-L1 is mutually exclusive in certain cancers. Accordingly, provided herein are methods using BTN1A1 and PD-L1 as biomarkers and companion diagnostics for cancer.

BTN1A1 is highly and specifically expressed in cancer cells. Provided herein are also methods for detecting expression of BTN1A1 in a sample from a subject using molecules described herein that have an antigen binding fragment that immunospecifically binds to BTN1A1. Accordingly, provided herein are also uses of the molecules described herein as a cancer diagnostic. In some embodiments, provided herein are methods to detect BTN1A1 in a sample from a subject by contacting the sample with molecules described herein to form a complex between the molecule and BTN1A1, and detecting the complex in the sample. In some embodiments, provided herein are methods to provide or aid cancer diagnosis of a subject, including contacting a sample from the subject with molecules described herein to form a complex between the molecule and BTN1A1, detecting the complex, and diagnosing the subject as likely having cancer if the complex is detected in the sample. In some embodiments, the methods include detecting the presence of glycosylated BTN1A1 in the sample using an molecules described herein having an antigen binding fragment that immunospecifically binds to glycosylated BTN1A1.

In some embodiments, the methods further include detecting the presence of PD-L1. Methods for detecting PD-L1 expression in a sample are known in the art, including, e.g., antibody-based detection methods (e.g., ELISA, FACS, immunocytochemistry) or nucleic acid-based detection methods (e.g., PCR, microarrays, DNA sequencing).

In some embodiments, the molecules have an antigen binding fragment that immunospecifically binds to glycosylated BTN1A1. In some embodiments, the molecules have an antigen binding fragment that immunospecifically binds to BTN1A1 glycosylated at positions N55, N215, and/or N449. In some embodiments, the antigen binding fragment immunospecifically binds to BTN1A1 glycosylated at position N55. In some embodiments, the antigen binding fragment immunospecifically binds to BTN1A1 glycosylated at position N215. In some embodiments, the antigen binding fragment immunospecifically binds to BTN1A1 glycosylated at position N449. In some embodiments, the antigen binding fragment immunospecifically binds to one or more glycosylation motifs. In some embodiments, the antigen binding fragment immunospecifically binds to BTN1A1 glycosylated at positions N55 and N215. In some embodiments, the antigen binding fragments immunospecifically binds to BTN1A1 glycosylated at positions N215 and N449. In some embodiments, the antigen binding fragments immunospecifically binds to BTN1A1 glycosylated at positions N55 and N449. In some embodiments, the antigen binding fragments immunospecifically binds to BTN1A1 glycosylated at positions N55, N215 and N449. In some embodiments, the molecules have an antigen binding fragment that immunospecifically binds to a BTN1A1 dimer (e.g., a glycosylated BTN1A1 dimer). In some embodiments, the BTN1A1 dimer is glycosylated at any one or more positions of N55, N215 and N449 or one or both BTN1A1 monomers in the BTN1A1 dimer. For example, the glycosylated BTN1A1 dimer can be glycosylated at any one, two, three, four, five, or six positions N55, N215 and N449 in the BTN1A1 dimer.

In some embodiments, the molecules are anti-BTN1A1 antibodies. In some embodiments, the molecules are anti-glycosylated BTN1A1 antibodies. In some embodiments, the molecules are anti-BTN1A1 dimer antibodies.

Provided herein are also methods for detecting expression of BTN1A1 in a sample from a subject using molecules described herein that have an antigen binding fragment that includes the VH or VL domain of the murine monoclonal antibody STC703, STC810, STC820, STC1011, STC1012, STC1029, STC2602, STC2714, STC2739, STC2778, or STC2781, as depicted in Tables 2a-12b. In some embodiments, the molecules can have an antigen binding fragment that includes both the VH and VL domain of the murine monoclonal antibody STC703, STC810, STC820, STC1011, STC1012, STC1029, STC2602, STC2714, STC2739, STC2778, or STC2781, as depicted in Tables 2a-12b. In some embodiments, the methods further include detecting expression of PD-L1.

Also provided herein are methods for detecting expression of BTN1A1 in a sample from a subject using molecules described herein that have an antigen binding fragment that includes one or more VH CDRs having the amino acid sequence of any one of the VH CDRs of the murine monoclonal antibody STC703, STC810, STC820, STC1011, STC1012, STC1029, STC2602, STC2714, STC2739, STC2778, or STC2781, as depicted in Tables 2a-12b. In some embodiments, the molecules can have antigen binding fragment that includes one or more VL CDRs having the amino acid sequence of any one of the VL CDRs of the murine monoclonal antibody STC703, STC810, STC820, STC1012, STC1011 STC1029, STC2602, STC2714, STC2739, STC2778, or STC2781, as depicted in Tables 2a-12b. In some embodiments, the molecules can have antigen binding fragments that includes at least one VH CDR and at least one VL CDR of the murine monoclonal antibody STC703, STC810, STC820, STC1011, STC1012, STC1029, STC2602, STC2714, STC2739, STC2778, or STC2781, as depicted in Tables 2a-12b. In some embodiments, the methods further include detecting expression of PD-L1.

Also provided herein are methods for detecting expression of BTN1A1 in a sample from a subject using molecules described herein that have an antigen binding fragment that competitively blocks (e.g., in a dose-dependent manner) a BTN1A1 epitope described herein. The BTN1A1 epitope can be an epitope of STC703, STC810, STC820, STC1011, STC1012, STC1029, STC2602, STC2714, STC2739, STC2778, or STC2781. In some embodiments, the methods further include detecting expression of PD-L1.

Also provided herein are methods for detecting expression of BTN1A1 in a sample from a subject using molecules described herein that have an antigen binding fragment that immunospecifically binds to an epitope of BTN1A1 as described herein. The BTN1A1 epitope can be an epitope of STC703, STC810, STC820, STC1011, STC1012, STC1029, STC2602, STC2714, STC2739, STC2778, or STC2781. In some embodiments, the methods further include detecting expression of PD-L1.

In some embodiments, detecting BTN1A1 in a sample includes measuring the expression level of BTN1A1 in the sample using molecules described herein. In some embodiments, detecting BTN1A1 further includes comparing the expression level of BTN1A1 in the sample from the subject to a reference level. In some embodiments, the methods include measuring the expression level of the BTN1A1 in a sample using the molecules described herein, comparing the expression level of the BTN1A1 in the sample with a reference level, and diagnosing the subject as likely having cancer, or as likely to be responsive to a molecule including an antigen binding fragment that immunospecifically binds to BTN1A1, if the expression level of BTN1A1 in the sample is higher than the reference level.

In some embodiments, detecting PD-L1 in a sample includes measuring the expression level of PD-L1 in the sample using molecules described herein. In some embodiments, detecting PD-L1 further includes comparing the expression level of PD-L1 in the sample from the subject to a reference level. In some embodiments, the methods include measuring the expression level of the PD-L1 in a sample using the molecules described herein, comparing the expression level of the PD-L1 in the sample with a reference level, and diagnosing the subject as likely to be responsive to a molecule including an antigen binding fragment that immunospecifically binds to BTN1A1 (e.g., glycosylated BTN1A1 or a BTN1A1 dimer, such as a glycosylated BTN1A1 dimer) if the expression level of PD-L1 in the sample is lower than the reference level.

In some embodiments, measuring the BTN1A1 level includes measuring the level of glycosylated BTN1A1 using molecules having an antigen binding fragment that immunospecifically binds to glycosylated BTN1A1, such as anti-glycosylated BTN1A1 antibodies. In some embodiments, measuring the level of glycosylated BTN1A1 in a sample further includes comparing the level of glycosylated BTN1A1 in the sample with a reference level, and diagnosing the subject as likely having cancer or as likely to be responsive to a molecule including an antigen binding fragment that immunospecifically binds to glycosylated-BTN1A1 if the level of glycosylated BTN1A1 in the sample is higher than the reference level.

In some embodiments, measuring the BTN1A1 level includes measuring the level of BTN1A1 dimers using molecules having an antigen binding fragment that immunospecifically binds to BTN1A1 dimers, such as anti-BTN1A1 dimer antibodies. In some embodiments, measuring the level of BTN1A1 dimers in a sample further includes comparing the level of glycosylated BTN1A1 in the sample with a reference level, and diagnosing the subject as likely having cancer or as likely to be responsive to a molecule including an antigen binding fragment that immunospecifically binds to a BTN1A1 dimer if the level of BTN1A1 dimers in the sample is higher than the reference level.

In some embodiments, the reference level can be the expression level of BTN1A1 or PD-L1 in a sample from a healthy individual. In some embodiments, the reference level can be the average or medium expression level of BTN1A1 or PD-L1 in samples from a population of healthy individuals. The reference level can also be a cutoff value determined by statistic analysis of the expression levels of BTN1A1 or PD-L1 from samples of a population. Statistic methods that can be used to determine such cutoff value are well known in the art. For example, Receiver Operator Characteristic (ROC) analysis can be utilized to determine the reference expression ratio. A review of the ROC analysis can be found in Soreide, *J Clin Pathol,* 10:1136 (2008), which is herby incorporated by reference in its entirety.

In some embodiments, the subject can be a healthy subject undergoing a routine medical checkup. In some embodiments, the healthy subject is at risk of having cancer, as determined by the presence of certain risk factors that are well known in the art. Such risk factors include, without limitation, a genetic predisposition, a personal disease history, a familial disease history, a lifestyle factor, an environmental factor, a diagnostic indicator, and the like. In some embodiments, the subject is asymptomatic. An asymptomatic subject further includes a cancer patient who display mild early diagnostic indicators of cancer, but is otherwise symptom or complaint free. In some embodiments, the subject has cancer.

In some embodiments, the subject is suspected of having cancer. In some embodiments, the subject has a genetic predisposition for developing cancer or a family history of cancer. In some embodiments, the subject is exposed to certain lifestyle factors promoting the development of cancer or the subject shows clinical disease manifestations of cancer. In some embodiments, the subject is a patient who is receiving a clinical workup to diagnose cancer or to assess the risk of developing cancer.

The cancer can be a metastatic cancer. The cancer can be a hematological cancer or a solid tumor. In some embodiments, the cancer is a hematological cancer selected from the group consisting of leukemia, lymphoma, and myeloma. In some embodiments, the cancer is a solid tumor selected from the group consisting of breast cancer, lung cancer, thymic cancer, thyroid cancer, head & neck cancer, prostate cancer, esophageal cancer, tracheal cancer, brain cancer, liver cancer, bladder cancer, kidney cancer, stomach cancer, pancreatic cancer, ovarian cancer, uterine cancer, cervical cancer, testicular cancer, colon cancer, rectal cancer or skin cancer, both melanomatous and non-melanomatous skin cancers. The cancer can also be any other type of cancer as described herein.

In some embodiments, the cancer is an anti-PD1 therapy or an anti-PD-L1 therapy resistant or refractory cancer. In some embodiments, the cancer is an anti-PD1 therapy resistant or refractory cancer. In some embodiments, the cancer is an anti-PD-L1 therapy resistant or refractory cancer. In some embodiments, the cancer is a breast cancer or a lung cancer. In some embodiments, the cancer is a mammary carcinoma. In some embodiments, the cancer is a Lewis lung carcinoma.

In some embodiments, the subject is treatment naïve. In some embodiments, the subject is undergoing treatments for cancer (e.g., chemotherapy). In some embodiments, the subject is in remission. In some embodiments, the remission is drug-induced. In some embodiments, the remission is drug-free.

In some embodiments, the methods of detecting BTN1A1, glycosylated BTN1A1, a BTN1A1 dimer, or PD-L1 include obtaining a sample from a subject. The subject can be a human. The subject can be a cancer patient. The sample can be a whole blood sample, a bone marrow sample, a partially purified blood sample, PBMCs, tissue biopsy, circulating tumor cells, circulating elements such as protein complexes or exosomes. In some embodiments, the sample is a blood sample. In some embodiments, the sample is tissue biopsy.

In some embodiments, the methods provided herein include detecting BTN1A1 or PD-L1 in a sample using a variety of immunohistochemistry (IHC) approaches or other immunoassay methods using molecules described herein, including anti-BTN1A1 antibodies, anti-glycosylated BTN1A1 antibodies, anti-BTN1A1 dimer antibodies, and anti-PD-L1 antibodies.

IHC staining of tissue sections has been shown to be a reliable method of assessing or detecting presence of proteins in a sample. Immunohistochemistry techniques utilize an antibody to probe and visualize cellular antigens in situ, generally by chromogenic or fluorescent methods. Thus, antibodies or antisera, preferably polyclonal antisera, and most preferably monoclonal antibodies specific for BTN1A1 or PD-L1 can be used. As discussed in greater detail below, the antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, including antisera, polyclonal antisera or a monoclonal antibody specific for the primary antibody. Immunohistochemistry protocols and kits are well known in the art and are commercially available. Automated systems for slide preparation and IHC processing are available commercially. The Ventana® BenchMark XT system is an example of such an automated system.

Standard immunological and immunoassay procedures can be found in *Basic and Clinical Immunology* (Stites & Terr eds., 7th ed. 1991). Moreover, the immunoassays can be performed in any of several configurations, which are reviewed extensively in *Enzyme Immunoassay* (Maggio, ed., 1980); and Harlow & Lane, supra. For a review of the general immunoassays, see also *Methods in Cell Biology: Antibodies in Cell Biology*, volume 37 (Asai, ed. 1993); *Basic and Clinical Immunology* (Stites & Ten, eds., 7th ed. 1991).

Commonly used assays to detect BTN1A1, glycosylated BTN1A1, BTN1A1 dimers or PD-L1 include an enzyme-linked immunosorbent assay (ELISA), a fluorescent immunosorbent assay (FIA), a chemiluminescent immunosorbent assay (CLIA), a radioimmunoassay (RIA), an enzyme multiplied immunoassay (EMI), a solid phase radioimmunoassay (SPROA), a fluorescence polarization (FP) assay, a fluorescence resonance energy transfer (FRET) assay, a time-resolved fluorescence resonance energy transfer (TR-FRET) assay and a surface plasmon resonance (SPR) assay.

In some embodiments, the ELISA is a sandwich ELISA. In some embodiments, the ELISA is a direct ELISA. In some embodiments, the ELISA includes the initial step of immobilizing the molecules described herein on a solid support (e.g., on the wall of a microtiter plate well or of a cuvette).

The assays to detect BTN1A1, glycosylated BTN1A1, BTN1A1 dimers or PD-L1 include noncompetitive assays, e.g., sandwich assays, and competitive assays. Typically, an assay such as an ELISA assay can be used. ELISA assays are known in the art, e.g., for assaying a wide variety of tissues and samples, including blood, plasma, serum or bone marrow.

A wide range of immunoassay techniques using such an assay format are available, see, e.g., U.S. Pat. Nos. 4,016,043, 4,424,279, and 4,018,653, which are hereby incorporated by reference in their entireties. These include both single-site and two-site or "sandwich" assays of the non-competitive types, as well as in the traditional competitive binding assays. These assays also include direct binding of a labeled antibody to a target antigen. Sandwich assays are commonly used assays. A number of variations of the sandwich assay technique exist. For example, in a typical forward assay, an unlabelled anti-BTN1A1 antibody is immobilized on a solid substrate, and the sample to be tested brought into contact with the bound antibody. After a suitable period of incubation, for a period of time sufficient to allow formation of an antibody-antigen complex, a second anti-BTN1A1 antibody, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative by simple observation of the visible signal, or can be quantitated by comparing with a control sample containing standard amounts of the antigen.

Variations on the forward assay include a simultaneous assay, in which both sample and labeled antibody are added simultaneously to the bound antibody. These techniques are well known to those skilled in the art, including any minor variations as will be readily apparent. In a typical forward sandwich assay, for example, a first anti-BTN1A1 or a first anti-PD-L1 antibody is either covalently or passively bound to a solid surface. The solid surface can be glass or a polymer, the most commonly used polymers being cellulose, polyacrylamide, nylon, polystyrene, polyvinyl chloride, or polypropylene. The solid supports can be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g., from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the antigen. The second anti-BTN1A1 antibody or second anti-PD-L1 antibody is linked to a reporter molecule which is used to indicate the binding of the second antibody to the molecular marker.

In some embodiments, flow cytometry (FACS) can be used to detect the level of BTN1A1, glycosylated BTN1A1 BTN1A1 dimers, or PD-L1 in a sample. The flow cytometer detects and reports the intensity of the fluorichrome-tagged antibody, which indicates the level of BTN1A1, glycosylated BTN1A1, BTN1A1 dimers, or PD-L1. Non-fluorescent cytoplasmic proteins can also be observed by staining permeablized cells. The stain can either be a fluorescence compound able to bind to certain molecules, or a fluorichrome-tagged antibody to bind the molecule of choice.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase, and alkaline phosphatase, and other are discussed herein. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which can be further quantitated, usually spectrophotometrically, to give an indication of the amount of BTN1A1, glycosylated BTN1A1, BTN1A1 dimer, or PD-L1 present in the sample. Alternately, fluorescent compounds, such as fluorescein and rhodamine, can be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of BTN1A1, glycosylated BTN1A1, BTN1A1 dimer, or PD-L1. Immunofluorescence and EIA techniques are both well established in the art and are discussed herein.

As such, provided herein are methods of cancer diagnosis include detecting the presence or expression levels of BTN1A1 in a sample from a subject using the molecules described therein having an antigen binding fragment that immunospecifically binds to BTN1A1. In some embodiments, the methods further include administering a cancer treatment to the subject diagnosed to have cancer. The cancer treatment can be any cancer therapy as described herein or otherwise known in the art. In some embodiments, the cancer treatment includes administering a therapeutically effective amount of anti-BTN1A1 antibodies to the subject. In some embodiments, the cancer treatment includes administering a therapeutically effective amount of an anti-PD1 therapy or an anti-PD-L1 therapy.

5.7 Evaluating Efficacy of Treatment

The expression level of BTN1A1 in a subject can correlate with cancer development. An increase in BTN1A1 level can indicate cancer progression, and a decrease in BTN1A1 level can indicate cancer regression. Accordingly, provided herein are also methods to evaluate the efficacy of a particular cancer treatment in a subject by monitoring the BTN1A1 level in samples of the subject over a course of the treatment using molecules described herein having an antigen binding fragment that immunospecifically binds to BTN1A1. In some embodiments, the methods include detecting the expression levels of BTN1A1. In some embodiments, the methods include detecting the levels of glycosylated BTN1A1. In some embodiments, the methods include detecting the levels of BTN1A1 dimers.

In some embodiments, the molecules have an antigen binding fragment that immunospecifically binds to glycosylated BTN1A1. In some embodiments, the molecules have an antigen binding fragment that immunospecifically binds to BTN1A1 glycosylated at positions N55, N215, and/or N449. In some embodiments, the antigen binding fragment immunospecifically binds to BTN1A1 glycosylated at position N55. In some embodiments, the antigen binding fragment immunospecifically binds to BTN1A1 glycosylated at position N215. In some embodiments, the antigen binding fragment immunospecifically binds to BTN1A1 glycosylated at position N449. In some embodiments, the antigen binding fragment immunospecifically binds to one or more glycosylation motifs. In some embodiments, the antigen binding fragment immunospecifically binds to BTN1A1 glycosylated at positions N55 and N215. In some embodiments, the molecules are anti-BTN1A1 antibodies. In some embodiments, the molecules are anti-glycosylated BTN1A1 antibodies. In some embodiments, the molecules have an antigen binding fragment that immunospecifically binds to a BTN1A1 dimer (e.g., a glycosylated BTN1A1 dimer). In some embodiments, the BTN1A1 dimer is glycosylated at any one or more positions of N55, N215 and N449 or one or both BTN1A1 monomers in the BTN1A1 dimer. For example, the glycosylated BTN1A1 dimer can be glycosylated at any one, two, three, four, five, or six positions N55, N215 and N449 in the BTN1A1 dimer.

In some embodiments, provided herein are also methods to evaluate the efficacy of a particular cancer treatment in a subject by monitoring the BTN1A1 level in samples of the subject over a course of the treatment using molecules described herein having an antigen binding fragment that immunospecifically binds to BTN1A1. In one embodiment, the molecules can have an antigen binding fragment that includes the VH or VL domain of the murine monoclonal antibody STC703, STC810, STC820, STC1012, STC1011, STC1029, STC2602, STC2714, STC2739, STC2778, or STC2781, as depicted in Tables 2a-12b. In one embodiment, the molecules can have an antigen binding fragment that includes both the VH and VL domain of the murine monoclonal antibody STC703, STC810, STC820, STC1011, STC1012, STC1029, STC2602, STC2714, STC2739, STC2778, or STC2781, as depicted in Tables 2a-12b. In another embodiment, the molecules can have an antigen binding fragment that includes one or more VH CDRs having the amino acid sequence of any one of the VH CDRs of the murine monoclonal antibody STC703, STC810, STC820, STC1011, STC1012, STC1029, STC2602, STC2714, STC2739, STC2778, or STC2781, as depicted in Tables 2a-12b. In another embodiment, the molecules can have antigen binding fragment that includes one or more VL CDRs having the amino acid sequence of any one of the VL CDRs of the murine monoclonal antibody STC703, STC810, STC820, STC1011, STC1012, STC1029, STC2602, STC2714, STC2739, STC2778, or STC2781, as depicted in Tables 2a-12b. In yet another embodiment, the molecules can have antigen binding fragment that includes at least one VH CDR and at least one VL CDR of the murine monoclonal antibody STC703, STC810, STC820, STC1011, STC1012, STC1029, STC2602, STC2714, STC2739, STC2778, or STC2781, as depicted in Tables 2a-12b.

In some embodiments, provided herein are also methods to evaluate the efficacy of a particular cancer treatment in a subject by monitoring the BTN1A1 level in samples of the subject over a course of the treatment using molecules described herein having an antigen binding fragment. In some embodiments, the molecules can have an antigen binding fragment that competitively blocks (e.g., in a dose-dependent manner) a BTN1A1 epitope described herein. The BTN1A1 epitope can be an epitope of STC703, STC810, STC820, STC1011, STC1012, STC1029, STC2602, STC2714, STC2739, STC2778, or STC2781. In some embodiments, the molecules can have an antigen binding fragment that immunospecifically binds to an epitope of BTN1A1 as described herein. The BTN1A1 epitope can be an epitope of STC703, STC810, STC820, STC1011, STC1012, STC1029, STC2602, STC2714, STC2739, STC2778, or STC2781.

In some embodiment, provided herein are methods of evaluating the efficacy of a particular cancer treatment in a patient, including: a) contacting two or more samples obtained from the patient at a first and at least one subsequent time point throughout the course of the treatment with a molecule described herein; b) measuring the levels of BTN1A1 in the two or more samples, and c) comparing the levels of BTN1A1 in the two or more samples, where a decreased level of BTN1A1 in a sample obtained at a subsequent time point relative to the level of BTN1A1 in the sample obtained at the first time point indicate that the cancer treatment is efficacious. The molecule can be an anti-BTN1A1 antibody. In some embodiments, the BTN1A1 level can be the level of glycosylated BTN1A1. In some embodiments, the BTN1A1 leve can be the level of a BTN1A1 dimer (e.g., a glycosylated BTN1A1 dimer). The molecule can also be an anti-glycosylated BTN1A1 antibody or an anti-BTN1A1 dimer antibody. In some embodiments, the molecule is STC703, STC810, STC820, STC1011, STC1012, STC1029, STC2602, STC2714, STC2739, STC2778, or STC2781.

In some embodiments, the methods include contacting two or more samples obtained from the patient at a first and at least one subsequent time point throughout the course of the treatment with a molecule described herein to form complexes between the molecule and BTN1A1 in the samples and measuring the levels of BTN1A1 in the two or more samples by measuring the complexes in the sample.

In some embodiments, the levels of BTN1A1, glycosylated BTN1A1, or BTN1A1 dimers from two or more samples are measured in one assay. In other embodiments, the levels the levels of BTN1A1, glycosylated BTN1A1, or BTN1A1 dimers from two or more samples are measured in multiple assays. In some embodiments, the level of BTN1A1, glycosylated BTN1A1, or BTN1A1 dimers is measured the same day as the sample is obtained from the subject. In some embodiments, the level of BTN1A1, glycosylated BTN1A1, or BTN1A1 dimers is measured without storage of the sample obtained from the subject.

The sample from a cancer patient can be a whole blood sample, a bone marrow sample, a partially purified blood sample, PBMCs, tissue biopsy, circulating tumor cells, circulating elements such as protein complexes or exosomes. In some embodiments, the sample is a blood sample. In some embodiments, the sample is tissue biopsy. As a person of ordinary skill in the art would understand, any methods of determining the expression level of a protein in a sample as described herein or otherwise known in the art can be used to determine the level of BTN1A1 in a sample from a cancer patient. In some embodiments, the methods include an immunoassay. The immunoassay can be an immunohistochemistry approach, including using molecules described herein to probe and visualize BTN1A1. The immunoassay can include FIA, CLIA, MA, EMI, SPROA, FP assay, FRET assay, TR-FRET assay or SPR assay.

The cancer treatment or cancer therapy can be any therapy described herein or otherwise known in the art, including but not limited to: a surgical therapy, chemotherapy, biological targeted therapy, small molecular targeted therapy, radiation therapy, cryotherapy, hormonal therapy, immunotherapy and cytokine therapy. In some embodiments, the cancer treatment include a FDA-approved cancer treatment, including an experimental cancer treatment in clinical development. In some embodiments, the cancer treatment includes treatments with a combination of two or more drugs, or two or more types of therapies.

In some embodiments, the cancer treatment includes administering an anti-BTN1A1 antibody to the cancer patient.

In some embodiments, one or more samples were obtained at the beginning of the course of the cancer treatment and one or more samples were obtained at later time points throughout the course of the treatment. In some embodiments, the subsequent time points are 2 or more, 3 or more, 4 or more, 5 or more, 6 or more, 7 or more, 8 or more, 9 or more, 10 or more, 15 or more, 20 or more, 25 or more or 30 or more time points.

In some embodiments, the method further includes adjusting the treatment if the treatment is determined to be not efficacious. Adjusting the treatment can include, for example, adjusting the dose of a drug treatment, increasing the frequency of a drug treatment, treating with a different drug or combination of drugs, or ending the treatment.

In some embodiments, the method further includes repeating a treatment if the treatment is determined to be efficacious.

In some embodiments, the level of BTN1A1, glycosylated BTN1A1, or BTN1A1 dimers in the samples obtained at the first time point is decreased by more than 10%, more than 20%, more than 30%, more than 40%, more than 50%, more than 60%, more than 70%, more than 80%, more than 90%, more than 95%, or more than 99% at a subsequent time point.

5.8 Patient Selection

Provided herein are uses of molecules having an antigen binding fragment that immunospecifically binds to BTN1A1 to predict responsiveness of a cancer patient to a cancer treatment by determining the presence or expression level of BTN1A1 in a sample from the patient. In some embodiments, the methods include detecting BTN1A1 in a sample from a cancer patient by contacting the sample with a molecule described herein to form a complex between the molecule and BTN1A1, and predicting that the subject will likely be responsive to a cancer treatment if the complex is detected. In some embodiments, the methods include detecting the presence of glycosylated BTN1A1 in the sample using molecules having an antigen-binding fragment that immunospecifically binds to glycosylated BTN1A1. In some embodiments, the methods include detecting the presence of a BTN1A1 dimer (e.g., a glycosylated BTN1A1 dimer) in the sample using molecules having an antigen binding fragment that immunospecifically binds to a BTN1A1 dimer (e.g., a glycosylated BTN1A1 dimer). In some embodiments, the method further includes determining the presence or expression level of PD-L1.

In some embodiments, the molecules have an antigen binding fragment that immunospecifically binds to glycosylated BTN1A1. In some embodiments, the molecules have an antigen binding fragment that immunospecifically binds to BTN1A1 glycosylated at positions N55, N215, and/or N449. In some embodiments, the antigen binding fragment immunospecifically binds to BTN1A1 glycosylated at position N55. In some embodiments, the antigen binding fragment immunospecifically binds to BTN1A1 glycosylated at position N215. In some embodiments, the antigen binding fragment immunospecifically binds to BTN1A1 glycosylated at position N449. In some embodiments, the antigen binding fragment immunospecifically binds to one or more glycosylation motifs. In some embodiments, the antigen binding fragment immunospecifically binds to BTN1A1 glycosylated at positions N55 and N215. In some embodiments, the antigen binding fragments immunospecifically binds to BTN1A1 glycosylated at positions N215 and N449. In some embodiments, the antigen binding fragments immunospecifically binds to BTN1A1 glycosylated at positions N55 and N449. In some embodiments, the antigen binding fragments immunospecifically binds to BTN1A1 glycosylated at positions N55, N215 and N449. In some embodiments, the molecules have an antigen binding fragment that immunospecifically binds to a BTN1A1 dimer (e.g., a glycosylated BTN1A1 dimer). In some embodiments, the BTN1A1 dimer is glycosylated at any one or more positions of N55, N215 and N449 or one or both BTN1A1 monomers in the BTN1A1 dimer. For example, the glycosylated BTN1A1 dimer can be glycosylated at any one, two, three, four, five, or six positions N55, N215 and N449 in the BTN1A1 dimer.

In some embodiments, the molecules are anti-BTN1A1 antibodies. In some embodiments, the molecules are anti-glycosylated BTN1A1 antibodies. In some embodiments, the molecules are anti-BTN1A1 dimer antibodies.

In one embodiment, the molecules provided herein that can be used for patient selection can have an antigen binding fragment that includes the VH or VL domain of the murine monoclonal antibody STC703, STC810, STC820, STC1011, STC1012, STC1029, STC2602, STC2714, STC2739, STC2778, or STC2781, as depicted in Tables 2a-12b. In one embodiment, the molecules can have an antigen binding fragment that includes both the VH and VL domain of the murine monoclonal antibody STC703, STC810, STC820, STC1011, STC11012, STC1029, STC2602, STC2714, STC2739, STC2778, or STC2781, as depicted in Tables 2a-12b. In another embodiment, the molecules can have an antigen binding fragment that includes one or more VH CDRs having the amino acid sequence of any one of the VH CDRs of the murine monoclonal antibody STC703, STC810, STC820, STC1011, STC1012, STC1029, STC2602, STC2714, STC2739, STC2778, or STC2781, as depicted in Tables 2a-12b. In another embodiment, the molecules can have antigen binding fragment that includes one or more VL CDRs having the amino acid sequence of any one of the VL CDRs of the murine monoclonal antibody STC703, STC810, STC820, STC1011, STC1012, STC1029, STC2602, STC2714, STC2739, STC2778, or STC2781, as depicted in Tables 2a-12b. In yet another embodiment, the molecules can have antigen binding fragment that includes at least one VH CDR and at least one VL CDR of the murine monoclonal antibody STC703, STC810, STC820, STC1011, STC1012, STC1029, STC2602, STC2714, STC2739, STC2778, or STC2781, as depicted in Tables 2a-12b.

In some embodiments, the molecules provided herein that can be used for patient selection can have an antigen binding fragment that competitively blocks (e.g., in a dose-dependent manner) a BTN1A1 epitope described herein. The BTN1A1 epitope can be an epitope of STC703, STC810, STC820, STC1011, STC1012, STC1029, STC2602, STC2714, STC2739, STC2778, or STC2781. In some embodiments, the molecules can have an antigen binding fragment that immunospecifically binds to an epitope of an BTN1A1 antibody described herein. The BTN1A1 epitope can be an epitope of STC703, STC810, STC820, STC1011, STC1012, STC1029, STC2602, STC2714, STC2739, STC2778, or STC2781.

In other embodiments, detecting BTN1A1, e.g., alone or in combination with PD-L1, in a sample includes measuring the expression level of BTN1A1, e.g., alone or in combination with PD-L1, in the sample using molecules described herein. In some embodiments, detecting BTN1A1, e.g., alone or in combination with PD-L1, further includes comparing the expression level of BTN1A1, e.g., alone or in combination with PD-L1, in the sample from the subject to a reference level. In some embodiments, the methods include measuring the expression level of the BTN1A1, e.g., alone or in combination with PD-L1, in a sample using an anti-BTN1A1 antibody, comparing the expression level of BTN1A1, e.g., alone or in combination with PD-L1, in the sample with a reference level, and predicting that the subject will likely be responsive to a cancer treatment if the expression level of BTN1A1 in the sample is higher than the BTN1A1 reference level, and, optionally, if the expression level of PD-L1 is lower than the PD-L1 reference level.

In some embodiments, measuring the BTN1A1 level, e.g., alone or in combination with PD-L1, includes measuring the level of glycosylated BTN1A1, e.g., alone or in combination with PD-L1, using an anti-glycosylated BTN1A1 antibody. In some embodiments, measuring the level of glycosylated BTN1A1 in a sample, e.g., alone or in combination with PD-L1, further includes comparing the level of glycosylated BTN1A1, e.g., alone or in combination with PD-L1, in the sample with a reference level, and predicting that the subject will likely be responsive to a cancer treatment if the level of glycosylated BTN1A1 in the sample is higher than the reference level for glycosylated BTN1A1, and, optionally, if the expression level of PD-L1 is lower than the reference level for PD-L1.

In some embodiments, measuring the BTN1A1 level, e.g., alone or in combination with PD-L1, includes measuring the level of BTN1A1 dimers, e.g., alone or in combination with PD-L1, using an anti-BTN1A1 dimer antibody (e.g., STC703, STC810, STC2714). In some embodiments, measuring the level of BTN1A1 dimers, e.g., alone or in combination with PD-L1, in a sample further includes comparing the level of BTN1A1 dimers, e.g., alone or in combination with PD-L1, in the sample with a reference level, and predicting that the subject will likely be responsive to a cancer treatment if the level of BTN1A1 dimers in the sample is higher than the reference level for BTN1A1 dimers, and, optionally, if the expression level of PD-L1 is lower than the reference level for PD-L1.

The sample from a cancer patient can be a whole blood sample, a bone marrow sample, a partially purified blood sample, PBMCs, tissue biopsy, circulating tumor cells, circulating elements such as protein complexes or exosomes. In some embodiments, the sample is a blood sample. Methods to detect the presence of BTN1A1 or PD-L1 or measure the expression level of BTN1A1 or PD-L1 are described herein or otherwise known in the art.

The cancer treatment or cancer therapy can be any therapy described herein or otherwise known in the art, including but not limited to: a surgical therapy, chemotherapy, biological targeted therapy, small molecular targeted therapy, radiation therapy, cryotherapy, hormonal therapy, immunotherapy and cytokine therapy. In some embodiments, the cancer treatment include a FDA-approved cancer treatment, including an experimental cancer treatment in clinical development. In some embodiments, the cancer treatment includes treatments with a combination of two or more drugs, or two or more types of therapies.

In some embodiments, the cancer treatment includes administering an anti-BTN1A1 antibody to the cancer patient. In some embodiments, the cancer treatment further includes administering an anti-PD-1 therapy or an anti-PD-L1 therapy.

5.9 Kit

Provided herein are kits containing a molecule described herein and one or more ancillary agents. In some embodiments, provided herein is a kit for preparing and/or administering a therapy provided herein. The kit can have one or more sealed vials containing any of the pharmaceutical compositions described herein. The kit can include, for example, a molecule having an antigen binding fragment that immunospecifically binds to BTN1A1, glycosylated BTN1A1, or a BTN1A1 dimer as well as reagents to prepare, formulate, and/or administer the molecule or perform one or more steps of the methods disclosed herein.

In some embodiments, the antigen binding fragment immunospecifically binds to glycosylated BTN1A1. In some embodiments, the antigen binding fragment immunospecifically binds to BTN1A1 glycosylated at positions N55, N215, and/or N449. In some embodiments, the antigen binding fragment immunospecifically binds to BTN1A1 glycosylated at position N55. In some embodiments, the antigen binding fragment immunospecifically binds to BTN1A1 glycosylated at position N215. In some embodiments, the antigen binding fragment immunospecifically binds to BTN1A1 glycosylated at position N449. In some embodiments, the antigen binding fragment immunospecifically binds to one or more glycosylation motifs. In some embodiments, the antigen binding fragment immunospecifically binds to BTN1A1 glycosylated at positions N55 and N215. In some embodiments, the antigen binding fragment immunospecifically binds to a BTN1A1 dimer (e.g., a glycosylated BTN1A1 dimer). In some embodiments, the BTN1A1 dimer is glycosylated at any one or more positions of N55, N215 and N449 or one or both BTN1A1 monomers in the BTN1A1 dimer. For example, the glycosylated BTN1A1 dimer can be glycosylated at any one, two, three, four, five, or six positions N55, N215 and N449 in the BTN1A1 dimer.

In some embodiments, the molecule is an anti-BTN1A1 antibody. In some embodiments, the anti-BTN1A1 antibody is anti-glycosylated BTN1A1 antibody. In some embodiments, the anti-BTN1A1 antibody is an anti-BTN1A1 dimer antibody (e.g., STC703, STC810, or STC2714). In some embodiments, the anti-BTN1A1 antibody is humanized antibody or human antibody.

In one embodiment, the kits provided herein can include molecules having an antigen binding fragment that includes the VH or VL domain of the murine monoclonal antibody STC703, STC810, STC820, STC1011, STC1012, STC1029, STC2602, STC2714, STC2739, STC2778, or STC2781, as depicted in Tables 2a-12b. In one embodiment, kits provided herein can include molecules having an antigen binding fragment that includes both the VH and VL domain of the murine monoclonal antibody STC703, STC810, STC820, STC1011, STC1012, STC1029, STC2602, STC2714, STC2739, STC2778, or STC2781, as depicted in Tables 2a-12b. In another embodiment, kits provided herein can include molecules having an antigen binding fragment that includes one or more VH CDRs having the amino acid sequence of any one of the VH CDRs of the murine monoclonal antibody STC703, STC810, STC820, STC1011, STC1012, STC1029, STC2602, STC2714, STC2739, STC2778, or STC2781, as depicted in Tables 2a-12b. In another embodiment, the molecules can have antigen binding fragment that includes one or more VL CDRs having the amino acid sequence of any one of the VL CDRs of the murine monoclonal antibody STC703, STC810, STC820, STC1011, STC1012, STC1029, STC2602, STC2714, STC2739, STC2778, or STC2781, as depicted in Tables 2a-12b. In yet another embodiment, the molecules can have antigen binding fragment that includes at least one VH CDR and at least one VL CDR of the murine monoclonal antibody STC703, STC810, STC820, STC1011, STC1012, STC1029, STC2602, STC2714, STC2739, STC2778, or STC2781, as depicted in Tables 2a-12b.

In some embodiments, kits provided herein can include molecules having an antigen binding fragment that competitively blocks (e.g., in a dose-dependent manner) a BTN1A1 epitope described herein. The BTN1A1 epitope can be an epitope of STC703, STC810, STC820, STC1011, STC1012, STC1029, STC2602, STC2714, STC2739, STC2778, or STC2781, as described herein. In some embodiments, kits provided herein can include molecules having an antigen binding fragment that immunospecifically binds to an epitope of BTN1A1 as described herein. The BTN1A1 epitope can be an epitope of STC703, STC810, STC820, STC1011, STC1012, STC1029, STC2602, STC2714, STC2739, STC2778, or STC2781.

In some embodiments, the kit further includes a second anticancer agent. The second anticancer agent can be a chemotherapeutic agent, a immunotherapeutic agent, a hormonal therapeutic agent, or a cytokine.

In some embodiments, the second anticancer agent is an anti-PD1-therapy or an anti-PD-L1 therapy. In some embodiments, the second anticancer agent is an anti-PD1-therapy. In some embodiments, the second anticancer agent is an anti-PD-L1 therapy. In some embodiments, the seconde anticancer agent is an anti-PD1 therapy and an anti-PD-L1 therapy. In some embodiments, the anti-PD-1 therapy or the anti-PD-L1 therapy includes an anti-PD-1 or anti-PD-L1 antibody or antibody fragment, or a soluble PD-1 or PD-L1 ligand, or Fc-fusion protein thereof. In some embodiments, the anti-PD-1 therapy includes nivolumab (Opdivo), pembrolizumab (Keytruda), pidilizumab, AMP-514, or AMP-224. In some embodiments, the anti-PD-1 therapy includes an anti-PD-1 antibody provided in International Application No. PCT/US2016/64394. In some embodiments, the anti-PD-L1 therapy includes YW243.55.S70, MPDL3280A, MEDI-4736, MSB-0010718C, or MDX-1105. In some embodiments, the anti-PD-L1 therapy includes an antibody provided in International Application No. PCT/US2016/024691, published as WO 2016/160792 A1, and International Application No. PCT/US2017/024027.

Provided herein are also kits that can be used as a companion diagnostic for cancer. In some embodiments, the kits can be used to provide or aid cancer diagnosis. In some embodiments, the kits can be used to evaluate the efficacy of a cancer treatment. In some embodiments, the kits can be used to predict the responsiveness of a patient to a cancer treatment. In some embodiments, the kits can be used to select patients for a particular cancer treatment. The kit can include, for example, reagents for detecting BTN1A1 in a sample. In some embodiments, the kit includes a reagent for detecting PD-L1 (e.g., an anti-PD-L1 antibody).

The reagent can be a molecule having an antigen binding fragment that immunospecifically binds to BTN1A1, glycosylated BTN1A1, or a BTN1A1 dimer. In some embodiments, the molecules have an antigen binding fragment that immunospecifically binds to glycosylated BTN1A1. In some embodiments, the molecules have an antigen binding fragment that immunospecifically binds to BTN1A1 glycosylated at positions N55, N215, and/or N449. In some embodiments, the antigen binding fragment immunospecifically binds to BTN1A1 glycosylated at position N55. In some embodiments, the antigen binding fragment immunospecifically binds to BTN1A1 glycosylated at position N215. In some embodiments, the antigen binding fragment immunospecifically binds to BTN1A1 glycosylated at position N449. In some embodiments, the antigen binding fragment immunospecifically binds to one or more glycosylation motifs. In some embodiments, the antigen binding fragment immunospecifically binds to BTN1A1 glycosylated at positions N55 and N215. In some embodiments, the molecules are anti-BTN1A1 antibodies. In some embodiments, the molecules are anti-glycosylated BTN1A1 antibodies. In some embodiments, the molecules are anti-BTN1A1 dimer antibodies (e.g., STC703, STC810, or STC2714). In some embodiments, the BTN1A1 dimer is glycosylated at any one or more positions of N55, N215 and N449 or one or both BTN1A1 monomers in the BTN1A1 dimer. For example, the glycosylated BTN1A1 dimer can be glycosylated at any one, two, three, four, five, or six positions N55, N215 and N449 in the BTN1A1 dimer.

The cancer therapies can be any therapy described herein or otherwise known in the art, including but not limited to: a surgical therapy, chemotherapy, biological targeted therapy, small molecular targeted therapy, radiation therapy, cryotherapy, hormonal therapy, immunotherapy and cytokine therapy. In some embodiments, the cancer therapy includes administering to a cancer patient molecules described herein that have an antigen binding fragment that immunospecifically binds to BTN1A1, such as anti-BTN1A1 antibodies, including anti-glycosylated BTN1A1 antibodies and anti-BTN1A1 dimer antibodies.

In some embodiments, the ancillary reagent for the diagnostic kit can be a secondary antibody, a detection reagent, an immobilization buffer, a blocking buffer, a washing buffer, a detection buffer, or any combination thereof.

Secondary antibodies can include, for example, an anti-human IgA antibody, an anti-human IgD antibody, an anti-human IgE antibody, an anti-human IgG antibody, or an anti-human IgM antibody. In some embodiments, the secondary antibodies are anti-bovine antibodies. Secondary detection antibodies can be monoclonal or polyclonal antibodies. Secondary antibodies can be derived from any mammalian organism, including mice, rats, hamsters, goats, camels, chicken, rabbit, and others. Secondary antibodies can be conjugated to enzymes (e.g., horseradish peroxidase (HRP), alkaline phosphatase (AP), luciferase, and the like) or dyes (e.g., colorimetric dyes, fluorescent dyes, fluorescence resonance energy transfer (FRET)-dyes, time-resolved (TR)-FRET dyes, and the like). In some embodiments, the secondary antibody is a polyclonal rabbit-anti-human IgG antibody, which is HRP-conjugated.

In some embodiments, the detection reagent contains a fluorescent detection reagent or a luminescent detection reagent. In some other embodiments, the luminescent detection reagent contains luminol or luciferin.

A large selection of washing buffers are known in the art, such as tris(hydroxymethyl)aminomethane (Tris)-based buffers (e.g., Tris-buffered saline, TBS) or phosphate buffers (e.g., phosphate-buffered saline, PBS). Washing buffers can include detergents, such as ionic or non-ionic detergents. In some embodiments, the washing buffer is a PBS buffer (e.g., about pH 7.4) including Tween®20 (e.g., about 0.05% Tween®20).

Any dilution buffer known in the art can be included in a kit of this disclosure. Dilution buffers can include a carrier protein (e.g., bovine serum albumin, BSA) and a detergent (e.g., Tween®20). In some embodiments, the dilution buffer is PBS (e.g., about pH 7.4) including BSA (e.g., about 1% BSA) and Tween®20 (e.g., about 0.05% Tween®20).

In some embodiments, the detection reagent is a colorimetric detection reagent, a fluorescent detection reagent, or a chemiluminescent detection reagent. In some embodiments, the colorimetric detection reagent includes PNPP (p-nitrophenyl phosphate), ABTS (2,2'-azino-bis(3-ethylbenzothiazoline-6-sulphonic acid)) or OPD (o-phenylenediamine). In some embodiments, the fluorescent detection reagent includes QuantaBlu™ or QuantaRed™ (Thermo Scientific, Waltham, MA). In some embodiments, the luminescent detection reagent includes luminol or luciferin. In some embodiments, the detection reagent includes a trigger (e.g., $H_2O_2$) and a tracer (e.g., isoluminol-conjugate).

Any detection buffer known in the art can be included in a kit of this disclosure. In some embodiments the detection buffer is a citrate-phosphate buffer (e.g., about pH 4.2).

Any stop solution known in the art can be included in a kit of this disclosure. The stop solutions of this disclosure terminate or delay the further development of the detection reagent and corresponding assay signals. Stop solutions can include, for example, low-pH buffers (e.g., glycine-buffer, pH 2.0), chaotrophic agents (e.g., guanidinium chloride, sodium-dodecylsulfate (SDS)) or reducing agents (e.g., dithiothreitol, mecaptoethanol), or the like.

In some embodiments, the kits provided herein include a cleaning reagent for an automated assay system. An automated assay system can include systems by any manufacturer. In some embodiments, the automated assay systems include, for example, the BIO-FLASH™, the BEST 2000™, the DS2™, the ELx50 WASHER, the ELx800 WASHER, the ELx800 READER, and the Autoblot S20™. A cleaning reagent can include any cleaning reagent known in the art. In some embodiments, the cleaning reagent is the cleaning reagent recommended by the manufacturer of the automated assay system.

In some embodiments, the kits can also include a suitable container means, which is a container that does not react with components of the kit, such as an eppendorf tube, an assay plate, a syringe, a bottle, or a tube. The container can be made from sterilizable materials, such as plastic or glass.

In some embodiments, the kits further include a solid support. The solid support can include any support known in the art on which a protein of this disclosure can be immobilized. In some embodiments, solid the solid substrates are microtiter well plates, slides (e.g., glass slides), chips (e.g., protein chips, biosensor chips, such as Biacore chips), microfluidic cartridges, cuvettes, beads (e.g., magnetic beads) or resins.

In some other embodiments, the kits provided herein include instruction for using the subunits of the kit for detecting BTN1A1 or glycosylated BTN1A1 in the sample from the subject.

The kits provided herein can be tailored to specific assay technologies. In some embodiments, the kit is an ELISA kit, Dot Blot kit, chemiluminescence immunoassay (CIA) kit or multiplex kit. In some embodiments, the ELSA kit can include a washing buffer, a sample diluents, a secondary antibody-enzyme conjugate, a detection reagent and a stop solution. In some embodiments, the Dot Blot kit includes a washing buffer, a sample diluents, a secondary antibody-enzyme conjugate, a detection reagent, and a stop solution. In some embodiments, the CIA kit includes a washing buffer, a sample diluent, a tracer (e.g., isoluminol-conjugate) and a trigger (e.g., $H_2O_2$). In some embodiments, the multiplex kit includes a washing buffer, a sample diluents and a secondary antibody-enzyme conjugate.

In some embodiments, the kit of the present invention has a packaging that includes a label indicating the kit is used for diagnosis, prognosis or monitoring of a cancer. In some embodiments, the kit is used as companion diagnostics for cancer treatments. In some other embodiments, the packaging has a label indicates that the kit is used with a cancer drug. In some embodiments, the kit is used to select a patient for a specific cancer treatment.

In some embodiments, the packaging of the kit includes an FDA-approved label. FDA approved labels can include notification of an FDA-approved use and instructions. In some embodiments, the kit is labeled for Research Use Only (RUO) or for Investigational Use Only (IUO). In some embodiments, the kit is labeled for In Vitro Diagnostic Use (IVD). In some embodiments, the kit is labeled in accordance with Title 21, Code of Federal Regulations, Section 809, Subpart B (21 CFR 89, Subpart B).

6. EXAMPLES

It is understood that modifications which do not substantially change the nature and spirit of the various embodiments described herein are also contemplated. Accordingly, the following examples are intended to illustrate but not in any way limiting.

6.1 Example 1: BTN1A1 is Expressed in Various Cancer Types

To assess BTN1A1 expression levels across different cancer types a cBioPortal search was performed. CBioPortal (Gao et al. (2013) Sci. Signal. 6(269)pl1.; Cerami et al. (2012) Cancer Discov. 2(5) 401-4) allows the mining of results from 150 published cancer genomics studies.

FIG. 1 illustrates results from the cBioPortal search for BTN1A1. The frequency of mutations (green), deletions (blue), and amplifications (red) was plotted by cancer type. BTN1A1 was found to be expressed in a variety of cancer types, including breast cancer, neuroendocrine prostate cancer (NEPC), diffuse large B-cell lymphoma, melanoma, National Cancer Institute cancer panel (NCI 60), uveal melanoma, pancreas cancer, ovarian cancer, uterine cancer, lung adenocarcinoma, desmoplastic small-round-cell tumor, bladder cancer, colorectal cancer, lung squamous cell carcinoma, liver cancer, lung cancer, stomach cancer, cholangiocarcinoma, esophagus squamous cell carcinoma, head and neck cancer, sarcoma, prostate cancer, liver cancer, pancreas cancer, pheochromocytoma and paraganglioma (PCPG), cervical cancer, glioma, and acute myeloid leukemia (AML).

6.2 Example 2: Expression of BTN1A1 and PD-L1 is Mutually Exclusive

To assess BTN1A1 expression patterns relative to other immune checkpoints, a tissue microarray analysis of several tissues was performed. Specifically, paraffin embedded cancerous human lung, prostate, pancreas and liver tissue slices were stained for BTN1A1 and PD-L1 (3,3'-diaminobenzidine (DAB) and hematoxylin counterstain) and analyzed by brightfield microscopy.

FIGS. 2A-D show exemplary images of lung squamous carcinoma (FIG. 2A), prostate adenocarcinoma (FIG. 2B), pancreatic adenocarcinoma (FIG. 2C), and hepatocellular carcinoma (FIG. 2D) samples. Two samples are shown for each tissue type (top and bottom rows of FIGS. 2A-D). Different slices from each sample were stained with PD-L1 (left columns in FIGS. 2A-D) or BTN1A1 (right columns in FIGS. 2A-D). Each sample in FIGS. 2A-D showed strong BTN1A1 staining; PD-L1 staining was not detected in any of the sample. Thus, BTN1A1 and PD-L1 expression was found to be mutually exclusive in prostate adenocarcinoma, pancreatic adenocarcinoma, and hepatocellular carcinoma samples.

FIGS. 3A-D show fluorescence microscope images of a typical human lung squamous cell carcinoma tissue slice. An OPAL™ multiplex immunohistochemistry kit (Perkin Elmer, Waltham, MA) was used to costain for PD-L1 (FIG. 3A; green), BTN1A1 (FIG. 3B; red), and Cytokeratin (FIG. 3C; purple). FIG. 3D shows merged images of FIGS. 3A-C. A Vectra® 3.0 phenoptics platform (Perkin Elmer) was used to image and deconvolute the images. PD-L1 and BTN1A1 were both found to be expressed in the tumor area shown in FIGS. 3A-D. A mosaic PD-L1 and BTN1A1 expression pattern was generally observed in human lung squamous cell carcinoma tissue slices and PD-L1 and BTN1A1 expression found to be mutually exclusive in any given region of a tissue slice.

FIGS. 4A-D show further fluorescence microscope images of an additional human lung squamous cell carcinoma tissue slice, which illustrate typical PD-L1 (FIG. 4A; green), BTN1A1 (FIG. 4B; red), and Cytokeratin (FIG. 4C; purple) expression. FIG. 4D shows merged images of FIGS. 4A-C. The characteristic mosaic PD-L1 and BTN1A1 expression pattern was also observed in the human lung squamous cell carcinoma tissue slice of FIGS. 4A-D.

6.3 Example 3: Anti-BTN1A1 Antibodies Synergize with Anti-PD1 Antibodies to Induce IL-2 and IFNγ Secretion in a Mixed Lymphocyte Reaction A Mixed Lymphocyte Reaction (MLR) was used to assess the ability of anti-glycosylated BTN1A1 antibodies to synergize with anti-PD1 antibodies.

In brief, 300 ng/mL STC810 was tested alone or in combination with 20 ng/mL of STM418, an anti-PD-1 blocking mAb developed by STCube. Allogenic dendritic cells and total T-cells were enriched from PBMC and co-cultured (DC:T=1:10) in the presence of antibody for 72 h. Culture supernatants were subjected to ELISA for IL-2 and IFNγ quantitation by ELISA.

As shown in FIG. 5A and FIG. 5B, no effect on IL-2 or IFNγ secretion was observed with 20 ng/mL anti-PD-1 mAb STM418 alone. However, combination with anti-PD-1 was found to increase STC810-induced IL-2 and IFNγ secretion. STC810 at 1,000 ng/ml was found to increase IL-2 and IFNγ secretion to comparable levels as STC810 at 300 ng/ml (data not shown). Mouse IgG was used as a negative control. P values were calculated by Students' t-test (n=3).

This Example demonstrates that anti-glycosylated BTN1A1 antibodies can synergize with anti-PD1 antibodies to induce IL-2 and IFNγ secretion in a mixed lymphocyte reaction.

6.4 Example 4: Development of Anti-Mouse BTN1A1 Antibodies

Three different anti-mouse BTN1A1 antibodies, STC1011, STC1012, and STC1029 were developed and characterized by STCube to facilitate animal studies.

The binding affinity between BTN1A1 and monoclonal anti-BTN1A1 antibodies STC1011, STC1012, and STC1029 was measured by Surface Plasmon Resonance (BIAcore™). Sensorgrams and saturation curves of antibody titrations of with human IgG1-Fc-tagged mouse BTN1A1-ECD (dimer) were recorded.

An Protein capture chip (BIAcore™) was coated with STC1011, STC1012, STC1029, or a control IgG1 antibody. No interaction between the IgG1 control and mouse BTN1A1-His was observed. Mouse BTN1A1-ECD-Fc was injected into the microfluidic channel on a Biacore™ X-100 instrument. $K_D$ values were obtained using fitting tools of the BIAevaluation software (BIAcore). FIGS. 6A-C provide sensograms showing real-time binding of dimeric BTN1A1-ECD-Fc (2-64 nM with 2-fold dilution) to immobilized STC1011, STC1012, and STC1029. Signals of IgG1 antibody control cells were subtracted from test cell signals to produce the sensograms shown in FIGS. 6A-C.

The $K_D$ values for BTN1A1-ECD-Fc binding to STC1011, STC1012, and STC1029, as measured by Biacore™ assays, are provided in Table 15 below. STC1011, STC1012, and STC1029 were found to bind BTN1A1-ECD-Fc with high affinity.

TABLE 15

$K_D$ of STC1011, STC1012, or STC1029 Determined by Biacore ™

| | $k_a$ (1/Ms) | $k_d$ (1/s) | $K_D$ (M) | Rmax (RU) |
|---|---|---|---|---|
| STC1011 | | | | |
| STC1012 | 1.46E+05 | 5.99E−04 | 4.10E−09 | 98.815 |
| STC1029 | 2.51E+05 | 4.27E−04 | 1.69E−09 | 84.753 |

BTN1A1-glycosylation dependent cellular internalization of STC1012 was analyzed using live cell imaging. To facilitate this assay, pHRodo-labeled STC1012 antibody was developed. pHRodo is a conjugatable fluorescent tag which is inactive at neutral pH and activated in a low pH environment, such as the acidic environment in a cell's lysosome. Generally, when a pH-Rodo-labeled antibody is internalized into a cell after binding to its target on the cell surface and degraded, red fluorescence will be observed in the cell cytosol. Such fluorescence can be quantitated by fluorescence microscopy, e.g., by counting red objects in an image or as relative units of red fluorescence per image. In brief, HEK293T cells expressing BTN1A1 WT or BTN1A1 2NQ were plated in a 96-well plate at 2,000 cells/well and pH-Rodo®-labeled (ThermoFisher Inc., Waltham, MA) STC1012 (5 μg/ml) or an IgG control antibody (5 μg/ml) were added to each well. Red fluorescence was tracked over 40 h using an IncuCyte ZOOM® live cell imaging system (Essen Bioscience, Inc; Ann Arbor, MI).

FIG. 7A and FIG. 7B show that STC1012 internalization into a cell is not dependent on BTN1A1 glycosylation.

Figure 1:
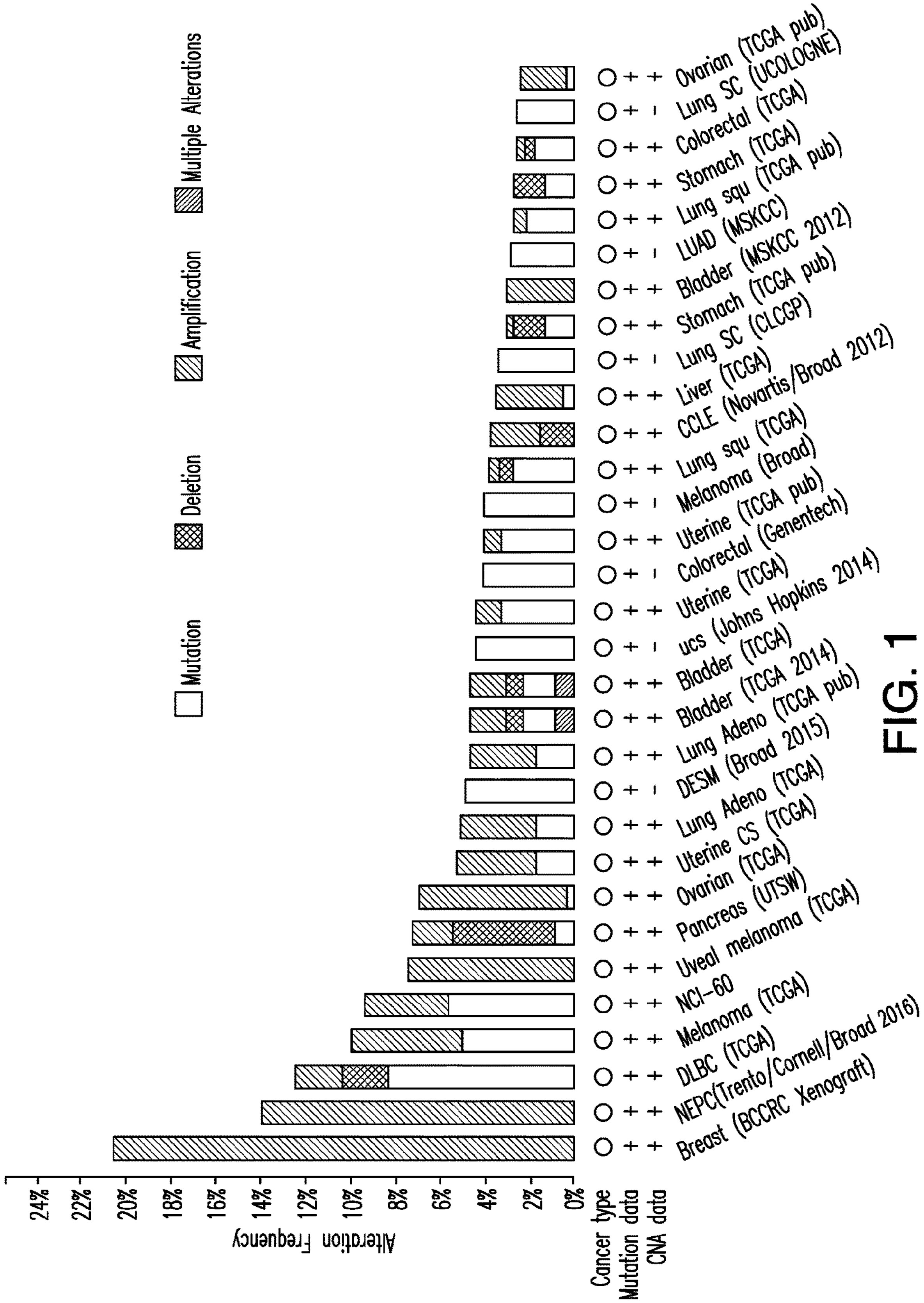
Figure 1:
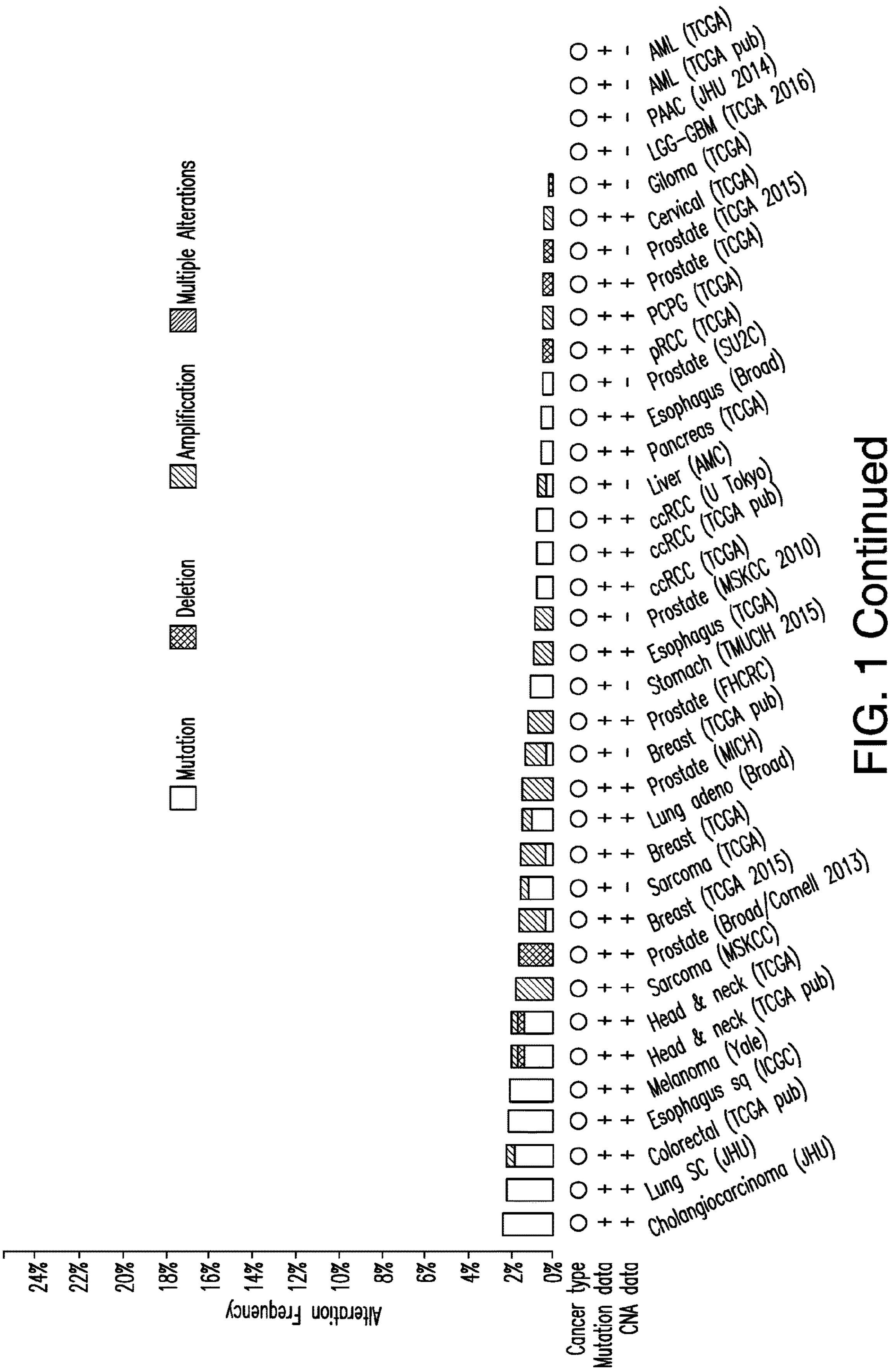
Figure 2A:
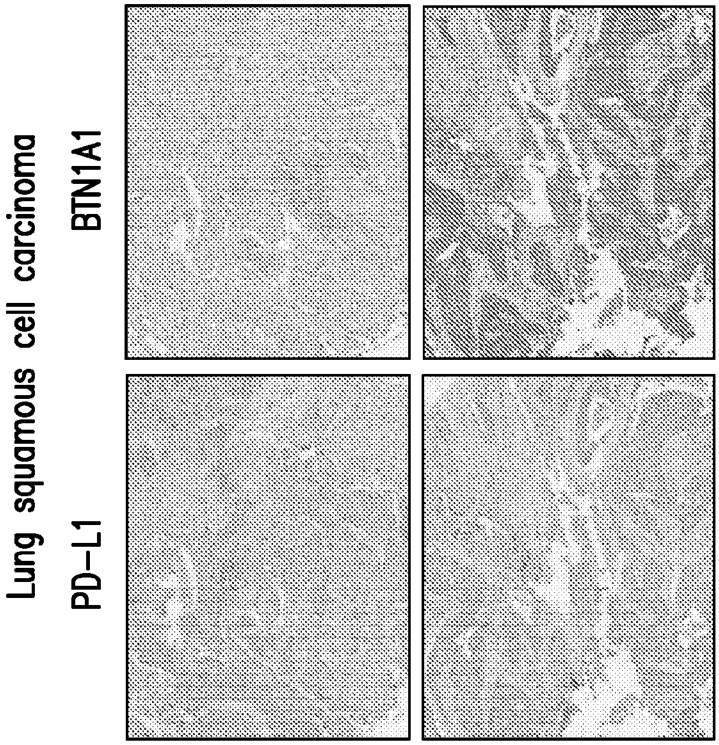
Figure 2B:
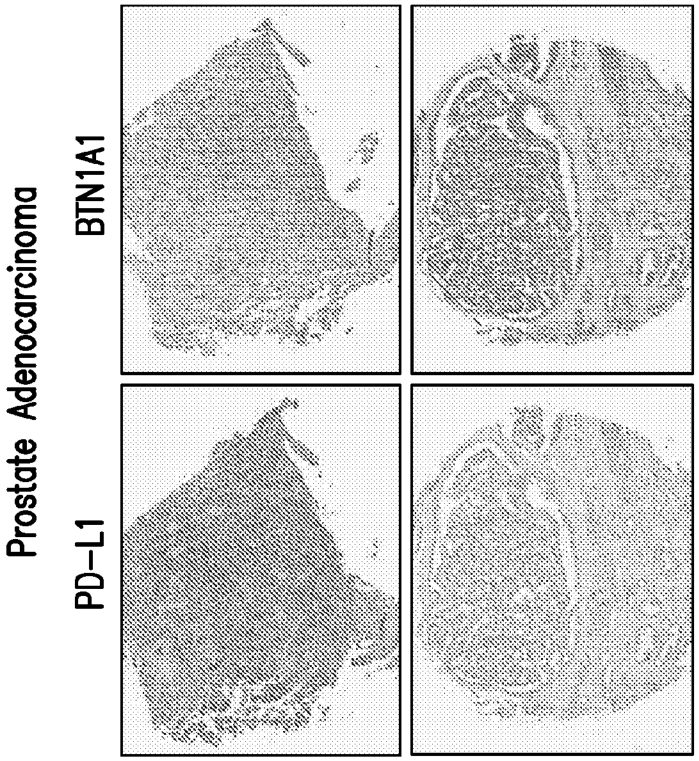
Figure 2C:
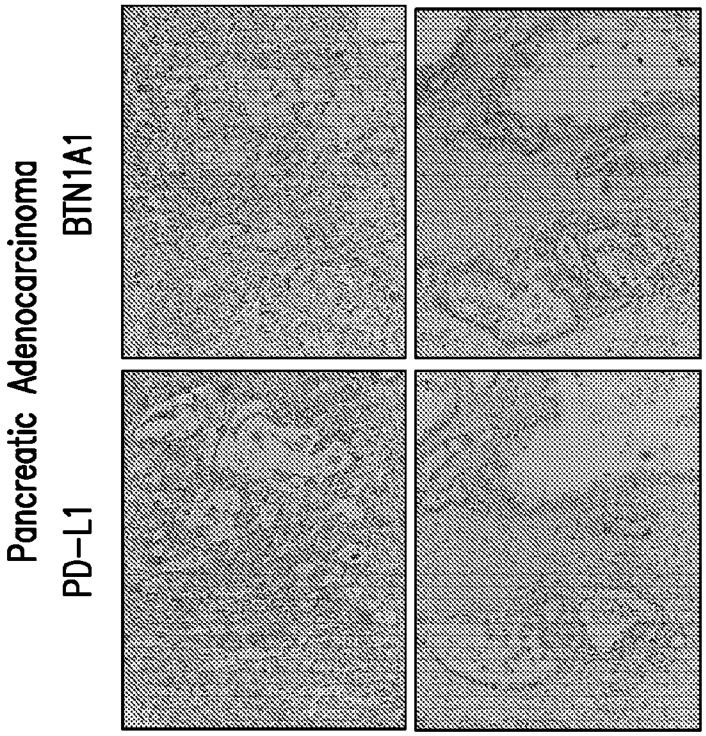
Figure 2D:
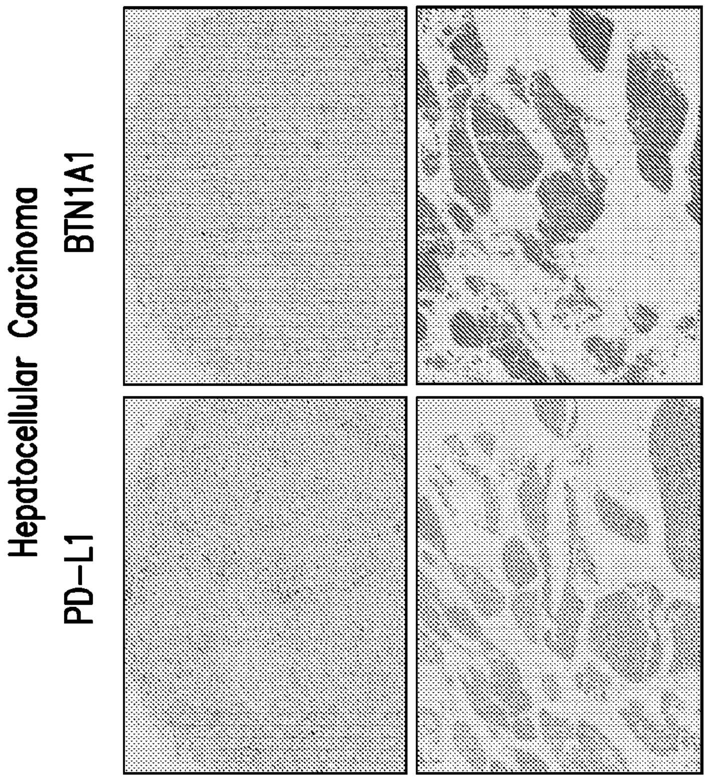
Figure 3A:
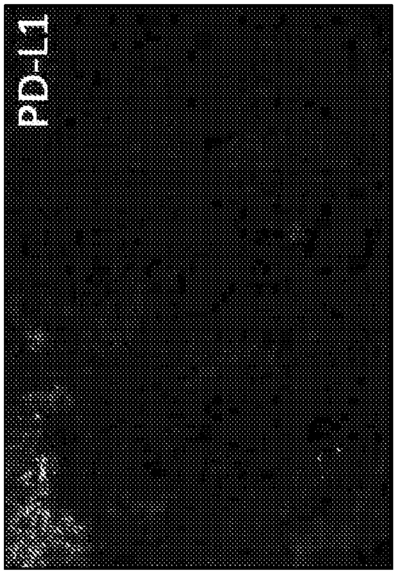
Figure 3B:
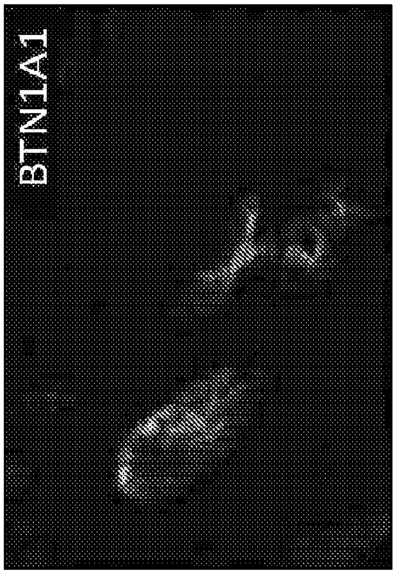
Figure 3C:
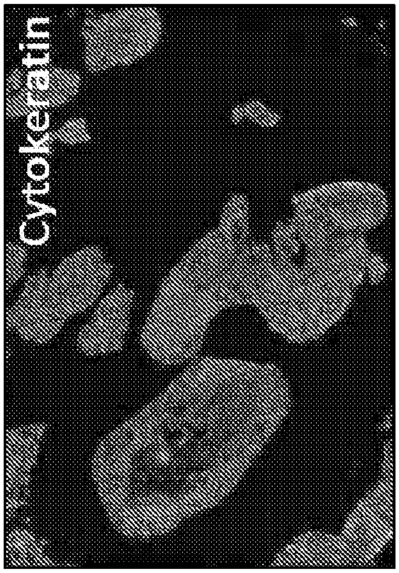
Figure 3D:
Figure 4A:
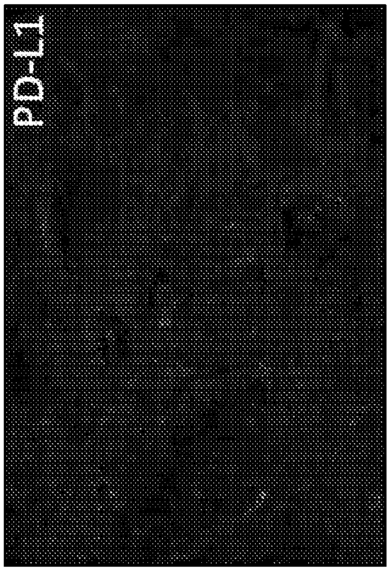
Figure 4B:
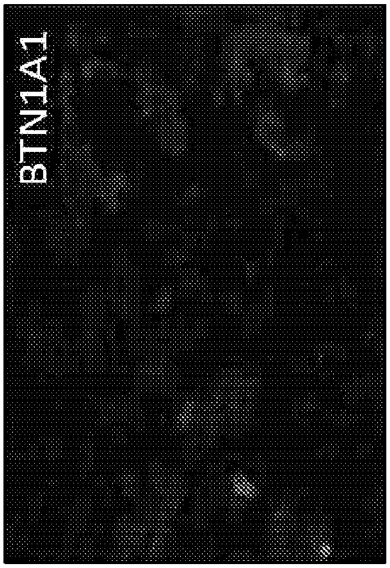
Figure 4C:
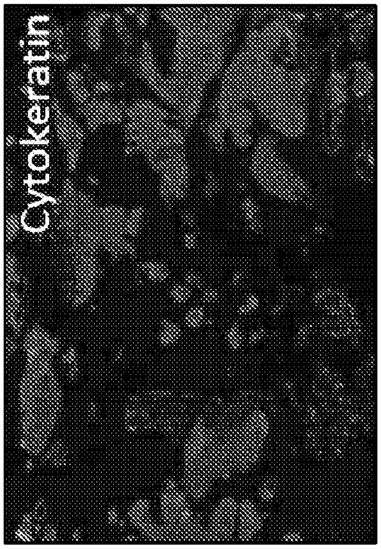
Figure 4D:
Figure 5B:
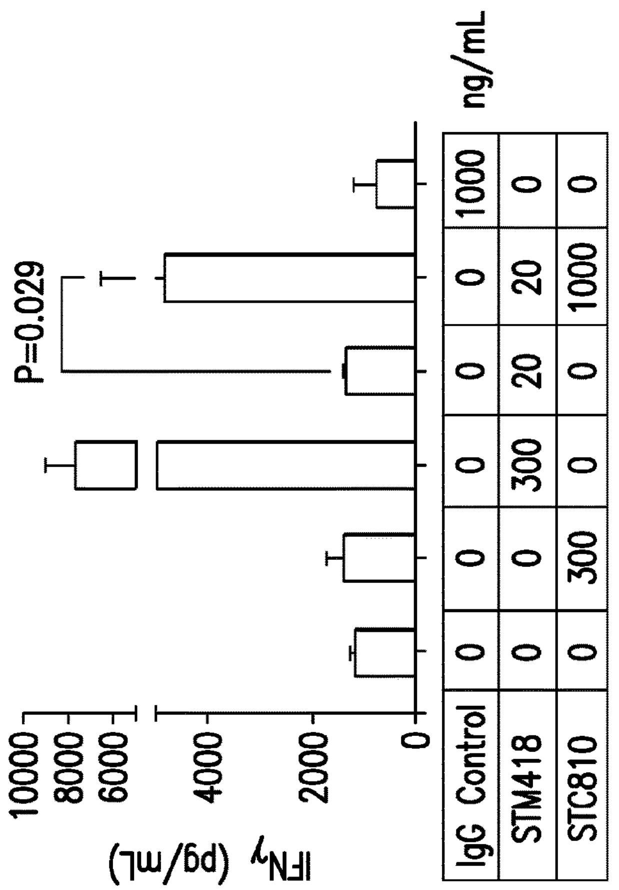
Figure 5A:
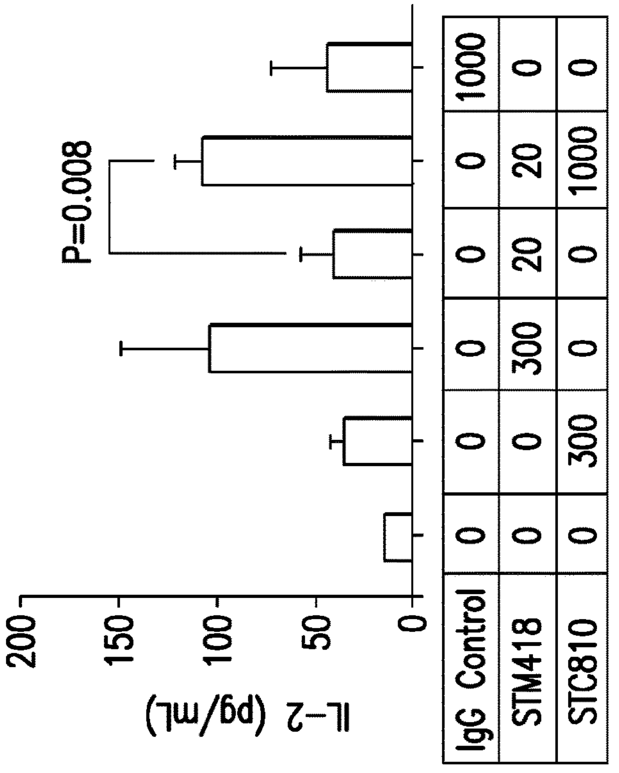
Figure 6A:
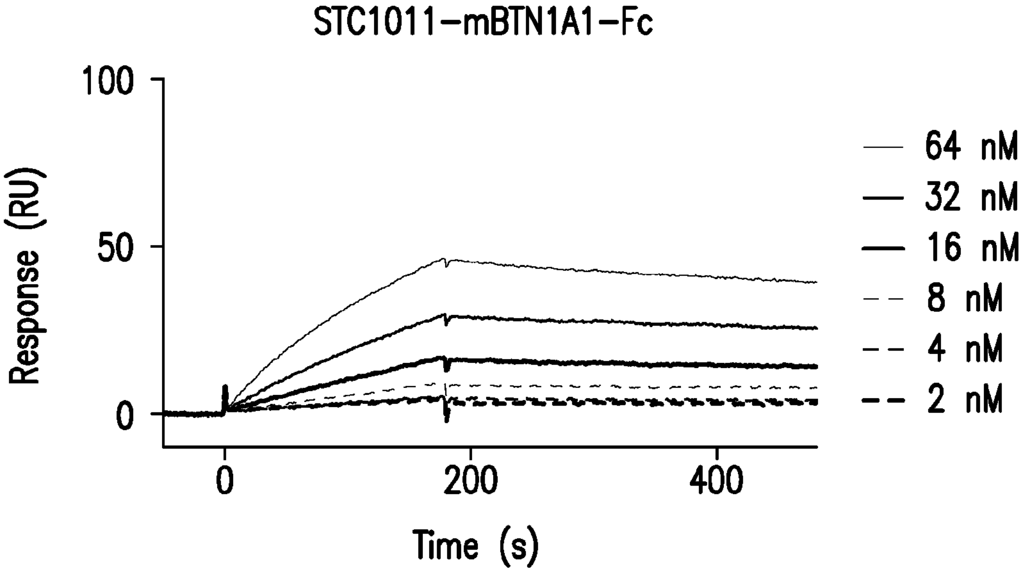
Figure 6B:
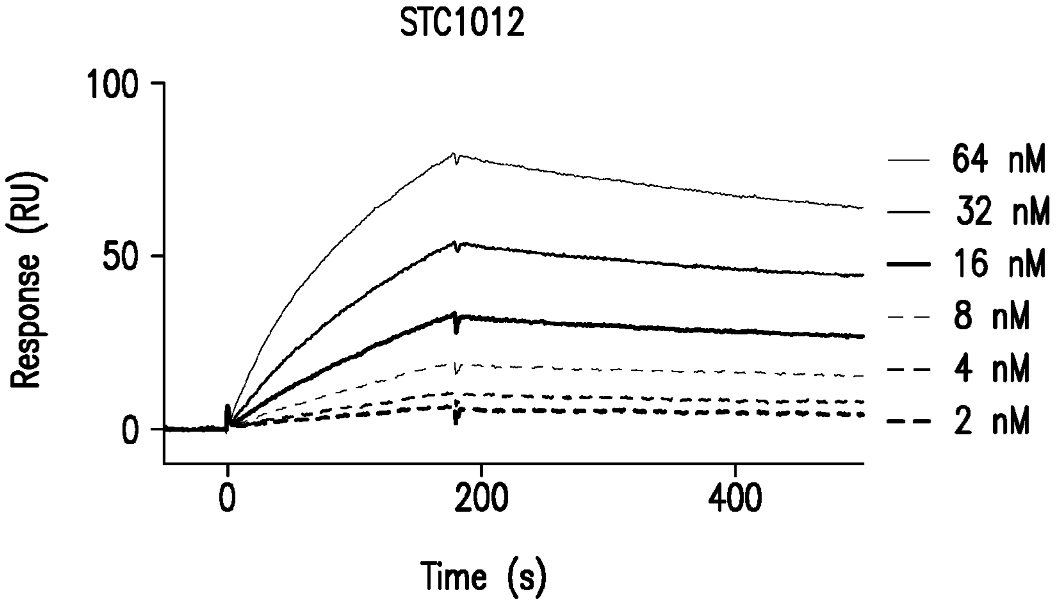
Figure 6C:
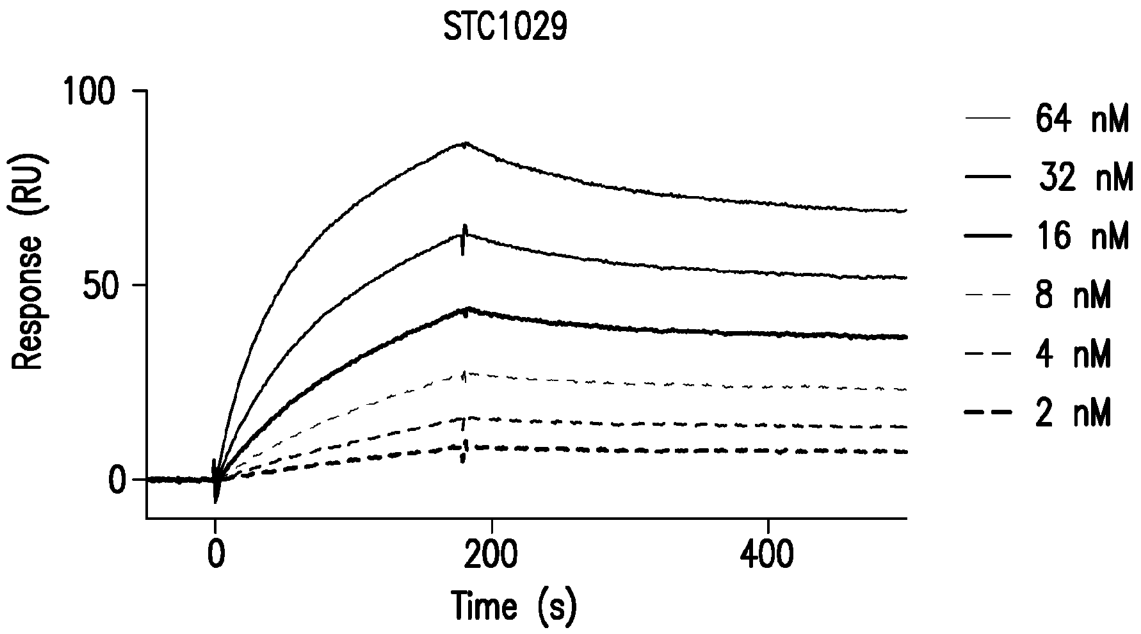
Figure 7A:
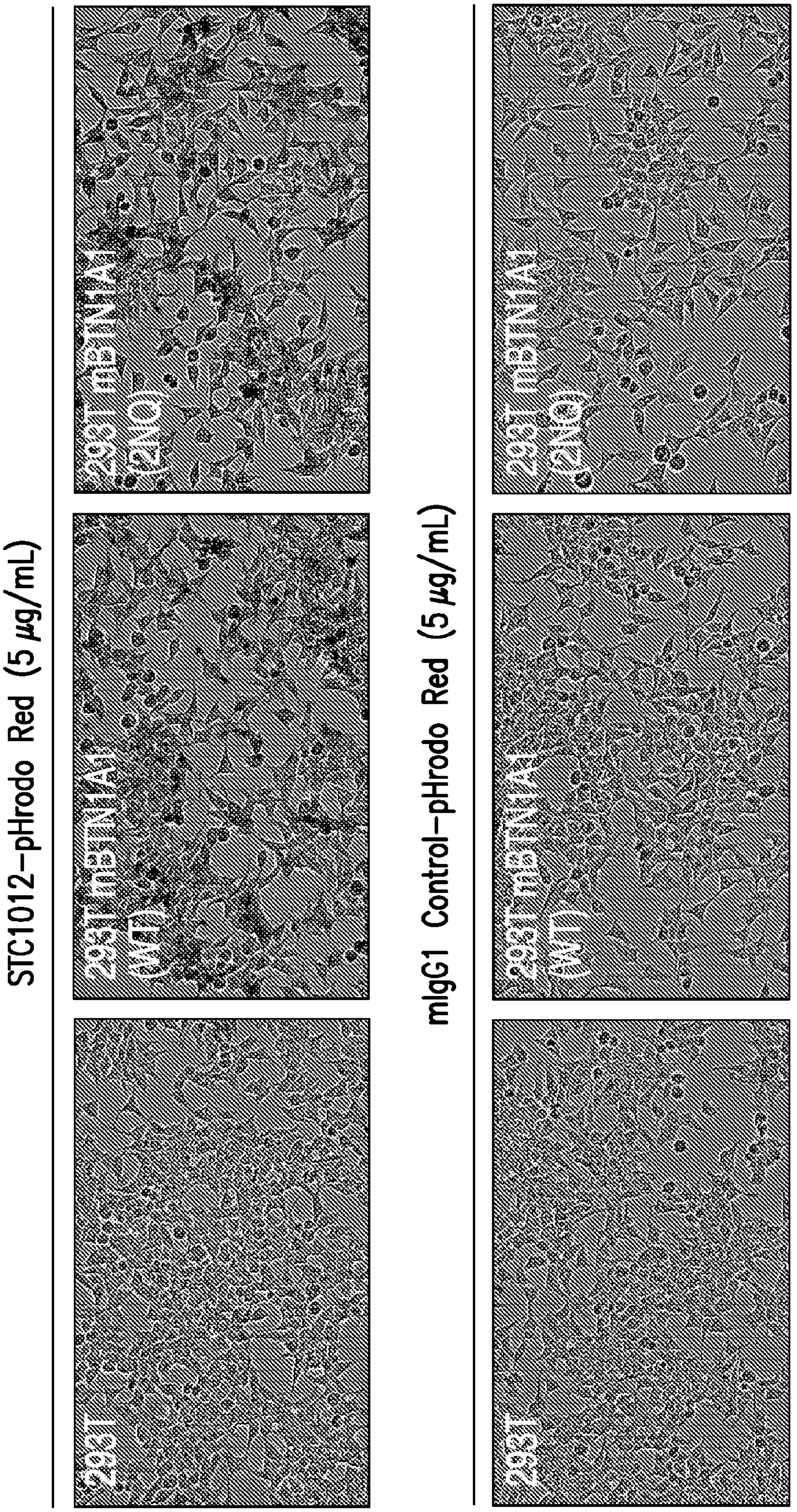
FIG. 7A shows representative images of fluorescence or internalized STC1012. Specific fluorescence indicating STC1012 internalization was observed with BTN1A1 WT expressing cells and with BTN1A1-2NQ expressing cells.
Figure 7B:
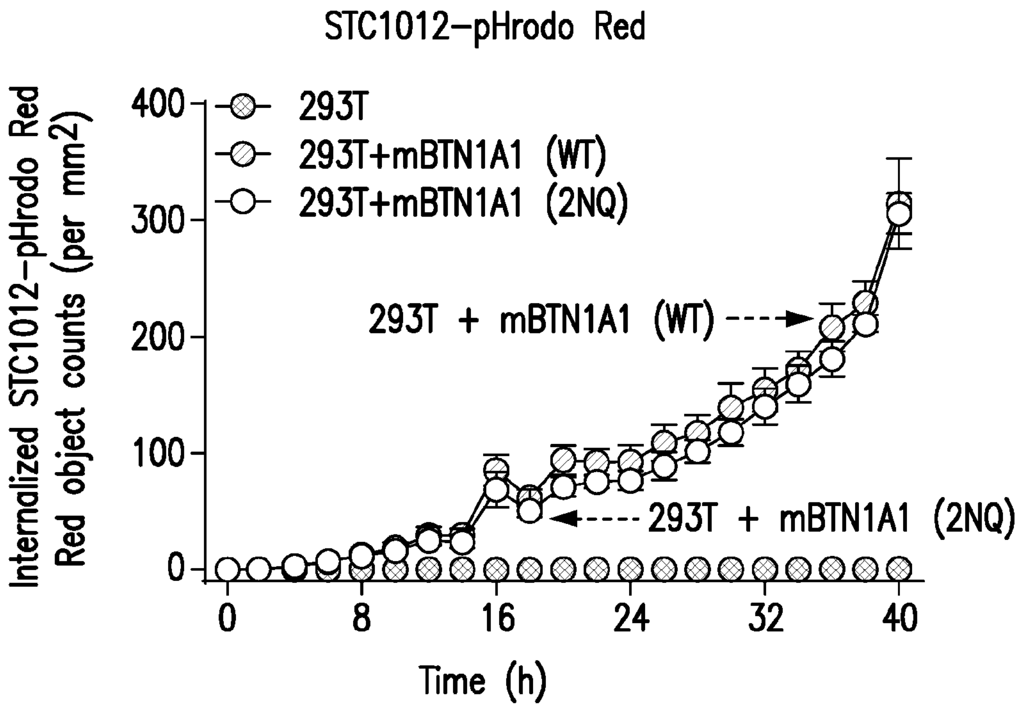
FIG. 7B shows a scatter plot of fluorescence counts indicating internalized STC1012 over time. Steadily increasing internalization of STC810 over a 40 h period was observed with BTN1A1-WT expressing cells and with BTN1A1-2NQ expressing cells.
Figure 7C:
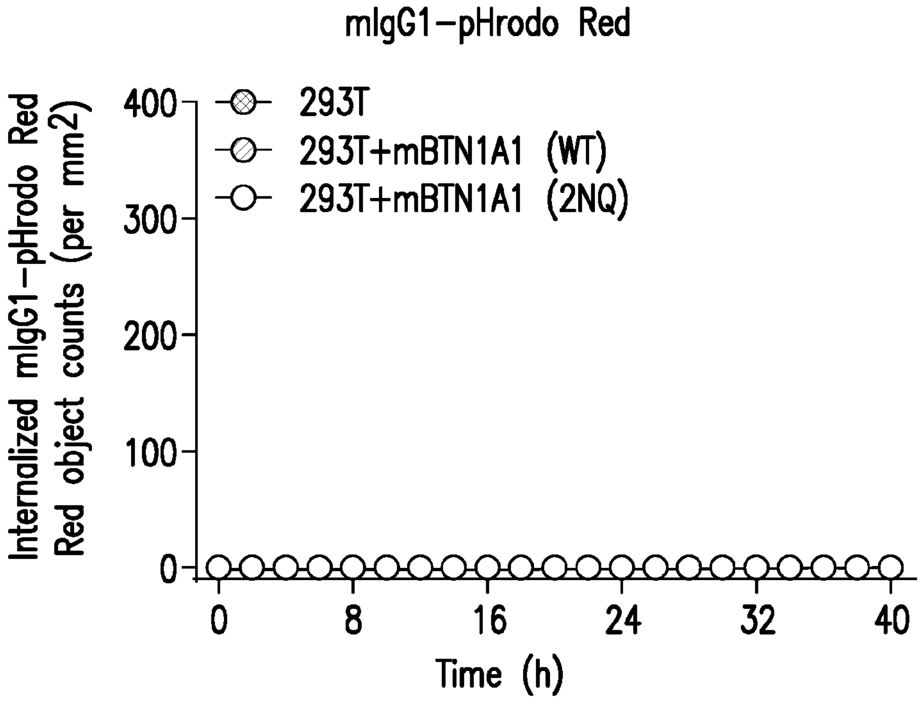
Figure 8B:
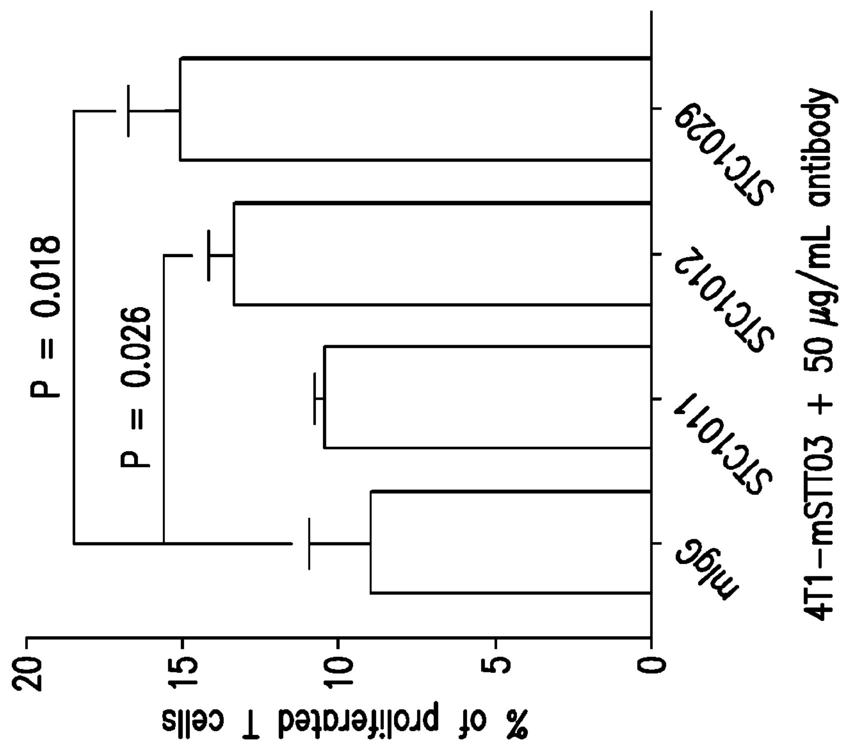
Figure 8A:
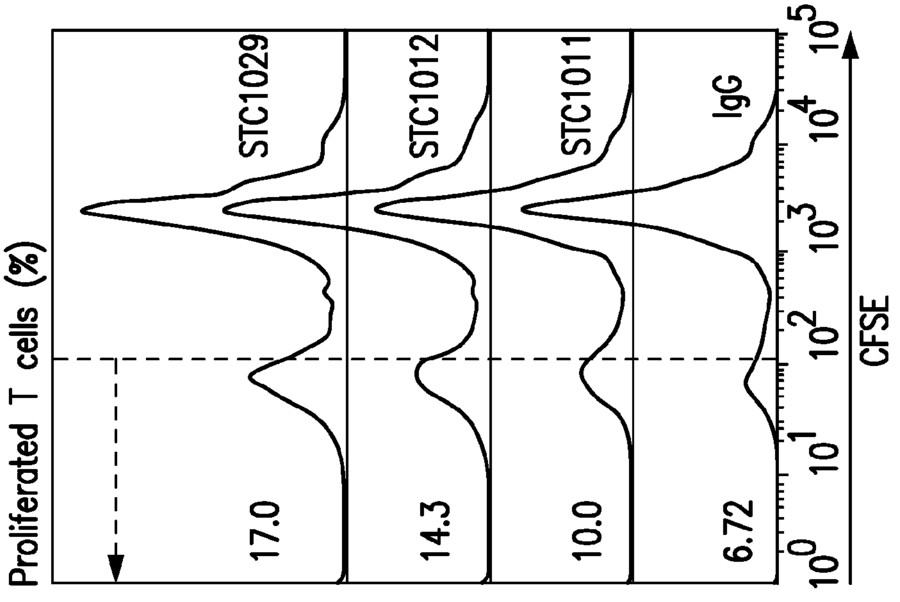

The effect of STC1011, STC1012, and STC1029 on T-cell proliferation was analyzed by contacting a coculture of mitomycin C-treated 4T1-BTN1A1 cells ($4\times10^4$/well) and mouse splenocytes ($2\times10^5$/well) with anti-mouse BTN1A1 antibodies (50m/mL) for 72 h. T-cell proliferation was measured by flow cytometry of CFSE-stained cells. As shown in FIG. 8A and FIG. 8B, STC1011, STC1012, and STC1029 were found to increase T-cell proliferation relative to an IgG control antibody. P values were calculated by Students' T-test (n=3).

6.5 Example 5: Anti-BTN1A1 Antibodies can Retard Tumor Growth in PD-1-Refractory Cancer The efficacy of anti-BTN1A1 antibodies to for the treatment of PD-1 refractory cancer was tested in a 4T1 orthotopic syngeneic breast cancer Balb/c mouse model and a LLC syngenic lung cancer C57BL/6 mouse model. Both models are known to be unresponsive to PD-1 or PD-L1-targeting therapies.

Figure 9:
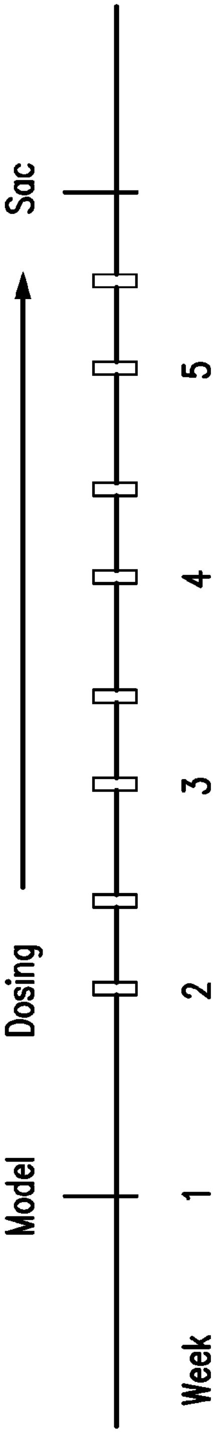

FIG. 9 shows a graph illustrating the dosing schedule for anti-BTN1A1 antibody administration to mice bearing a mammary carcinoma (4T1) or a Lewis lung carcinoma (LLC) implant. In brief, on day 0, the tumor model was engrafted into the $4^{th}$ left mammary fat pad (4T1) or flank (LLC) of mice. At a tumor volume of 50-80 $mm^3$ (4T1) or 75 $mm^3$ (LLC), the mice were randomized into treatment groups based on tumor volume, and dosing of an anti- BTN1A1 antibody (STC1012) or an IgG control antibody began. Dosing at 5 mg/kg (4T1) or 200m/mouse (LLC) was performed twice per week for 4 weeks intraperitonially (IP) until the end of the study. Tumor volumes were calculated as L (length)*W(width)$^2$*0.5 (4T1) or L*W$^2$*π/6 (LLC).

Figure 10:
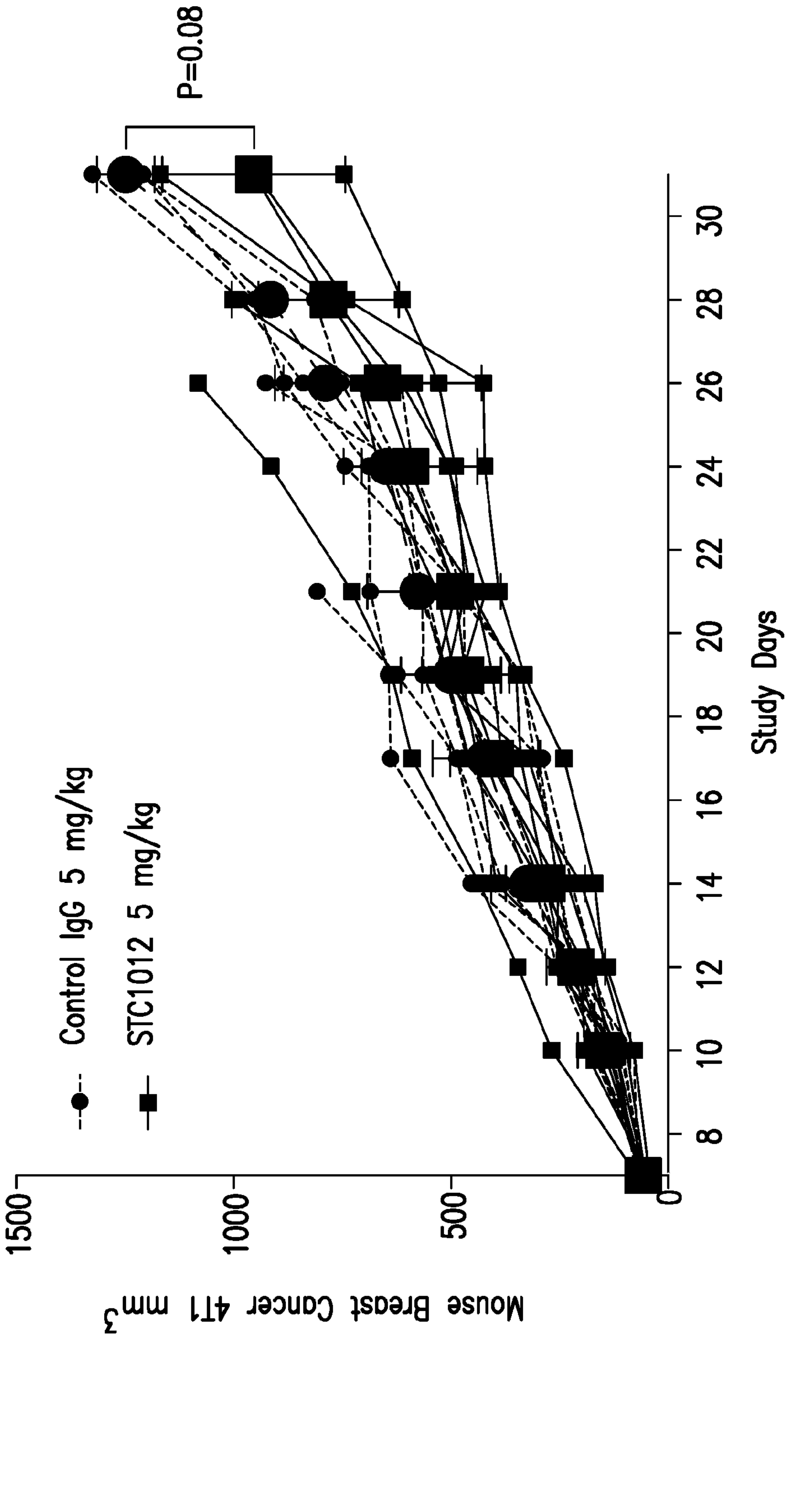

FIG. 10 shows a scatter plot illustrating progressing 4T1 tumor growth in Balb/c mice that were treated with anti-mouse BTN1A1 antibody STC1012 or an IgG antibody-control. Tumor growth in individual animals is plotted. At 50-80 mm$^3$ tumor volume, IP dosing began twice per week with 5 mg/kg IgG or STC1012. On day 31, the observed difference in tumor volume between control and treated group was 24%, P=0.08. Mice lost below 1500 mm$^3$ were due to ulceration.

Figure 11:
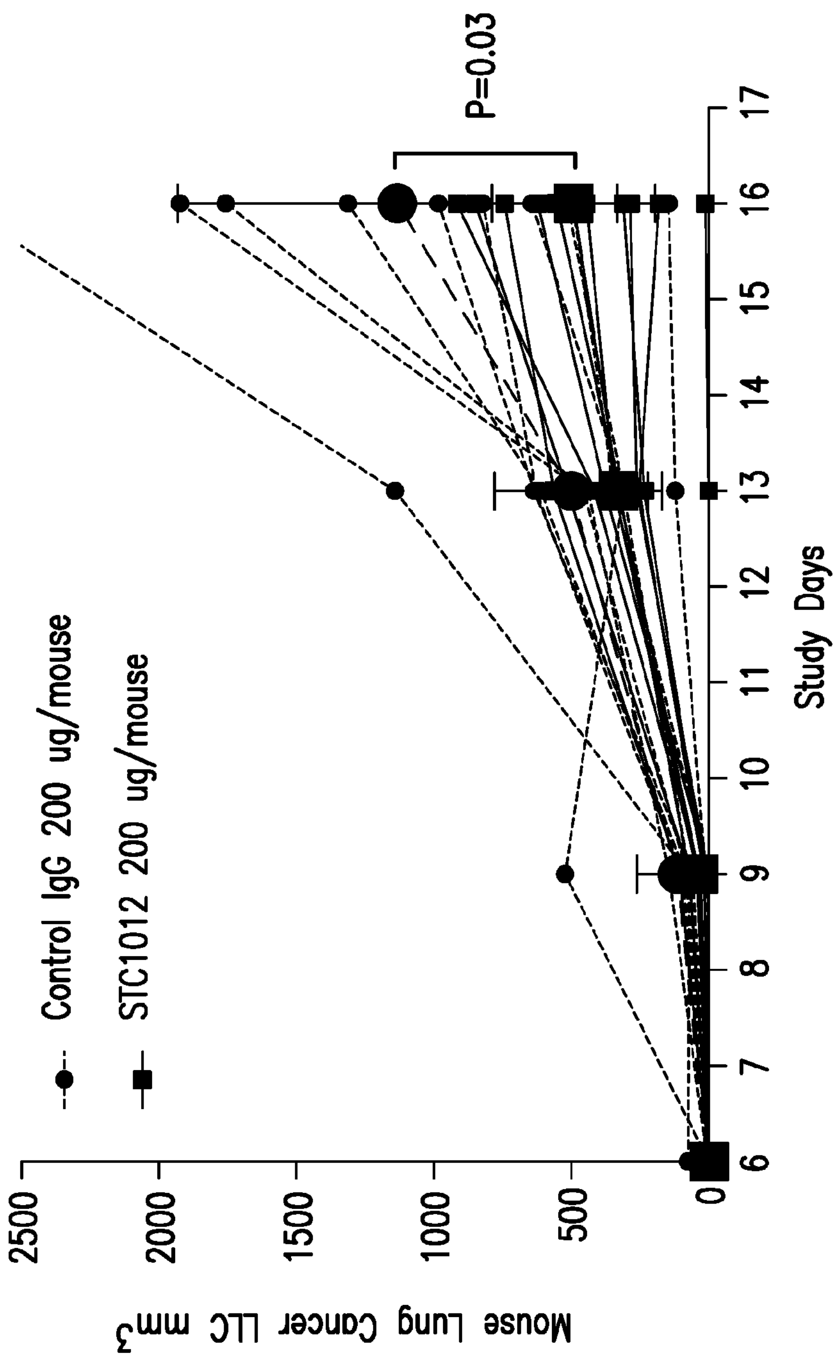

FIG. 11 shows a scatter plot illustrating progressing LLC tumor growth in C57BL/6 mice that were treated with anti-mouse BTN1A1 antibody STC1012 or an IgG antibody-control. Tumor growth in individual animals is plotted. At 75 mm$^3$ tumor volume, IP dosing began twice per week with 200 μg/mouse IgG or STC1012. On day 16, the observed difference in tumor volume between control and treated group was 52%, P=0.03.

Figure 12:
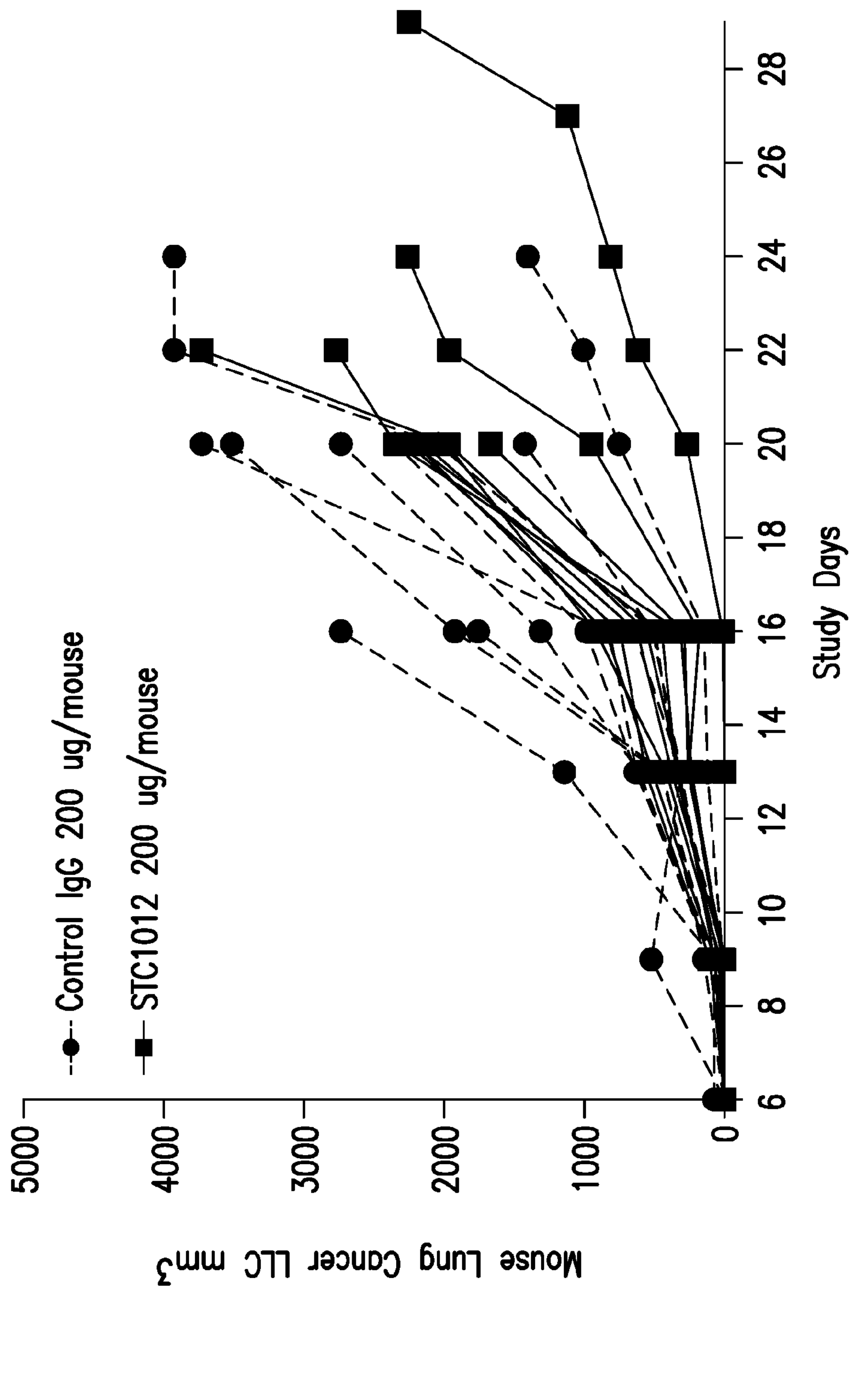
Figure 13A:
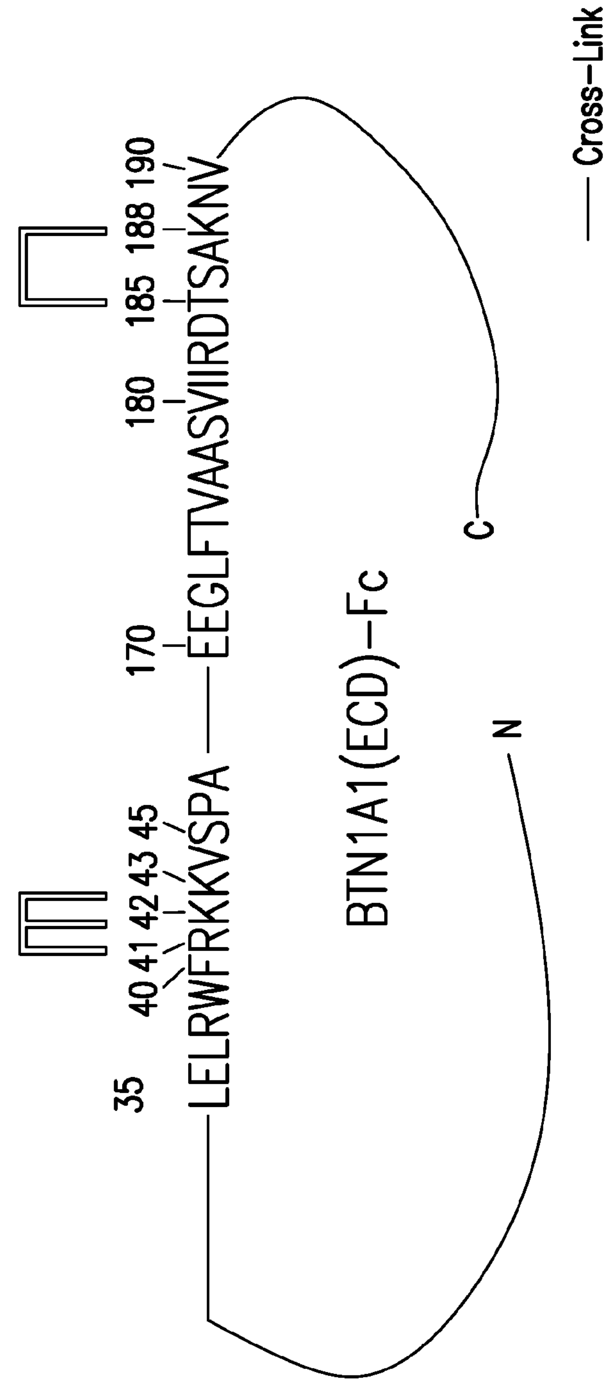
Figure 13B:
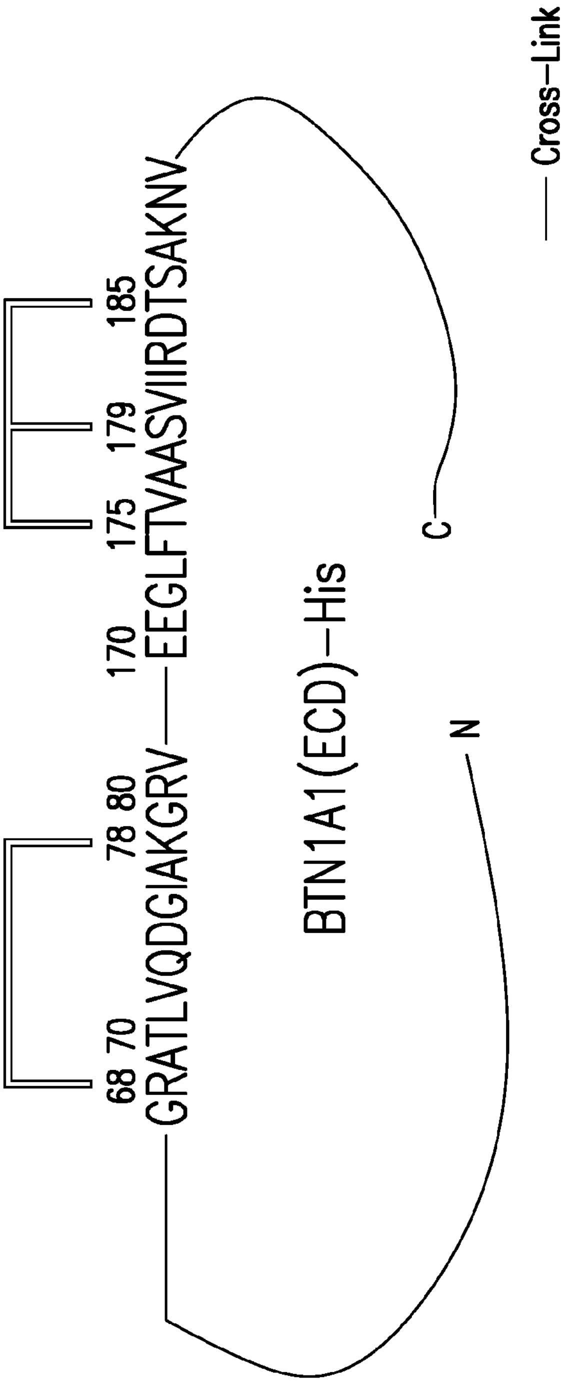

FIG. 12 shows a scatter plot illustrating progressing LLC tumor growth for individual animals beyond day 16 (see FIG. 11).

In sum, this example demonstrates that anti-BTN1A1 antibodies can be efficacious in treating PD-1 or PD-L1-therapy refractory cancers.

6.6 Example 6: Production and Screening of Dimer-Specific BTN1A1 Monoclonal Antibodies Immunization.

To generate dimer-specific BTN1A1 monoclonal antibodies, a dimer form of BTN1A1 (BTN1A1-Fc) was produced by inserting the extracellular domain of the gene into Fc fusion vector (pFUSE-hIgG1-Fc, Invivogen). Hybridomas producing monoclonal antibodies generated against dimer form of BTN1A1 were obtained by the fusion of SP2/0 murine myeloma cells with spleen cells isolated from human BTN1A1-Fc-immunized BALB/c mice (n=6) (Antibody Solution, Inc.) according to standardized protocol. Before fusion, sera from the immunized mice were validated for binding to the BTN1A1 immunogen using FACS analysis. The hybridomas that produced antibodies were again tested for specificity.

FACS.

To identify anti-BTN1A1-Fc MAbs that were specific for and which preferentially bound human BTN1A1-Fc antigen, different types of assays were performed. In a screening assay to detect preferential binding of MAbs to BTN1A1, antibody binding was determined based on the measurement of fluorescence intensity through FACS analysis (using cell membrane bound proteins). By way of example, the assay was performed using the HEK293T human embryonic kidney cell line. Illustratively, HEK293T cells overexpressing BTN1A1 were were incubated with anti-BTN1A1 antibodies existing in hybridoma culture supernatant. After washing, secondary antibodies conjugated with FITC were added as detection agent. Fluorescence intensity (measured fluorescence intensity, MFI) was measured via FACS I flow cytometry analysis to assess the relative binding of the anti-BTN1A1 antibodies to membrane bound BTN1A1 WT on cells. Antibodies that exhibited significantly higher MFI on WT BTN1A1 were selected for further evaluation. Based on the binding analysis, sixty seven candidate MAb-producing hybridomas were selected, grown in ADCF medium, and their supernatant containing monoclonal antibody was concentrated and purified.

ELISA.

In order to exclude the possibility that the observed binding was due to human Fc binding, ELISA was performed using human BTN1A1-Fc and human IgG1 control. The antigens BTN1A1-Fc and human IgG1 were coated onto ELISA plate. Antibodies were added to each well and binding was for each antibody determined by standard direct ELISA against the antigens. Human IgG1 binding antibodies were excluded from the candidates.

Octet.

To determine the binding affinity, the selected antibodies that showed high binding activity in FACS and ELISA were subjected to Octet kinetic analysis. Using a biosensor coated with anti-mouse Fc capture antibody, $K_D$ was determined by Kon and Koff. Antibodies with higher affinity (nanomolar range) were selected. Epitope binning is also used to categorize the epitope binding characteristics of panels of antibodies against a single target. This epitope binning experiment was designed to determine whether two different antibodies bind to the same epitope. If two antibodies bind to the same epitope of the antigen, then the binding of the first antibody will preclude the binding if the second antibody. If each antibody in a tested pair binds to a completely independent epitope, then binding of the first antibody will have no effect on the binding of the second. Through repeated testing, the antibodies are grouped according to epitope binding specificity. This experiment was performed using the Octet Red96 System (Pall ForteBio) with Bio-Layer Interferometry (BLI) to detect and analyze the interaction of biological molecules. Antigen was bound to the disposable sensors, then additional binding of antibody to the antigen was measured by change in delay of the reflection of the light passing through the sensor. A longer delay is indicative of more mass bound to the sensor, and this value is used to determine the degree of protein-antibody interaction. In this experiment, antibodies were categorized by 5 different classes that do not share the binding site.

TABLE 16

Screening Results of Antibodies by FACS, ELISA and Octet.

| Code | FACS (MFI) | ELISA (Native Ag) | ELISA (Denatured Ag) | Octet (KD) |
|---|---|---|---|---|
| STC2602 | 69.5 | 1.389 | 0.128 | 2.35E−09 |
| STC2701 | 1091 | 0.777 | 0.519 | |
| STC2702 | 1080 | 0.889 | 0.659 | |
| STC2703 | 2609 | 0.901 | 0.603 | |
| STC2704 | 121 | 1.02 | 1.098 | |
| STC2705 | 952 | 0.717 | 0.376 | |
| STC2706 | 902 | 0.691 | 0.349 | |
| STC2707 | 922 | 0.762 | 0.532 | |
| STC2708 | 1407 | 0.882 | 0.538 | |
| STC2709 | 587 | 0.555 | 0.302 | |
| STC2710 | 1410 | 0.856 | 0.517 | |
| STC2711 | 31.4 | 1.038 | 1.138 | |
| STC2712 | 4663 | 0.939 | 0.915 | |
| STC2713 | 2811 | 0.87 | 0.863 | |
| STC2714 | 4934 | 1.195 | 0.981 | 1.57E−09 |
| STC2715 | 5936 | 1.213 | 0.912 | 6.24E−07 |
| STC2716 | 241 | 1.183 | 1.244 | |
| STC2717 | 4670 | 1.183 | 1.193 | |
| STC2718 | 1803 | 0.937 | 0.645 | |
| STC2719 | 827 | 0.814 | 0.47 | |
| STC2720 | 605 | 0.743 | 0.343 | |
| STC2721 | 2566 | 1.04 | 0.85 | |
| STC2722 | 640 | 0.657 | 0.246 | |
| STC2723 | 443 | 0.931 | 0.737 | 2.37E−06 |

TABLE 16-continued

Screening Results of Antibodies by FACS, ELISA and Octet.

| Code | FACS (MFI) | ELISA (Native Ag) | ELISA (Denatured Ag) | Octet (KD) |
|---|---|---|---|---|
| STC2724 | 961 | 1.233 | 1.212 | |
| STC2725 | 132 | 1.077 | 0.959 | |
| STC2726 | 921 | 0.945 | 0.621 | |
| STC2727 | 5173 | 1.291 | 1.003 | 1.90E−10 |
| STC2728 | 1664 | 1.299 | 1.23 | |
| STC2729 | 1324 | 1.015 | 0.504 | |
| STC2730 | 985 | 0.932 | 0.395 | |
| STC2731 | 1703 | 1.204 | 0.933 | |
| STC2732 | 718 | 0.736 | 0.389 | |
| STC2733 | 2121 | 1.116 | 0.567 | |
| STC2734 | 321 | 0.959 | 0.824 | |
| STC2735 | 3699 | 1.043 | 0.895 | |
| STC2736 | 578 | 0.704 | 0.284 | |
| STC2737 | 2658 | 1.074 | 0.849 | |
| STC2738 | 832 | 0.897 | 0.417 | |
| STC2739 | 841 | 0.956 | 0.418 | 8.85E−11 |
| STC2740 | 702 | 0.702 | 0.329 | |
| STC2741 | 4887 | 1.297 | 1.058 | |
| STC2742 | 3615 | 1.385 | 1.278 | |
| STC2743 | 926 | 0.927 | 0.383 | |
| STC2744 | 656 | 0.877 | 0.362 | |
| STC2745 | 430 | 1.218 | 1.344 | |
| STC2746 | 1387 | | | |
| STC2747 | 530 | 0.385 | 0.798 | |
| STC2748 | 653 | 0.421 | 0.898 | |
| STC2749 | 1170 | 0.886 | 0.961 | |
| STC2750 | 1173 | 0.892 | 1.339 | |
| STC2751 | 4334 | 1.288 | 1.25 | |
| STC2752 | 508 | 1.165 | 1.276 | |
| STC2753 | 887 | 0.937 | 0.957 | |
| STC2754 | 1406 | 0.865 | 1.057 | |
| STC2755 | 356 | 1.215 | 1.254 | |
| STC2756 | 162 | 1.086 | 1.229 | |
| STC2757 | 602 | 1.175 | 1.157 | |
| STC2758 | 1233 | 1.014 | 1.204 | |
| STC2759 | 6077 | 1.047 | 1.289 | 2.42E−09 |
| STC2760 | 5558 | 1.179 | 1.403 | 1.63E−09 |
| STC2761 | 865 | 0.674 | 1.125 | |
| STC2762 | 726 | 1.148 | 1.252 | |
| STC2763 | 497 | 0.55 | 0.9 | |
| STC2764 | 1933 | 1.042 | 1.07 | |
| STC2765 | 768 | 0.729 | 1.022 | |
| STC2766 | 452 | 1.215 | 1.228 | |
| STC2767 | 904 | 0.862 | 1.109 | |
| STC2768 | 4732 | 2.006 | 1.686 | 9.07E−08 |
| STC2769 | 5036 | 2.099 | 1.576 | 4.37E−08 |
| STC2770 | 5428 | 1.992 | 1.681 | 6.54E−09 |
| STC2771 | 4965 | 1.932 | 1.643 | 1.81E−09 |
| STC2772 | 6434 | 1.937 | 1.485 | 1.27E−09 |
| STC2773 | 4604 | 2.116 | 1.626 | 4.45E−09 |
| STC2774 | 6467 | 2.009 | 1.391 | <1.0E−12 |
| STC2775 | 6410 | 1.945 | 1.544 | 2.57E−09 |
| STC2776 | 6480 | 2.195 | 1.695 | <1.0E−12 |
| STC2777 | 6780 | 2.039 | 1.634 | <1.0E−12 |
| STC2778 | 2341 | 1.799 | 1.442 | 4.36E−10 |
| STC2779 | 4879 | 2.042 | 1.455 | <1.0E−12 |
| STC2780 | 6325 | 2.059 | 1.628 | <1.0E−12 |
| STC2781 | 6446 | 2.103 | 1.383 | 1.77E−10 |

Antibody Sequencing.

To identify the DNA sequence of the antibody, total RNA was isolated from hybridoma cells using the RNeasy Mini RNA kit (Qiagen) and cDNA was generated using SuperScript II One-Step RT-PCR system (ThermoFisher). The variable region of the heavy chain (VH) and of the variable region (VL) of the light chain, which contains the complementarity determining regions (CDRs), were amplified using specific primer sets from the SMARTer® RACE cDNA Amplification Kit (Takara/Clontech), which was then used as the template in a PCR. The product was ligated into the pRACE expression vector. The PCR products ligated into pRACE in-fusion vectors were transformed into Top10 competent *E. coli* cells (ThermoFisher). The cloned vectors were selected, purified, and sequenced. The sequencing results were analyzed with the abYsis website (www.bioinf.org.uk/abysis2.7). The CDR region peptide sequences were corroborated by three different prediction methods. The sequences of the HC and LC of each antibody were aligned using Clustal Omega (www.ebi.ac.uk/Tools/msa/clustalo/). The antibody sequencing results revealed that most of antibodies have the same sequences in heavy and light chain.

T Cell-Mediated Killing of Cancer Cells.

Figure 14:
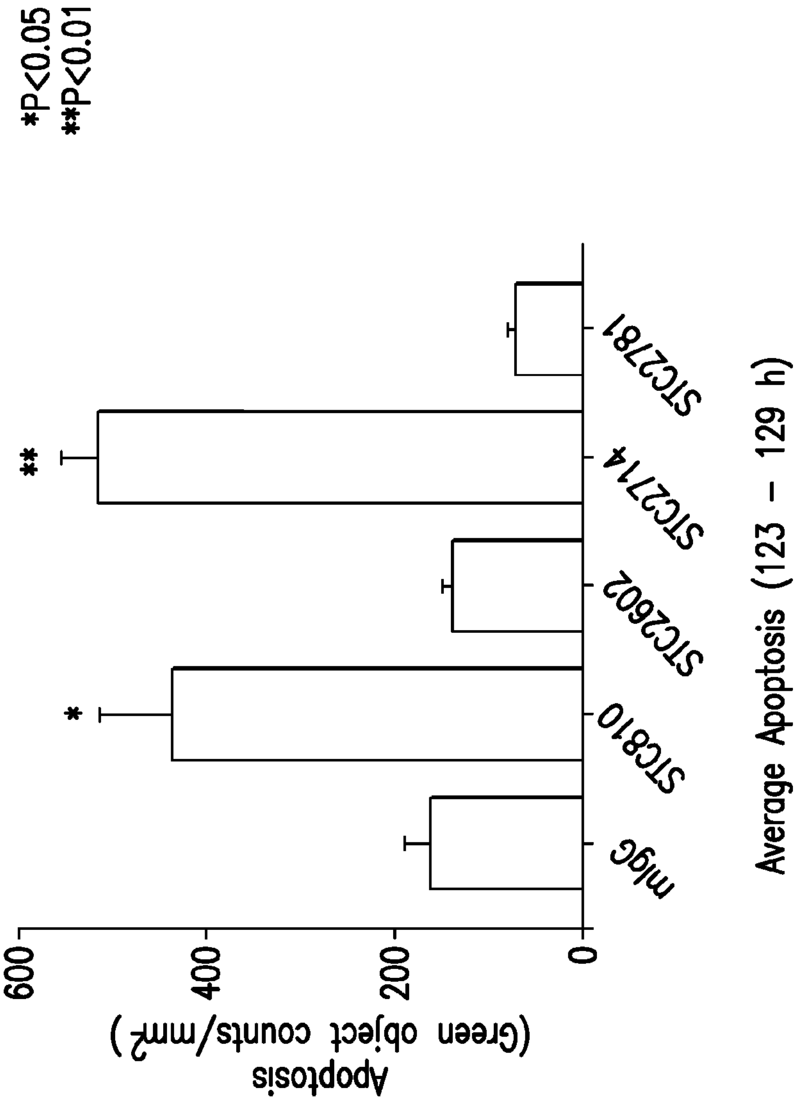

T cell killing assay is an effective minimized system in which to test the efficacy of immune checkpoint blockade agents, but BTN1A1 and its receptors may each be expressed by multiple cell types and T cells are only one component of the immune response to cancer. So in order to develop an in vitro model that better represents the immune environment in which cancer cell killing must occur, a cancer cell killing assay was developed using T cells from whole, naïve peripheral blood monocyte populations. To evaluate the killing of cancer cells by naïve T cells, PC3 human prostate cancer cells were stably transfected with human BTN1A1, then plated into a 96 well plate. Isolated T cells were added to each well, along with the indicated concentration of BTN1A1 antibodies. Finally, a cell-permeable reagent which is fluorescent only after cleavage by Caspase 3/7 was added as an apoptosis indicator. Apoptosis was enhanced in PC3 cells by the inclusion of STC2714 in the media, indicating that STC2714 blocks a suppressive signal mediated from the cancer cell to T cells in the context of the whole circulating immune component (FIG. 14).

Western Blot for Detection of Dimer-Specific BTN1A1 Antibody.

Figure 15:
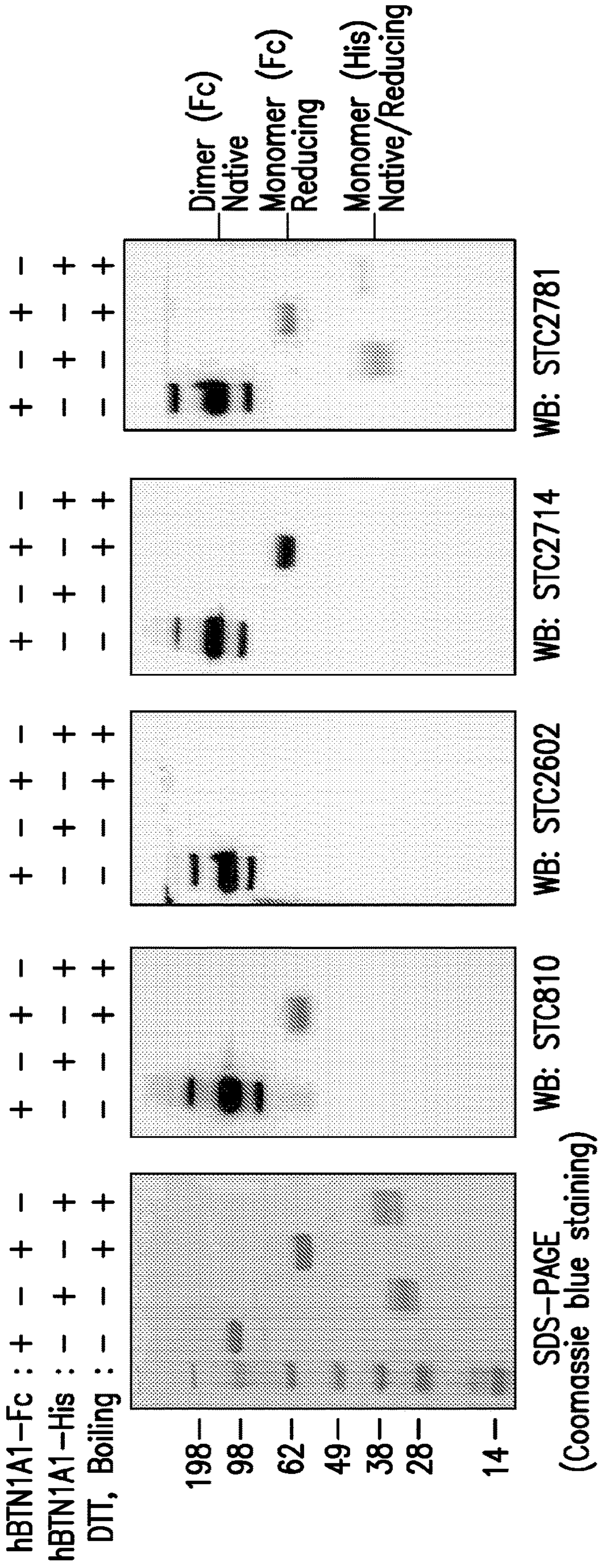

To determine the conformational specificity, Western blot analysis was performed using both dimer form of BTN1A1 (Fc fusion protein extracellular domain of BTN1A1) and monomer form of BTN1A1 (His-tagged protein of extracellular domain of BTN1A1). Proteins were treated with DTT (a reducing agent) and boiling or without reducing and denaturing by boiling. After running the proteins on, Western blot was performed by a standard protocol (FIG. 15). In a native condition (without a reducing agent and boiling), STC2714 recognized only Fc fusion protein, a dimerized form of BTN1A1 ECD, but not His-tagged protein, a monomer form of BTN1A1 ECD. Reduced BTN1A1-Fc also could be detected by STC2714, suggesting that this protein could be restored to a dimer form on the membrane during incubation. This result proposed that STC2714 is a dimer-specific antibody.

Binding Affinity of STC2714 to Dimer Form of BTN1A1.

Figure 16A:
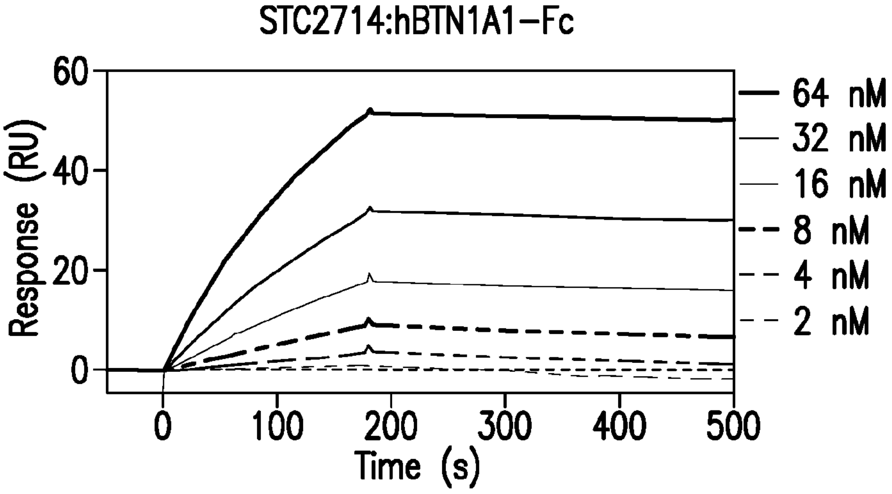
Figure 16B:
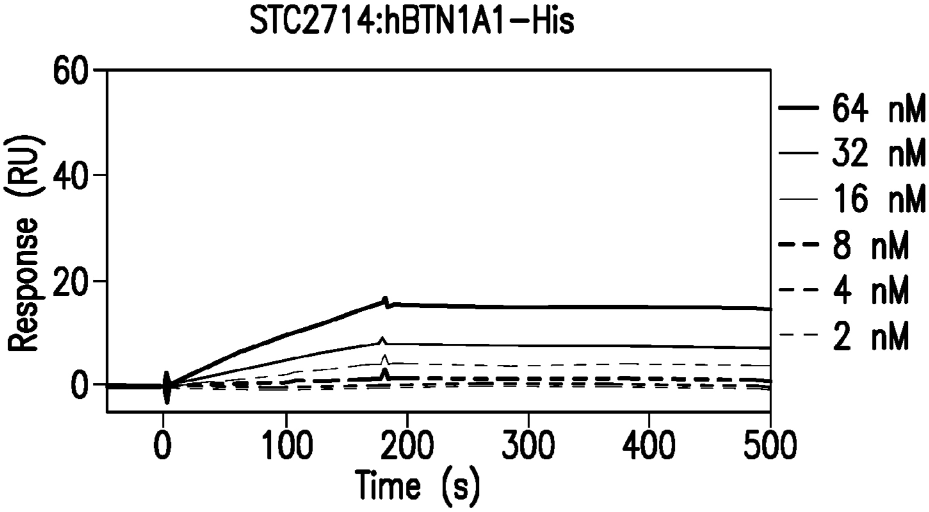

The $K_D$ value of STC2714 was determined using a Biacore X-100 system (GE Healthcare Life Science). The $K_D$ value was obtained by the process of association and dissociation of BTN1A1-Fc (a dimer form) and BTN1A1-His (a monomer form) in the mobile phase to STC2714 bound to a gold sensor chip immobilized with anti-mouse IgG antibody. A representative association/dissociation graph is shown in FIGS. 16A and B. STC2714 binds BTN1A1-Fc with high affinity ($K_D$=2.5 nM); while this antibody has 31.4 nM of $K_D$ to BTN1A1-His. This suggests that STC2714 has stronger affinity to a dimer form of BTN1A1 than to a monomer form of BTN1A1.

Throughout this application various publications have been referenced. The disclosures of these publications in their entireties are hereby incorporated by reference in this application in order to more fully describe the state of the art to which this disclosure pertains. While examples of certain particular embodiments are provided herein, it will be apparent to those skilled in the art that various changes and modifications may be made. Such modifications are also intended to fall within the scope of the appended claims.

What is claimed is:

1. A method of treating cancer in a subject in need thereof, comprising administering to the subject a therapeutically effective amount of a molecule comprising an antigen binding fragment that immunospecifically binds to BTN1A1, wherein the cancer expresses PD-L1 at a level lower than or equal to a PD-L1 reference level; wherein the PD-L1 reference level is the average or medium expression level of PD-L1 in a population of healthy individuals; and wherein the antigen binding fragment comprises:

(i) a heavy chain variable region ($V_H$) comprising a $V_H$ complementarity-determining region (CDR) 1, a $V_H$ CDR2, and a $V_H$ CDR3 having an amino acid sequence of a $V_H$ CDR1, a $V_H$ CDR2, and a $V_H$ CDR3, respectively, of a $V_H$ having an amino acid sequence of SEQ ID NO:31; and (ii) a light chain variable region ($V_L$) comprising a $V_L$ CDR1, a $V_L$ CDR2, and a $V_L$ CDR3 having an amino acid sequence of a $V_L$ CDR1, a $V_L$ CDR2, and a $V_L$ CDR3, respectively, of a $V_L$ having an amino acid sequence of SEQ ID NO:33.

2. The method of claim 1, wherein the antigen binding fragment thereof comprises:

(a) a $V_H$ comprising: a $V_H$ CDR1 having the amino acid sequence of SEQ ID NO:35, a $V_H$ CDR2 having the amino acid sequence of SEQ ID NO:36; and a $V_H$ CDR3 having the amino acid sequence of SEQ ID NO:37; and a $V_L$ comprising: a $V_L$ CDR1 having the amino acid sequence of SEQ ID NO:47; a $V_L$ CDR2 having the amino acid sequence of SEQ ID NO:48; and a $V_L$ CDR3 having the amino acid sequence of SEQ ID NO:49; or (b) a $V_H$ comprising: a $V_H$ CDR1 having the amino acid sequence of SEQ ID NO:38, a $V_H$ CDR2 having the amino acid sequence of SEQ ID NO:39; and a $V_H$ CDR3 having the amino acid sequence of SEQ ID NO:40; and a $V_L$ comprising: a $V_L$ CDR1 having the amino acid sequence of SEQ ID NO:50; a $V_L$ CDR2 having the amino acid sequence of SEQ ID NO:51; and a $V_L$ CDR3 having the amino acid sequence of SEQ ID NO:52; or (c) a $V_H$ comprising: a $V_H$ CDR1 having the amino acid sequence of SEQ ID NO:41, a $V_H$ CDR2 having the amino acid sequence of SEQ ID NO:42; and a $V_H$ CDR3 having the amino acid sequence of SEQ ID NO:43; and a $V_L$ comprising: a $V_L$ CDR1 having the amino acid sequence of SEQ ID NO:53; a $V_L$ CDR2 having the amino acid sequence of SEQ ID NO:54; and a $V_L$ CDR3 having the amino acid sequence of SEQ ID NO:55; or (d) a $V_H$ comprising: a $V_H$ CDR1 having the amino acid sequence of SEQ ID NO:44, a $V_H$ CDR2 having the amino acid sequence of SEQ ID NO:45; and a $V_H$ CDR3 having the amino acid sequence of SEQ ID NO:46; and a $V_L$ comprising: a $V_L$ CDR1 having the amino acid sequence of SEQ ID NO:56; a $V_L$ CDR2 having the amino acid sequence of SEQ ID NO:57; and a $V_L$ CDR3 having the amino acid sequence of SEQ ID NO:58.

3. The method of claim 1, wherein the antigen binding fragment thereof comprises a $V_L$ comprising an amino acid sequence having at least 95% identity to the amino acid sequence of SEQ ID NO:33.

4. The method of claim 1, wherein the antigen binding fragment thereof comprises a $V_L$ comprising the amino acid sequence of SEQ ID NO:33.

5. The method of claim 1, wherein the antigen binding fragment thereof comprises a $V_H$ comprising an amino acid sequence having at least 95% identity to the amino acid sequence of SEQ ID NO:31.

6. The method of claim 1, wherein the antigen binding fragment thereof comprises a $V_H$ comprising the amino acid sequence of SEQ ID NO:31.

7. The method of claim 1, wherein the antigen binding fragment thereof comprises a $V_L$ comprising an amino acid sequence having at least 95% identity to the amino acid sequence of SEQ ID NO:33; and a $V_H$ comprising an amino acid sequence having at least 95% identity to the amino acid sequence of SEQ ID NO:31.

8. The method of claim 1, wherein the antibody or the antigen-binding fragment thereof comprises a $V_L$ comprising the amino acid sequence of SEQ ID NO: 33; and a $V_H$ comprising the amino acid sequence of SEQ ID NO:31.

9. The method of claim 1, wherein the molecule is an antibody.

10. The method of claim 1, wherein the molecule is a monoclonal antibody or a humanized antibody.

11. The method of claim 9, wherein the antibody is an IgG, IgM, or IgA.

12. The method of claim 1, wherein the molecule comprising the antigen binding fragment that immunospecifically binds to BTN1A1 is a Fab', a F(ab') 2, a F(ab') 3, a monovalent scFv, or a bivalent scFv.

13. The method of claim 1, further comprising administering to the subject a radiation therapy.

14. The method of claim 13, wherein the radiation therapy is a high-dose radiation therapy.

15. The method of claim 1, further comprising administering to the subject a therapeutically effective amount of an anti-PD-1 therapy or an anti-PD-L1 therapy.

16. The method of claim 1, wherein the cancer is a breast cancer, a neuroendocrine prostate cancer (NEPC), a diffuse large B-cell lymphoma, a melanoma, a cancer from the National Cancer Institute cancer panel (NCI 60), a uveal melanoma, a pancreas cancer, an ovarian cancer, a uterine cancer, a lung adenocarcinoma, a desmoplastic small-round-cell tumor, a bladder cancer, a colorectal cancer, a lung squamous cell carcinoma, a liver cancer, a lung cancer, a stomach cancer, a cholangiocarcinoma, an esophagus squamous cell carcinoma, a head and neck cancer, a sarcoma, a prostate cancer, a liver cancer, a pancreas cancer, a pheochromocytoma or paraganglioma (PCPG), a cervical cancer, a glioma, or an acute myeloid leukemia (AML).

17. The method of claim 1, wherein the cancer is a breast cancer or a lung cancer.

18. The method of claim 1, wherein the cancer is a mammary carcinoma or a Lewis lung carcinoma.

19. The method of claim 1, wherein the cancer expresses BTN1A1 at a level higher than or equal to a BTN1A1 reference level; wherein the BTN1A1 reference level is the average or medium expression level of BTN1A1 in a population of healthy individuals.

20. The method of claim 1, wherein the treatment produces at least one therapeutic effect selected from a group consisting of a reduction in size of a tumor, a reduction in number of metastatic lesions over time, a complete response, a partial response, and a stable disease.

* * * * *

SEQUENCE LISTING

<160> NUMBER OF SEQ ID NOS: 332

<210> SEQ ID NO 1
<211> LENGTH: 526
<212> TYPE: PRT
<213> ORGANISM: Artificial Sequence
<220> FEATURE:
<223> OTHER INFORMATION: Synthetic polypeptide

<400> SEQUENCE: 1

```
Met Ala Val Phe Pro Ser Ser Gly Leu Pro Arg Cys Leu Leu Thr Leu
1               5                   10                  15

Ile Leu Leu Gln Leu Pro Lys Leu Asp Ser Ala Pro Phe Asp Val Ile
            20                  25                  30

Gly Pro Pro Glu Pro Ile Leu Ala Val Val Gly Glu Asp Ala Lys Leu
        35                  40                  45

Pro Cys Arg Leu Ser Pro Asn Ala Ser Ala Glu His Leu Glu Leu Arg
    50                  55                  60

Trp Phe Arg Lys Lys Val Ser Pro Ala Val Leu Val His Arg Asp Gly
65                  70                  75                  80

Arg Glu Gln Glu Ala Glu Gln Met Pro Glu Tyr Arg Gly Arg Ala Thr
                85                  90                  95

Leu Val Gln Asp Gly Ile Ala Lys Gly Arg Val Ala Leu Arg Ile Arg
            100                 105                 110

Gly Val Arg Val Ser Asp Asp Gly Glu Tyr Thr Cys Phe Phe Arg Glu
        115                 120                 125

Asp Gly Ser Tyr Glu Glu Ala Leu Val His Leu Lys Val Ala Ala Leu
    130                 135                 140

Gly Ser Asp Pro His Ile Ser Met Gln Val Gln Glu Asn Gly Glu Ile
145                 150                 155                 160

Cys Leu Glu Cys Thr Ser Val Gly Trp Tyr Pro Glu Pro Gln Val Gln
                165                 170                 175

Trp Arg Thr Ser Lys Gly Glu Lys Phe Pro Ser Thr Ser Glu Ser Arg
            180                 185                 190

Asn Pro Asp Glu Glu Gly Leu Phe Thr Val Ala Ala Ser Val Ile Ile
        195                 200                 205

Arg Asp Thr Ser Ala Lys Asn Val Ser Cys Tyr Ile Gln Asn Leu Leu
    210                 215                 220

Leu Gly Gln Glu Lys Lys Val Glu Ile Ser Ile Pro Ala Ser Ser Leu
225                 230                 235                 240

Pro Arg Leu Thr Pro Trp Ile Val Ala Val Ala Val Ile Leu Met Val
                245                 250                 255

Leu Gly Leu Leu Thr Ile Gly Ser Ile Phe Phe Thr Trp Arg Leu Tyr
            260                 265                 270

Asn Glu Arg Pro Arg Glu Arg Arg Asn Glu Phe Ser Ser Lys Glu Arg
        275                 280                 285

Leu Leu Glu Glu Leu Lys Trp Lys Lys Ala Thr Leu His Ala Val Asp
    290                 295                 300

Val Thr Leu Asp Pro Asp Thr Ala His Pro His Leu Phe Leu Tyr Glu
305                 310                 315                 320

Asp Ser Lys Ser Val Arg Leu Glu Asp Ser Arg Gln Lys Leu Pro Glu
                325                 330                 335

Lys Thr Glu Arg Phe Asp Ser Trp Pro Cys Val Leu Gly Arg Glu Thr
            340                 345                 350

Phe Thr Ser Gly Arg His Tyr Trp Glu Val Glu Val Gly Asp Arg Thr
```

-continued

```
        355                 360                 365

Asp Trp Ala Ile Gly Val Cys Arg Glu Asn Val Met Lys Lys Gly Phe
    370                 375                 380

Asp Pro Met Thr Pro Glu Asn Gly Phe Trp Ala Val Glu Leu Tyr Gly
385                 390                 395                 400

Asn Gly Tyr Trp Ala Leu Thr Pro Leu Arg Thr Pro Leu Pro Leu Ala
                405                 410                 415

Gly Pro Pro Arg Arg Val Gly Ile Phe Leu Asp Tyr Glu Ser Gly Asp
            420                 425                 430

Ile Ser Phe Tyr Asn Met Asn Asp Gly Ser Asp Ile Tyr Thr Phe Ser
        435                 440                 445

Asn Val Thr Phe Ser Gly Pro Leu Arg Pro Phe Phe Cys Leu Trp Ser
    450                 455                 460

Ser Gly Lys Lys Pro Leu Thr Ile Cys Pro Ile Ala Asp Gly Pro Glu
465                 470                 475                 480

Arg Val Thr Val Ile Ala Asn Ala Gln Asp Leu Ser Lys Glu Ile Pro
                485                 490                 495

Leu Ser Pro Met Gly Glu Asp Ser Ala Pro Arg Asp Ala Asp Thr Leu
            500                 505                 510

His Ser Lys Leu Ile Pro Thr Gln Pro Ser Gln Gly Ala Pro
        515                 520                 525


<210> SEQ ID NO 2
<211> LENGTH: 1581
<212> TYPE: DNA
<213> ORGANISM: Artificial Sequence
<220> FEATURE:
<223> OTHER INFORMATION: Synthetic polynucleotide

<400> SEQUENCE: 2

atggcagttt tcccaagctc cggtctcccc agatgtctgc tcaccctcat tctcctccag      60

ctgcccaaac tggattcagc tccctttgac gtgattggac ccccggagcc catcctggcc     120

gttgtgggtg aggacgccaa gctgccctgt cgcctgtctc cgaacgcgag cgccgagcac     180

ttggagctac gctggttccg aaagaaggtt tcgccggccg tgctggtgca tagggacggg     240

cgcgagcagg aagccgagca gatgcccgag taccgcgggc gggcgacgct ggtccaggac     300

ggcatcgcca aggggcgcgt ggccttgagg atccgtggcg tcagagtctc tgacgacggg     360

gagtacacgt gctttttcag ggaggatgga agctacgaag aagccctggt gcatctgaag     420

gtggctgctc tgggctctga ccctcacatc agtatgcaag ttcaagagaa tggagaaatc     480

tgtctggagt gcacctcagt gggatggtac ccagagcccc aggtgcagtg gagaacttcc     540

aagggagaga agtttccatc tacatcagag tccaggaatc ctgatgaaga aggtttgttc     600

actgtggctg cttcagtgat catcagagac acttctgcga aaaatgtgtc ctgctacatc     660

cagaatctcc ttcttggcca ggagaagaaa gtagaaatat ccataccagc ttcctccctc     720

ccaaggctga ctccctggat agtggctgtg gctgtcatcc tgatggttct aggacttctc     780

accattgggt ccatattttt cacttggaga ctatacaacg aaagacccag agagaggagg     840

aatgaattca gctctaaaga gagactcctg gaagaactca aatggaaaaa ggctaccttg     900

catgcagttg atgtgactct ggacccagac acagctcatc cccacctctt tctttatgag     960

gattcaaaat ctgttcgact ggaagattca cgtcagaaac tgcctgagaa aacagagaga    1020

tttgactcct ggccctgtgt gttgggccgt gagaccttca cctcaggaag gcattactgg    1080

gaggtggagg tgggagacag gactgactgg gcaatcggcg tgtgtaggga gaatgtgatg    1140
```

-continued

```
aagaaaggat ttgaccccat gactcctgag aatgggttct gggctgtaga gttgtatgga   1200

aatgggtact gggccctcac tcctctccgg acccctctcc cattggcagg gcccccacgc   1260

cgggttggga ttttcctaga ctatgaatca ggagacatct ccttctacaa catgaatgat   1320

ggatctgata tctatacttt ctccaatgtc actttctctg gcccccctccg gcccttcttt   1380

tgcctatggt ctagcggtaa aaagcccctg accatctgcc caattgctga tgggcctgag   1440

agggtcacag tcattgctaa tgcccaggac ctttctaagg agatcccatt gtcccccatg   1500

ggggaggact ctgcccctag ggatgcagac actctccatt ctaagctaat ccctacccaa   1560

cccagccaag ggcaccttta a                                             1581
```

<210> SEQ ID NO 3
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 3

```
Gln Gly Gln Met Gln Gln Ser Gly Ala Glu Leu Val Lys Pro Gly Ala
1               5                   10                  15

Ser Val Lys Leu Ser Cys Lys Thr Ser Gly Phe Thr Phe Ser Ser Arg
            20                  25                  30

Tyr Ile Ser Trp Leu Lys Gln Lys Pro Arg Gln Ser Leu Glu Trp Ile
        35                  40                  45

Ala Trp Ile Tyr Ala Gly Thr Gly Gly Thr Ser Tyr Asn Gln Lys Phe
    50                  55                  60

Thr Gly Lys Ala Gln Leu Thr Val Asp Thr Ser Ser Ser Thr Ala Tyr
65                  70                  75                  80

Met Gln Leu Ser Ser Leu Thr Ser Glu Asp Ser Ala Ile Tyr Tyr Cys
                85                  90                  95

Ala Arg Arg Arg Gly Leu Gly Tyr Phe Asp Tyr Trp Gly Gln Gly Thr
            100                 105                 110

Thr Leu Thr Val Ser Ser
        115
```

<210> SEQ ID NO 4
<211> LENGTH: 354
<212> TYPE: DNA
<213> ORGANISM: Artificial Sequence
<220> FEATURE:
<223> OTHER INFORMATION: Synthetic polynucleotide

<400> SEQUENCE: 4

```
cagggtcaga tgcagcagtc tggagctgag ctggtgaagc ctggggcttc agtgaagctg     60

tcctgcaaga cttctggctt caccttcagc agtaggtata taagttggtt gaagcagaag    120

cctcgacaga gtcttgagtg gattgcatgg atttatgctg gaactggtgg cactagttat    180

aatcagaagt tcacaggcaa ggcccaactg actgtagaca catcctccag cacagcctac    240

atgcaactca gcagcctgac atctgaggac tctgccatct attactgtgc aagacggagg    300

ggactagggt actttgacta ctggggccaa ggcaccactc tcacagtctc ctca          354
```

<210> SEQ ID NO 5
<211> LENGTH: 107
<212> TYPE: PRT
<213> ORGANISM: Artificial Sequence
<220> FEATURE:

<223> OTHER INFORMATION: Synthetic polypeptide

<400> SEQUENCE: 5

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Phe Ser Leu Lys Ile Asn Ser Leu Gln Ser
65                  70                  75                  80

Glu Asp Phe Gly Asn Tyr Tyr Cys Gln His Phe Trp Gly Ser Pro Trp
                85                  90                  95

Thr Phe Gly Gly Gly Thr Lys Leu Glu Ile Lys
            100                 105
```

<210> SEQ ID NO 6
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 6

```
gacatccaga tgactcagtc tccagcctcc ctatctgtgt ctgtgggaga aactgtcacc     60

atcacatgtc gagcaagtga gaatatttac agtaatttag catggtatca gcagaaacag    120

ggaaaatctc ctcagctcct ggtctatgct gcaacaaact tagcagatgg tgtgccatca    180

aggttcagtg gcagtggatc aggcacacag ttttccctca agatcaacag cctgcagtct    240

gaagattttg ggaattatta ctgtcaacat ttttggggtt ctccgtggac gttcggtgga    300

ggcaccaagc tggaaatcaa a                                              321
```

<210> SEQ ID NO 7
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 7

```
Gly Phe Thr Phe Ser Ser Arg
1               5
```

<210> SEQ ID NO 8
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 8

```
Tyr Ala Gly Thr Gly Gly
1               5
```

<210> SEQ ID NO 9
<211> LENGTH: 9
<212> TYPE: PRT
<213> ORGANISM: Artificial Sequence
<220> FEATURE:

<223> OTHER INFORMATION: Synthetic polypeptide

<400> SEQUENCE: 9

Arg Arg Gly Leu Gly Tyr Phe Asp Tyr
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 10

Gly Phe Thr Phe Ser Ser Arg Tyr Ile Ser
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 11

Trp Ile Tyr Ala Gly Thr Gly Gly Thr Ser
1               5                   10

<210> SEQ ID NO 12
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 12

Arg Arg Gly Leu Gly Tyr Phe Asp Tyr
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 13

Ser Arg Tyr Ile Ser
1               5

<210> SEQ ID NO 14
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 14

Trp Ile Tyr Ala Gly Thr Gly Gly Thr Ser Tyr Asn Gln Lys Phe Thr
1               5                   10                  15

Gly

<210> SEQ ID NO 15
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 15

Arg Arg Gly Leu Gly Tyr Phe Asp Tyr
1 5

<210> SEQ ID NO 16
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 16

Ser Ser Arg Tyr Ile Ser
1 5

<210> SEQ ID NO 17
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 17

Trp Ile Ala Trp Ile Tyr Ala Gly Thr Gly Gly Thr Ser
1 5 10

<210> SEQ ID NO 18
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 18

Ala Arg Arg Arg Gly Leu Gly Tyr Phe Asp
1 5 10

<210> SEQ ID NO 19
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 19

Arg Ala Ser Glu Asn Ile Tyr Ser Asn Leu Ala
1 5 10

<210> SEQ ID NO 20
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 20

Ala Ala Thr Asn Leu Ala Asp
1 5

<210> SEQ ID NO 21
<211> LENGTH: 9
<212> TYPE: PRT
<213> ORGANISM: Artificial Sequence
<220> FEATURE:

-continued

<223> OTHER INFORMATION: Synthetic polypeptide

<400> SEQUENCE: 21

Gln His Phe Trp Gly Ser Pro Trp Thr
1 5

<210> SEQ ID NO 22
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 22

Arg Ala Ser Glu Asn Ile Tyr Ser Asn Leu Ala
1 5 10

<210> SEQ ID NO 23
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 23

Ala Ala Thr Asn Leu Ala Asp
1 5

<210> SEQ ID NO 24
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 24

Gln His Phe Trp Gly Ser Pro Trp Thr
1 5

<210> SEQ ID NO 25
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 25

Arg Ala Ser Glu Asn Ile Tyr Ser Asn Leu Ala
1 5 10

<210> SEQ ID NO 26
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 26

Ala Ala Thr Asn Leu Ala Asp
1 5

<210> SEQ ID NO 27
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 27

Gln His Phe Trp Gly Ser Pro Trp Thr
1 5

<210> SEQ ID NO 28
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 28

Tyr Ser Asn Leu Ala Trp Tyr
1 5

<210> SEQ ID NO 29
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 29

Leu Leu Val Tyr Ala Ala Thr Asn Leu Ala
1 5 10

<210> SEQ ID NO 30
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 30

Gln His Phe Trp Gly Ser Pro Trp
1 5

<210> SEQ ID NO 31
<211> LENGTH: 125
<212> TYPE: PRT
<213> ORGANISM: Artificial Sequence
<220> FEATURE:
<223> OTHER INFORMATION: Synthetic polypeptide

<400> SEQUENCE: 31

Glu Val Gln Leu Gln Gln Ser Gly Pro Glu Leu Val Lys Pro Gly Ala
1 5 10 15

Ser Val Lys Ile Ser Cys Lys Ala Ser Gly Tyr Thr Phe Thr His Tyr
20 25 30

Asn Met Asp Trp Val Lys Gln Ser His Gly Lys Ser Leu Glu Trp Ile
35 40 45

Gly Tyr Ile Tyr Pro Ser Asn Gly Gly Thr Gly Tyr Asn Gln Lys Phe
50 55 60

Lys Ser Arg Ala Thr Leu Thr Val Asp Lys Ser Ser Ser Thr Ala Tyr
65 70 75 80

Met Glu Leu His Ser Leu Thr Ser Glu Asp Ser Ala Val Tyr Tyr Cys
85 90 95

Ala Arg Gly Ala Tyr His Tyr Gly Ser Ser Tyr Ala Tyr Trp Tyr Phe
100 105 110

Asp Val Trp Gly Ala Gly Thr Thr Val Thr Val Ser Ser
115 120 125

<210> SEQ ID NO 32
<211> LENGTH: 375
<212> TYPE: DNA
<213> ORGANISM: Artificial Sequence
<220> FEATURE:
<223> OTHER INFORMATION: Synthetic polynucleotide

<400> SEQUENCE: 32
gaggtccagc tgcagcagtc tggacctgag ctggtgaagc ctggggcttc agtgaagata 60
tcctgcaagg cttctggata cacattcact cactacaaca tggactgggt gaagcagagc 120
catggaaaga gccttgaatg gattggatat atttatcctt ccaatggtgg tactggctac 180
aaccagaaat tcaagagcag ggccacattg actgtagaca agtcctccag cacagcctac 240
atggaactcc acagcctgac atctgaggac tctgcagtct attactgtgc aagaggggcc 300
tatcactacg gtagttccta cgcctactgg tacttcgatg tctggggcgc agggaccacg 360
gtcaccgtct cctca 375

<210> SEQ ID NO 33
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 33

Asp Ile Gln Met Thr Gln Thr Thr Ser Ser Leu Ser Ala Ser Leu Gly
1 5 10 15

Asp Arg Val Thr Ile Ser Cys Ser Ala Ser Gln Asp Ile Ser Asn Tyr
20 25 30

Leu Asn Trp Tyr Gln Gln Lys Pro Asp Glu Thr Val Lys Leu Leu Ile
35 40 45

Ser Tyr Thr Ser Ser Leu His Ser Gly Val Pro Ser Arg Phe Ser Gly
50 55 60

Ser Gly Ser Gly Thr Asp Tyr Ser Leu Thr Ile Ser Asn Leu Ala Pro
65 70 75 80

Glu Asp Ile Ala Thr Tyr Tyr Cys Gln Gln Ser Ser Lys Leu Pro Phe
85 90 95

Thr Phe Gly Ser Gly Thr Glu Leu Glu Ile Lys Arg Ala
100 105

<210> SEQ ID NO 34
<211> LENGTH: 327
<212> TYPE: DNA
<213> ORGANISM: Artificial Sequence
<220> FEATURE:
<223> OTHER INFORMATION: Synthetic polynucleotide

<400> SEQUENCE: 34
gatatccaga tgacacagac tacatcctcc ctgtctgcct ctctgggaga cagagtcacc 60
atcagttgca gtgcaagtca ggacattagc aattatttaa actggtatca gcagaaacca 120
gatgaaactg ttaaactcct gatctcttac acatcaagtt tacactcagg agtcccatca 180
agattcagtg gcagtgggtc tgggacagat tattctctca ccatcagcaa cctggcacct 240
gaagatattg ccacttacta ttgtcagcag tctagtaagc ttccattcac gttcggctcg 300
gggacagagt tggaaataaa acgggct 327

<210> SEQ ID NO 35

<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 35

Gly Tyr Thr Phe Thr His Tyr
1 5

<210> SEQ ID NO 36
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 36

Tyr Pro Ser Asn Gly Gly
1 5

<210> SEQ ID NO 37
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 37

Gly Ala Tyr His Tyr Gly Ser Ser Tyr Ala Tyr Trp Tyr Phe Asp Val
1 5 10 15

<210> SEQ ID NO 38
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 38

Gly Tyr Thr Phe Thr His Tyr Asn Met Asp
1 5 10

<210> SEQ ID NO 39
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 39

Tyr Ile Tyr Pro Ser Asn Gly Gly Thr Gly
1 5 10

<210> SEQ ID NO 40
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 40

Gly Ala Tyr His Tyr Gly Ser Ser Tyr Ala Tyr Trp Tyr Phe Asp Val
1 5 10 15

<210> SEQ ID NO 41
<211> LENGTH: 5

```
<212> TYPE: PRT
<213> ORGANISM: Artificial Sequence
<220> FEATURE:
<223> OTHER INFORMATION: Synthetic polypeptide

<400> SEQUENCE: 41

His Tyr Asn Met Asp
1               5


<210> SEQ ID NO 42
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 42

Tyr Ile Tyr Pro Ser Asn Gly Gly Thr Gly Tyr Asn Gln Lys Phe Lys
1               5                   10                  15

Ser


<210> SEQ ID NO 43
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 43

Gly Ala Tyr His Tyr Gly Ser Ser Tyr Ala Tyr Trp Tyr Phe Asp Val
1               5                   10                  15


<210> SEQ ID NO 44
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 44

Thr His Tyr Asn Met Asp
1               5


<210> SEQ ID NO 45
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 45

Trp Ile Gly Tyr Ile Tyr Pro Ser Asn Gly Gly Thr Gly
1               5                   10


<210> SEQ ID NO 46
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 46

Ala Arg Gly Ala Tyr His Tyr Gly Ser Ser Tyr Ala Tyr Trp Tyr Phe
1               5                   10                  15

Asp
```

<210> SEQ ID NO 47
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 47

Ser Ala Ser Gln Asp Ile Ser Asn Tyr Leu Asn
1               5                   10

<210> SEQ ID NO 48
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 48

Tyr Thr Ser Ser Leu His Ser
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 49

Gln Gln Ser Ser Lys Leu Pro Phe Thr
1               5

<210> SEQ ID NO 50
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 50

Ser Ala Ser Gln Asp Ile Ser Asn Tyr Leu Asn
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 51

Tyr Thr Ser Ser Leu His Ser
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 52

Gln Gln Ser Ser Lys Leu Pro Phe Thr
1               5

<210> SEQ ID NO 53
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 53

Ser Ala Ser Gln Asp Ile Ser Asn Tyr Leu Asn
1 5 10

<210> SEQ ID NO 54
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 54

Tyr Thr Ser Ser Leu His Ser
1 5

<210> SEQ ID NO 55
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 55

Gln Gln Ser Ser Lys Leu Pro Phe Thr
1 5

<210> SEQ ID NO 56
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 56

Ser Asn Tyr Leu Asn Trp Tyr
1 5

<210> SEQ ID NO 57
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 57

Leu Leu Ile Ser Tyr Thr Ser Ser Leu His
1 5 10

<210> SEQ ID NO 58
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 58

Gln Gln Ser Ser Lys Leu Pro Phe
1 5

<210> SEQ ID NO 59

<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 59

```
Gln Gly Gln Met Gln Gln Ser Gly Ala Glu Leu Val Lys Pro Gly Ala
1               5                   10                  15

Ser Val Lys Leu Ser Cys Lys Thr Ser Gly Phe Thr Phe Ser Ser Arg
            20                  25                  30

Tyr Ile Ser Trp Leu Lys Gln Lys Pro Arg Gln Ser Leu Glu Trp Ile
        35                  40                  45

Ala Trp Ile Tyr Ala Gly Thr Gly Gly Thr Ser Tyr Asn Gln Lys Phe
    50                  55                  60

Thr Gly Lys Ala Gln Leu Thr Val Asp Thr Ser Ser Ser Thr Ala Tyr
65                  70                  75                  80

Met Gln Leu Ser Ser Leu Thr Ser Glu Asp Ser Ala Ile Tyr Tyr Cys
                85                  90                  95

Ala Arg Arg Arg Gly Gly Gly Tyr Phe Asp Tyr Trp Gly Gln Gly Thr
            100                 105                 110

Thr Leu Thr Val Ser Ser
        115
```

<210> SEQ ID NO 60
<211> LENGTH: 354
<212> TYPE: DNA
<213> ORGANISM: Artificial Sequence
<220> FEATURE:
<223> OTHER INFORMATION: Synthetic polynucleotide

<400> SEQUENCE: 60

```
cagggtcaga tgcagcagtc tggagctgag ctggtgaagc ctggggcttc agtgaagctg     60

tcctgcaaga cttctggctt caccttcagc agtaggtata taagttggtt gaagcagaag    120

cctcgacaga gtcttgagtg gattgcatgg atttatgctg gaactggtgg tactagctat    180

aatcagaagt tcacaggcaa ggcccaactg actgtagaca catcctccag cacagcctac    240

atgcaactca gcagcctgac atctgaggac tctgccatct attactgtgc aagacgaagg    300

ggcggcggtt actttgacta ctggggccaa ggcaccactc tcacagtctc ctca          354
```

<210> SEQ ID NO 61
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 61

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Phe Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80
```

Glu Asp Phe Gly Ser Tyr Tyr Cys Gln His Phe Trp Gly Ser Pro Trp
            85                  90                  95

Thr Phe Gly Gly Gly Thr Lys Leu Glu Ile Lys
            100                 105

<210> SEQ ID NO 62
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 62
gacatccaga tgactcagtc tccagcctcc ctatctgtat ctgtgggaga aactgtcacc      60
atcacatgtc gagcaagtga gaatattttc agtaatttag catggtatca gcagaaacag     120
ggaaaatctc ctcagctcct ggtctatgct gcaacaaact tagcagatgg tgtgccatca     180
aggttcagtg gcagtggatc aggcacacag tattccctca agatcaacag cctgcagtct     240
gaggattttg ggagttatta ctgtcaacat ttttggggtt ctccgtggac gttcggtgga     300
ggcaccaagc tggaaatcaa a                                               321

<210> SEQ ID NO 63
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 63

Gly Phe Thr Phe Ser Ser Arg
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 64

Tyr Ala Gly Thr Gly Gly
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 65

Arg Arg Gly Gly Gly Tyr Phe Asp Tyr
1               5

<210> SEQ ID NO 66
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 66

Gly Phe Thr Phe Ser Ser Arg Tyr Ile Ser
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 67

```
Trp Ile Tyr Ala Gly Thr Gly Gly Thr Ser
1               5                   10
```

<210> SEQ ID NO 68
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 68

```
Arg Arg Gly Gly Gly Tyr Phe Asp Tyr
1               5
```

<210> SEQ ID NO 69
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 69

```
Ser Arg Tyr Ile Ser
1               5
```

<210> SEQ ID NO 70
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 70

```
Trp Ile Tyr Ala Gly Thr Gly Gly Thr Ser Tyr Asn Gln Lys Phe Thr
1               5                   10                  15

Gly
```

<210> SEQ ID NO 71
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 71

```
Arg Arg Gly Gly Gly Tyr Phe Asp Tyr
1               5
```

<210> SEQ ID NO 72
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 72

```
Ser Ser Arg Tyr Ile Ser
```

1 5

<210> SEQ ID NO 73
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 73

Trp Ile Ala Trp Ile Tyr Ala Gly Thr Gly Gly Thr Ser
1 5 10

<210> SEQ ID NO 74
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 74

Ala Arg Arg Arg Gly Gly Gly Tyr Phe Asp
1 5 10

<210> SEQ ID NO 75
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 75

Arg Ala Ser Glu Asn Ile Phe Ser Asn Leu Ala
1 5 10

<210> SEQ ID NO 76
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 76

Ala Ala Thr Asn Leu Ala Asp
1 5

<210> SEQ ID NO 77
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 77

Gln His Phe Trp Gly Ser Pro Trp Thr
1 5

<210> SEQ ID NO 78
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 78

Arg Ala Ser Glu Asn Ile Phe Ser Asn Leu Ala
1 5 10

<210> SEQ ID NO 79
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 79

Ala Ala Thr Asn Leu Ala Asp
1 5

<210> SEQ ID NO 80
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 80

Gln His Phe Trp Gly Ser Pro Trp Thr
1 5

<210> SEQ ID NO 81
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 81

Arg Ala Ser Glu Asn Ile Phe Ser Asn Leu Ala
1 5 10

<210> SEQ ID NO 82
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 82

Ala Ala Thr Asn Leu Ala Asp
1 5

<210> SEQ ID NO 83
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 83

Gln His Phe Trp Gly Ser Pro Trp Thr
1 5

<210> SEQ ID NO 84
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 84

Phe Ser Asn Leu Ala Trp
1 5

<210> SEQ ID NO 85
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 85

Leu Leu Val Tyr Ala Ala Thr Asn Leu Ala
1 5 10

<210> SEQ ID NO 86
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 86

Gln His Phe Trp Gly Ser Pro Trp
1 5

<210> SEQ ID NO 87
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 87

Glu Val Gln Leu Gln Gln Ser Gly Pro Glu Leu Val Lys Pro Gly Asp
1 5 10 15

Ser Val Lys Met Ser Cys Lys Ala Ser Gly Tyr Thr Phe Thr Asp Tyr
20 25 30

Tyr Met Asp Trp Val Lys Gln Ser His Gly Lys Ser Leu Glu Trp Ile
35 40 45

Gly Tyr Ile Ser Pro Asn Asn Gly Gly Thr Lys Tyr Asn Gln Lys Phe
50 55 60

Lys Gly Lys Ala Thr Leu Thr Val Asp Lys Ser Ser Ser Thr Ala Tyr
65 70 75 80

Met Glu Leu His Ser Leu Thr Ser Glu Asp Ser Ala Val Tyr Tyr Cys
85 90 95

Ala Arg Glu Pro Asp Leu Leu Tyr Tyr Phe Asp Tyr Trp Gly Gln Gly
100 105 110

Thr Thr Leu Thr Val Ser Ser
115

<210> SEQ ID NO 88
<211> LENGTH: 358
<212> TYPE: DNA
<213> ORGANISM: Artificial Sequence
<220> FEATURE:
<223> OTHER INFORMATION: Synthetic polynucleotide

<400> SEQUENCE: 88
gaggtccagc tgcaacagtc tggacctgag ctggtgaagc ctggggattc agtgaagatg 60
tcctgcaagg cttctggcta cacattcact gactactaca tggactgggt gaagcagagc 120
catggaaaga gccttgagtg gattggatat atttctccta acaatggtgg tactaagtac 180
aatcagaagt tcaagggcaa ggccacattg actgttgaca agtcctccag cacagcctac 240
atggagctcc acagcctgac atctgaggac tctgcagtct attactgtgc aagagagccc 300
gacctgcttt actactttga ctactggggc caaggcacca ctctcacagt ctcctcag 358

<210> SEQ ID NO 89
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 89

Asp Ile Val Met Ser Gln Ser Pro Ser Ser Leu Ala Val Ser Val Gly
1 5 10 15

Glu Lys Val Ile Met Ser Cys Lys Ser Ser Gln Ser Leu Leu Tyr Phe
20 25 30

Ser Asn Gln Lys Asn Tyr Leu Ala Trp Tyr Gln Gln Lys Pro Gly Gln
35 40 45

Ser Pro Arg Leu Leu Ile Tyr Trp Ala Ser Thr Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Lys Ala Glu Asp Leu Ala Val Tyr Tyr Cys Gln Gln
85 90 95

Tyr Tyr Ser Tyr Pro Trp Thr Phe Gly Gly Gly Thr Lys Leu Glu Ile
100 105 110

Lys

<210> SEQ ID NO 90
<211> LENGTH: 340
<212> TYPE: DNA
<213> ORGANISM: Artificial Sequence
<220> FEATURE:
<223> OTHER INFORMATION: Synthetic polynucleotide

<400> SEQUENCE: 90
gacattgtga tgtcacagtc tccatcctcc ctagctgtgt cagttggaga gaaggttatt 60
atgagctgca agtccagtca gagcctttta tattttagca atcaaaagaa ctacttggcc 120
tggtaccagc agaaaccagg gcagtctcct agactgctga tttactgggc atccactagg 180
gaatctgggg tccctgatcg cttcacaggc agtggatctg ggacagattt cactctcacc 240
atcagcagtg tgaaggctga agacctggca gtttattact gtcagcaata ttatagctat 300
ccgtggacgt tcggtggagg caccaagctg gaaatcaaac 340

<210> SEQ ID NO 91
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 91

Gly Tyr Thr Phe Thr Asp Tyr
1 5

<210> SEQ ID NO 92
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 92

Ser Pro Asn Asn Gly Gly Thr
1 5

<210> SEQ ID NO 93
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 93

Glu Pro Asp Leu Leu Tyr Tyr Phe Asp Tyr
1 5 10

<210> SEQ ID NO 94
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 94

Gly Tyr Thr Phe Thr Asp Tyr Tyr Met Asp
1 5 10

<210> SEQ ID NO 95
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 95

Tyr Ile Ser Pro Asn Asn Gly Gly Thr Lys
1 5 10

<210> SEQ ID NO 96
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 96

Glu Pro Asp Leu Leu Tyr Tyr Phe Asp Tyr
1 5 10

<210> SEQ ID NO 97
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 97

Asp Tyr Tyr Met Asp
1 5

<210> SEQ ID NO 98
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 98

Tyr Ile Ser Pro Asn Asn Gly Gly Thr Lys Tyr Asn Gln Lys Phe Lys
1 5 10 15

Gly

<210> SEQ ID NO 99
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 99

Glu Pro Asp Leu Leu Tyr Tyr Phe Asp Tyr
1 5 10

<210> SEQ ID NO 100
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 100

Thr Asp Tyr Tyr Met Asp
1 5

<210> SEQ ID NO 101
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 101

Ser Leu Glu Trp Ile Gly Tyr Ile Ser Pro Asn Asn Gly Gly Thr Lys
1 5 10 15

<210> SEQ ID NO 102
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 102

Ala Arg Glu Pro Asp Leu Leu Tyr Tyr Phe Asp
1 5 10

<210> SEQ ID NO 103
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 103

Ser Ala Ser Gln Asp Ile Ser Asn Tyr Leu Asn
1 5 10

<210> SEQ ID NO 104
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 104

Tyr Thr Ser Ser Leu His Ser
1 5

<210> SEQ ID NO 105
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 105

Gln Gln Ser Ser Lys Leu Pro Phe Thr
1 5

<210> SEQ ID NO 106
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 106

Ser Ala Ser Gln Asp Ile Ser Asn Tyr Leu Asn
1 5 10

<210> SEQ ID NO 107
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 107

Tyr Thr Ser Ser Leu His Ser
1 5

<210> SEQ ID NO 108
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 108

Gln Gln Ser Ser Lys Leu Pro Phe Thr
1 5

<210> SEQ ID NO 109
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 109

Ser Ala Ser Gln Asp Ile Ser Asn Tyr Leu Asn
1 5 10

<210> SEQ ID NO 110
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 110

Tyr Thr Ser Ser Leu His Ser
1 5

<210> SEQ ID NO 111
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 111

Gln Gln Ser Ser Lys Leu Pro Phe Thr
1 5

<210> SEQ ID NO 112
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 112

Ser Asn Tyr Leu Asn Trp Tyr
1 5

<210> SEQ ID NO 113
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 113

Leu Leu Ile Ser Tyr Thr Ser Ser Leu His
1 5 10

<210> SEQ ID NO 114
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 114

Gln Gln Ser Ser Lys Leu Pro Phe
1 5

<210> SEQ ID NO 115
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 115

Glu Val Met Leu Val Glu Ser Gly Gly Ala Leu Val Lys Pro Gly Gly
1 5 10 15

Ser Leu Lys Leu Ser Cys Ala Ala Ser Gly Phe Thr Phe Ser Asn Tyr
20 25 30

Val Met Ser Trp Val Arg Gln Thr Pro Glu Lys Arg Leu Glu Trp Val
35 40 45

Ala Thr Ile Ser Ser Gly Gly Ser Tyr Thr Asn Tyr Pro Asp Ser Val
50 55 60

Lys Gly Arg Phe Ile Ile Ser Arg Asp Asn Ala Arg Asn Thr Leu Tyr

```
65                  70                  75                  80

Leu Gln Met Ser Ser Leu Arg Ser Glu Asp Thr Ala Ile Tyr Tyr Cys
                85                  90                  95

Val Arg Glu Gly Asp Gly Phe Tyr Val Phe Asp Tyr Trp Gly Leu Gly
            100                 105                 110

Thr Thr Leu Thr Val Ser Ser
        115
```

<210> SEQ ID NO 116
<211> LENGTH: 357
<212> TYPE: DNA
<213> ORGANISM: Artificial Sequence
<220> FEATURE:
<223> OTHER INFORMATION: Synthetic polynucleotide

<400> SEQUENCE: 116

```
gaagtgatgc tggtggagtc tgggggagcc ttagtgaagc ctggagggtc cctgaaactc     60

tcctgtgcag cctctggatt cactttcagc aattatgtca tgtcttgggt tcgccagact    120

ccagagaaga ggctggagtg ggtcgcaacc attagtagtg gtggtagtta caccaattat    180

ccagacagtg tgaagggtcg attcatcatc tccagagaca atgccaggaa caccctgtac    240

ctgcaaatga gcagtctgag gtctgaggac acggccatat attactgtgt aagagagggg    300

gatggtttct acgtctttga ctactggggc ctaggcacca ctctcacagt ctcctca       357
```

<210> SEQ ID NO 117
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 117

```
Asp Ile Val Met Ser Gln Ser Pro Ser Ser Leu Ala Val Ser Val Gly
1               5                   10                  15

Glu Lys Val Ile Met Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Trp Thr Phe Gly Gly Gly Thr Lys Leu Glu Ile
            100                 105                 110

Lys
```

<210> SEQ ID NO 118
<211> LENGTH: 339
<212> TYPE: DNA
<213> ORGANISM: Artificial Sequence
<220> FEATURE:
<223> OTHER INFORMATION: Synthetic polynucleotide

<400> SEQUENCE: 118

```
gacattgtga tgtcacagtc tccatcctcc ctagctgtgt cagttggaga gaaggttatt     60

atgagctgca agtccagtca gagcctttta tatagtggca atcaaaagaa ctacttggcc    120
```

tggtaccagc agaaaccagg gcagtctcct aaactgctga tttactgggc atccactagg 180
gaatctgggg tccctgatcg cttcacaggc agtggatctg ggacagattt cactctcacc 240
atcagcagtg tgaaggctga agacctggca gtttattact gtcagcaata ttatagctat 300
ccgtggacgt tcggtggagg caccaagctg gaaatcaaa 339

<210> SEQ ID NO 119
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 119

Gly Phe Thr Phe Ser Asn Tyr
1 5

<210> SEQ ID NO 120
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 120

Ser Ser Gly Gly Ser Tyr
1 5

<210> SEQ ID NO 121
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 121

Glu Gly Asp Gly Phe Tyr Val Phe Asp Tyr
1 5 10

<210> SEQ ID NO 122
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 122

Gly Phe Thr Phe Ser Asn Tyr Val Met Ser
1 5 10

<210> SEQ ID NO 123
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 123

Thr Ile Ser Ser Gly Gly Ser Tyr Thr Asn
1 5 10

<210> SEQ ID NO 124
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 124

Glu Gly Asp Gly Phe Tyr Val Phe Asp Tyr
1 5 10

<210> SEQ ID NO 125
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 125

Asn Tyr Val Met Ser
1 5

<210> SEQ ID NO 126
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 126

Thr Ile Ser Ser Gly Gly Ser Tyr Thr Asn Tyr Pro Asp Ser Val Lys
1 5 10 15

Gly

<210> SEQ ID NO 127
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 127

Glu Gly Asp Gly Phe Tyr Val Phe Asp Tyr
1 5 10

<210> SEQ ID NO 128
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 128

Ser Asn Tyr Val Met Ser
1 5

<210> SEQ ID NO 129
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 129

Trp Val Ala Thr Ile Ser Ser Gly Gly Ser Tyr Thr Asn
1 5 10

<210> SEQ ID NO 130
<211> LENGTH: 11
<212> TYPE: PRT

<213> ORGANISM: Artificial Sequence
<220> FEATURE:
<223> OTHER INFORMATION: Synthetic polypeptide

<400> SEQUENCE: 130

Val Arg Glu Gly Asp Gly Phe Tyr Val Phe Asp
1 5 10

<210> SEQ ID NO 131
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 131

Lys Ser Ser Gln Ser Leu Leu Tyr Ser Gly Asn Gln Lys Asn Tyr Leu
1 5 10 15

Ala

<210> SEQ ID NO 132
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 132

Trp Ala Ser Thr Arg Glu Ser
1 5

<210> SEQ ID NO 133
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 133

Gln Gln Tyr Tyr Ser Tyr Pro Trp Thr
1 5

<210> SEQ ID NO 134
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 134

Lys Ser Ser Gln Ser Leu Leu Tyr Ser Gly Asn Gln Lys Asn Tyr Leu
1 5 10 15

Ala

<210> SEQ ID NO 135
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 135

Trp Ala Ser Thr Arg Glu Ser
1 5

<210> SEQ ID NO 136
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 136

Gln Gln Tyr Tyr Ser Tyr Pro Trp Thr
1 5

<210> SEQ ID NO 137
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 137

Lys Ser Ser Gln Ser Leu Leu Tyr Ser Gly Asn Gln Lys Asn Tyr Leu
1 5 10 15

Ala

<210> SEQ ID NO 138
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 138

Trp Ala Ser Thr Arg Glu Ser
1 5

<210> SEQ ID NO 139
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 139

Gln Gln Tyr Tyr Ser Tyr Pro Trp Thr
1 5

<210> SEQ ID NO 140
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 140

Leu Tyr Ser Gly Asn Gln Lys Asn Tyr Leu Ala Trp Tyr
1 5 10

<210> SEQ ID NO 141
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 141

Leu Leu Ile Tyr Trp Ala Ser Thr Arg Glu
1 5 10

<210> SEQ ID NO 142
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 142

```
Gln Gln Tyr Tyr Ser Tyr Pro Trp
1               5
```

<210> SEQ ID NO 143
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 143

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Lys Gln Ser His Gly Lys Ser Leu Glu Trp Ile
        35                  40                  45

Gly Arg Ile Asn Pro Tyr Asn Gly Asp Thr Phe Tyr Asn Gln Lys Phe
    50                  55                  60

Lys Asp Lys Ala Thr Leu Thr Val Asp Thr Ser Ser Ser Thr Ala His
65                  70                  75                  80

Met Glu Leu Arg Ser Leu Thr Ser Glu Glu Ser Ala Val Tyr Tyr Cys
                85                  90                  95

Ala Arg Trp Thr Thr Val Ile Asn Phe Asp Tyr Trp Gly Gln Gly Thr
            100                 105                 110

Thr Leu Thr Val Ser Ser
        115
```

<210> SEQ ID NO 144
<211> LENGTH: 354
<212> TYPE: DNA
<213> ORGANISM: Artificial Sequence
<220> FEATURE:
<223> OTHER INFORMATION: Synthetic polynucleotide

<400> SEQUENCE: 144

```
gaggttcagc tgcagcagtc tggacctgag ctggtgaagc ctggggcttc agtgaagata     60

tcctgcaagg cttctggtta ctcatttact ggctacttta tgaactgggt gaaacagagc    120

catggaaaga gccttgagtg gattggacgt attaatcctt ataatggtga tactttttac    180

aaccagaagt tcaaggacaa ggccacatta actgtagaca catcctctag cacagcccac    240

atggagctcc ggagcctgac atctgaggag tctgcagtct attattgtgc aagatggact    300

acggtaataa actttgacta ccggggccaa ggcaccactc tcacagtctc ctca          354
```

<210> SEQ ID NO 145
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 145

```
Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Tyr Asp
            20                  25                  30

Val Val Trp Tyr Gln Gln Lys Pro Gly Gln Ser Pro Lys Leu Leu Met
        35                  40                  45

Tyr Tyr Val Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Pro
                85                  90                  95

Thr Phe Gly Gly Gly Thr Lys Leu Glu Ile Lys
            100                 105
```

<210> SEQ ID NO 146
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 146

```
agtattgtga tgacccagac tcccaaattc ctgcttgtgt cagcaggaga cagggttacc      60
ataacctgca aggccagtca gagtgtgagt tatgatgtag tttggtacca acagaagcca     120
gggcagtctc ctaaactgct gatgtattat gtatccaatc gctacactgg agtccctgat     180
cgcttcactg gcagtggata tgggacggat ttcactttca ccatcagcac tgtgcaggct     240
gaagacctgg cagtttattt ctgtcagcag gattatagct ctcctccgac gttcggtgga     300
ggcaccaagc tggaaatcaa a                                                321
```

<210> SEQ ID NO 147
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 147

```
Gly Tyr Ser Phe Thr Gly Tyr
1               5
```

<210> SEQ ID NO 148
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 148

```
Asn Pro Tyr Asn Gly Asp
1               5
```

<210> SEQ ID NO 149
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 149

-continued

```
Trp Thr Thr Val Ile Asn Phe Asp Tyr
1               5


<210> SEQ ID NO 150
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 150

Gly Tyr Ser Phe Thr Gly Tyr Phe Met Asn
1               5                   10


<210> SEQ ID NO 151
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 151

Arg Ile Asn Pro Tyr Asn Gly Asp Thr Phe
1               5                   10


<210> SEQ ID NO 152
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 152

Trp Thr Thr Val Ile Asn Phe Asp Tyr
1               5


<210> SEQ ID NO 153
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 153

Gly Tyr Phe Met Asn
1               5


<210> SEQ ID NO 154
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 154

Arg Ile Asn Pro Tyr Asn Gly Asp Thr Phe Tyr Asn Gln Lys Phe Lys
1               5                   10                  15

Asp


<210> SEQ ID NO 155
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 155
```

Trp Thr Thr Val Ile Asn Phe Asp Tyr
1 5

<210> SEQ ID NO 156
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 156

Thr Gly Tyr Phe Met Asn
1 5

<210> SEQ ID NO 157
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 157

Trp Ile Gly Arg Ile Asn Pro Tyr Asn Gly Asp Thr Phe
1 5 10

<210> SEQ ID NO 158
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 158

Ala Arg Trp Thr Thr Val Ile Asn Phe Asp
1 5 10

<210> SEQ ID NO 159
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 159

Lys Ala Ser Gln Ser Val Ser Tyr Asp Val Val
1 5 10

<210> SEQ ID NO 160
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 160

Tyr Val Ser Asn Arg Tyr Thr
1 5

<210> SEQ ID NO 161
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 161

Gln Gln Asp Tyr Ser Ser Pro Pro Thr
1 5

<210> SEQ ID NO 162
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 162

Lys Ala Ser Gln Ser Val Ser Tyr Asp Val Val
1 5 10

<210> SEQ ID NO 163
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 163

Tyr Val Ser Asn Arg Tyr Thr
1 5

<210> SEQ ID NO 164
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 164

Gln Gln Asp Tyr Ser Ser Pro Pro Thr
1 5

<210> SEQ ID NO 165
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 165

Lys Ala Ser Gln Ser Val Ser Tyr Asp Val Val
1 5 10

<210> SEQ ID NO 166
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 166

Tyr Val Ser Asn Arg Tyr Thr
1 5

<210> SEQ ID NO 167
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 167

Gln Gln Asp Tyr Ser Ser Pro Pro Thr 1 5

<210> SEQ ID NO 168
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 168

Ser Tyr Asp Val Val Trp Tyr
1 5

<210> SEQ ID NO 169
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 169

Leu Leu Met Tyr Tyr Val Ser Asn Arg Tyr
1 5 10

<210> SEQ ID NO 170
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 170

Gln Gln Asp Tyr Ser Ser Pro Pro
1 5

<210> SEQ ID NO 171
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 171

Arg Lys Lys Val Ser Pro Ala Val Leu
1 5

<210> SEQ ID NO 172
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 172

Thr Val Ala Ala Ser Val Ile Ile Arg Asp Thr Ser Ala Lys Asn Val
1 5 10 15

Ser Cys Tyr

<210> SEQ ID NO 173
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 173

Ile Arg Asp Thr Ser Ala Lys Asn
1 5

<210> SEQ ID NO 174
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 174

Leu Glu Leu Arg Trp Phe Arg Lys Lys Val Ser Pro Ala
1 5 10

<210> SEQ ID NO 175
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 175

Glu Glu Gly Leu Phe Thr Val Ala Ala Ser Val Ile Ile Arg Asp Thr
1 5 10 15

Ser Ala Lys Asn Val
20

<210> SEQ ID NO 176
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 176

Ala Thr Leu Val Gln Asp Gly Ile Ala Lys Gly Arg
1 5 10

<210> SEQ ID NO 177
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 177

Asn Pro Asp Glu Glu Gly Leu Phe Thr Val Ala Ala Ser Val Ile Ile
1 5 10 15

Arg Asp Thr Ser Ala Lys
20

<210> SEQ ID NO 178
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 178

Thr Val Ala Ala Ser Val Ile Ile Arg Asp Thr Ser Ala Lys Asn Val
1 5 10 15

Ser Cys Tyr

<210> SEQ ID NO 179
<211> LENGTH: 12

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 179

Ala Glu Gln Xaa Pro Glu Tyr Arg Gly Arg Ala Thr
1               5                   10


<210> SEQ ID NO 180
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 180

Gly Arg Ala Thr Leu Val Gln Asp Gly Ile Ala Lys Gly Arg Val
1               5                   10                  15


<210> SEQ ID NO 181
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 181

Glu Glu Gly Leu Phe Thr Val Ala Ala Ser Val Ile Ile Arg Asp Thr
1               5                   10                  15

Ser Ala Lys Asn Val
            20


<210> SEQ ID NO 182
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 182

Tyr Cys Ala Arg Gly Ala Tyr
1               5


<210> SEQ ID NO 183
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 183

Thr Phe Thr His Tyr
1               5


<210> SEQ ID NO 184
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 184
```

Phe Thr Phe Gly Ser Gly Thr Glu
1               5

<210> SEQ ID NO 185
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 185

Ser Leu Glu Trp Ile Gly Tyr Ile Tyr Pro Ser Asn Gly Gly Thr Gly
1               5                   10                  15

Tyr Asn Gln Lys Phe Lys Ser Arg
            20

<210> SEQ ID NO 186
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 186

Leu Leu Ile Ser Tyr Thr Ser Ser Leu His Ser Gly Val Pro Ser Arg
1               5                   10                  15

<210> SEQ ID NO 187
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 187

Thr Phe Thr His Tyr
1               5

<210> SEQ ID NO 188
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 188

Leu His Ser Gly Val Pro Ser Arg
1               5

<210> SEQ ID NO 189
<211> LENGTH: 443
<212> TYPE: PRT
<213> ORGANISM: Artificial Sequence
<220> FEATURE:
<223> OTHER INFORMATION: Synthetic polypeptide

<400> SEQUENCE: 189

Ala Pro Phe Asp Val Ile Gly Pro Pro Glu Pro Ile Leu Ala Val Val
1               5                   10                  15

Gly Glu Asp Ala Glu Leu Pro Cys Arg Leu Ser Pro Asn Ala Ser Ala
            20                  25                  30

Glu His Leu Glu Leu Arg Trp Phe Arg Lys Lys Val Ser Pro Ala Val
        35                  40                  45

Leu Val His Arg Asp Gly Arg Glu Gln Glu Ala Glu Gln Met Pro Glu
    50                  55                  60

```
Tyr Arg Gly Arg Ala Thr Leu Val Gln Asp Gly Ile Ala Lys Gly Arg
65                  70                  75                  80

Val Ala Leu Arg Ile Arg Gly Val Arg Val Ser Asp Asp Gly Glu Tyr
                85                  90                  95

Thr Cys Phe Phe Arg Glu Asp Gly Ser Tyr Glu Glu Ala Leu Val His
            100                 105                 110

Leu Lys Val Ala Ala Leu Gly Ser Asp Pro His Ile Ser Met Gln Val
        115                 120                 125

Gln Glu Asn Gly Glu Ile Cys Leu Glu Cys Thr Ser Val Gly Trp Tyr
    130                 135                 140

Pro Glu Pro Gln Val Gln Trp Arg Thr Ser Lys Gly Glu Lys Phe Pro
145                 150                 155                 160

Ser Thr Ser Glu Ser Arg Asn Pro Asp Glu Glu Gly Leu Phe Thr Val
                165                 170                 175

Ala Ala Ser Val Ile Ile Arg Asp Thr Ser Ala Lys Asn Val Ser Cys
            180                 185                 190

Tyr Ile Gln Asn Leu Leu Leu Gly Gln Glu Lys Lys Val Glu Ile Ser
        195                 200                 205

Ile Pro Ala Ser Ser Leu Pro Arg Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440
```

<210> SEQ ID NO 190
<211> LENGTH: 222
<212> TYPE: PRT
<213> ORGANISM: Artificial Sequence
<220> FEATURE:

<223> OTHER INFORMATION: Synthetic polypeptide

<400> SEQUENCE: 190

```
Ala Pro Phe Asp Val Ile Gly Pro Pro Glu Pro Ile Leu Ala Val Val
1               5                   10                  15

Gly Glu Asp Ala Glu Leu Pro Cys Arg Leu Ser Pro Asn Ala Ser Ala
            20                  25                  30

Glu His Leu Glu Leu Arg Trp Phe Arg Lys Lys Val Ser Pro Ala Val
        35                  40                  45

Leu Val His Arg Asp Gly Arg Glu Gln Glu Ala Glu Gln Met Pro Glu
    50                  55                  60

Tyr Arg Gly Arg Ala Thr Leu Val Gln Asp Gly Ile Ala Lys Gly Arg
65                  70                  75                  80

Val Ala Leu Arg Ile Arg Gly Val Arg Val Ser Asp Asp Gly Glu Tyr
                85                  90                  95

Thr Cys Phe Phe Arg Glu Asp Gly Ser Tyr Glu Glu Ala Leu Val His
            100                 105                 110

Leu Lys Val Ala Ala Leu Gly Ser Asp Pro His Ile Ser Met Gln Val
        115                 120                 125

Gln Glu Asn Gly Glu Ile Cys Leu Glu Cys Thr Ser Val Gly Trp Tyr
    130                 135                 140

Pro Glu Pro Gln Val Gln Trp Arg Thr Ser Lys Gly Glu Lys Phe Pro
145                 150                 155                 160

Ser Thr Ser Glu Ser Arg Asn Pro Asp Glu Glu Gly Leu Phe Thr Val
                165                 170                 175

Ala Ala Ser Val Ile Ile Arg Asp Thr Ser Ala Lys Asn Val Ser Cys
            180                 185                 190

Tyr Ile Gln Asn Leu Leu Leu Gly Gln Glu Lys Lys Val Glu Ile Ser
        195                 200                 205

Ile Pro Ala Ser Ser Leu Pro Arg His His His His His His
    210                 215                 220
```

<210> SEQ ID NO 191
<211> LENGTH: 524
<212> TYPE: PRT
<213> ORGANISM: ARTIFICIAL SEQUENCE
<220> FEATURE:
<223> OTHER INFORMATION: Synthetic polypeptide

<400> SEQUENCE: 191

```
Met Ala Val Pro Thr Asn Ser Cys Leu Leu Val Cys Leu Leu Thr Leu
1               5                   10                  15

Thr Val Leu Gln Leu Pro Thr Leu Asp Ser Ala Ala Pro Phe Asp Val
            20                  25                  30

Thr Ala Pro Gln Glu Pro Val Leu Ala Leu Val Gly Ser Asp Ala Glu
        35                  40                  45

Leu Thr Cys Gly Phe Ser Pro Asn Ala Ser Ser Glu Tyr Met Glu Leu
    50                  55                  60

Leu Trp Phe Arg Gln Thr Arg Ser Lys Ala Val Leu Leu Tyr Arg Asp
65                  70                  75                  80

Gly Gln Glu Gln Glu Gly Gln Gln Met Thr Glu Tyr Arg Gly Arg Ala
                85                  90                  95

Thr Leu Ala Thr Ala Gly Leu Leu Asp Gly Arg Ala Thr Leu Leu Ile
            100                 105                 110

Arg Asp Val Arg Val Ser Asp Gln Gly Glu Tyr Arg Cys Leu Phe Lys
        115                 120                 125
```

```
Asp Asn Asp Asp Phe Glu Glu Ala Ala Val Tyr Leu Lys Val Ala Ala
    130                 135                 140

Val Gly Ser Asp Pro Gln Ile Ser Met Thr Val Gln Glu Asn Gly Glu
145                 150                 155                 160

Met Glu Leu Glu Cys Thr Ser Ser Gly Trp Tyr Pro Glu Pro Gln Val
                165                 170                 175

Gln Trp Arg Thr Gly Asn Arg Glu Met Leu Pro Ser Thr Ser Glu Ser
            180                 185                 190

Lys Lys His Asn Glu Glu Gly Leu Phe Thr Val Ala Val Ser Met Met
        195                 200                 205

Ile Arg Asp Ser Ser Ile Lys Asn Met Ser Cys Cys Ile Gln Asn Ile
    210                 215                 220

Leu Leu Gly Gln Gly Lys Glu Val Glu Ile Ser Leu Pro Ala Pro Phe
225                 230                 235                 240

Val Pro Arg Leu Thr Pro Trp Ile Val Ala Val Ala Ile Ile Leu Leu
                245                 250                 255

Ala Leu Gly Phe Leu Thr Ile Gly Ser Ile Phe Phe Thr Trp Lys Leu
            260                 265                 270

Tyr Lys Glu Arg Ser Ser Leu Arg Lys Lys Glu Phe Gly Ser Lys Glu
        275                 280                 285

Arg Leu Leu Glu Glu Leu Arg Cys Lys Lys Thr Val Leu His Glu Val
    290                 295                 300

Asp Val Thr Leu Asp Pro Asp Thr Ala His Pro His Leu Phe Leu Tyr
305                 310                 315                 320

Glu Asp Ser Lys Ser Val Arg Leu Glu Asp Ser Arg Gln Ile Leu Pro
                325                 330                 335

Asp Arg Pro Glu Arg Phe Asp Ser Trp Pro Cys Val Leu Gly Arg Glu
            340                 345                 350

Thr Phe Thr Ser Gly Arg His Tyr Trp Glu Val Glu Val Gly Asp Arg
        355                 360                 365

Thr Asp Trp Ala Ile Gly Val Cys Arg Glu Asn Val Val Lys Lys Gly
    370                 375                 380

Phe Asp Pro Met Thr Pro Asp Asn Gly Phe Trp Ala Val Glu Leu Tyr
385                 390                 395                 400

Gly Asn Gly Tyr Trp Ala Leu Thr Pro Leu Arg Thr Ser Leu Arg Leu
                405                 410                 415

Ala Gly Pro Pro Arg Arg Val Gly Val Phe Leu Asp Tyr Asp Ala Gly
            420                 425                 430

Asp Ile Ser Phe Tyr Asn Met Ser Asn Gly Ser Leu Ile Tyr Thr Phe
        435                 440                 445

Pro Ser Ile Ser Phe Ser Gly Pro Leu Arg Pro Phe Phe Cys Leu Trp
    450                 455                 460

Ser Cys Gly Lys Lys Pro Leu Thr Ile Cys Ser Thr Ala Asn Gly Pro
465                 470                 475                 480

Glu Lys Val Thr Val Ile Ala Asn Val Gln Asp Asp Ile Pro Leu Ser
                485                 490                 495

Pro Leu Gly Glu Gly Cys Thr Ser Gly Asp Lys Asp Thr Leu His Ser
            500                 505                 510

Lys Leu Ile Pro Phe Ser Pro Ser Gln Ala Ala Pro
        515                 520
```

<210> SEQ ID NO 192
<211> LENGTH: 1575

<212> TYPE: DNA
<213> ORGANISM: Artificial Sequence
<220> FEATURE:
<223> OTHER INFORMATION: Synthetic polynucleotide

<400> SEQUENCE: 192
atggcagttc ccaccaactc ctgcctcctg gtctgtctgc tcaccctcac tgtcctacag 60
ctgcccacgc tggattcggc agctcccttc gatgtgaccg cacctcagga gccagtgttg 120
gccctagtgg gctcagatgc cgagctgacc tgtggctttt ccccaaacgc gagctcagaa 180
tacatggagc tgctgtggtt tcgacagacg aggtcgaaag cggtacttct ataccgggat 240
ggccaggagc aggagggcca gcagatgacg gagtaccgcg ggagggcgac gctggcgaca 300
gccgggcttc tagacggccg cgctactctg ctgatccgag atgtcagggt ctcagaccag 360
ggggagtacc ggtgcctttt caaagacaac gacgacttcg aggaggccgc cgtatacctc 420
aaagtggctg ctgtgggttc agatcctcaa atcagtatga cggttcaaga gaatggagaa 480
atggagctgg agtgcacctc ctctggatgg tacccagagc ctcaggtgca gtggagaaca 540
ggcaacagag agatgctacc atccacgtca gagtccaaga agcataatga ggaaggcctg 600
ttcactgtgg cagtttcaat gatgatcaga gacagctcca taaagaacat gtcctgctgc 660
atccagaata tcctccttgg ccaggggaag gaagtagaga tctccttacc agctcccttc 720
gtgccaaggc tgactccctg gatagtagct gtggctatca tcttactggc cttaggattt 780
ctcaccattg ggtccatatt tttcacttgg aaactataca aggaaagatc cagtctgcgg 840
aagaaggaat ttggctctaa agagagactt ctggaagaac tcagatgcaa aaagactgta 900
ctgcatgaag ttgacgtgac tctggatcca gacacagccc acccccacct cttcctgtat 960
gaagattcaa agtcagttcg attggaagat tcacgtcaga tcctgcctga tagaccagag 1020
agatttgact cctggccctg tgtgttgggc cgtgagacct ttacttcagg gagacattac 1080
tgggaggtgg aggtgggaga tagaactgac tgggccattg gtgtgtgtag ggagaatgtg 1140
gtgaagaaag ggtttgaccc catgactcct gataatgggt tctgggctgt ggagttgtat 1200
ggaaatgggt actgggccct caccccactc aggacctctc tccgattagc agggccccct 1260
cgcagagttg gggtttttct ggactatgac gcaggagaca tttccttcta caacatgagt 1320
aacggatctc ttatctatac tttccctagc atctctttct ctggcccccct ccgtcccttc 1380 ttttgtctgt ggtcctgtgg taaaaagccc ctgaccatct gttcaactgc caatgggcct 1440
gagaaagtca cagtcattgc taatgtccag gacgacattc ccttgtcccc gctgggggaa 1500
ggctgtactt ctggagacaa agacactctc cattctaaac tgatcccgtt ctcacctagc 1560
caagcggcac cataa 1575

<210> SEQ ID NO 193
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 193

Glu Val Gln Leu Gln Gln Ser Gly Pro Glu Leu Val Lys Pro Gly Ala
1 5 10 15

Ser Val Lys Ile Ser Cys Lys Ala Ser Gly Phe Ser Phe Ile Gly Tyr
20 25 30

Tyr Ile Asp Trp Val Lys Gln Ser Pro Gly Lys Ser Leu Glu Trp Ile
35 40 45

```
Gly Tyr Ile Tyr Pro Ser Asn Gly Glu Thr Ser Tyr His Gln Lys Cys
    50                  55                  60

Lys Gly Lys Ala Thr Leu Thr Val Asp Lys Ser Ser Ser Thr Val Asn
65                  70                  75                  80

Met Gln Leu Asn Ser Leu Thr Ser Glu Asp Ser Ala Val Tyr Tyr Cys
                85                  90                  95

Ala Arg Tyr Gly Asn Tyr Asp Trp Phe Phe Asp Val Trp Gly Ala Gly
            100                 105                 110

Thr Thr Val Thr Val Ser Ser
        115
```

<210> SEQ ID NO 194
<211> LENGTH: 357
<212> TYPE: DNA
<213> ORGANISM: Artificial Sequence
<220> FEATURE:
<223> OTHER INFORMATION: Synthetic polynucleotide

<400> SEQUENCE: 194

```
gaagtccagc tgcagcagtc tggacctgag ctggtgaagc ctggggcttc agtgaagata      60

tcctgcaagg cttctggttt ttctttcatt ggctactaca tagactgggt gaagcagagt     120

cctggaaaga gccttgagtg gattggatat atttatcctt ccaatggtga aaccagctac     180

caccagaagt gcaagggcaa ggccacattg actgtagaca aatcctccag cacagtcaac     240

atgcagctca acagtctgac atctgaggac tctgcagtct attactgtgc aagatatggt     300

aactacgact ggttcttcga tgtctggggc gcagggacca cggtcaccgt ttcctca        357
```

<210> SEQ ID NO 195
<211> LENGTH: 106
<212> TYPE: PRT
<213> ORGANISM: Artificial Sequence
<220> FEATURE:
<223> OTHER INFORMATION: Synthetic polypeptide

<400> SEQUENCE: 195

```
Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Phe Trp Ile Tyr
        35                  40                  45

Ser Thr Ser Asn Leu Ala Ser Gly Val Pro Ile Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Tyr Thr
                85                  90                  95

Phe Gly Gly Gly Thr Lys Leu Glu Ile Lys
            100                 105
```

<210> SEQ ID NO 196
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 196

-continued

```
caaattgttc tcacccagtc tccagcaatc atgtctgcat ctccagggga gaaggtcacc     60

ataacctgca gtgccagttc aagtgtaagt tacatgcact ggttccagca gaagccaggc    120

acttctccca aattttggat ttatagcaca tccaacctgg cttctggagt ccctattcgc    180

ttcagtggca gtggatctgg gacctcttac tctctcacaa tcagccgaat ggaggctgaa    240

gatgctgcca cttattactg ccagcaaagg agtagttacc cgtacacgtt cggagggggg    300

accaagctgg aaataaaacg g                                              321
```

```
<210> SEQ ID NO 197
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 197

Gly Phe Ser Ile Gly Tyr
1               5


<210> SEQ ID NO 198
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 198

Tyr Pro Ser Asn Gly Glu
1               5


<210> SEQ ID NO 199
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 199

Tyr Gly Asn Tyr Asp Trp Phe Phe Asp Val
1               5                   10


<210> SEQ ID NO 200
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 200

Gly Phe Ser Ile Gly Tyr Tyr Ile Asp
1               5


<210> SEQ ID NO 201
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 201

Tyr Ile Tyr Pro Ser Asn Gly Glu Thr Ser
1               5                   10


<210> SEQ ID NO 202
```

<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 202

Tyr Gly Asn Tyr Asp Trp Phe Phe Asp Val
1               5                   10

<210> SEQ ID NO 203
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 203

Gly Tyr Tyr Ile Asp
1               5

<210> SEQ ID NO 204
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 204

Tyr Ile Tyr Pro Ser Asn Gly Glu Thr Ser Tyr His Gln Lys Cys Lys
1               5                   10                  15

Gly

<210> SEQ ID NO 205
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 205

Tyr Gly Asn Tyr Asp Trp Phe Phe Asp Val
1               5                   10

<210> SEQ ID NO 206
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 206

Ile Gly Tyr Tyr Ile Asp
1               5

<210> SEQ ID NO 207
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 207

Trp Ile Gly Tyr Ile Tyr Pro Ser Asn Gly Glu Thr Ser
1               5                   10

<210> SEQ ID NO 208
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 208

Ala Arg Tyr Gly Asn Tyr Asp Trp Phe Phe Asp
1 5 10

<210> SEQ ID NO 209
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 209

Ser Ala Ser Ser Ser Val Ser Tyr Met His
1 5 10

<210> SEQ ID NO 210
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 210

Ser Thr Ser Asn Leu Ala Ser
1 5

<210> SEQ ID NO 211
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 211

Gln Gln Arg Ser Ser Tyr Pro Tyr Thr
1 5

<210> SEQ ID NO 212
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 212

Ser Ala Ser Ser Ser Val Ser Tyr Met His
1 5 10

<210> SEQ ID NO 213
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 213

Ser Thr Ser Asn Leu Ala Ser
1 5

<210> SEQ ID NO 214

<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 214

Gln Gln Arg Ser Ser Tyr Pro Tyr Thr
1               5

<210> SEQ ID NO 215
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 215

Ser Ala Ser Ser Ser Val Ser Tyr Met His
1               5                   10

<210> SEQ ID NO 216
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 216

Ser Thr Ser Asn Leu Ala Ser
1               5

<210> SEQ ID NO 217
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 217

Gln Gln Arg Ser Ser Tyr Pro Tyr Thr
1               5

<210> SEQ ID NO 218
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 218

Ser Tyr Met His Trp Phe
1               5

<210> SEQ ID NO 219
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 219

Phe Trp Ile Tyr Ser Thr Ser Asn Leu Ala
1               5                   10

<210> SEQ ID NO 220
<211> LENGTH: 8

<212> TYPE: PRT
<213> ORGANISM: Artificial Sequence
<220> FEATURE:
<223> OTHER INFORMATION: Synthetic polypeptide

<400> SEQUENCE: 220

Gln Gln Arg Ser Ser Tyr Pro Tyr
1               5

<210> SEQ ID NO 221
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 221

Gln Ile Gln Leu Val Gln Ser Gly Pro Glu Leu Lys Lys Pro Gly Ala
1               5                   10                  15

Thr Val Lys Ile Ser Cys Lys Ala Ser Gly Tyr Thr Phe Thr Ile Phe
            20                  25                  30

Gly Met Asn Trp Val Lys Gln Ala Pro Gly Lys Gly Leu Glu Trp Met
        35                  40                  45

Gly Trp Ile Asn Thr Asn Thr Gly Glu Pro Thr Tyr Ala Glu Glu Phe
    50                  55                  60

Lys Gly Arg Phe Ala Phe Ser Leu Glu Thr Ser Ala Ser Thr Ala Phe
65                  70                  75                  80

Leu Gln Ile Asn Asn Leu Lys Asn Glu Asp Thr Ala Thr Tyr Phe Cys
                85                  90                  95

Ala Arg Val Gly Tyr Tyr Asp Phe Asp Tyr Trp Gly Gln Gly Thr Thr
            100                 105                 110

Leu Thr Val Ser Ser
        115

<210> SEQ ID NO 222
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 222
cagatccagt tggtgcagtc tggacctgag ctgaagaagc ctggagcgac agtcaagatc 60
tcctgcaagg cttctggata taccttcaca atctttggaa tgaactgggt gaagcaggct 120
ccaggaaagg gtttagagtg gatgggctgg ataaacacca acactggaga gccaacatat 180
gctgaagagt tcaagggacg gtttgccttc tctttggaaa cctctgccag cactgccttt 240
ttgcagatca acaacctcaa aaatgaggac acggctacat atttctgtgc aagagtgggg 300
tactacgact ttgactactg gggccaaggc accactctca cagtctcctc a 351

<210> SEQ ID NO 223
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 223

Asp Val Val Met Thr Gln Thr Pro Leu Thr Leu Ser Val Thr Val Gly
1               5                   10                  15

```
Gln Pro Ala Ser Ile Ser Cys Lys Ser Ser Gln Ser Leu Leu Asp Ser
            20                  25                  30

Asp Gly Lys Thr Phe Leu Asn Trp Phe Leu Gln Arg Pro Gly Gln Ser
        35                  40                  45

Pro Lys Arg Leu Ile Tyr Leu Val Ser Lys Lys Asp Ser Gly Val Pro
    50                  55                  60

Asp Arg Phe Thr Gly Ser Gly Ala Gly Thr Asp Phe Thr Leu Lys Ile
65                  70                  75                  80

Ser Arg Val Glu Ala Glu Asp Leu Gly Val Tyr Tyr Cys Arg Gln Gly
                85                  90                  95

Thr His Phe Pro Trp Thr Phe Gly Gly Gly Thr Arg Leu Glu Ile Lys
            100                 105                 110


<210> SEQ ID NO 224
<211> LENGTH: 336
<212> TYPE: DNA
<213> ORGANISM: Artificial Sequence
<220> FEATURE:
<223> OTHER INFORMATION: Synthetic polynucleotide

<400> SEQUENCE: 224

gatgttgtga tgacccagac tccactcact ttgtcggtta ccgttggaca accagcctcc      60

atctcttgca agtcaagtca gagcctctta gatagtgatg gaaagacatt tttgaattgg     120

ttcttacaga ggccaggcca gtctccaaag cgcctaatct atctggtgtc taaaaaggac     180

tctggagtcc ctgacaggtt cactggcagt ggagcaggga cagatttcac actgaaaatc     240

agcagagtgg aggctgagga tttgggagtt tattattgcc ggcaaggtac acattttccg     300

tggacgttcg gtggaggcac caggctggaa atcaaa                               336


<210> SEQ ID NO 225
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 225

Gly Tyr Thr Phe Phe Ile Phe
1               5


<210> SEQ ID NO 226
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 226

Asn Thr Asn Thr Gly Glu
1               5


<210> SEQ ID NO 227
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 227

Val Gly Tyr Tyr Asp Phe Asp Tyr
1               5
```

```
<210> SEQ ID NO 228
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 228

Gly Tyr Thr Phe Phe Ile Phe Gly Met Asn
1               5                   10


<210> SEQ ID NO 229
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 229

Trp Ile Asn Thr Asn Thr Gly Glu Pro Thr
1               5                   10


<210> SEQ ID NO 230
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 230

Val Gly Tyr Tyr Asp Phe Asp Tyr
1               5


<210> SEQ ID NO 231
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 231

Ile Phe Gly Met Asn
1               5


<210> SEQ ID NO 232
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 232

Trp Ile Asn Thr Asn Thr Gly Glu Pro Thr Tyr Ala Glu Glu Phe Lys
1               5                   10                  15

Gly


<210> SEQ ID NO 233
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 233

Val Gly Tyr Tyr Asp Phe Asp Tyr
1               5
```

<210> SEQ ID NO 234
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 234

Thr Ile Phe Gly Met Asn
1 5

<210> SEQ ID NO 235
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 235

Trp Met Gly Trp Ile Asn Thr Asn Thr Gly Glu Pro Thr
1 5 10

<210> SEQ ID NO 236
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 236

Ala Arg Val Gly Tyr Tyr Asp Phe Asp
1 5

<210> SEQ ID NO 237
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 237

Lys Ser Ser Gln Ser Leu Leu Asp Ser Asp Gly Lys Thr Phe Leu Asn
1 5 10 15

<210> SEQ ID NO 238
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 238

Leu Val Ser Lys Lys Asp Ser
1 5

<210> SEQ ID NO 239
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 239

Arg Gln Gly Thr His Phe Pro Trp Thr
1 5

<210> SEQ ID NO 240
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 240

Lys Ser Ser Gln Ser Leu Leu Asp Ser Asp Gly Lys Thr Phe Leu Asn
1 5 10 15

<210> SEQ ID NO 241
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 241

Leu Val Ser Lys Lys Asp Ser
1 5

<210> SEQ ID NO 242
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 242

Arg Gln Gly Thr His Phe Pro Trp Thr
1 5

<210> SEQ ID NO 243
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 243

Lys Ser Ser Gln Ser Leu Leu Asp Ser Asp Gly Lys Thr Phe Leu Asn
1 5 10 15

<210> SEQ ID NO 244
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 244

Leu Val Ser Lys Lys Asp Ser
1 5

<210> SEQ ID NO 245
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 245

Arg Gln Gly Thr His Phe Pro Trp Thr
1 5

<210> SEQ ID NO 246
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 246

```
Leu Asp Ser Asp Gly Lys Thr Phe Leu Asn Trp Phe Leu
1               5                   10
```

<210> SEQ ID NO 247
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 247

```
Arg Leu Ile Tyr Leu Val Ser Lys Lys Asp
1               5                   10
```

<210> SEQ ID NO 248
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 248

```
Arg Gln Gly Thr His Phe Pro Trp
1               5
```

<210> SEQ ID NO 249
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 249

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Thr His
            20                  25                  30

Gly Val Asn Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95

Arg Pro Tyr Tyr Tyr Gly Ala Met Asp Tyr Trp Gly Gln Gly Thr Ser
            100                 105                 110

Val Thr Val Ser Ser
        115
```

<210> SEQ ID NO 250
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 250
caggtacaac tgaagcagtc aggacctggc ctagtgcagc cctcacagag cctgtccatc 60
acctgcacag tctctggttt ctcattaact acccatggtg taaactgggt tcgccagtct 120
ccaggaaagg gtctggagtg gctgggagtg atatggagtg gtggaagcac agactataat 180
gcagctttca tatccagact gagcatcagc aaggacaatt ccaagagcca agttttcttt 240
aaaatgaaca gtctgcaagc taatgacaca gccatatatt actgtgccag accctactac 300
tatggagcta tggactactg gggtcaagga acctcagtca ccgtctcctc a 351

<210> SEQ ID NO 251
<211> LENGTH: 106
<212> TYPE: PRT
<213> ORGANISM: Artificial Sequence
<220> FEATURE:
<223> OTHER INFORMATION: Synthetic polypeptide

<400> SEQUENCE: 251

Gln Ile Val Leu Thr Gln Ser Pro Ser Ile Met Ser Ala Ser Pro Gly
1 5 10 15

Glu Lys Val Thr Ile Thr Cys Ser Ala Ser Ser Ser Val Ser Tyr Ile
20 25 30

His Trp Phe Gln Gln Lys Pro Gly Thr Ser Pro Lys Leu Trp Ile Tyr
35 40 45

Ser Thr Ser Asn Leu Ala Ser Gly Val Pro Ala Arg Phe Ser Gly Ser
50 55 60

Gly Ser Gly Thr Ser Tyr Ser Leu Thr Ile Ser Arg Met Glu Ala Glu
65 70 75 80

Asp Ala Ala Thr Tyr Tyr Cys Gln Gln Arg Ser Ile Tyr Pro Leu Thr
85 90 95

Phe Gly Ala Gly Thr Lys Leu Glu Leu Lys
100 105

<210> SEQ ID NO 252
<211> LENGTH: 318
<212> TYPE: DNA
<213> ORGANISM: Artificial Sequence
<220> FEATURE:
<223> OTHER INFORMATION: Synthetic polynucleotide

<400> SEQUENCE: 252
caaattgttc tcacccagtc tccatcaatc atgtctgcat ctccagggga gaaggtcacc 60
ataacctgca gtgccagctc aagtgtaagt tacatacact ggttccagca gaagccaggc 120
acttctccca aactctggat ctatagcaca tccaacctgg cttctggagt ccctgctcgc 180
ttcagtggca gtggatctgg gacctcttac tctctcacaa tcagccgaat ggaggctgaa 240
gatgctgcca cttattactg ccagcaaagg agtatttacc cgctcacgtt cggtgctggg 300
accaagctgg agctgaaa 318

<210> SEQ ID NO 253
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 253

Gly Phe Ser Leu Thr Thr His 1 5

<210> SEQ ID NO 254
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 254

Trp Ser Gly Gly Ser
1 5

<210> SEQ ID NO 255
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 255

Pro Tyr Tyr Tyr Gly Ala Met Asp Tyr
1 5

<210> SEQ ID NO 256
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 256

Gly Phe Ser Leu Thr Thr His Gly Val Asn
1 5 10

<210> SEQ ID NO 257
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 257

Val Ile Trp Ser Gly Gly Ser Thr Asp
1 5

<210> SEQ ID NO 258
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 258

Pro Tyr Tyr Tyr Gly Ala Met Asp Tyr
1 5

<210> SEQ ID NO 259
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 259

Thr His Gly Val Asn
1 5

<210> SEQ ID NO 260
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 260

Val Ile Trp Ser Gly Gly Ser Thr Asp Tyr Asn Ala Ala Phe Ile Ser
1 5 10 15

<210> SEQ ID NO 261
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 261

Pro Tyr Tyr Tyr Gly Ala Met Asp Tyr
1 5

<210> SEQ ID NO 262
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 262

Thr Thr His Gly Val Asn
1 5

<210> SEQ ID NO 263
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 263

Val Trp Gly Val Ile Trp Ser Gly Gly Ser Thr Asp
1 5 10

<210> SEQ ID NO 264
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 264

Ala Arg Pro Tyr Tyr Tyr Gly Ala Met Asp
1 5 10

<210> SEQ ID NO 265
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 265

Ser Ala Ser Ser Ser Val Ser Tyr Ile His
1 5 10

<210> SEQ ID NO 266
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 266

Ser Thr Ser Asn Leu Ala Ser
1 5

<210> SEQ ID NO 267
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 267

Gln Gln Arg Ser Ile Tyr Pro Leu Thr
1 5

<210> SEQ ID NO 268
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 268

Ser Ala Ser Ser Ser Val Ser Tyr Ile His
1 5 10

<210> SEQ ID NO 269
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 269

Ser Thr Ser Asn Leu Ala Ser
1 5

<210> SEQ ID NO 270
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 270

Gln Gln Arg Ser Ile Tyr Pro Leu Thr
1 5

<210> SEQ ID NO 271
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 271

Ser Ala Ser Ser Ser Val Ser Tyr Ile His
1 5 10

<210> SEQ ID NO 272
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 272

Ser Thr Ser Asn Leu Ala Ser
1               5

<210> SEQ ID NO 273
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 273

Gln Gln Arg Ser Ile Tyr Pro Leu Thr
1               5

<210> SEQ ID NO 274
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 274

Ser Tyr Ile His Trp Phe
1               5

<210> SEQ ID NO 275
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 275

Leu Trp Ile Tyr Ser Thr Ser Asn Leu Ala
1               5                   10

<210> SEQ ID NO 276
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 276

Gln Gln Arg Ser Ile Tyr Pro Leu
1               5

<210> SEQ ID NO 277
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 277

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ser Phe Thr Asn Tyr
            20                  25                  30

```
Gly Met Asn Trp Val Lys Gln Ala Pro Gly Lys Gly Leu Lys Trp Met
        35                  40                  45

Gly Trp Ile Asn Ile Tyr Thr Gly Glu Thr Thr Tyr Gly Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Arg Ser Glu Asp Thr Ala Thr Tyr Phe Cys
                85                  90                  95

Val Arg Gly Gly Thr Met Ile Met Tyr Trp Gly Gln Gly Thr Thr Leu
            100                 105                 110

Thr Val Ser Ser
        115


<210> SEQ ID NO 278
<211> LENGTH: 348
<212> TYPE: DNA
<213> ORGANISM: Artificial Sequence
<220> FEATURE:
<223> OTHER INFORMATION: Synthetic polynucleotide

<400> SEQUENCE: 278

cagatccagt tggtgcagtc tggacctgag ctgaagaagc ctggagagac agtcaagatc      60

tcctgcaagg cttctgggta tagcttcaca aactatggaa tgaactgggt gaagcaggct     120

ccaggaaagg gtttaaagtg gatgggctgg ataaatatct acactggaga gacaacatat     180

ggtgatgatt tcaagggacg gtttgccttc tctttggaaa cctctgccag cactgcctat     240

ttgcagatca acaacctcag aagtgaggac acggctacat atttctgtgt aagagggggg     300

actatgatta tgtactgggg ccaaggcacc actctcacag tctcctca                  348


<210> SEQ ID NO 279
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 279

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp His Gln Gln Lys Ser His Glu Ser Pro Arg Leu Leu Ile
        35                  40                  45

Lys Tyr Ala Ser Gln Ser Met Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asp Ser Trp Pro Leu
                85                  90                  95

Thr Phe Gly Ala Gly Thr Lys Leu Glu Leu Lys
            100                 105


<210> SEQ ID NO 280
<211> LENGTH: 321
<212> TYPE: DNA
<213> ORGANISM: Artificial Sequence
<220> FEATURE:
<223> OTHER INFORMATION: Synthetic polynucleotide
```

<400> SEQUENCE: 280
gatattgtgc taactcagtc tccagccacc ctgtctgtga ctccaggaga tagcgtcagt 60
ctttcctgca gggccagcca aagtattagc aacaacctac actggcatca acaaaaatca 120
catgagtctc caaggcttct catcaagtat gcttcccagt ccatgtctgg gatcccctcc 180
aggttcagtg gcagtggatc agggacagat ttcactctca gtatcaacag tgtggagact 240
gaagattttg gaatgtattt ctgtcaacag agtgacagct ggccgctcac gttcggtgct 300
gggaccaagc tggagctgaa a 321

<210> SEQ ID NO 281
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 281

Gly Tyr Ser Phe Thr Asn Tyr
1 5

<210> SEQ ID NO 282
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 282

Asn Ile Tyr Thr Gly Glu
1 5

<210> SEQ ID NO 283
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 283

Gly Gly Thr Met Ile Met Tyr
1 5

<210> SEQ ID NO 284
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 284

Gly Tyr Ser Phe Thr Asn Tyr Gly Met Asn
1 5 10

<210> SEQ ID NO 285
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 285

Trp Ile Asn Ile Tyr Thr Gly Glu Thr Thr
1 5 10

<210> SEQ ID NO 286
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 286

Gly Gly Thr Met Ile Met Tyr
1 5

<210> SEQ ID NO 287
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 287

Asn Tyr Gly Met Asn
1 5

<210> SEQ ID NO 288
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 288

Trp Ile Asn Ile Tyr Thr Gly Glu Thr Thr Tyr Gly Asp Asp Phe Lys
1 5 10 15

Gly

<210> SEQ ID NO 289
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 289

Gly Gly Thr Met Ile Met Tyr
1 5

<210> SEQ ID NO 290
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 290

Thr Asn Tyr Gly Met Asn
1 5

<210> SEQ ID NO 291
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 291

Trp Met Gly Trp Ile Asn Ile Tyr Thr Gly Glu Thr Thr 1 5 10

<210> SEQ ID NO 292
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 292

Val Arg Gly Gly Thr Met Ile Met
1 5

<210> SEQ ID NO 293
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 293

Arg Ala Ser Gln Ser Ile Ser Asn Asn Leu His
1 5 10

<210> SEQ ID NO 294
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 294

Tyr Ala Ser Gln Ser Met Ser
1 5

<210> SEQ ID NO 295
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 295

Gln Gln Ser Asp Ser Trp Pro Leu Thr
1 5

<210> SEQ ID NO 296
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 296

Arg Ala Ser Gln Ser Ile Ser Asn Asn Leu His
1 5 10

<210> SEQ ID NO 297
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 297

Tyr Ala Ser Gln Ser Met Ser
1 5

<210> SEQ ID NO 298
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 298

Gln Gln Ser Asp Ser Trp Pro Leu Thr
1               5

<210> SEQ ID NO 299
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 299

Arg Ala Ser Gln Ser Ile Ser Asn Asn Leu His
1               5                   10

<210> SEQ ID NO 300
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 300

Tyr Ala Ser Gln Ser Met Ser
1               5

<210> SEQ ID NO 301
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 301

Gln Gln Ser Asp Ser Trp Pro Leu Thr
1               5

<210> SEQ ID NO 302
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 302

Ser Asn Asn Leu His Trp His
1               5

<210> SEQ ID NO 303
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 303

Leu Leu Ile Lys Tyr Ala Ser Gln Ser Met
1               5                   10

<210> SEQ ID NO 304
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 304

```
Gln Gln Ser Asp Ser Trp Pro Leu
1               5
```

<210> SEQ ID NO 305
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 305

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ser Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Ile Tyr Thr Gly Glu Thr Thr Tyr Gly Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Ser Glu Asp Thr Ala Thr Tyr Phe Cys
                85                  90                  95

Val Arg Gly Gly Thr Met Ile Met Tyr Trp Gly Gln Gly Thr Thr Leu
            100                 105                 110

Thr Val Ser Ser
        115
```

<210> SEQ ID NO 306
<211> LENGTH: 348
<212> TYPE: DNA
<213> ORGANISM: Artificial Sequence
<220> FEATURE:
<223> OTHER INFORMATION: Synthetic polynucleotide

<400> SEQUENCE: 306

```
cagatccagt tggtgcagtc tggacctgag ctgaagaagc ctggagagac agtcaagatc     60

tcctgcaagg cttctgggta tagcttcaca aactatggaa tgaactgggt gaagcaggct    120

ccaggaaagg gtttaaagtg gatgggctgg ataaatatct acactggaga gacaacatat    180

ggtgatgatt tcaagggacg gtttgccttc tctttggaaa cctctgccag cactgcctat    240

ttgcagatca acaacctcaa aagtgaggac acggctacat atttctgtgt aagagggggg    300

actatgatta tgtactgggg ccaaggcacc actctcacag tctcctca                348
```

<210> SEQ ID NO 307
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 307

-continued

```
Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Phe Gly Gly Gly Thr Lys Leu Glu Ile Lys
            100                 105


<210> SEQ ID NO 308
<211> LENGTH: 330
<212> TYPE: DNA
<213> ORGANISM: Artificial Sequence
<220> FEATURE:
<223> OTHER INFORMATION: Synthetic polynucleotide

<400> SEQUENCE: 308

gacattgtgc tgacacagtc tcctgcttcc ttagctgtat ctctggggca gagggccacc      60

atctcataca gggccagcaa aagtgtcagt acatctggct atagttatat gcactggaac     120

caacagaaac caggacagcc acccagactc ctcatctatc ttgtatccaa cctagaatct     180

ggggtccctg ccaggttcag tggcagtggg tctgggacag acttcaccct caacatccat     240

cctgtggagg aggaggatgc tgcaacctat tactgtcagc acattaggga gctttacacg     300

ttcggagggg ggaccaagct ggaaataaaa                                      330


<210> SEQ ID NO 309
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 309

Gly Tyr Ser Phe Thr Asn Tyr
1               5


<210> SEQ ID NO 310
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 310

Asn Ile Tyr Thr Gly Glu
1               5


<210> SEQ ID NO 311
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 311
```

Gly Gly Thr Met Ile Met Tyr
1 5

<210> SEQ ID NO 312
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 312

Gly Tyr Ser Phe Thr Asn Tyr Gly Met Asn
1 5 10

<210> SEQ ID NO 313
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 313

Trp Ile Asn Ile Tyr Thr Gly Glu Thr Thr
1 5 10

<210> SEQ ID NO 314
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 314

Gly Gly Thr Met Ile Met Tyr
1 5

<210> SEQ ID NO 315
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 315

Asn Tyr Gly Met Asn
1 5

<210> SEQ ID NO 316
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 316

Trp Ile Asn Ile Tyr Thr Gly Glu Thr Thr Tyr Gly Asp Asp Phe Lys
1 5 10 15

Gly

<210> SEQ ID NO 317
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 317

-continued

```
Gly Gly Thr Met Ile Met Tyr
1               5


<210> SEQ ID NO 318
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 318

Thr Asn Tyr Gly Met Asn
1               5


<210> SEQ ID NO 319
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 319

Trp Met Gly Trp Ile Asn Ile Tyr Thr Gly Glu Thr Thr
1               5                   10


<210> SEQ ID NO 320
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 320

Val Arg Gly Gly Thr Met Ile Met
1               5


<210> SEQ ID NO 321
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 321

Arg Ala Ser Lys Ser Val Ser Thr Ser Gly Tyr Ser Tyr Met His
1               5                   10                  15


<210> SEQ ID NO 322
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 322

Leu Val Ser Asn Leu Glu Ser
1               5


<210> SEQ ID NO 323
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 323
```

-continued

Gln His Ile Arg Glu Leu Tyr Thr
1 5

<210> SEQ ID NO 324
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 324

Arg Ala Ser Lys Ser Val Ser Thr Ser Gly Tyr Ser Tyr Met His
1 5 10 15

<210> SEQ ID NO 325
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 325

Leu Val Ser Asn Leu Glu Ser
1 5

<210> SEQ ID NO 326
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 326

Gln His Ile Arg Glu Leu Tyr Thr
1 5

<210> SEQ ID NO 327
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 327

Arg Ala Ser Lys Ser Val Ser Thr Ser Gly Tyr Ser Tyr Met His
1 5 10 15

<210> SEQ ID NO 328
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 328

Leu Val Ser Asn Leu Glu Ser
1 5

<210> SEQ ID NO 329
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 329

Gln His Ile Arg Glu Leu Tyr Thr

-continued

```
1               5


<210> SEQ ID NO 330
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 330

Ser Thr Ser Gly Tyr Ser Tyr Met His Trp Asn
1               5                   10


<210> SEQ ID NO 331
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 331

Leu Leu Ile Tyr Leu Val Ser Asn Leu Glu
1               5                   10


<210> SEQ ID NO 332
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 332

Gln His Ile Arg Glu Leu Tyr
1               5
```